US009670200B2

(12) United States Patent
Almarsson et al.

(10) Patent No.: US 9,670,200 B2
(45) Date of Patent: Jun. 6, 2017

(54) QUATERNARY AMMONIUM SALT PRODRUGS

(75) Inventors: Örn Almarsson, Shrewsbury, MA (US); Laura Cook Blumberg, Lincoln, MA (US); Julius F. Remenar, Framingham, MA (US)

(73) Assignee: Alkermes Pharma Ireland Limited, Dublin (IE)

( * ) Notice: Subject to any disclaimer, the term of this patent is extended or adjusted under 35 U.S.C. 154(b) by 154 days.

(21) Appl. No.: 12/978,178

(22) Filed: Dec. 23, 2010

(65) Prior Publication Data

US 2011/0178068 A1   Jul. 21, 2011

Related U.S. Application Data

(60) Provisional application No. 61/293,171, filed on Jan. 7, 2010, provisional application No. 61/293,163, filed on Jan. 7, 2010, provisional application No. 61/293,153, filed on Jan. 7, 2010, provisional application No. 61/293,124, filed on Jan. 7, 2010.

(51) Int. Cl.

| C07D 471/04 | (2006.01) |
|---|---|
| A61K 31/343 | (2006.01) |
| A61K 31/40 | (2006.01) |
| A61K 31/444 | (2006.01) |
| A61K 31/452 | (2006.01) |
| A61K 31/473 | (2006.01) |
| A61K 33/02 | (2006.01) |
| C07D 211/52 | (2006.01) |
| C07D 221/18 | (2006.01) |
| C07D 307/87 | (2006.01) |
| C07D 495/04 | (2006.01) |
| A61K 31/407 | (2006.01) |
| A61K 31/519 | (2006.01) |
| A61K 31/551 | (2006.01) |
| C07D 207/09 | (2006.01) |
| C07D 491/044 | (2006.01) |
| C07F 9/6561 | (2006.01) |

(52) U.S. Cl.
CPC .......... *C07D 471/04* (2013.01); *A61K 31/343* (2013.01); *A61K 31/40* (2013.01); *A61K 31/407* (2013.01); *A61K 31/444* (2013.01); *A61K 31/452* (2013.01); *A61K 31/473* (2013.01); *A61K 31/519* (2013.01); *A61K 31/551* (2013.01); *C07D 207/09* (2013.01); *C07D 211/52* (2013.01); *C07D 221/18* (2013.01); *C07D 307/87* (2013.01); *C07D 491/044* (2013.01); *C07D 495/04* (2013.01); *C07F 9/6561* (2013.01)

(58) Field of Classification Search
None
See application file for complete search history.

(56) References Cited

U.S. PATENT DOCUMENTS

| 3,998,815 A | 12/1976 | Bodor |
| 4,264,765 A * | 4/1981 | Bodor .................... C07H 17/08 536/7.2 |
| 4,727,151 A | 2/1988 | Bodor |

(Continued)

FOREIGN PATENT DOCUMENTS

| EP | 1 891 956 A1 | 2/2008 |
| WO | 2005079807 A1 | 9/2005 |

(Continued)

OTHER PUBLICATIONS

Bodor "Prodrugs versus soft drugs" Chapter 11, Design of Prodrugs Elsevier Science Publisher B. V. (1985), pp. 333-354.*
Davidsen et al. Journal of Medicinal Chemistry, 37 (26), (1994), pp. 4423-4429.*
Nielsen et al European Journal of Pharmaceutical Sciences 26 (2005) 421-428.*
Nielsen, A.B., et al., "Bioreversible quaternary N-acyloxymethyl derivatives of the tertiary amines bupivacaine and lidocaine—synthesis, aqueous solubility and stability in buffer, human plasma and simulated intestinal fluid," *European Journal of Pharmaceutical Sciences 24*, pp. 433-440 (2005).

(Continued)

*Primary Examiner* — Nyeemah A Grazier
(74) *Attorney, Agent, or Firm* — Elmore Patent Law Group, P.C.; Carolyn Elmore; Darlene Vanstone

(57) ABSTRACT

The invention provides a method of sustained delivery of a tertiary amine-containing parent drug comprising administering to a patient an effective amount of a prodrug compound of the invention wherein upon administration to the patient, release of the parent drug from the prodrug is sustained release. Prodrug compounds suitable for use in the methods of the invention are labile quaternary ammonium salts of tertiary amine-containing parent drugs (or tertiary imine-containing parent drugs) that are derivatized through aldehyde-linked prodrug moieties that reduce the solubility of the prodrug compound at a reference pH as compared to the parent drug. The physical, chemical and solubility properties of these derivatives can be further modulated by the choice of counterion $X^-$. In one embodiment, the present invention provides a prodrug compound of Formula I:

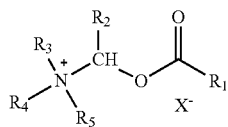

Formula I where $R_1$-$R_5$ are defined in the written description of the invention. The prodrug compounds of the invention can be used to treat any condition for which the tertiary amine-containing parent drug or tertiary imine-containing parent drug is useful as a treatment.

17 Claims, 4 Drawing Sheets

(56) References Cited

U.S. PATENT DOCUMENTS

| | | | |
|---|---|---|---|
| 4,992,550 | A | 2/1991 | Hughes |
| 5,236,927 | A | 8/1993 | Jones et al. |
| 5,783,589 | A | 7/1998 | Latimer et al. |
| 5,985,856 | A | 11/1999 | Stella et al. |
| 6,180,095 | B1 | 1/2001 | Greenwald et al. |
| 6,608,084 | B1 | 8/2003 | Bourzat et al. |
| 6,758,099 | B2 * | 7/2004 | Cima et al. ............... 73/861 |
| 2002/0176841 | A1 * | 11/2002 | Barker et al. ............ 424/78.12 |
| 2005/0169992 | A1 * | 8/2005 | Jao ................. A61K 31/7004 424/468 |
| 2006/0084692 | A1 | 4/2006 | Erik Wong et al. |
| 2006/0293217 | A1 * | 12/2006 | Barker et al. ................ 514/2 |
| 2007/0154546 | A1 * | 7/2007 | Zhang ............... A61K 9/0019 424/468 |
| 2008/0085888 | A1 | 4/2008 | Breining et al. |
| 2009/0053329 | A1 | 2/2009 | Peters et al. |
| 2011/0003828 | A1 | 1/2011 | Blumberg et al. |
| 2011/0015156 | A1 | 1/2011 | Remenar et al. |
| 2011/0166128 | A1 * | 7/2011 | Remenar et al. ............ 514/220 |
| 2011/0166156 | A1 * | 7/2011 | Blumberg et al. ....... 514/254.04 |
| 2011/0166194 | A1 | 7/2011 | Blumberg et al. |
| 2011/0319422 | A1 | 12/2011 | Blumberg et al. |
| 2012/0015866 | A1 | 1/2012 | Blumberg et al. |

FOREIGN PATENT DOCUMENTS

| | | |
|---|---|---|
| WO | 2009111540 A1 | 9/2009 |
| WO | WO 2011/084848 A2 | 7/2011 |

OTHER PUBLICATIONS

Krise, et al., "Novel Prodrug Approach for Tertiary Amines: Synthesis and Preliminary Evaluation of N-Phosphonooxymethyl Prodrugs," J. Med Chem 42: pp. 3094-3100 (1999).

Bogardus, J., et al., "Kinetics and Mechanism of Hydrolysis of Labile Quaternary Ammonium Derivatives of Tertiary Amines," Journal of Pharmaceutical Sciences 71(7): pp. 729-735 (Jul. 1982).

Yata, N., "Concept of Prodrug," Prog. Med., vol. 5, pp. 2152-2156 (1985).

Simplicio, A., "Prodrugs for Amines," Molecules 13, pp. 519-547 (2008).

Ichikawa, T., et al., "Optically Active Antifungal Azoles, Synthesis and Antifungal Activity of the Water-Soluble Prodrugs of . . . ," Chem. Pharm. Bull 49(9): pp. 1102-1109 (2001).

Druzgala, P., et al., "Water Soluble Pilocarpine Prodrugs with Sustained Intra-ocular Activity in Normotensive Rabbits and in Glaucomatous Beagles," Journal of Controlled Release 28(1/3): pp. 282-283 (1994).

\* cited by examiner

QUATERNARY AMMONIUM SALT PRODRUGS

RELATED APPLICATION(S)

This application claims the benefit of U.S. Provisional Application Nos. 61/293,171, 61/293,163, 61/293,153 and 61/293,124 all filed on Jan. 7, 2010. The entire teachings of the above application(s) are incorporated herein by reference.

BACKGROUND OF THE INVENTION (i) Field of the Invention

The present invention relates to prodrug delivery systems for tertiary amine-containing drugs.

(ii) Background of the Invention

Drug delivery systems are often critical for the safe, effective administration of a biologically active agent. Perhaps the importance of these systems is best realized when patient compliance and consistent dosing are taken under consideration. For instance, reducing the dosing requirement for a drug from four-times-a-day to a single dose per day would have significant value in terms of ensuring patient compliance and optimization of therapy.

Optimization of a drug's bioavailability has many potential benefits. For patient convenience and enhanced compliance it is generally recognized that less frequent dosing is desirable. By extending the period through which the drug is released, a longer duration of action per dose is expected. This will then lead to an overall improvement of dosing parameters such as taking a drug once a day where it has previously required four times a day dosing or once a week or even less frequently when daily dosing was previously required. Many drugs are presently given at a once-a-day dosing frequency. Yet, not all of these drugs have pharmacokinetic properties that are suitable for dosing intervals of exactly twenty-four hours. Extending the period through which these drugs are released would also be beneficial.

One of the fundamental considerations in drug therapy involves the relationship between blood levels and therapeutic activity. For most drugs, it is of primary importance that serum levels remain between a minimally effective concentration and a potentially toxic level. In pharmacokinetic terms, the peaks and troughs of a drug's blood levels ideally fit well within the therapeutic window of serum concentrations. For certain therapeutic agents, this window is sufficiently narrow that dosage formulation becomes critical.

In an attempt to address the need for improved bioavailability profiles, several drug release modulation technologies have been developed. Enteric coatings have been used as a protector of pharmaceuticals in the stomach and microencapsulating active agents using protenoid microspheres, liposomes or polysaccharides have been effective in abating enzyme degradation of the active agent. Enzyme inhibiting adjuvants have also been used to prevent enzyme degradation.

A wide range of pharmaceutical formulations provide sustained release through microencapsulation of the active agent in amides of dicarboxylic acids, modified amino acids or thermally condensed amino acids. Slow release rendering additives can also be intermixed with a large array of active agents in tablet formulations.

While microencapsulation and enteric coating technologies impart enhanced stability and time-release properties to active agent substances these technologies suffer from several shortcomings. Incorporation of the active agent is often dependent on diffusion into the microencapsulating matrix, which may not be quantitative and may complicate dosage reproducibility. In addition, encapsulated drugs rely on diffusion out of the matrix, degradation of the matrix, or both which is highly dependent the chemical properties and on the water solubility of the active agent. Conversely, water-soluble microspheres swell by an infinite degree and, unfortunately, may release the active agent in bursts with limited active agent available for sustained release. Furthermore, in some technologies, control of the degradation process required for active agent release is unreliable. For example, an enterically coated active agent depends on pH to release of the active agent and, due to the variability of pH and residence times, it is difficult to control the rate of release.

Several implantable drug delivery systems have utilized polypeptide attachment to drugs. Additionally, other large polymeric carriers incorporating drugs into their matrices are used as implants for the gradual release of drug. Yet another technology combines the advantages of covalent drug attachment with liposome formation where the active ingredient is attached to highly ordered lipid films.

However there is still a need for an active agent delivery system that is able to deliver certain active agents which have been heretofore not formulated or difficult to formulate in a sustained release formulation for release over a sustained period of time and which is convenient for patient dosing.

It is known that tertiary amines are an extremely important in various classes of compounds from drug discovery. Many of these drugs are useful in therapeutic areas such as for their effects on the central nervous system (CNS) of a patient that would benefit from sustained release formulations. Tertiary amine-containing drugs have been derivatized to form compounds that enhance solubility of the parent tertiary amine-containing drug and improve targeting of the drug in the body and ultimately release the parent drug in its original form for pharmacological action. These compounds derivatized from tertiary amine containing parent drugs are referred to in the prior art as "delivery systems", "transient delivery systems", "prodrugs", or promoieties and comprise quaternary ammonium salts of parent drug compounds that are labile to enzymatic and/or chemical cleavage in vivo.

However, the derivatives, promoieties and prodrugs of parent tertiary amine-containing drugs of the prior art are concerned with increasing solubility of these drugs, protecting labile moieties on the parent drugs and achieving rapid release of the parent drug from the prodrug moiety with minimal toxicity. Thus far there have been no prodrugs of tertiary amine containing drugs that provide sustained release or zero order kinetics by, for example, decreasing the solubility of the parent drug. There is a generally recognized need for sustained delivery of tertiary amine-containing drugs that reduces the daily dosing requirement and allows for controlled and sustained release of the parent tertiary amine-containing drug and also avoids irregularities of release and cumbersome formulations encountered with typical dissolution controlled sustained release methods.

SUMMARY OF THE INVENTION

The present invention accomplishes this by extending the period during which a tertiary amine-containing parent drug is released and absorbed after administration to the patient and providing a longer duration of action per dose than is currently expected. In one embodiment, the compounds suitable for use in the methods of the invention are labile quaternary ammonium salts of tertiary amine-containing parent drugs that are derivatized through aldehyde-linked prodrug moieties that reduce the solubility and polarity of the prodrug compound as compared to the underivatized parent drug.

In addition, it has also been discovered that the reduction or elimination in pH-dependence of solubility of the prodrug compounds of the invention relative to their parent drugs can be exploited in novel ways. The reduced solubility of the prodrug of the invention is maintained even if the prodrug is administered into an environment of fluctuating pH such as would be encountered in the stomach or at the site of injection. The pH independence of aqueous solubility for a prodrug of the invention also reduces or eliminates the problem of "dose dumping" (i.e. the undesirable rapid release of active agent upon administration of a sustained release formulation) which may occur in a sustained release formulation that is susceptible to changes in solubility in response to fluctuations in pH of the surrounding environment. The physical, chemical and solubility properties of the prodrugs can be further modulated by the choice of counterion $X^-$.

In one embodiment, the invention provides a method of sustained delivery of a tertiary amine-containing parent drug comprising administering to a patient an effective amount of a prodrug compound of formula I wherein upon administration to the patient, release of the parent drug from the prodrug is sustained release:

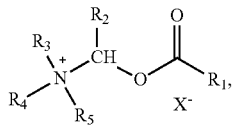

Formula I wherein $R_1$ is i) an aliphatic group comprising at least 1, carbon atom, preferably at least 5 carbon atoms, preferably at least 7 carbon atoms and preferably at least 9 carbon atoms; ii) a straight chain or branched, substituted or unsubstituted $C_5$-$C_{24}$-alkyl group, a straight chain or branched, substituted or unsubstituted $C_5$-$C_{24}$-alkenyl group or a straight chain or branched, substituted or unsubstituted $C_5$-$C_{24}$-alkynyl group; iii) a straight chain or branched, substituted or unsubstituted $C_7$-$C_{24}$-alkyl group, a straight chain or branched, substituted or unsubstituted $C_7$-$C_{24}$-alkenyl group or a straight chain or branched, substituted or unsubstituted $C_7$-$C_{24}$-alkynyl group; iv) a straight chain or branched, substituted or unsubstituted $C_9$-$C_{24}$-alkyl group, a straight chain or branched, substituted or unsubstituted $C_9$-$C_{24}$-alkenyl group or a straight chain or branched, substituted or unsubstituted $C_9$-$C_{24}$-alkynyl group; v) an alkyl group comprising at least 1 carbon atom wherein said alkyl group comprises a substituted or unsubstituted $C_3$-$C_{12}$ cycloalkyl group vi) a secondary or tertiary alkyl group, such as $C_3$-$C_{12}$-cycloalkyl, 1-methyl-$C_3$-$C_{12}$-cycloalkyl, isopropyl, sec-butyl, t-butyl, pent-2-yl, hex-2-yl, hept-2-yl, cyclopentyl, neopentyl, 3-methylpent-3-yl, 3-ethylpent-3-yl; 2,3-dimethylbut-2-yl; 2-methylbut-2-yl, 2 methyl hex-2-yl, 1-methylcyclopropyl, 1-methylcyclopentyl, 1-methylcyclohexyl, 1-ethylcyclohexyl or a branched alkyl group vii) aryl or substituted aryl or viii) heteroaryl or substituted heteroaryl; $R_2$ is hydrogen, straight chain or branched, substituted or unsubstituted $C_1$-$C_6$ alkyl, or substituted or unsubstituted $C_3$-$C_{12}$ cycloalkyl and preferably $R_2$ is hydrogen or methyl and most preferably, R2 is hydrogen; $R_3$, $R_4$ and $R_5$, together with the nitrogen atom to which they are attached, form a tertiary amine-containing parent drug or a tertiary imine-containing parent drug; and $X^-$ is a pharmaceutically acceptable anion.

In one preferred embodiment, the prodrug compound of formula I further comprises a biocompatible delivery system for delivering the prodrug wherein the system is preferably capable of minimizing accelerated hydrolytic cleavage of the prodrug. Preferably the biocompatible delivery system is capable of minimizing hydrolytic cleavage by minimizing exposure of the prodrug to water and/or minimizing exposure to pH conditions deviating from the physiological range of pH (e.g. about 7). Preferred delivery systems include biocompatible polymeric matrix delivery systems comprising the prodrug and capable of minimizing diffusion of water into the matrix.

It is understood that the prodrug compound of formula I includes a tertiary amine (or imine)-containing parent drug that is further "substituted" as that term is defined herein, for any purpose including but not limited to, stabilization of the parent during synthesis of the prodrug and stabilization of the prodrug for administration to the patient. One example of a substituted tertiary amine-containing parent drug is a pharmaceutically acceptable ester of the tertiary amine-containing parent drug. Any of the tertiary amine-containing parent drugs and prodrugs of parent drugs of the invention may be substituted so long as the substituted tertiary amine-containing or substituted tertiary imine-containing parent drug which when administered to a patient in vivo becomes cleaved by chemical and/or enzymatic hydrolysis thereby releasing the parent drug moiety such that a sufficient amount of the compound intended to be delivered to the patient is available for its intended therapeutic use in a sustained release manner.

In one embodiment, $R_1$ is a branched alkyl group corresponding to one of the formulas below.

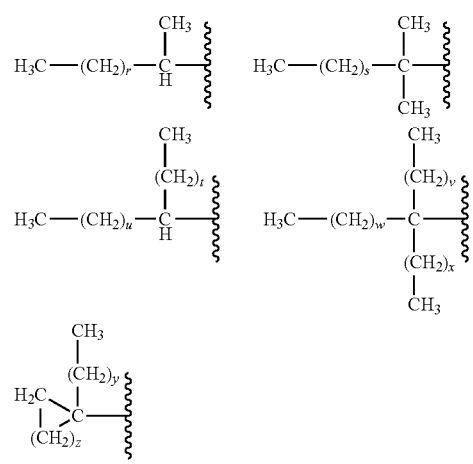

In these groups, r is 0 to 21 and s is 0 to 20. Each of t and u is independently 0 to 21, provided that the sum of t and u is from 0 to 21. Each of v, w and x is independently 0 to 20, provided that the sum of v, w and x is from 0 to 20. z is an integer from 1 to 10 and y is an integer from 0 to 20, provided that the sum of z and y is from 1 to 21. Preferably, r is an integer from 1 to 21; s is an integer from 1 to 20; the sum of t and u is from 5 to 21; the sum of v, w and x is from 4 to 20; and the sum of y and z is from 4 to 21.

In another embodiment, the invention provides a method for producing a prodrug compound of a tertiary amine-containing parent drug of Formula I comprising the step of reacting the tertiary amine of the parent drug of Formula IV:

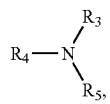

Formula IV wherein $R_3$, $R_4$ and $R_5$, together with the nitrogen atom to which they are attached, form the tertiary amine-containing parent drug compound, with a compound of Formula II:

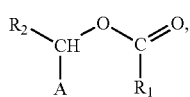

Formula II wherein A is a leaving group, and $R_1$ and $R_2$ are as defined for Formula I.

It is understood that the parent drug of Formula IV may be substituted with at least one chemical moiety. An example of a substituted parent drug includes, but is not limited to, a tertiary amine-containing parent drug substituted with at least one pharmaceutically acceptable ester. Substitution of the tertiary-amine containing parent drug prior to quaternization chemistry is, for example, useful in stabilizing reactive sites on the parent drug during synthesis of the prodrug.

The term "labile" as used herein refers to the capacity of the quaternary ammonium salt form of a tertiary amine containing parent drug to undergo enzymatic and/or chemical cleavage in vivo thereby releasing the original tertiary-amine containing parent drug. As used herein the term "prodrug" means the labile quaternary ammonium salt derivative compound of a tertiary amine-containing or tertiary imine-containing parent drug which when administered to a patient in vivo becomes cleaved by chemical and/or enzymatic hydrolysis thereby releasing the parent drug moiety such that a sufficient amount of the compound intended to be delivered to the patient is available for its intended therapeutic use in a sustained release manner. As used herein the term "parent drug" means any chemical compound that is useful in the prevention, diagnosis, treatment, or cure of disease for the relief of pain or to control or improve the underlying cause or symptoms associated with any physiological or pathological disorder in humans or animals. While a specific isomeric form of a parent drug may be preferred for use in treatment, the term "parent drug" as used herein is intended to encompass all isomers of the parent drug. A "tertiary amine-containing parent drug" is any parent drug comprising a tertiary amine moiety including aliphatic tertiary amines, cyclic tertiary amines and aromatic tertiary amines. A "tertiary imine-containing parent drug" is any parent drug comprising an imine moiety, i.e. a carbon nitrogen double bond. A "substituted parent drug" is used herein to mean a parent drug that is "substituted" as that term is defined herein. Parent drugs may be substituted for the purposes of stabilization of the parent drug during preparation of the prodrug or for the purposes of stabilizing the prodrug of the invention for any purpose including for administration to a patient.

The prodrug compounds of Formula I can be used to treat any condition for which the tertiary amine-containing parent drug is useful.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

Figure 1:
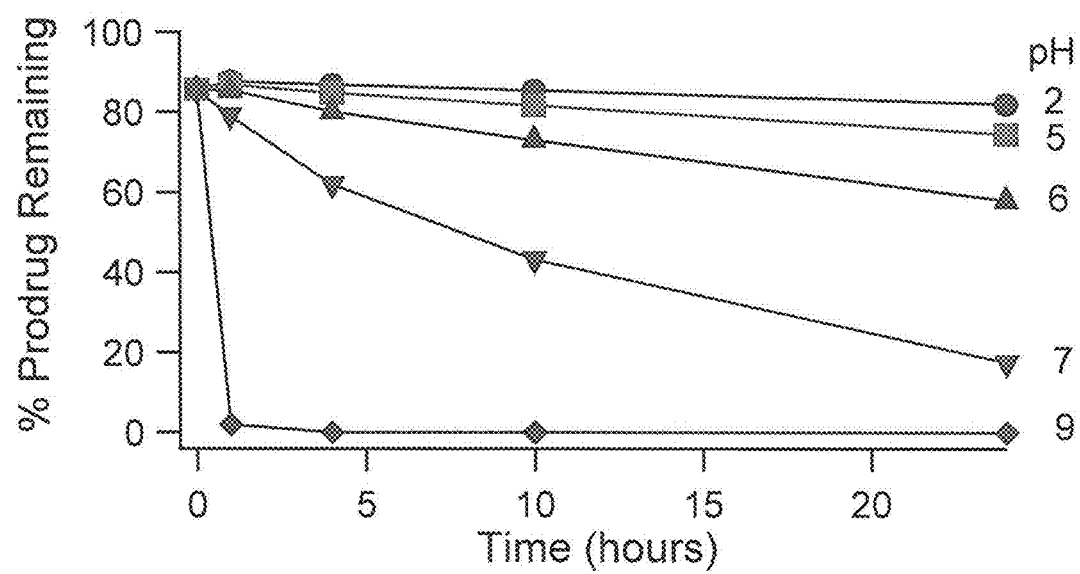
FIG. 1: Solution stability of asenapine octanoate prodrug as a function of pH.

The prodrug compounds of the present invention having the general structure of Formula I provide sustained or extended release to the parent compound. The terms "sustained release", "sustained delivery" and "extended release" are used interchangeably herein to indicate that the prodrugs of the invention provide release of the parent drug by any mechanism including slow first-order kinetics of absorption or zero-order kinetics of absorption, such that the parent drug which is released from the prodrug provides a longer duration of action than the duration of action of the parent drug when administered alone (i.e. not as a prodrug of the invention). In accordance with the invention, "sustained release" of the prodrugs of the invention may include other pharmacokinetic indices such as a lower maximum concentration (Cmax) of parent drug in the blood and/or an extended period of time for the parent drug to reach maximum concentration in the blood (Tmax) as compared to the Cmax and Tmax when the parent drug is administered alone. Sustained release may also decrease concentration fluctuations in the body, as indicated by plasma concentration-time profiles.

Without being limited to any theory, the mechanism for sustained release of the prodrugs of the invention may be due to several factors including, but not limited to, the decreased solubility of the prodrug as compared to the parent drug at a reference pH such as the pH wherein the parent drug (not in prodrug form) would generally be fully protonated (e.g. around a pH 5.0). Such lower solubility of the prodrug at the reference pH may result in more gradual dissolution and slower release of the parent drug by the action of serum enzymes or chemical hydrolysis. In addition or alternatively, the mechanism of sustained release may be the result of the pH-independent solubility properties characteristic of the prodrugs of the invention that result in controlled and sustained release of the parent drug from the prodrug.

In one embodiment, the prodrugs of the present invention provide an extended period during which an active agent is absorbed thereby providing a longer duration of action per dose than is currently expected. This leads to an overall improvement of dosing parameters and the potential for less frequent dosing or improved pharmacokinetics for the duration of the currently prescribed dosing intervals.

"Effective amounts" or a "therapeutically effective amount" of a prodrug of the invention is based on that amount of the parent drug which is deemed to provide clinically beneficial therapy to the patient. In one embodiment, the prodrug of the invention provides an effective amount for a longer period of time per dose than that of the parent drug per the same dose when delivered alone.

In one embodiment, the prodrugs of the invention provide a lower Cmax of the parent drug as compared to the parent drug when administered alone. A lower Cmax means that dose dumping is minimized or avoided and that the side effects of the drug (e.g. sedation or coma) are also generally reduced or eliminated.

The tertiary amine-containing parent drug may be any tertiary amine-containing drug that induces a desired local or systemic effect. Such drugs include broad classes of compounds. In general, this includes: analgesic agents; anesthetic agents; antiarthritic agents; respiratory drugs, including antiasthmatic agents; anticancer agents, including antineoplastic agents; anticholinergics; anticonvulsants; antidepressants; antidiabetic agents; antidiarrheals; antihelminthics; antihistamines; antihyperlipidemic agents; antihypertensive agents; anti-infective agents such as antibiotics and antiviral agents; antiinflammatory agents; antimigraine preparations; antinauseants; antiparkinsonism drugs; antipruritics; antipsychotics; antipyretics; antispasmodics; antitubercular agents; antiulcer agents; antiviral agents; anxiolytics; appetite suppressants; attention deficit disorder (ADD) and attention deficit hyperactivity disorder (ADHD) drugs; cardiovascular preparations including calcium channel blockers, CNS agents; beta-blockers and antiarrhythmic agents; central nervous system stimulants; serotonin agents (enhancers, transport or re-uptake inhibitors); alpha adrenergic antagonists or agonists; cough and cold preparations, including decongestants; antitussives; diuretics; genetic materials; gastrointestinal (GI) motility agents; herbal remedies; hormones; hormonolytics; hypnotics; hypoglycemic agents; immunosuppressive agents; leukotriene inhibitors; mitotic inhibitors; muscle relaxants; narcotic antagonists; opiod modulators; nicotine; nictone/acetylcholine antagonists or agonists; nutritional agents, such as vitamins, essential amino acids and fatty acids; ophthalmic drugs such as antiglaucoma agents; parasympatholytics; peptide drugs; psychostimulants; sedatives; steroids; sympathomimetics; tranquilizers; and vasodilators including general coronary, peripheral and cerebral.

Examples of tertiary amine-containing antibiotic parent drugs from which the prodrugs of the invention may be derived include: clindamycin, ofloxacin/levofloxacin, pefloxacin, quinupristine, rolitetracycline, and cefotiam.

Examples of tertiary amine-containing antifungal parent drugs from which the prodrugs of the invention may be derived include: butenafine, naftifine, and terbinafine.

Examples of tertiary amine-containing antimalarials and antiprotozoals parent drugs from which the prodrugs of the invention may be derived include: amodiaquine, quinacrine, sitamaquine, quinine.

Examples of tertiary amine-containing HIV protease inhibitor parent drugs from which the prodrugs of the invention may be derived include: saquinavir, indinavir, atazanavir and nelfinavir. Anti-HIV drugs also include maraviroc and aplaviroc for inhibition of HIV entry.

Examples of tertiary amine-containing anticonvulsants/ antispasmodics parent drugs from which the prodrugs of the invention may be derived include: atropine, darifenancin; dicyclomine; hyoscayamine, tiagabine, flavoxate; and alverine.

Examples of tertiary-amine containing antidepressant parent drugs from which the prodrugs of the invention are derived include amitriptyline, adinazolam, citalopram, cotinine, clomipramine, doxepin, escitalopram, femoxetine, imipramine, minaprine, moclobemide, mianserin, mirtazapine, nefazodone, nefopam, pipofenazine, promazine, ritanserin, trazodone, trimipramine and venlafaxine.

Examples of tertiary amine-containing antiemetic parent drugs from which the prodrugs of the invention are derived include aprepitant, buclizine, cilansetron, cyclizine, dolasetron, granisetron, meclizine, ondansetron, palonosetron, ramosetron, thiethylperazine, trimethobenzamide, scopolamine, and prochlorperazine.

Examples of tertiary amine-containing antihistamine parent drugs from which the prodrugs of the invention are derived include acetprometazine, azatadine, azelastine, brompheniramine, carbinoxamine, chlorpheniramine, clemastine, dexobrompheniramine, diphenhydramine, diphenylpyraline, doxepin, emadastine, loratadine, mequitazine, olopatadine, phenindamine, pheniramine, promethazine, tripelennamine, triprolidine, astemizole, cetirizine, fexofenadine, terfenadine, latrepirdine, ketotifen, cyproheptadine, hydroxyzine, clobenzepam doxylamine, cinnarizine, orphenadrine.

Examples of tertiary amine-containing antiparkinsonian parent drugs from which prodrugs of the invention are derived include cabergoline, ethopropazine, pergolide, selegiline, metixene, biperiden, cycrimine, procycladine and apomorphine.

Examples of tertiary amine-containing antipsychotic parent drugs from which prodrugs of the invention are derived include acetophenazine, amisulpride, aripiprazole, bifeprunox, blonanserin, cariprazine, carphenazine, clopenthixol, clozapine, dehydro aripiprazole, someperidone, droperidol, flupenthixol, fluphenazine, fluspirilene, haloperidol, iloperidone, lurasidone, mesoridazine, molindone, nemanopride, olanzapine, perospirone, perphenazine, PF-00217830 (Pfizer), pipotiazine, propericiazine, quetiapine, remoxipride, risperidone, sertindole, SLV-313 (Solvay/Wyeth), sulpiride, thioproperazine, thioridazine, thiothixene, trifluoperazine, ziprasidone, zotepine, pimozide, benzquinamide, triflupromazine, tetrabenazine, melperon, asenapine, chlorprothixene, spiperone and chlorpromazine.

Examples of tertiary amine-containing anxiolytic parent drugs from which prodrugs of the invention are derived include buspirone, and loxapine.

Examples of tertiary amine-containing nootroopic (memory and cognitive enhancers) parent drugs from which prodrugs of the invention are derived include donepezil, galantamine, latrepirdine, nicotine, TC-5616 (Targacept, Inc.) having the IUPAC name: N-[(2S,3S)-2-(pyridin-3-ylmethyl)-1-azabicyclo[2.2.2]oct-3-yl]-1-benzofuran-2-carboxamide.

Examples of tertiary amine-containing parent drugs for erectile dysfunction from which prodrugs of the invention are derived include apomorphine and sildenafil.

Examples of tertiary amine-containing parent drugs for migraine headache from which prodrugs of the invention are derived include almotriptan, naratriptan, rizatriptan, sumatriptan, zolmitriptan, dihydroergotamine, ergotamine, eletripan and lisuride.

Examples of tertiary amine-containing parent drugs for the treatment of alcoholism from which prodrugs of the invention are derived include naloxone and naltrexone.

Other narcotic antagonist amine containing parent drugs for treatment of substance abuse from which prodrugs of the invention are derived include: levallorphan, nalbuphine, nalorphine and nalmefene.

Examples of a tertiary amine-containing parent drug for the treatment of addiction from which a prodrug of the invention is derived include buprenorphine, isomethadone, levomethadyl acetate, methadyl acetate, nor-acetyl levomethadol, and normethadone.

Examples of tertiary amine-containing muscle relaxant parent drugs from which prodrugs are derived include cyclobenzaprine, nefopam, tolperisone, orphenadrine, and quinine.

Examples of tertiary amine-containing nonsteroidal anti-inflammatory parent drugs from which prodrugs of the invention are derived include etodolac, meloxicam, ketorolac, lornoxicam and tenoxicam. Examples of tertiary amine-containing opioid parent drugs from which prodrugs of the invention are derived include alfentanil, anileridine, buprenorphine, butorphanol, clonitazene, codeine, dihydrocodeine, dihydromorphin, fentanyl, hydromorphone, meperidine, metazocine, methadone, morphine, oxycodone, hyrdocodone, oxymorphone, pentazocine, remifentanil, and sufentanil.

Examples of other tertiary amine-containing analgesic parent drugs from which prodrugs of the invention are derived include methotrimeprazine, tramadol, nefopam, phenazocine, propiram, quinupramine, thebaine and propoxyphene.

Examples of tertiary amine-containing sedatives/hypnotics from which the prodrugs of the invention may be derived include: eszopiclone, flurazepam, propiomazine, and zopiclone.

Examples of tertiary amine-containing local analgesic parent drugs from which prodrugs of the invention are derived include bupivacaine, dexmedetomidine, dibucaine, dyclonine, lodicaine, mepivacaine, procaine, and tapentadol and ropivacaine.

Examples of tertiary amine-containing antianginals from which the prodrugs of the invention may be derived include ranozaline, bepridil.

Examples of tertiary amine-containing antiarrhythmics from which the prodrugs of the invention may be derived include: amiodarone, aprindine, encainide, moricizine, procainamide, diltiazem, verapamil, bepridil.

Examples of tertiary amine-containing antihypertensives from which the prodrugs of the invention may be derived include: azelnidipine, deserpidine, ketanserin, reserpine, and sildenafil.

Examples of tertiary amine-containing antithrombotics from which the prodrugs of the invention may be derived include: clopidogrel and ticlopidine.

Examples of tertiary amine-containing antineoplastic parent drugs from which prodrugs of the invention are derived include dasatinib, flavopiridol, gefitinib, imatinib, sunitinib, topotecan, vinblastine, vincristine, fincesine, vinorelbine, vinorelbine, tamoxifen, tremifene, and tesmilifene.

Examples of tertiary amine-containing drugs parent drugs for use in treating irritable bowel syndrome (IBS) from which the prodrugs of the invention are derived include asimadoline.

Examples of other tertiary amine-containing parent drugs from which the prodrugs of the invention are derived include: antimuscarinics and anticholinergics such as benzotropine, procyclidine and trihexylphenidyl; alpha andrenergic blockers such as dapiprazole, dexmedetomidine and nicergoline; anorexics such as diethylpropian, benzapehtamine, phendimetrazine, and sibutramine; antidiarrhels such as diphenoxylate and loperamide, antikinetic and antihypertensives such as clonidine; antiosteoporotics such as raloxifene; antipruritics such as methyldilazine; antitussives such as dextromethorphan; antiulceratives such as pirenzepine; cholinesterase inhibitors such as galantamine; gastroprokinetics such as alvimopan, cisapride, and piboserod; miglustat for treating glycosphingolipid lysosomal storage disorder; clomifene as gonad stimulating prinicipal; neuromuscular blockers such as dihydro-beta-erythrodoidine, niotropics such as rivastigmine, oxytocics such as methylergonovine; antiametics such as chloroquine; respiratory stimulants such as doxapram; muscarinic receptor antagonists for treating urinary incontinence such as oxybutynin and solifenacin; calcium channel blockers such as flunarizine; anthelmintics such as diethylcarbamazine and quinacrine; miotics such as physostigmine; neuroprotectives such as lubeluzole; immunosuppressants such as mycophenolate mofetil; and stimulants such as nicotine.

Preferred tertiary amine-containing parent drugs from which prodrugs of the invention are derived include amisulpride, aripiprazole, asenapine, cariprazine, citalopram, dehydroaripiprazole, escitalopram, galantamine, iloperidone, latrepirdine, lurasidone, olanzapine, paliperidone, perospirone, risperidone, and ziprasidone.

The compounds suitable for use in the methods of the invention are labile quaternary ammonium salts of tertiary amine-containing parent drugs that are derivatized through aldehyde-linked prodrug moieties that reduce the solubility and polarity of the prodrug compound as compared to the underivatized parent drug. The physical and chemical (including solubility) properties of these derivatives can be further modulated by the choice of counterion $X^-$. In one embodiment, a prodrug compound of the invention is less soluble at a reference pH than the parent drug. As used herein the term "reference pH" refers to the pH at which the aqueous solubility of a prodrug of the invention is compared to the aqueous solubility of the parent drug (not in prodrug form). Generally the reference pH is the pH at which the parent drug is fully protonated. It is understood that the term "fully protonated" as used herein includes a parent drug that is essentially fully protonated such that it is at least 95% protonated and preferably at least 99% protonated. Typically, the reference pH is about 5 and is preferably in the range of about 4 to about 6 and is more preferably in the range of about 4 to about 7. Preferably the aqueous solubility is measured in a phosphate buffer at room temperature. In one embodiment, the aqueous solubility of a prodrug compound of the invention at the reference pH is at least an order of magnitude lower than that of the aqueous solubility of the parent drug.

In one embodiment, a compound of the invention has an aqueous solubility in a phosphate buffer at room temperature of less than about 0.1 mg/ml, preferably less than about 0.01 mg/ml, preferably less than about 0.0001 mg/ml, and even more preferably less than about 0.00001 mg/ml at a pH of about 6.

In a preferred embodiment, a compound of the invention provides sustained delivery of the parent drug over hours, days, weeks or months when administered parenterally to a subject. For example, the compounds can provide sustained delivery of the parent drug for up to 7, 15, 30, 60, 75 or 90 days or longer. Without being bound by theory, it is believed that the compounds of the invention form an insoluble depot upon parenteral administration, for example subcutaneous, intramuscular or intraperitoneal injection.

In another preferred embodiment, the prodrug of the invention provides sustained delivery of the parent drug when delivered orally. The prodrugs of the invention are generally stable to hydrolysis in the low pH of the stomach. Given that the solubility of the prodrugs of the invention is pH-independent, crossing from the intestine having a low pH to the blood stream having a pH of around 7 will not cause the prodrugs to become soluble and dose dump. In a preferred embodiment, the orally delivered prodrugs further comprise a delivery system capable of enhancing sustained release and providing protection from enzymatic and chemical cleavage in the stomach and upper intestines. Additionally, such prodrug delivery system may comprise lipid-like features that may facilitate uptake via lymph fluid, mitigating exposure to the liver on the way to the systemic circulation. This latter property can be advantageous for drugs that experience metabolism in the liver to metabolites that are undesirable due to inactivity and/or toxicity.

The present invention is intended to encompass any parent drug compound or any substituted parent drug compound which contains a tertiary amine group and which is biologically active and can be derivatized according to the present invention to afford the corresponding compounds of formulas I or III. While the tertiary amine-containing parent drugs from which the prodrugs of the invention may be derived are numerous, many of the chemical structures of the prodrugs of the invention can be characterized by certain general structure types. One type includes those wherein the tertiary amine nitrogen is part of a cyclic (including bicyclic or tricyclic) aliphatic group such as piperidine, piperazine, morpholine, pyrrolidine, azapine, and diazapine. Another type includes those wherein the tertiary amine nitrogen is part of an alkyl amine group such as a diethyl and/or dimethyl amine. Examples of tertiary amine-containing parent drugs, and the functional tertiary amine group which provides the site of attachment of the aldehyde linked prodrug moiety are provided in the section below. Unless otherwise stated, the structural formula of a compound herein is intend to represent all enantiomers, racemates and diastereomers of that compound.

Prodrug Chemistry Via Tertiary Nitrogen of Piperazine Moiety

Aripiprazole

Aripiprazole is a known atypical antipsychotic agent that is used in the treatment of neurodisorders including bipolar disorder, schizophrenia and others. Its chemical name is 7-[4-[4-(2,3-dichlorophenyl)piperazin-1-yl]butoxy]-3,4-dihydro-1H-quinolin-2-one. Aripiprazole has the following structure:

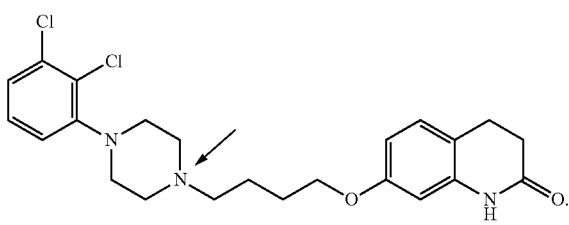 [SMILES: O=C1CCc2ccc(OCCCCN3CCN(c4cccc(Cl)c4Cl)CC3)cc2N1]

In a preferred embodiment, aripiprazole is covalently attached to the aldehyde prodrug moiety via the indicated tertiary nitrogen of the piperazine. However any other tertiary nitrogen on molecule is a potential site for covalent attachment to the prodrug moiety. In one embodiment, an aripiprazole prodrug of the invention has the following structure:

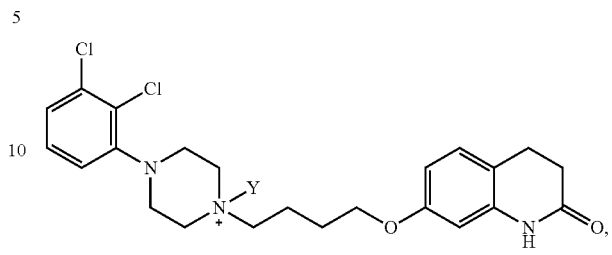

wherein the variable Y is selected from the structures of Table I and preferably from the structures of Table 2.

Dehydroaripiprazole

Dehydroaripiprazole is a known atypical antipsychotic agent that is useful in the treatment of neurodisorders including bipolar disorder, schizophrenia and others (as an active metabolite of ABILIFY®). Its chemical name is 7-[4-[4-(2,3-Dichlorophenyl)-1-Piperazinyl]Butoxy]-2(1H)-Quinolinone. Dehydroaripiprazole has the following structure:

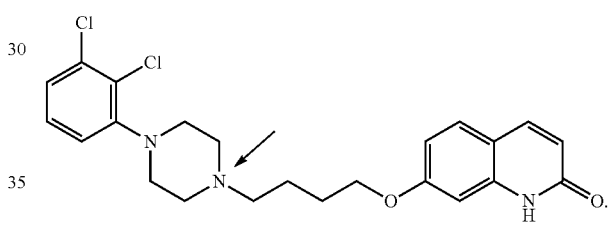

In a preferred embodiment dehydroaripiprazole is covalently attached to the aldehyde prodrug moiety via the indicated tertiary nitrogen of the piperazine. However any other tertiary nitrogen on molecule is a potential site for covalent attachment to the prodrug moiety. In one embodiment, a dehydroaripiprazole prodrug of the invention has the structure:

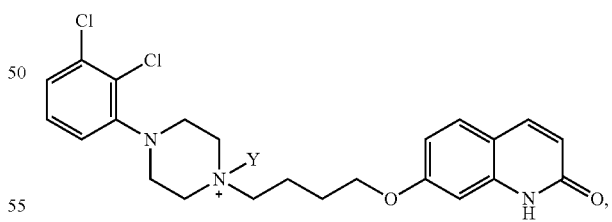

wherein the variable Y is selected from the structures of Tables 1-4, Table 5 and preferably from the structures of Table 2.

Olanzapine

Olanzapine is a known atypical antipsychotic that is used in the treatment of schizophrenia and bipolar disorder as well as other neurodisorders. Its chemical name is 2-methyl-4-(4-methyl-1-piperazinyl)-10H-thieno[2,3-b][1,5]benzodiazepine. Olanzapine has the following structure:

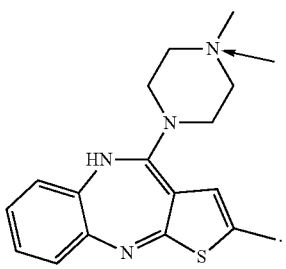 [SMILES: Cc1cc2c(s1)=Nc1ccccc1NC=2N1CCN(C)CC1]

In a preferred embodiment, olanzapine is covalently attached to the aldehyde prodrug moiety via the indicated tertiary nitrogen of the piperazine. However any other tertiary nitrogen on molecule is a potential site for covalent attachment to the prodrug moiety. In one embodiment, an olanzapine prodrug of the invention has the structure:

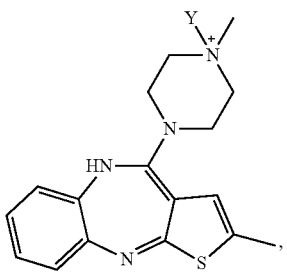

wherein the variable Y is selected from the structures of Tables 1-4, Table 5 and preferably from the structures of Table 2.

Cariprazine

Cariprazine is under development and has antipsychotic properties useful in the treatment of neurological disorders including biopolar depression. The chemical name for cariprazine is 3-(trans-4-{2-[4-(2,3-dichlorophenyl)piperazin-1-yl]ethyl}cyclohexyl)-1,1-dimethylurea. Cariprazine has the following structure:

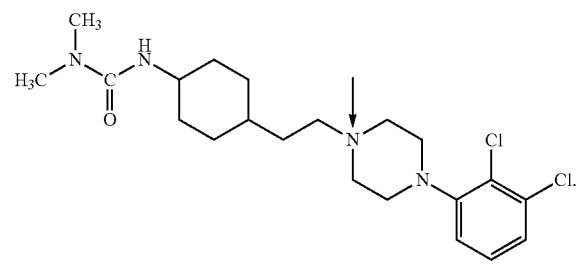

In a preferred embodiment, cariprazine is covalently attached to the aldehyde prodrug moiety via the indicated tertiary nitrogen of the piperazine. However any other tertiary nitrogen on molecule is a potential site for covalent attachment to the prodrug moiety. In one embodiment, a cariprazine prodrug of the invention has the structure:

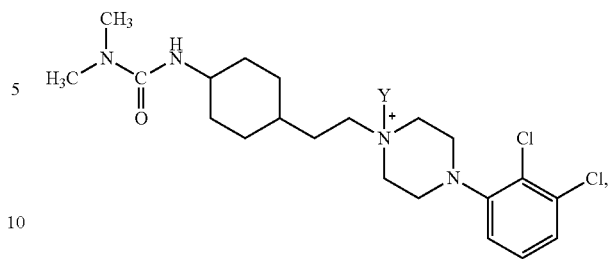

wherein the variable Y is selected from the structures of Tables 1-4, Table 5 and preferably from the structures of Table 2.

Ziprasidone

Ziprasidone is a known atypical antipsychotic agent useful in the treatment of neurological disorders including schizophrenia. Its chemical name is 5-[2-[4-(1,2-benzisothiazol-3-yl)-1-piperazinyl]ethyl]-6-chloro-1,3-dihydro-2H-indol-2-one. The structure of Ziprasidone is:

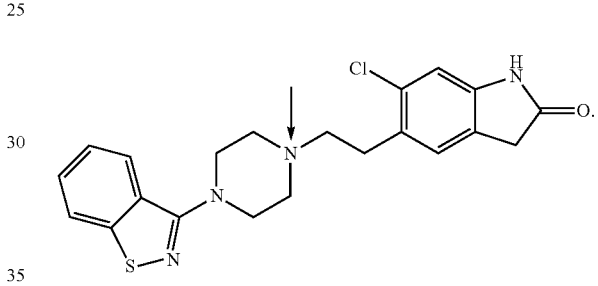

In a preferred embodiment, ziprasidone is covalently attached to the prodrug moiety via the indicated tertiary nitrogen of the piperazine. However any other tertiary nitrogen on molecule is a potential site for covalent attachment to the prodrug moiety. In one embodiment, a ziprasidone prodrug of the invention has the structure:

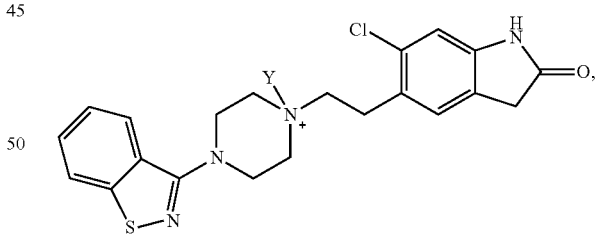

wherein the variable Y is selected from the structures of Tables 1-4, Table 5 and preferably from the structures of Table 2.

Lurasidone

Lurasidone is a known agent under development as an atypical antipsychotic agent useful in the treatment of schizophrenia and bipolar disorder. Its chemical name is: (3aR,4S,7R,7aS)-2-[((1R,2R)-2-{[4-(1,2-benzisothiazol-3-yl)-piperazin-1-yl]methyl}cyclohexyl)methyl]hexahydro-1H-4,7-methanisoindol-1,3-dione. The structure of Lurasidone is:

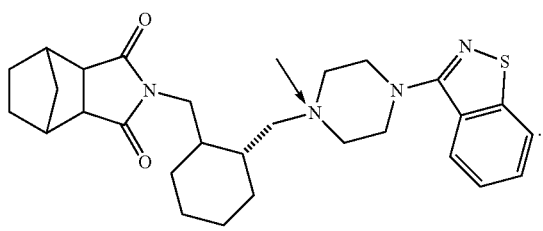 [SMILES: O=C1C2C3CCC(C3)C2C(=O)N1CC1CCCC[C@H]1CN1CCN(c2nsc3ccccc23)CC1]

In a preferred embodiment, lurasidone is covalently attached to the prodrug moiety via the indicated tertiary nitrogen of the piperazine. However any other tertiary nitrogen on molecule is a potential site for covalent attachment to the prodrug moiety. In one embodiment, a lurasidone prodrug of the invention has the structure:

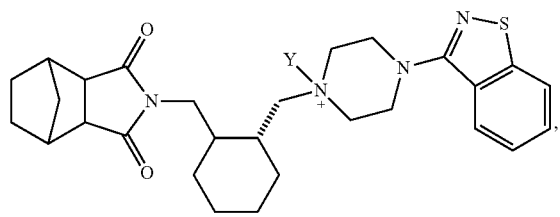

wherein the variable Y is selected from the structures of Tables 1-4, Table 5 and preferably from the structures of Table 2.

PF-00217830 (Pfizer)

PF-00217830 is a compound that is currently in development that has antipsychotic properties. The structure of PF-00217830 is:

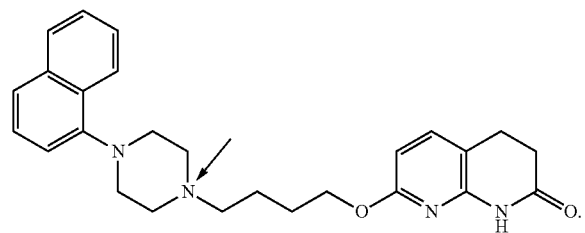 [SMILES: O=C1CCc2ccc(OCCCCN3CCN(c4cccc5ccccc45)CC3)nc2N1]

In a preferred embodiment, PF-00217830 is covalently attached to the prodrug moiety via the indicated tertiary nitrogen of the piperazine. However any other tertiary nitrogen on molecule is a potential site for covalent attachment to the prodrug moiety. In one embodiment, a PF-00217830 prodrug of the invention has the structure:

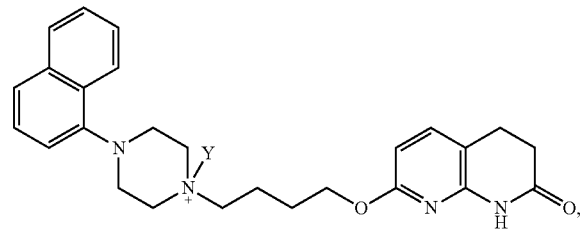

wherein the variable Y is selected from the structures of Tables 1-4, Table 5 and preferably from the structures of Table 2.

SLV-313 (Solvay/Wyeth)

SLV-313 is a compound that is currently in development that has antipsychotic properties. The structure of SLV-313 is:

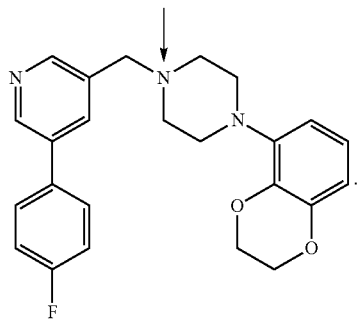 [SMILES: Fc1ccc(-c2cncc(CN3CCN(c4cccc5c4OCCO5)CC3)c2)cc1]

In a preferred embodiment, SLV-313 is covalently attached to the aldehyde prodrug moiety via the indicated tertiary nitrogen of the piperazine. However, any other tertiary nitrogen on molecule is a potential site for covalent attachment to the prodrug moiety. In one embodiment, a SLV-313 prodrug of the invention has the structure:

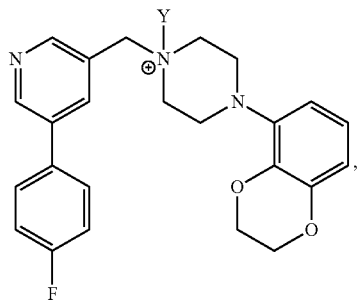

wherein the variable Y is selected from the structures of Tables 1-4, Table 5 and preferably from the structures of Table 2.

Bifeprunox

Bifeprunox is a known atypical antipsychotic agent that is under development for the treatment of neurodisorders. Its chemical name is 7-[4-(biphenyl-3-ylmethyl)piperazin-1-yl]-1,3-benzoxazol-2(3H)-one. The chemical structure of bifeprunox is:

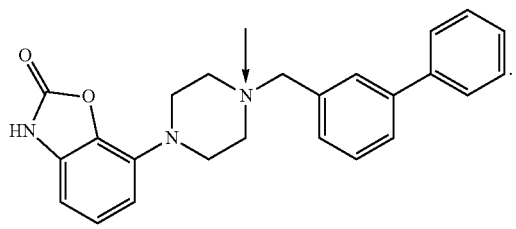

In a preferred embodiment, bifeprunox is covalently attached to the aldehyde prodrug moiety via the indicated tertiary nitrogen of the piperazine. However any other tertiary nitrogen on molecule is a potential site for cbifeprunox dehydroaripiprazole prodrug of the invention has the structure:

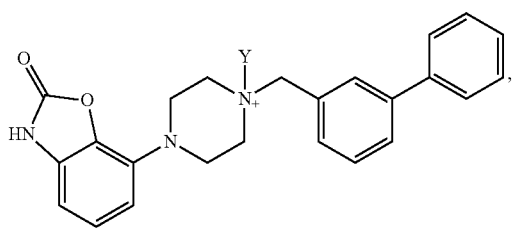

wherein the variable Y is selected from the structures of Tables 1-4, Table 5 and preferably from the structures of Table 2.

Clozapine

Clozapine is a known atypical antipsychotic agent that useful in the treatment of neurodisorders. Its chemical name is 8-chloro-11-(4-methylpiperazin-1-yl)-5H-dibenzo[b,e][1,4]diazepine. The structure of clozapine is:

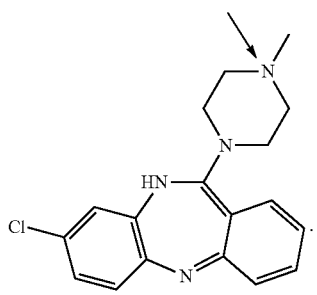 [SMILES: CN1CCN(C2=c3ccccc3=Nc3ccc(Cl)cc3N2)CC1]

In a preferred embodiment, clozapine is covalently attached to the aldehyde prodrug moiety via the indicated tertiary nitrogen of the piperazine. However any other tertiary nitrogen on molecule is a potential site for covalent attachment to the prodrug moiety. In one embodiment, a clozapine prodrug of the invention has the structure:

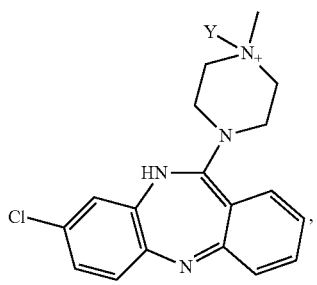

wherein the variable Y is selected from the structures of Tables 1-4, Table 5 and preferably from the structures of Table 2.

Perospirone

Perospirone is a known atypical antipsychotic agent that useful in the treatment of schizoprenia. Its chemical name is (3aR,7aS)-2-{4-[4-(1,2-benzisothiazol-3-yl)piperazin-1-yl]butyl}hexahydro-1H-isoindole-1,3(2H)-dione. The structure of perospirone is:

In a preferred embodiment, perospirone is covalently attached to the aldehyde prodrug moiety via the indicated tertiary nitrogen of the piperazine. However any other tertiary nitrogen on molecule is a potential site for covalent attachment to the prodrug moiety. In one embodiment, a perospirone prodrug of the invention has the structure:

wherein the variable Y is selected from the structures of Tables 1-4, Table 5 and preferably from the structures of Table 2.

Prodrug Chemistry Via the Tertiary Amine of the Piperidine Moiety

Risperidone

Risperidone is a known atypical antipsychotic pharmaceutical agent for use in the treatment of schizophrenia and other neurological disorders. The chemical name for risperidone is 4-[2-[4-(6-fluorobenzo[d]isoxazol-3-yl)-1-piperidyl]ethyl]-3-methyl-2,6-diazabicyclo[4.4.0]deca-1,3-dien-5-one. The structure of risperidone is:

In accordance with the invention, risperidone is covalently attached to the aldehyde-linked prodrug moiety by way of the tertiary nitrogen of the piperidinyl moiety. However any other tertiary nitrogen on molecule is a potential site for covalent attachment to the prodrug moiety. In one embodiment, a risperidone prodrug of the invention has the structure:

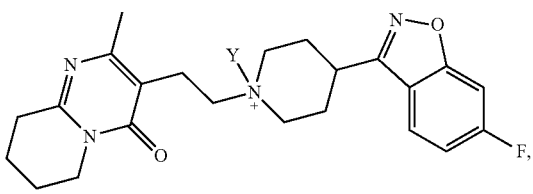

wherein the variable Y is selected from the structures of Tables 1-4, Table 5 and preferably from the structures of Table 2.

Paliperidone

Paliperidone is a known atypical antipsychotic pharmaceutical agent for use in the treatment of schizophrenia and other neurological disorders. The chemical name for paliperidone is 3-(2-(4-(6-fluorobenzo[d]isoxazol-3-yl)piperidin-1-yl)ethyl)-9-hydroxy-2-methyl-6,7,8,9-tetrahydro-4H-pyrido[1,2-a]pyrimidin-4-one (also referred to as 9-hydroxyrisperidone). The structure of paliperidone is:

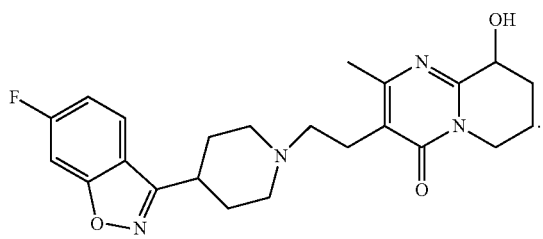

In accordance with the invention, paliperidone is covalently attached to the aldehyde-linked prodrug moiety by way of the tertiary nitrogen of the piperidinyl moiety. However any other tertiary nitrogen on molecule is a potential site for covalent attachment to the prodrug moiety. In one embodiment, a paliperidone prodrug of the invention has the structure:

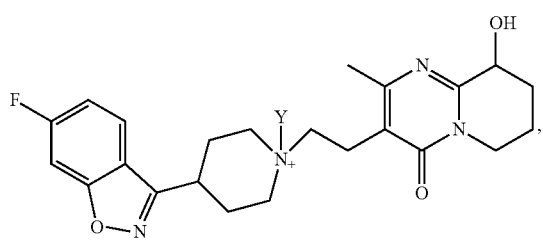

wherein the variable Y is selected from the structures of Tables 1-4, Table 5 and preferably from the structures of Table 2.

Haloperidol

Haloperidol is a known typical antipsychotic pharmaceutical agent for use in the treatment of schizophrenia and other neurological disorders. The chemical name for haloperidol is 4-[4-(4-chlorophenyl)-4-hydroxy-1-piperidyl]-1-(4-fluorophenyl)-butan-1-one. The structure of haloperidol is:

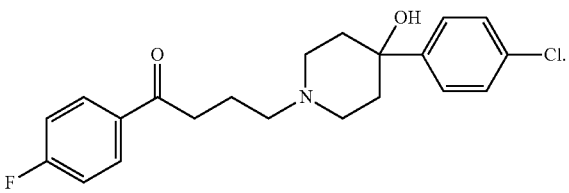 [SMILES: O=C(CCCN1CCC(O)(c2ccc(Cl)cc2)CC1)c1ccc(F)cc1]

In accordance with the invention, haloperidol is covalently attached to the aldehyde-linked prodrug moiety by way of the tertiary nitrogen of the piperidinyl moiety. However any other tertiary nitrogen on molecule is a potential site for covalent attachment to the prodrug moiety. In one embodiment, a haloperidol prodrug of the invention has the structure:

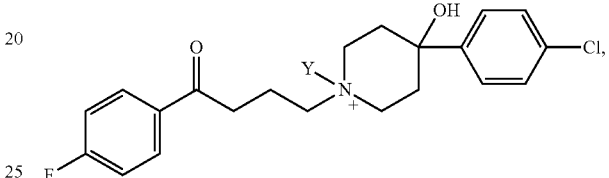

wherein the variable Y is selected from the structures of Tables 1-4, Table 5 and preferably from the structures of Table 2.

Iloperidone

Iloperidone is a known atypical antipsychotic pharmaceutical agent for use in the treatment of schizophrenia and other neurological disorders. The chemical name for iloperidol is 1-[4-[3-[4-(6-fluoro-1,2-benzisoxazol-3-yl)-1-piperidinyl]propoxy]-3-methoxyphenyl]ethanone. The structure of iloperidone is:

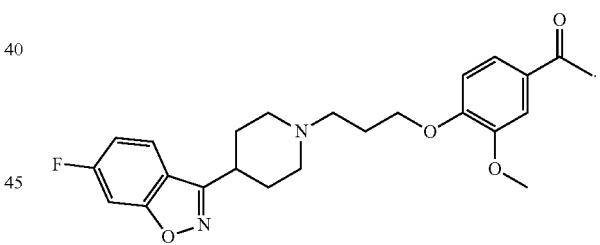

In accordance with the present invention iloperidone is covalently attached to the aldehyde prodrug moiety via the tertiary nitrogen of the piperidine ring. However any other tertiary nitrogen on molecule is a potential site for covalent attachment to the prodrug moiety. In one embodiment, an iloperidone prodrug of the invention has the structure:

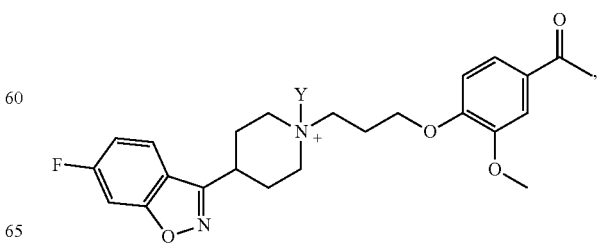

wherein the variable Y is selected from the structures of Tables 1-4, Table 5 and preferably from the structures of Table 2.

Latrepirdine

Latrepirdine is an antihistamine drug also known for its neuroprotective properties for use in treating diseases such as Alzheimer's Disease. Its chemical name is: 2,3,4,5-Tetrahydro-2,8-dimethyl-5-(2-(6-methyl-3-pyridyl)ethyl)-1H-pyrido(4,3-b)indole. The structure of latrepirdine is:

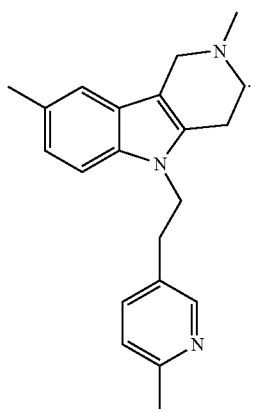 [SMILES: Cc1ccc2c(c1)c1c(n2CCc2ccc(C)nc2)CCN(C)C1]

In accordance with the present invention latrepirdine is covalently attached to the aldehyde prodrug moiety via the tertiary nitrogen of the piperidine ring. However any other tertiary nitrogen on molecule is a potential site for covalent attachment to the prodrug moiety. In one embodiment, a latrepirdine prodrug of the invention has the structure:

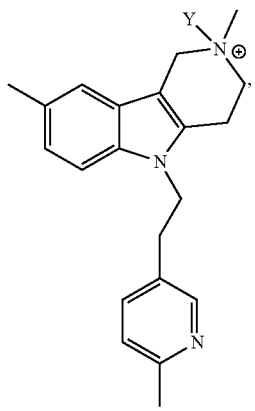

wherein the variable Y is selected from the structures of Tables 1-4, Table 5 and preferably from the structures of Table 2.

Apormophine

Apomorphine is a type of dopaminergic agonist, a morphine derivative which primarily affects the hypothalamic region of the brain. Drugs containing apomorphine are sometimes used in the treatment of Parkinson's disease or erectile dysfunction. The structure of apomorphine is:

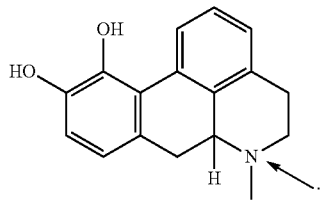 [SMILES: CN1CCc2cccc3c2C1Cc1ccc(O)c(O)c1-3]

In accordance with the present invention apomorphine is covalently attached to the aldehyde prodrug moiety via the tertiary nitrogen of the piperidine ring. In one embodiment, an apomorphine prodrug of the invention has the structure:

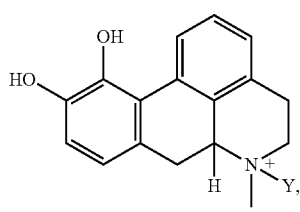

wherein the variable Y is selected from the structures of Tables 1-4, Table 5 and preferably from the structures of Table 2. In another embodiment, an apomorphine prodrug of the invention has the structure:

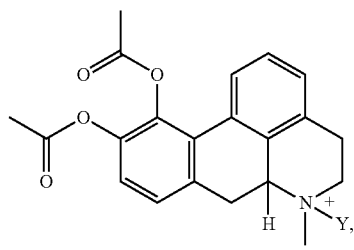

wherein the variable Y is selected from the structures of Tables 1-4, Table 5 and preferably from the structures of Table 2.

Loperamide

Loperamide is a known drug that is an opioid receptor agonist that is effective against diarrhea resulting from, for example, gastroenteritis and inflammatory bowel disease. The structure of loperamide is:

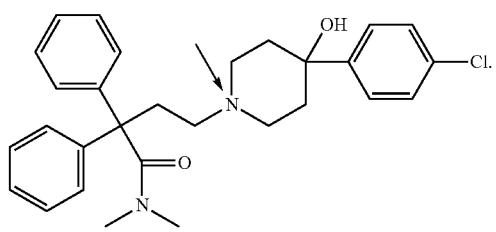 [SMILES: CN(C)C(=O)C(CCN1CCC(O)(c2ccc(Cl)cc2)CC1)(c1ccccc1)c1ccccc1]

In accordance with the present invention loperamide is covalently attached to the aldehyde prodrug moiety via the tertiary nitrogen of the piperidine ring. However any other tertiary nitrogen on molecule is a potential site for covalent attachment to the prodrug moiety. In one embodiment, a loperamide prodrug of the invention has the structure:

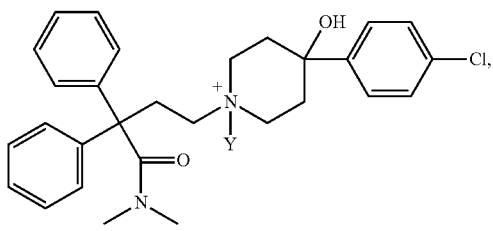

wherein the variable Y is selected from the structures of Tables 1-4, Table 5 and preferably from the structures of Table 2.

Prodrug Chemistry Via a Dimethyl Amine Moiety

Citalopram

Citalopram is a known antidepressant of the selective serotonin reuptake inhibitor (SSRI) class of pharmaceutical agents for use in the treatment of depression and anxiety. Its chemical name is: (RS)-1-[3-(dimethylamino)propyl]-1-(4-fluorophenyl)-1,3-dihydroisobenzofuran-5-carbonitrile.

The structure of citalopram is:

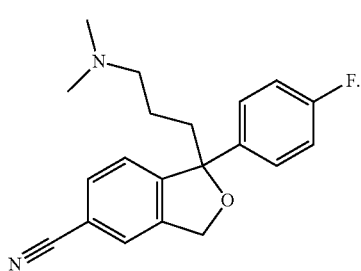

In a preferred embodiment, citalopram is covalently attached to the aldehyde-linked prodrug moiety by way of the diethylaminopropyl tertiary nitrogen. However, the prodrug moiety may be covalently attached to any other tertiary nitrogen moiety on the molecule. In one embodiment, a citalopram prodrug of the invention has the structure:

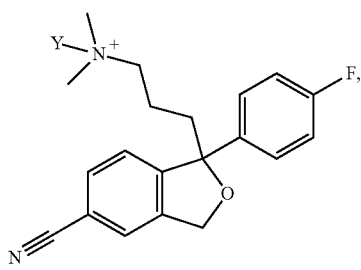

wherein the variable Y is selected from the structures of Tables 1-4, Table 5 and preferably from the structures of Table 2.

Escitalopram

Escitalopram is a known antidepressant of the selective serotonin reuptake inhibitor (SSRI) class of pharmaceutical agents for use in the treatment of depression and anxiety. Escitalopram is the S-enantiomer of the racemic citalopram. Its chemical name is (S)-1-[3-(dimethylamino)propyl]-1-(4-fluorophenyl)-1,3-dihydroisobenzofuran-5-carbonitrile. The structure of escitalopram is:

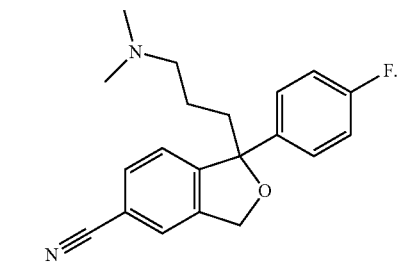 [SMILES: CN(C)CCCC1(c2ccc(F)cc2)OCc2cc(C#N)ccc21]

In a preferred embodiment, escitalopram is covalently attached to the aldehyde-linked prodrug moiety by way of the diethylaminopropyl tertiary nitrogen. However, the prodrug moiety may be covalently attached to any other tertiary nitrogen moiety on the molecule. In one embodiment, escitalopram prodrug of the invention has the structure:

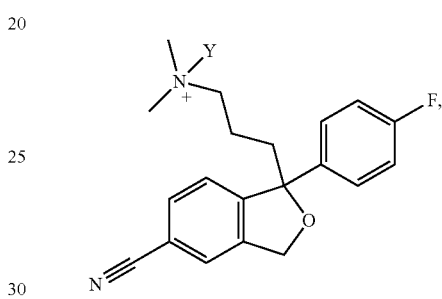

wherein the variable Y is selected from the structures of Tables 1-4, Table 5 and preferably from the structures of Table 2.

Tapentadol

Tapentadol is a known compound useful as a centrally-acting analgesic with a dual mode of action as an agonist at the μ-opioid receptor and as a norepinephrine reuptake inhibitor. Its chemical name is 3-[(1R,2R)-3-(dimethylamino)-1-ethyl-2-methylpropyl]phenol hydrochloride. The structure of Tapentadol is:

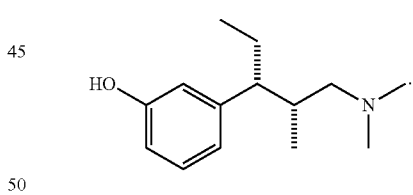

In a preferred embodiment, tapentadol is covalently attached to the aldehyde-linked prodrug moiety by way of the diethylaminopropyl tertiary nitrogen. In one embodiment, a tapentadol prodrug of the invention has the structure:

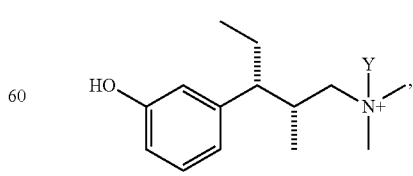

wherein the variable Y is selected from the structures of Tables 1-4, Table 5 and preferably from the structures of Table 2.

Levomethadyl Acetate

Levomethadyl acetate is a known compound useful in the treatment of narcotic addiction. Its chemical name is αS)-β-[(2S)-2-(Dimethylamino)propyl]-α-ethyl-β-phenylbenzeneethanol acetate (ester). The structure of levomethadyl acetate is:

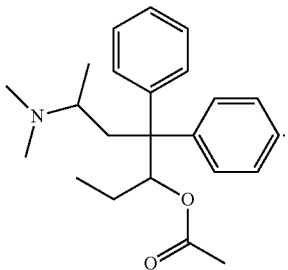 [SMILES: CCC(OC(C)=O)C(CC(C)N(C)C)(c1ccccc1)c1ccccc1]

In a preferred embodiment, of levomethadyl acetate is covalently attached to the aldehyde-linked prodrug moiety by way of the diethylaminopropyl tertiary nitrogen. In one embodiment, a levomethadyl acetate prodrug of the invention has the structure:

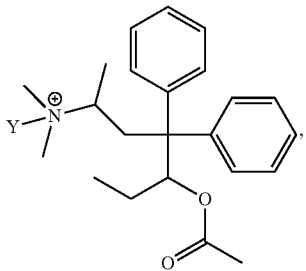

wherein the variable Y is selected from the structures of Tables 1-4, Table 5 and preferably from the structures of Table 2.

Prodrug Chemistry Via Pyrrolidine Moiety

Asenapine

Asenapine is a known antipsychotic pharmaceutical agent for treating neuro- and psychological disorders. Its chemical name is 5-Chloro-2,3,3a,12b-tetrahydro-2-methyl-1H-dibenz[2,3:6,7]oxepino[4,5-c]pyrrole. The structure of asenapine is:

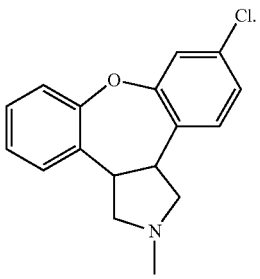 [SMILES: CN1CC2c3ccccc3Oc3cc(Cl)ccc3C2C1]

In accordance with the invention, asenapine is covalently attached to the aldehyde-linked prodrug moiety by way of the nitrogen on the pyrrolidine moiety. In one embodiment, an asenapine prodrug of the invention has the structure:

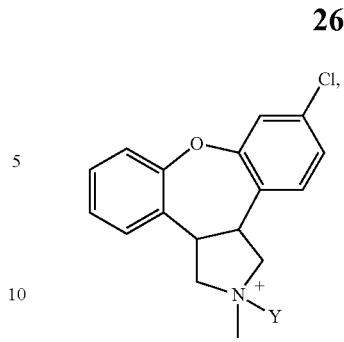

wherein the variable Y is selected from the structures of Tables 1-4, Table 5 and preferably from the structures of Table 2.

Asimadoline

Asimadoline is a compound known to be useful in the treatment of irritable bowel syndrome (IBS). Its chemical name is: N-[(1S)-2-[(3S)-3-hydroxypyrrolidin-1-yl]-1-phenylethyl]-N-methyl-2,2-di(phenyl)acetamide. The structure of asimadoline is:

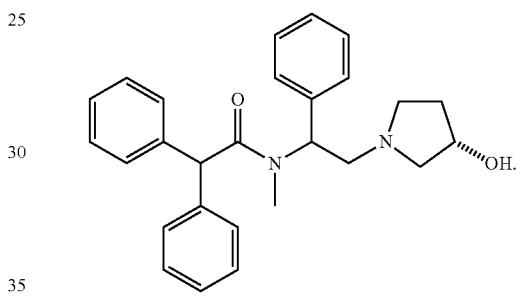

In accordance with the invention, asimadoline is covalently attached to the aldehyde-linked prodrug moiety by way of the nitrogen on the pyrrolidine moiety. In one embodiment, an asimadoline prodrug of the invention has the structure:

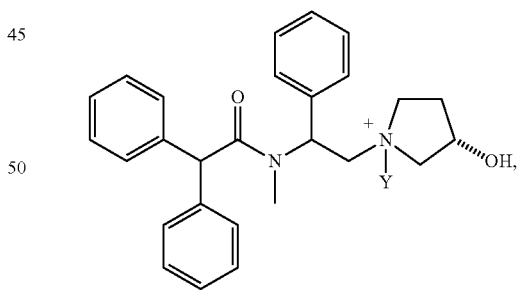

wherein the variable Y is selected from the structures of Tables 1-4, Table 5 and preferably from the structures of Table 2.

Prodrug Chemistry Via Azapine Moiety

Galantamine

Galantamine is an approved drug useful in the treatment of dementia and Alzheimer's disease and other forms of memory impairment. Its chemical name is: 4aS,6R,8aS)-5,6,9,10,11,12-hexahydro-3-methoxy-11-methyl-4aH-[1]benzofuro[3a,3,2-ef][2]benzazepin-6-ol. Its chemical structure is:

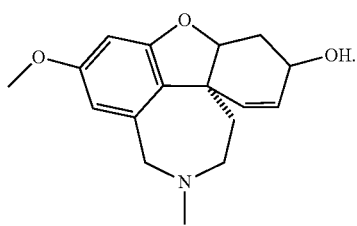

In a preferred embodiment, galantamine is covalently attached to the aldehyde-linked prodrug moiety by way of the nitrogen on the azapine ring. In one embodiment, a galantamine prodrug of the invention has the structure:

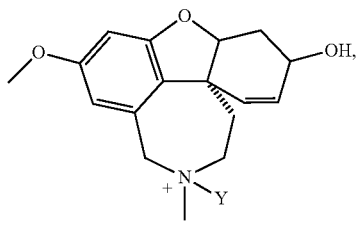

wherein the variable Y is selected from the structures of Tables 1-4, Table 5 and preferably from the structures of Table 2.

Prodrug Chemistry Via Azetidine Moiety

Azelnidipine

Azelnidipine is an approved drug known to have calcium channel blocking properties useful as an antihypertensive. Its chemical name is O3-[1-[di(phenyl)methyl]azetidin-3-yl]O5-propan-2-yl 2-amino-6-methyl-4-(3-nitrophenyl)-1,4-dihydropyridine-3,5-dicarboxylate. The structure of azelnidipine is:

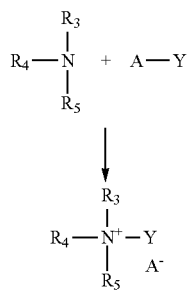

In a preferred embodiment, azelnidipine is covalently attached to the aldehyde-linked prodrug moiety by way of the nitrogen on the azetidine ring. However any other tertiary nitrogen on molecule is a potential site for covalent attachment to the prodrug moiety. In one embodiment, an azelnidipine prodrug of the invention has the structure:

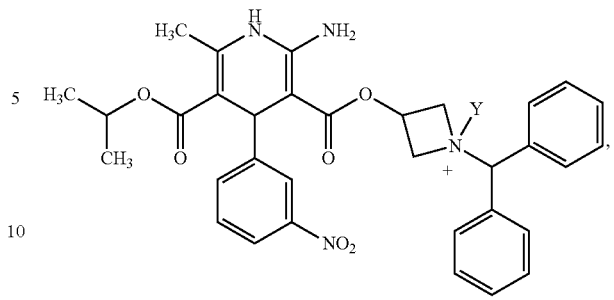

wherein the variable Y is selected from the structures of Tables 1-4, Table 5 and preferably from the structures of Table 2.

An example of a prodrug synthesis is depicted in Reaction Scheme I and involves nucleophilic attack by the tertiary amine of the parent drug causing displacement of leaving group A on the derivitizing agent thereby forming the prodrug. The leaving group can be of several types. Examples of suitable leaving groups include but are not limited to tosylate, triflate, iodide, bromide, chloride, acetate. $R_3$, $R_4$, $R_5$ and Y are as defined in Formula III.

Reaction Scheme 1

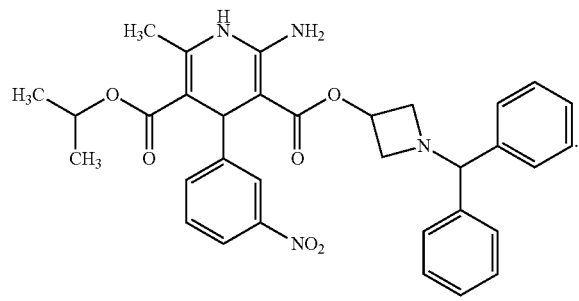

The compounds of the invention can be prepared as acid addition salts. Preferably, the acid is a pharmaceutically acceptable acid. Such acids are described in Stahl, P. H. and Wermuth, C. G. (eds.), *Handbook of Pharmaceutical Salts: Properties, Selection and Use*, Wiley VCH (2008). Pharmaceutically acceptable acids include acetic acid, dichloroacetic acid, adipic acid, alginic acid, L-ascorbic acid, L-aspartic acid, benzenesulfonic acid, 4-acetamidobenzoic acid, benzoic acid, p-bromophenylsulfonic acid; (+)-camphoric acid, (+)-camphor-10-sulfonic acid, capric acid, caproic acid, caprylic acid, carbonic acid, cinnamic acid, cyclamic acid, dodecylsulfuric acid, ethane-1,2-disulfonic acid, ethanesulfonic acid, 2-hydroxyethanesulfonic acid, sulfuric acid, boric acid, citric acid, formic acid, fumaric acid, galactaric acid, gentisic acid, D-glucoheptonic acid, D-gluconic acid, D-glucuronic acid, glutamic acid, glutaric acid, 2-oxoglutaric acid, glycerophosphoric acid, glycolic acid, hippuric acid, hydrochloric acid, hydrobromic acid, hydroiodic acid, isobutyric acid, DL-lactic acid, lactobionic acid, lauric acid, maleic acid, (−)-L-malic acid, malonic acid, DL-mandelic acid, methanesulfonic acid, naphthalene-1,5-disulfonic acid, naphthalene-2-sulfonic acid, 1-hydroxy-2-naphthoic acid, nicotinic acid, nitric acid, oleic acid, orotic acid, oxalic acid, palmitic acid, pamoic acid, phosphoric acid, propionic acid, (−)-L-pyroglutamic acid, salicyclic acid, 4-aminosalicyclic acid, sebacic acid, stearic acid, succinic acid, (+)-L-tartaric acid, thiocyanic acid, p-toluenesulfonic acid, and undecylenic acid.

The term "pharmaceutically acceptable anion" as used herein, refers to the conjugate base of a pharmaceutically acceptable acid. Such anions include the conjugate base of any the acids set forth above. Preferred pharmaceutically acceptable anions include acetate, bromide, camsylate, chloride, formate, fumarate, maleate, mesylate, nitrate, oxalate, phosphate, sulfate, tartrate, thiocyanate and tosylate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The synthesized compounds can be separated from a reaction mixture and further purified by a method such as column chromatography, high pressure liquid chromatography, trituration or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The compounds described herein may contain one or more asymmetric centers and thus give rise to enantiomers, diastereomers, and other stereoisomeric forms that may be defined, in terms of absolute stereochemistry, as (R)- or (S)—, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds, other unsaturation, or other centers of geometric asymmetry, and unless specified otherwise, it is intended that the compounds include both E and Z geometric isomers and/or cis- and trans-isomers. Likewise, all tautomeric forms are also intended to be included. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

In certain compounds of the invention, the quaternized nitrogen atom is a chiral center and both stereoisomers are converted in vivo to yield the parent drug. Such compounds can be formulated and used as a mixture of stereoisomers or as a composition having a single stereoisomer or an mixture with excess of one enantiomer. In certain compounds the parent drug, such as asenapine, is chiral and can be used as a racemic mixture. For such a racemic mixture, quaternization of the nitrogen atom produces an additional chiral center and up to four stereoisomers. Such compounds can be formulated and used as a mixture of four stereoisomers. Alternatively, the diastereomers are separated to yield pairs of enantiomers, and a racemic mixture of one pair of enantiomers is formulated and used. In another embodiment, a single stereoisomer is formulated and used. Additionally it is possible to separate the two enantiomers of Asenapine. Quaternization of a single enantiomer of Asenapine will provide two diastereomer products that can be either formulated and used as a mixture or separated and formulated and used as a single stereoisomer. Unless otherwise stated, the structural formula of a compound herein is intend to represent all enantiomers, racemates and diastereomers of that compound.

In another embodiment, the invention provides a method for sustained delivery of a tertiary amine-containing parent drug to a patient comprising administering a prodrug compound having the Formula III:

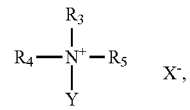

Formula III wherein
$R_3$, $R_4$ and $R_5$, together with the nitrogen atom to which they are attached, form a tertiary amine-containing parent drug, a substituted tertiary amine-containing parent drug or a tertiary imine-containing parent drug or a substituted tertiary imine containing parent drug;
Y is selected from:
a) $C(R_7R_8)OC(O)R_9$, where $R_7$ and $R_8$ are each independently hydrogen or an aliphatic group and preferably $R_7$ and $R_8$ are each independently selected from:
  i) hydrogen;
  ii) branched or unbranched, substituted or unsubstituted $C_1$-$C_6$ alkyl;
  iii) branched or unbranched, substituted or unsubstituted $C_2$-$C_6$ alkenyl; and
  iv) branched or unbranched, substituted or unsubstituted $C_2$-$C_6$ alkynyl;
$R_9$ is any aliphatic group that results in a prodrug having lower aqueous solubility at a reference pH (e.g. a pH at which the parent drug is fully protonated such as pH 5) as compared to the aqueous solubility of the parent drug, at the same reference pH and preferably, $R_9$ is selected from:
  i) branched or unbranched, substituted or unsubstituted $C_1$-$C_{24}$ alkyl;
  ii) branched or unbranched, substituted or unsubstituted $C_2$-$C_{24}$ alkenyl; iii) branched or unbranched, substituted or unsubstituted $C_2$-$C_{24}$ alkynyl;

iv) substituted or unsubstituted $C_3$-$C_{12}$ cycloalkyl;
v) aryl or substituted aryl; and
vi) heteroaryl or substituted heteroaryl;

b) $C(R_7R_8)OC(O)OR_9$, where $R_7$, $R_8$ and $R_9$ are previously defined;

c) $C(R_7R_8)OC(O)N(R_{10}R_{11})$, where $R_7$, $R_8$ are previously defined; where $R_{10}$ and $R_{11}$ are each independently hydrogen or any aliphatic group that results in a prodrug having lower aqueous solubility at a reference pH (e.g. a pH at which the parent drug is fully protonated such as pH 5) as compared to the aqueous solubility of the parent drug, at the same reference pH, provided that, at least one of $R_{10}$ and $R_{11}$ is an aliphatic group that results in a prodrug having lower aqueous solubility at a reference pH as compared to the aqueous solubility of the parent drug, at the same reference pH, and preferably, $R_{10}$ and $R_{11}$ are each independently hydrogen or an aliphatic group, provided that at least one of $R_{10}$ and $R_{11}$ is substituted or unsubstituted $C_1$-$C_{24}$-alkyl, substituted or unsubstituted $C_2$-$C_{24}$-alkenyl, substituted or unsubstituted $C_2$-$C_{24}$ alkynyl, and substituted or unsubstituted $C_3$-$C_{12}$ cycloalkyl, substituted or unsubstituted aryl, substituted or unsubstituted heteroaryl or $R_{10}$ and $R_{11}$ when taken together with the nitrogen to which they are attached form a heterocycle;

d) $C(R_7R_8)OP(O_3)^{2-}MV$, wherein $R_7$ and $R_8$ are previously defined and M and V are each independently a monovalent cation or M and V together form a divalent cation;

e) $C(R_7R_8)OP(O)(OR_{12})(OR_{13})$, where $R_7$ and $R_8$ are previously defined; where $R_{12}$ and $R_{13}$ are each independently hydrogen or any aliphatic group that results in a prodrug having lower aqueous solubility at a reference pH (e.g. pH 5) as compared to the aqueous solubility of the parent drug, at the same reference pH; provided that, at least one of $R_{12}$ and $R_{13}$ is an aliphatic group that results in a prodrug having lower aqueous solubility at a reference pH (e.g. pH 5) as compared to the aqueous solubility of the parent drug, at the same reference pH, and preferably, $R_{12}$ and $R_{13}$ are each independently hydrogen or an aliphatic group, provided that at least one of $R_{12}$ and $R_{12}$ is substituted or unsubstituted $C_1$-$C_{24}$-alkyl, substituted or unsubstituted $C_2$-$C_{24}$-alkenyl, substituted or unsubstituted $C_2$-$C_{24}$ alkynyl, and substituted or unsubstituted $C_3$-$C_{12}$ cycloalkyl; and $X^-$ is a pharmaceutically acceptable anion;

wherein the prodrug compound has lower aqueous solubility at a reference pH (e.g. pH 5) as compared to the aqueous solubility of the parent drug, at the same reference pH and wherein upon administration to the patient, release of the parent drug from the prodrug is sustained release.

In one preferred embodiment, the prodrug compound of formula III further comprises a biocompatible delivery system for delivering the prodrug wherein the system is capable of minimizing accelerated hydrolytic cleavage of the prodrug by minimizing exposure of the prodrug to water. Preferred delivery systems include biocompatible polymeric matrix delivery systems capable of minimizing diffusion of water in the matrix.

In one preferred embodiment, $R_7$ and $R_8$ are independently selected from:
i) hydrogen; and ii) branched or unbranched, substituted or unsubstituted $C_1$ to $C_3$ alkyl. In another embodiment, $R_7$ and $R_8$ are independently hydrogen, methyl or ethyl.

In one embodiment, $R_9$ is a secondary alkyl group or a tertiary alkyl group. Preferably $R_9$ is a secondary alkyl group or a tertiary alkyl group comprising at least 3 to about 24 carbon atoms ("$C_3$-$C_{24}$") or at least 4 to about 24 carbon atoms ("$C_4$-$C_{24}$"), and preferably at least 7 to about 24 carbon atoms and preferably about 8 to about 24 carbon atoms and even more preferably least 9 to about 24 carbon atoms. Examples of secondary and tertiary alky groups include, but are not limited to, $C_3$-$C_{12}$-cycloalkyl, 1-methyl-$C_3$-$C_{12}$-cycloalkyl, isopropyl, sec-butyl, t-butyl, pent-2-yl, hex-2-yl, hept-2-yl, cyclopentyl, neopentyl, 3-methylpent-3-yl, 3-ethylpent-3-yl; 2,3-dimethylbut-2-yl; 2-methylbut-2-yl, 2 methyl hex-2-yl, 1-methylcyclopropyl,1-methylcyclopentyl, 1-methylcyclohexyl, 1-ethylcyclohexyl or a branched alkyl group corresponding to one of the formulas below.

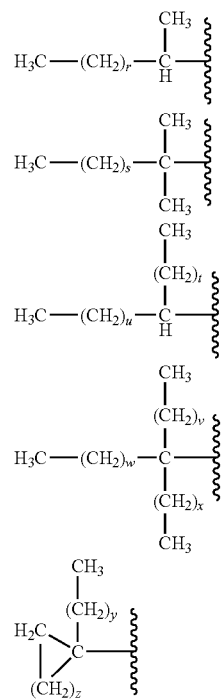

In these groups, r is 0 to 21 and s is 0 to 20. Each of t and u is independently 0 to 21, provided that the sum of t and u is from 0 to 21. Each of v, w and x is independently 0 to 20, provided that the sum of v, w and x is from 0 to 20. z is an integer from 1 to 10 and y is an integer from 0 to 20, provided that the sum of z and y is from 1 to 21. Preferably, r is an integer from 1 to 21; s is an integer from 1 to 20; the sum of t and u is from 5 to 21; the sum of v, w and x is from 4 to 20; and the sum of y and z is from 4 to 21.

In another preferred embodiment, $R_9$ is selected from branched or unbranched, substituted or unsubstituted $C_7$-$C_{24}$ alkyl; branched or unbranched, substituted or unsubstituted $C_8$-$C_{24}$ alkyl; or branched or unbranched, substituted or unsubstituted $C_9$-$C_{24}$ alkyl.

In another preferred embodiment $R_{10}$ and $R_{11}$ are each independently selected from i) secondary alkyl; ii) tertiary alkyl; and iii) hydrogen.

In a preferred embodiment, at least one of $R_{10}$ and $R_{11}$ is a branched or unbranched, substituted or unsubstituted-$C_7$-$C_{24}$ alkyl, $C_8$-$C_{24}$ alkyl or $C_9$-$C_{24}$ alkyl. In a preferred embodiment, at least one of $R_{12}$ and $R_{13}$ is a branched or unbranched, substituted or unsubstituted-$C_7$-$C_{24}$ alkyl, $C_8$-$C_{24}$ alkyl or $C_9$-$C_{24}$ alkyl.

The parent tertiary amine or imines of Formula III may be the same as those described for Formula I. The compounds of Formula III are also labile quaternary ammonium salts of tertiary amine-containing parent drugs that are derivatized through linked prodrug moieties that reduce the solubility of the prodrug compound at a reference pH as compared to the underivatized parent drug.

In one embodiment, variable Y in Formula III is selected from the group set forth in Tables 1-4 and Table 5 where the variables M and V are as described for Formula III. However, it is understood that in compounds of Formula III in which Y is —C(R$_8$)(R$_9$)—OPO$_3$MV or —CH(R$_8$)(R$_9$)—OP(O)$_2$(OR$_{11}$)M, it is possible for the phosphate moiety to serve as X— and for the quaternary ammonium group to serve as M.

In certain embodiments, Y is a group defined by one of the structures set forth below.

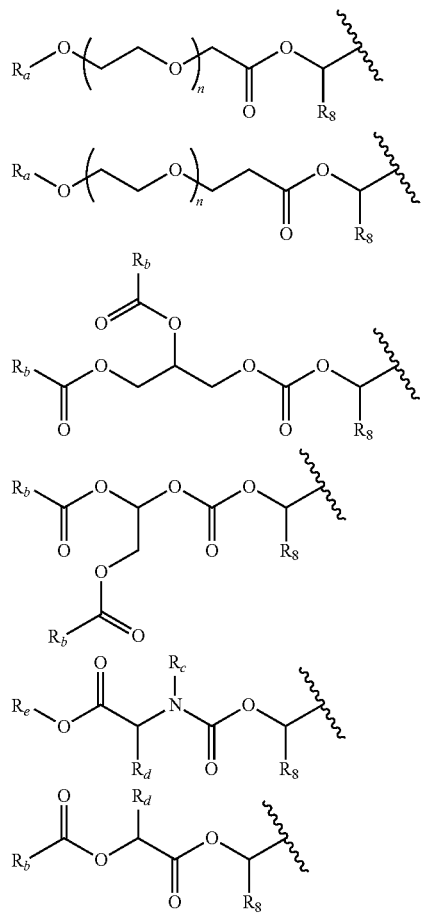

where n is 1 to about 1000, preferably 1 to about 100; R$_a$, R$_b$ and R$_e$ are each independently C$_1$-C$_{24}$-alkyl, substituted C$_1$-C$_{24}$-alkyl, C$_2$-C$_{24}$-alkenyl, substituted C$_2$-C$_{24}$-alkenyl, C$_2$-C$_{24}$-alkynyl, substituted C$_2$-C$_{24}$-alkenyl, C$_3$-C$_{12}$-cycloalkyl, substituted C$_3$-C$_{12}$-cycloalkyl, aryl or substituted aryl; R$_c$ is H or substituted or unsubstituted C$_1$-C$_6$-alkyl; R$_d$ is H, substituted or unsubstituted C$_1$-C$_6$-alkyl, substituted or unsubstituted aryl-C$_1$-C$_6$-alkyl or substituted or unsubstituted heteroaryl-C$_1$-C$_6$-alkyl; and R$_8$ is as defined above and is preferably hydrogen. Preferably R$_a$, R$_b$ and R$_e$ are each C$_1$-C$_{24}$-alkyl. Preferably R$_d$ is the side chain of one of the twenty naturally occurring amino acids, more preferably a neutral or hydrophobic side chain, such as hydrogen, methyl, isopropyl, isobutyl, benzyl, indolylmethyl, and sec-butyl. R$_c$ and R$_d$ can also, together with the carbon and nitrogen atoms to which they are attached, form a heterocycloalkyl group, preferably a pyrrolidine group.

Preferred Y groups of Tables 1-4, Table 5 and most preferably, preferred Y groups of Table 2, comprise at least 5 carbon atoms, preferably at least 7 carbon atoms, preferably at least 8 carbon atoms, preferably at least 9 carbon atoms and preferably greater than 9 carbon atoms. Unless otherwise stated, the structural formula of any compound depicted herein is intended to represent all enantiomers, racemates and diastereomers of that compound.

TABLE 1

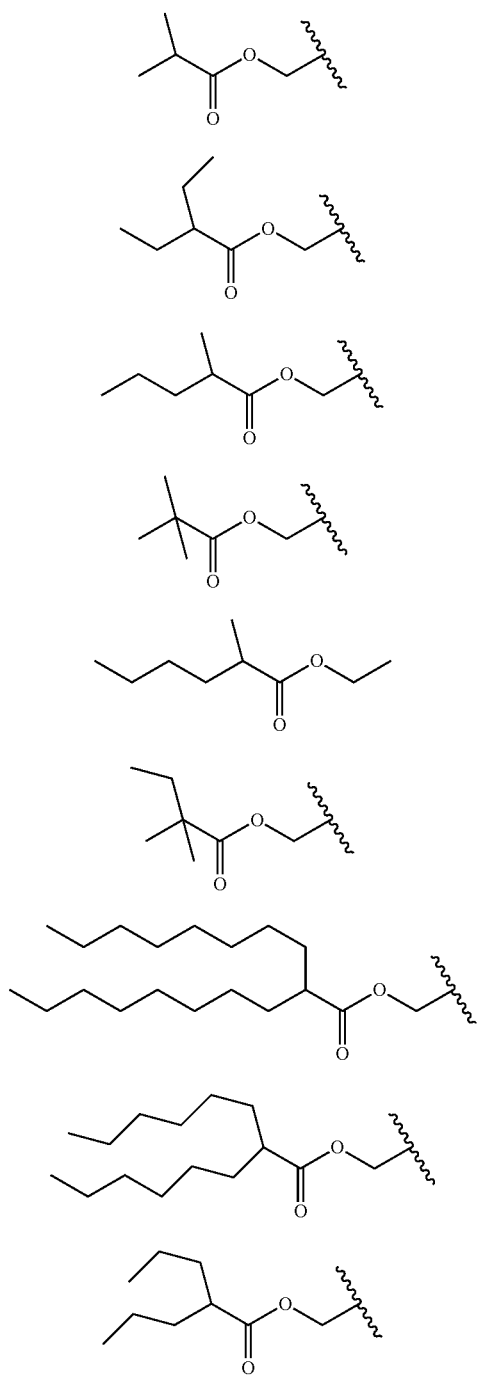

TABLE 1-continued
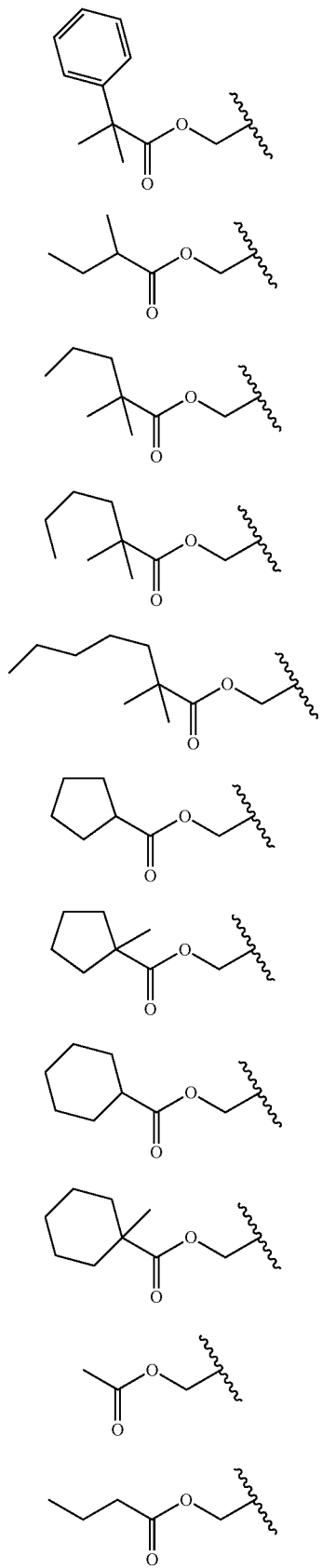
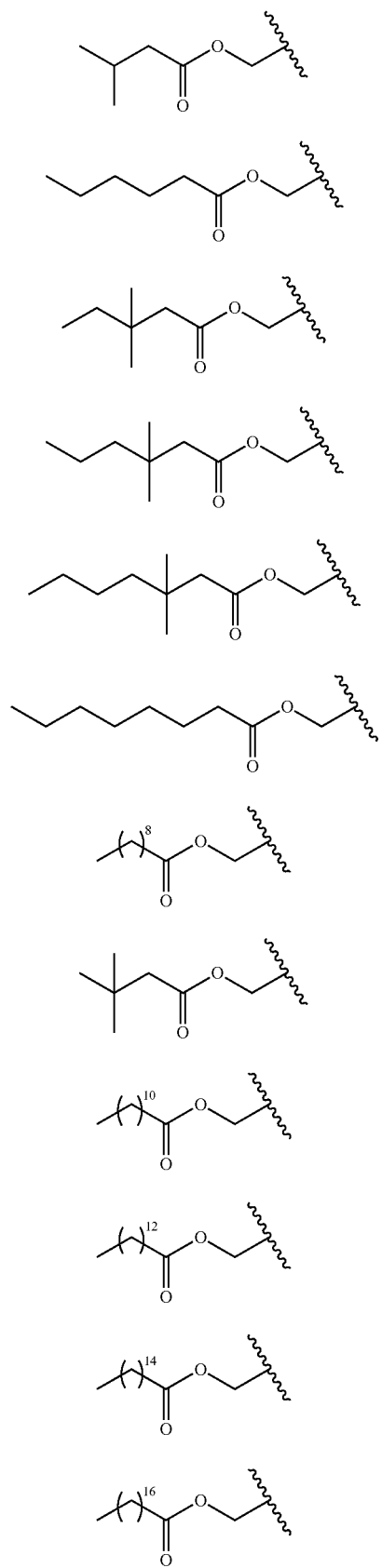

TABLE 1-continued
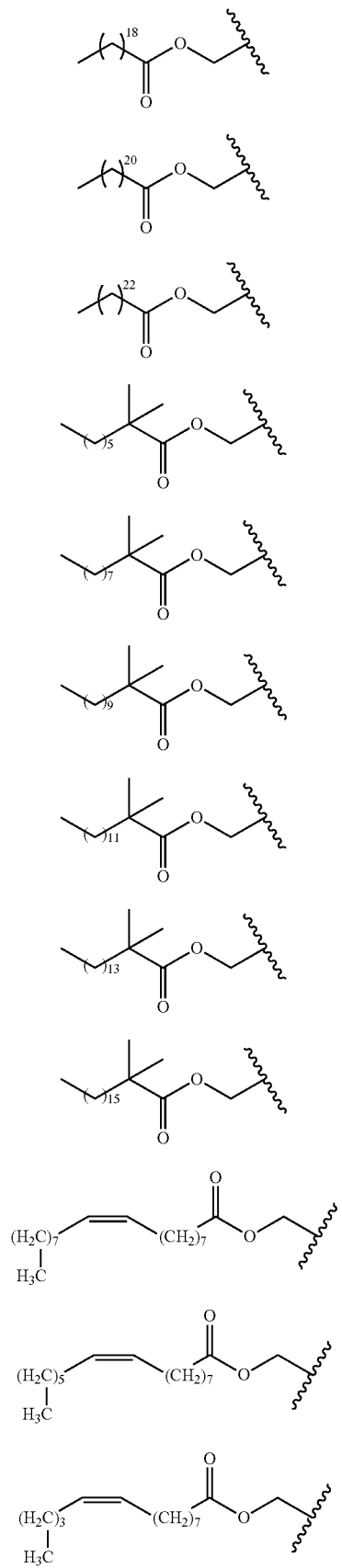
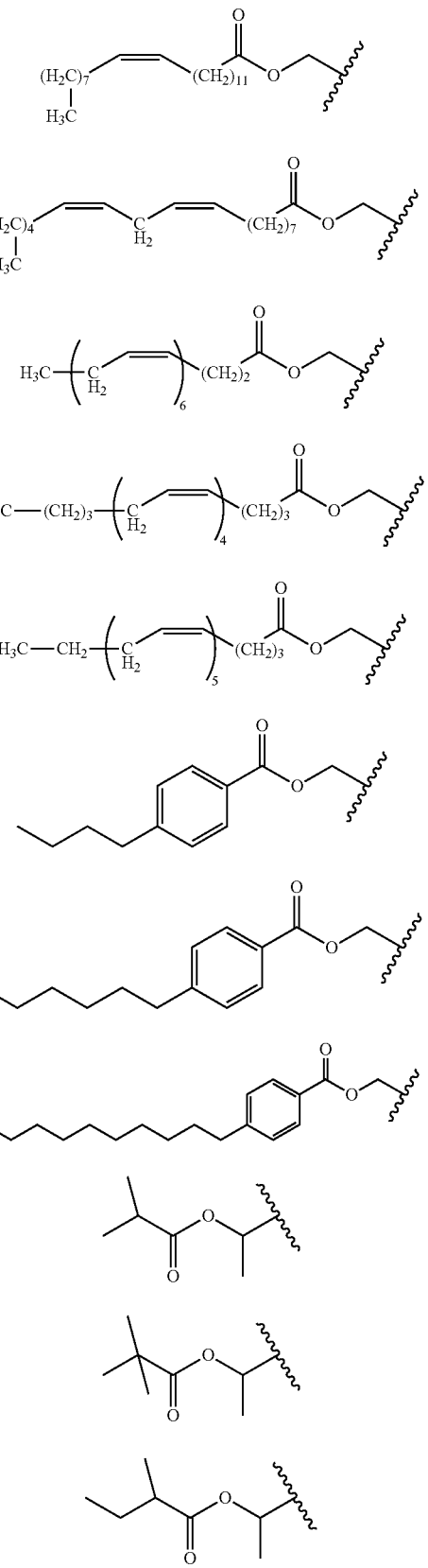

TABLE 1-continued
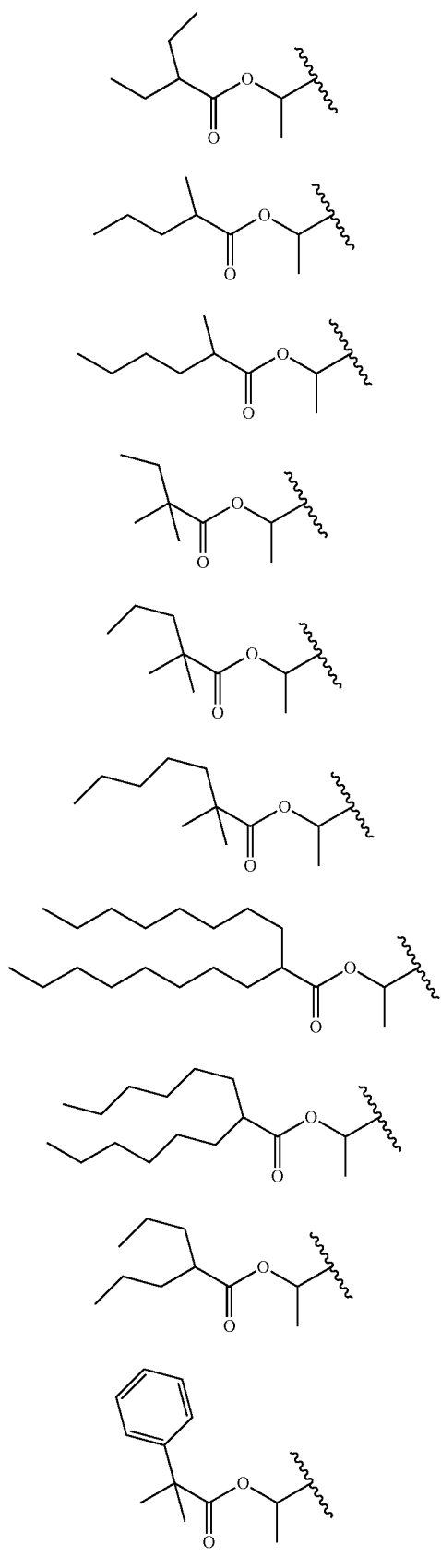
TABLE 1-continued
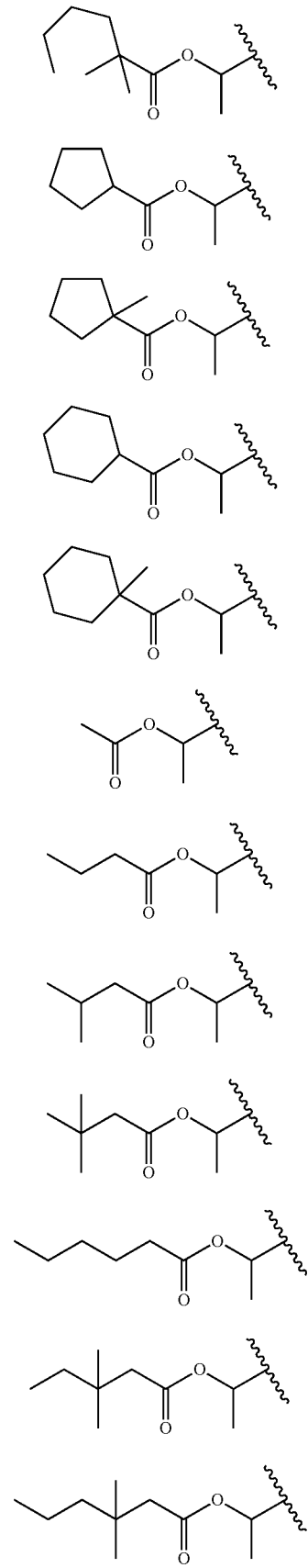

TABLE 1-continued
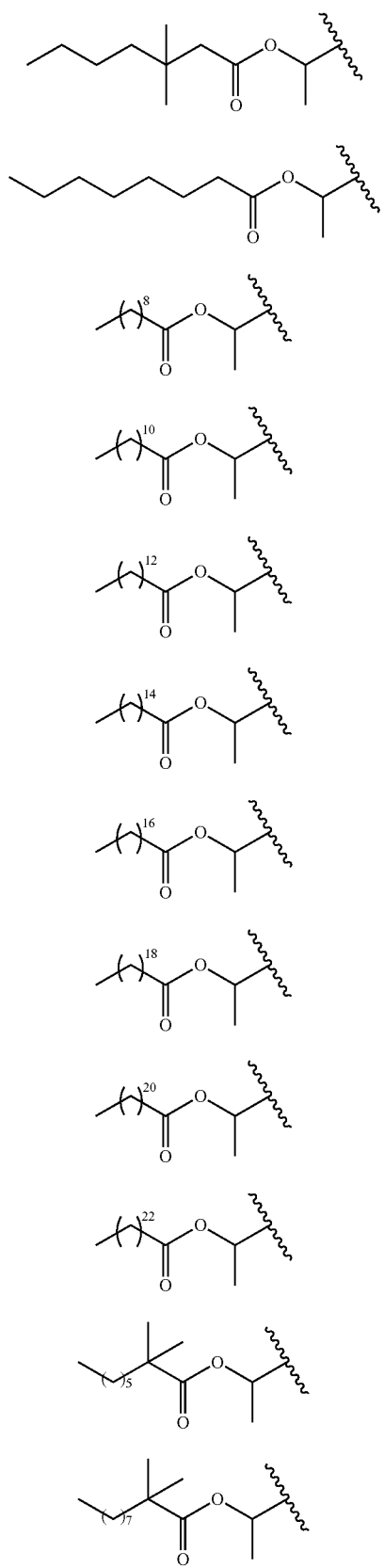
TABLE 1-continued
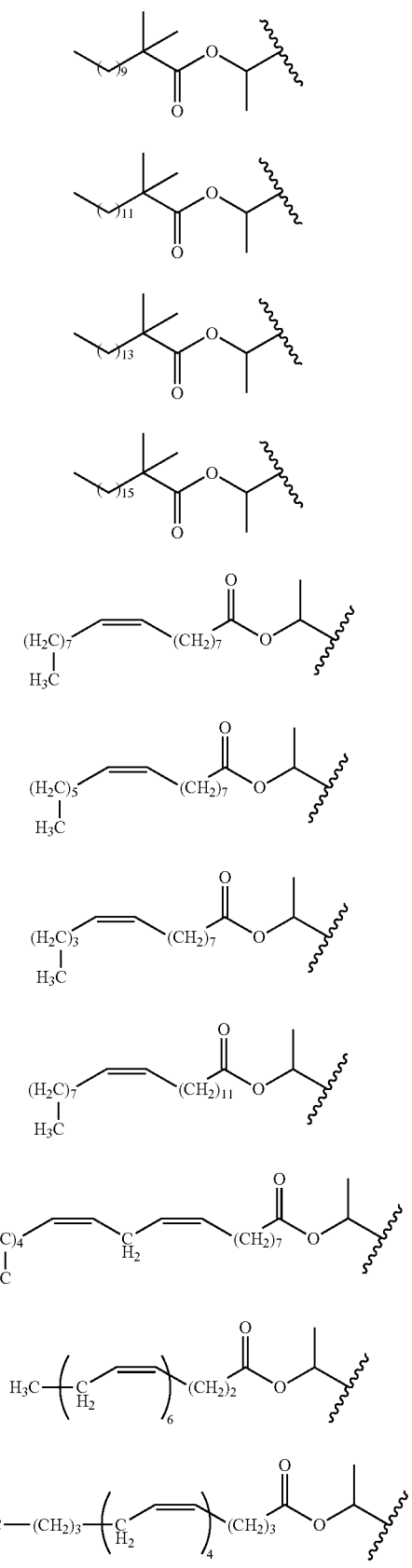

TABLE 1-continued

TABLE 1-continued
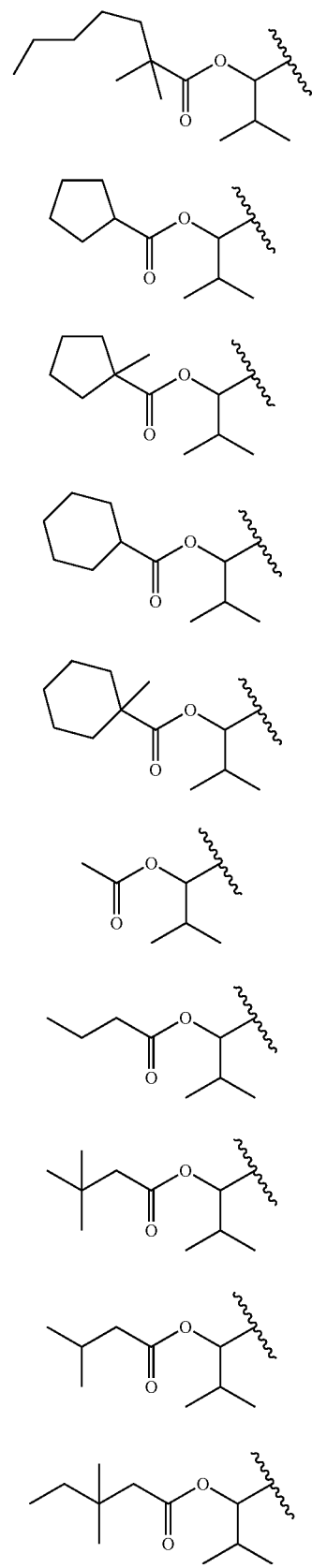
TABLE 1-continued
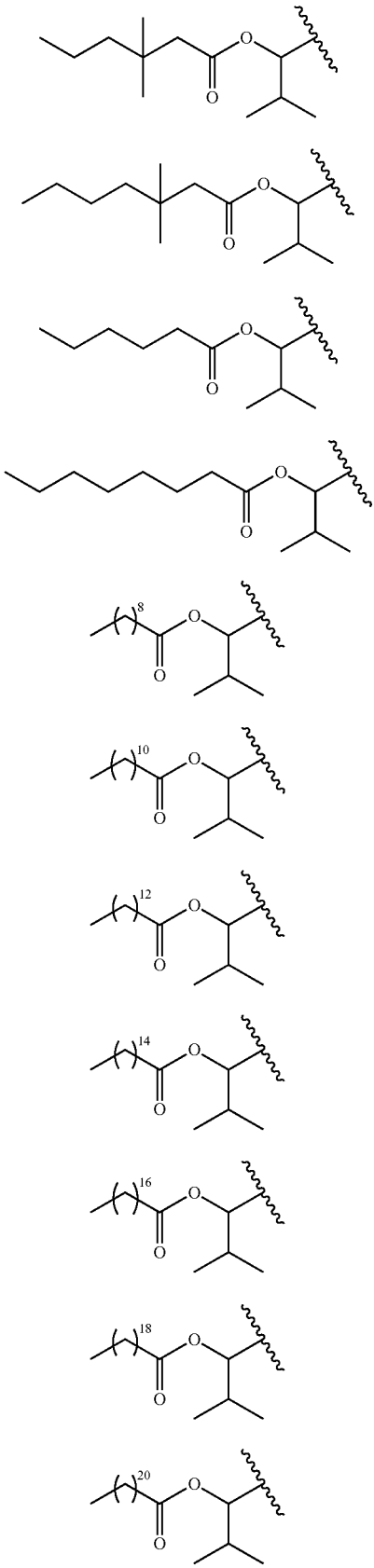

TABLE 1-continued

TABLE 1-continued
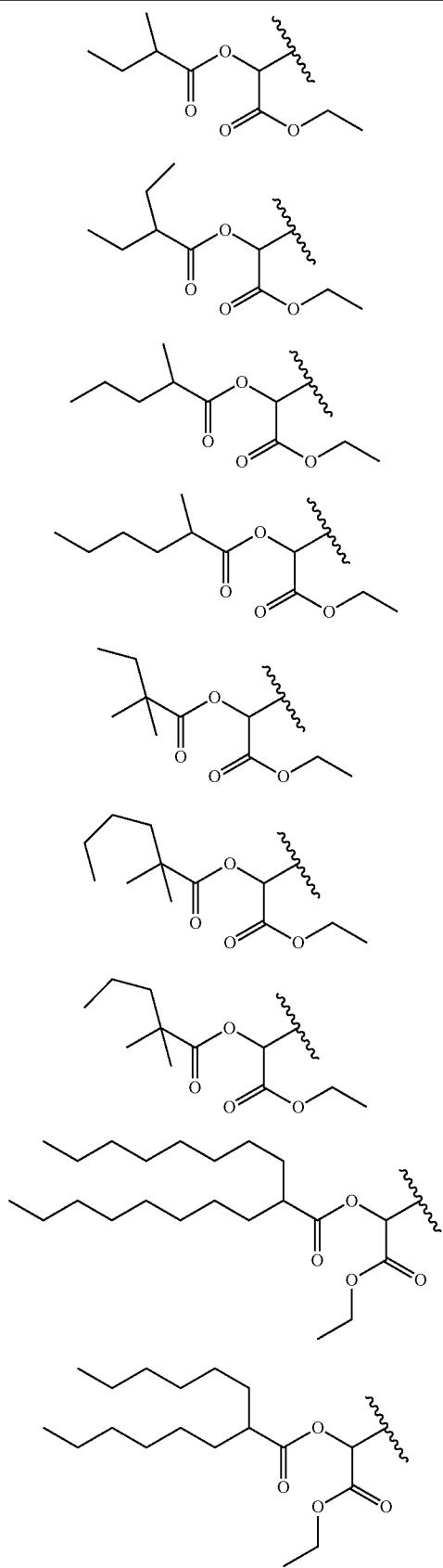
TABLE 1-continued
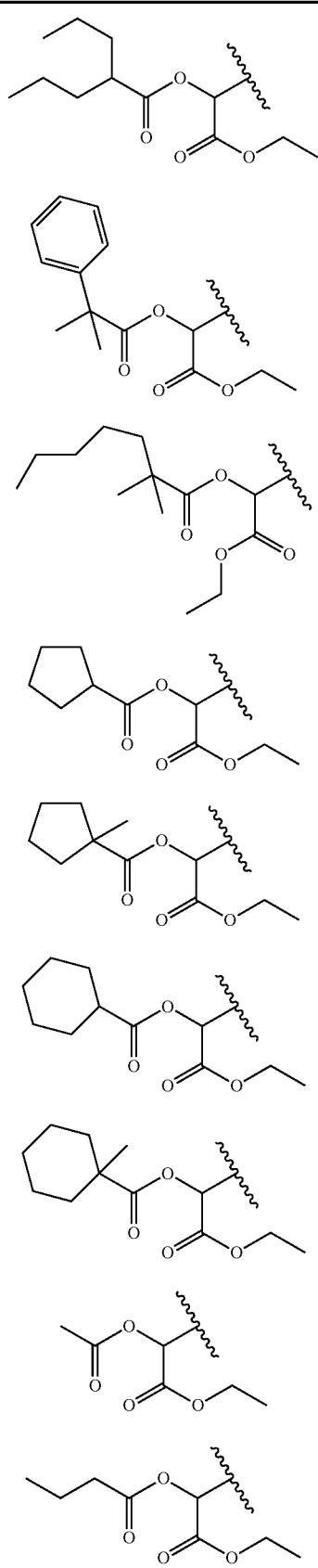

TABLE 1-continued
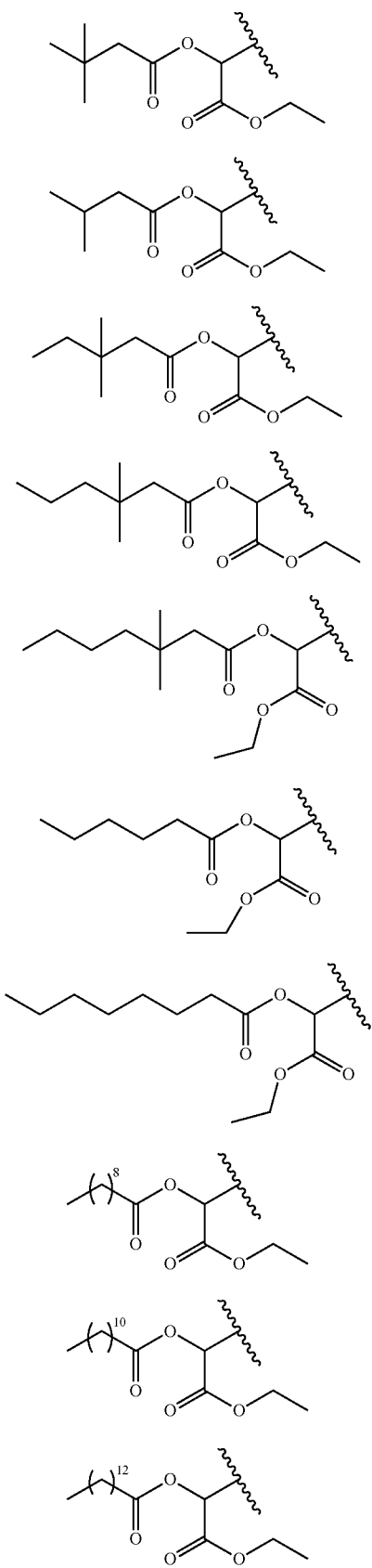
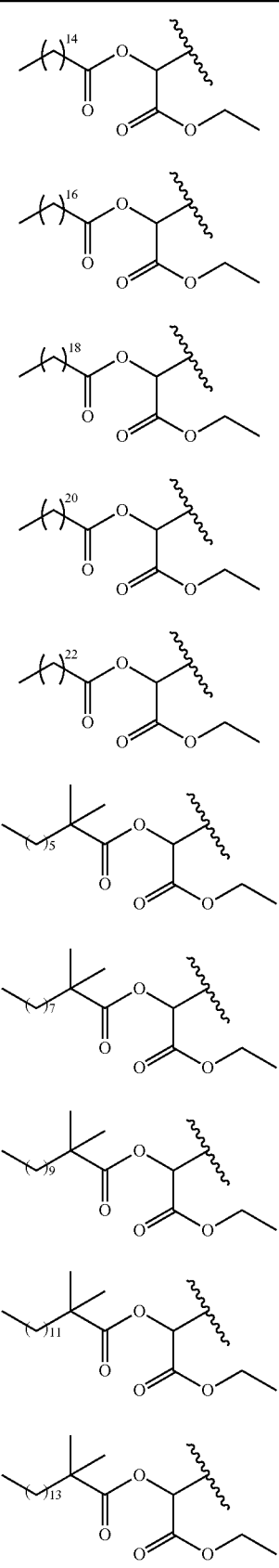

TABLE 1-continued
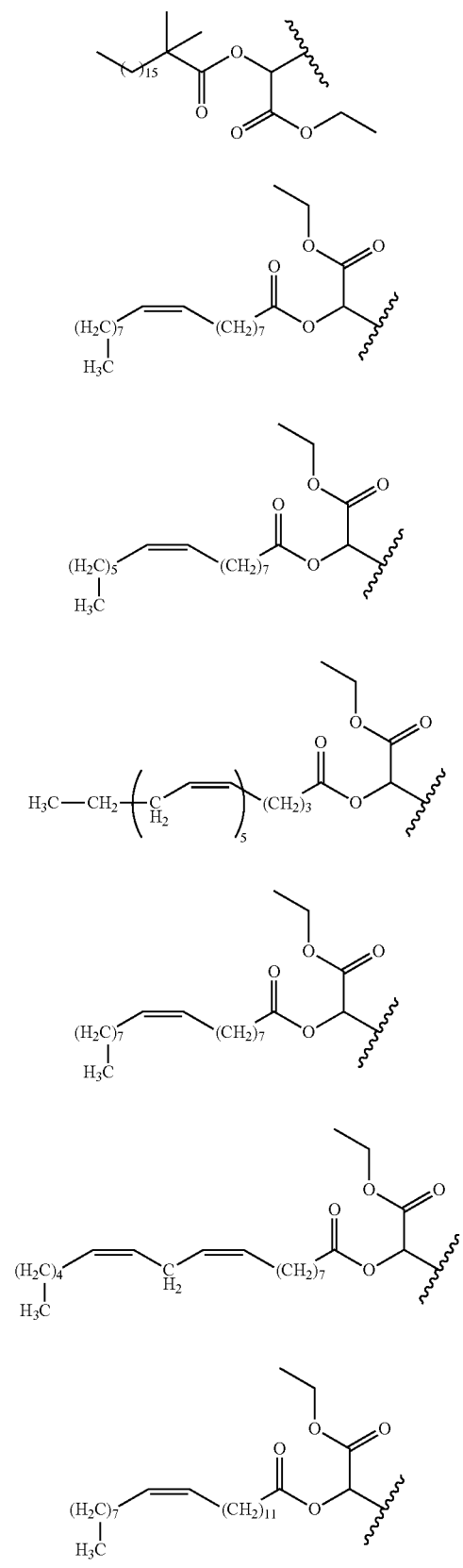
TABLE 1-continued
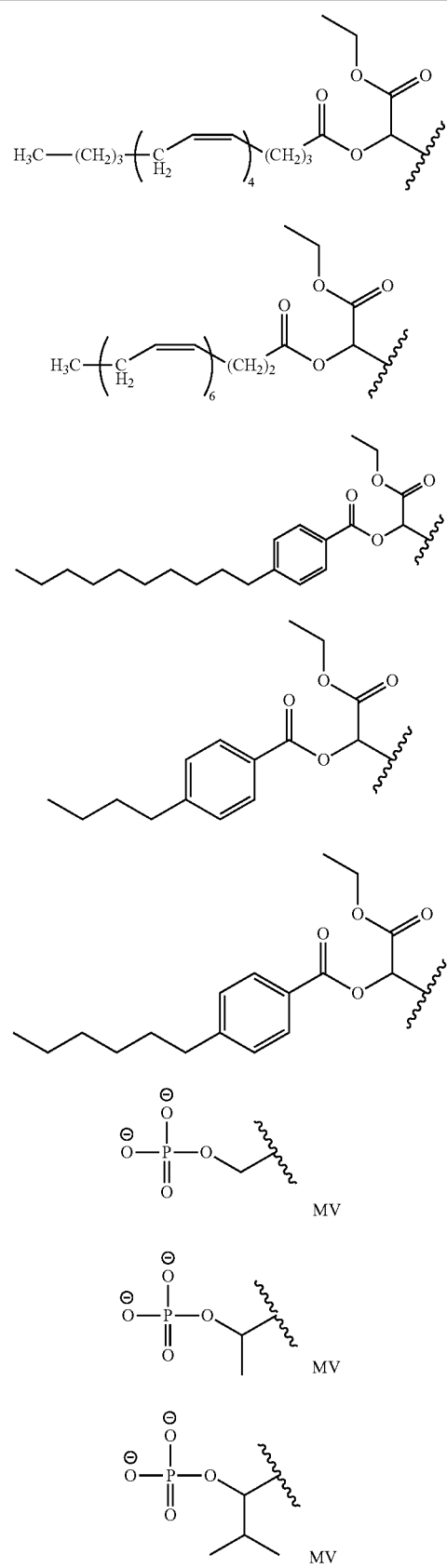

TABLE 1-continued
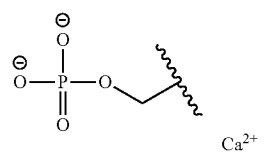 [SMILES: *COP(=O)([O-])[O-] ; [Ca+2]]
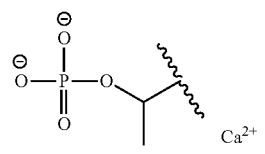
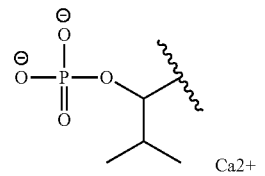
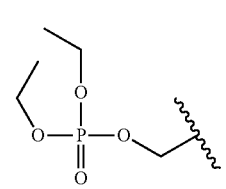 [SMILES: *COP(=O)(OCC)OCC]
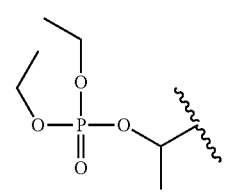 [SMILES: *C(C)OP(=O)(OCC)OCC]
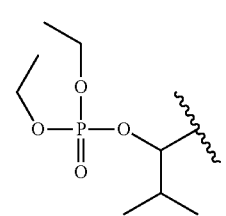 [SMILES: *C(OP(=O)(OCC)OCC)C(C)C]
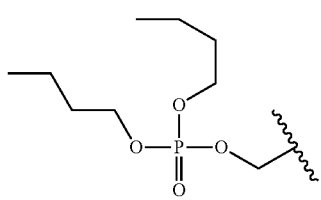 [SMILES: *COP(=O)(OCCCC)OCCCC]
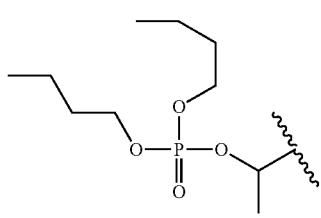 [SMILES: *C(C)OP(=O)(OCCCC)OCCCC]
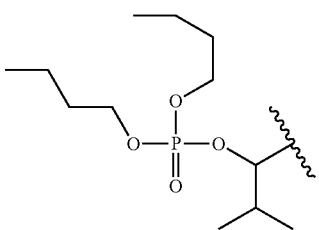 [SMILES: *C(OP(=O)(OCCCC)OCCCC)C(C)C]
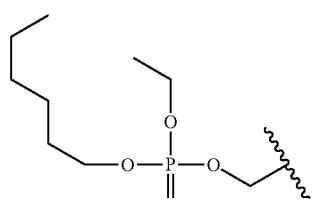
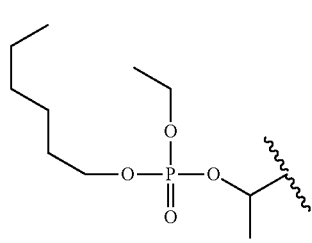 [SMILES: *C(C)OP(=O)(OCC)OCCCCCC]
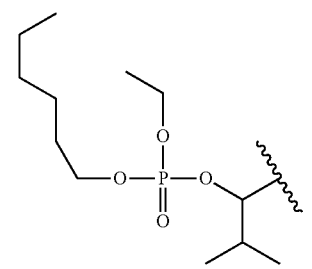 [SMILES: *C(OP(=O)(OCC)OCCCCCC)C(C)C]
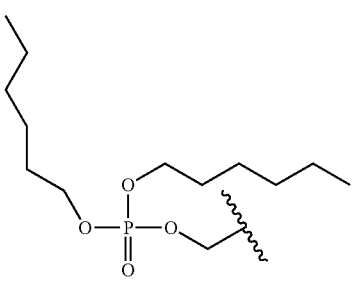 [SMILES: *COP(=O)(OCCCCCC)OCCCCCC]
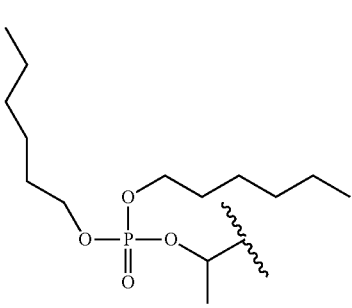 [SMILES: *C(C)OP(=O)(OCCCCCC)OCCCCCC]

TABLE 1-continued
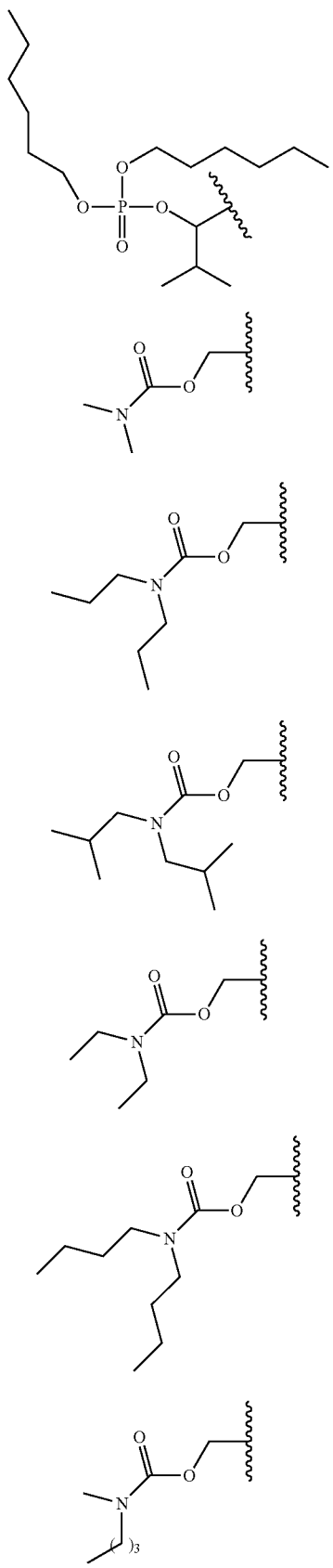
TABLE 1-continued
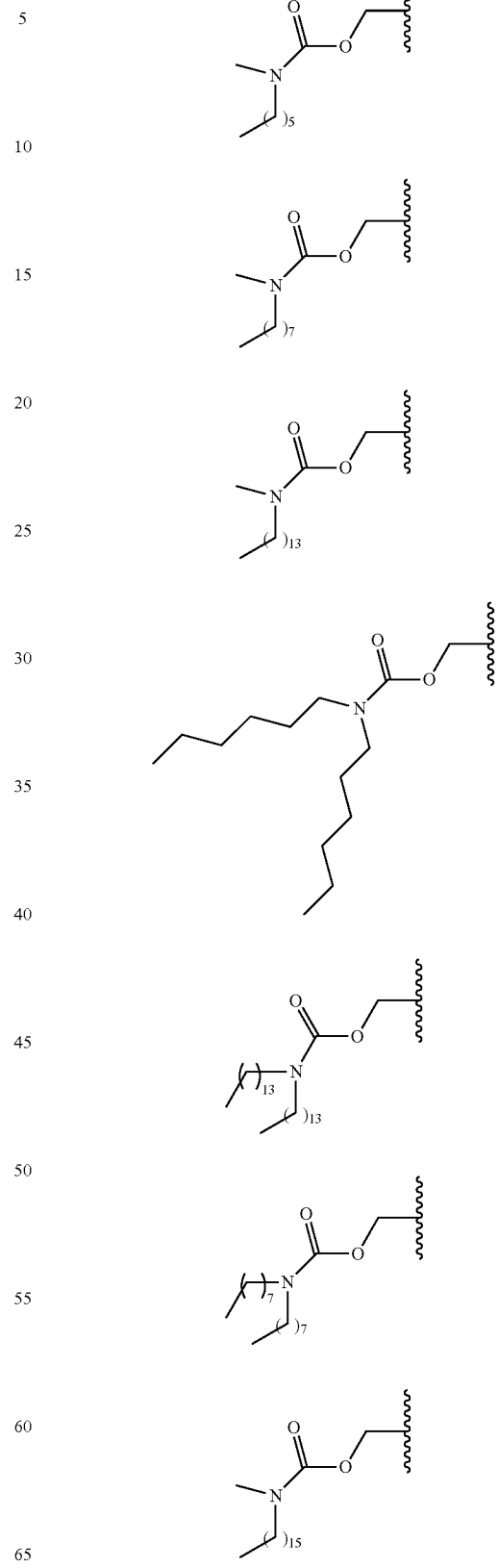

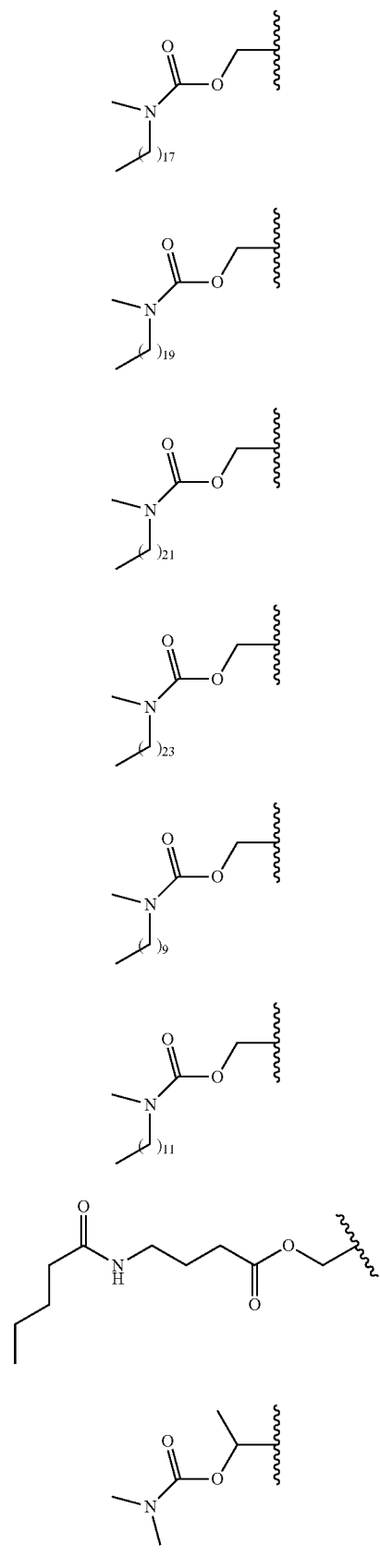

TABLE 1-continued
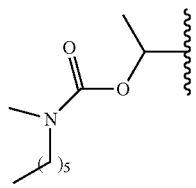
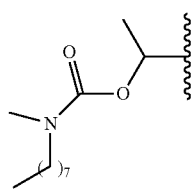
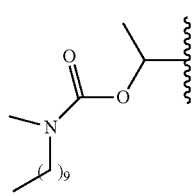
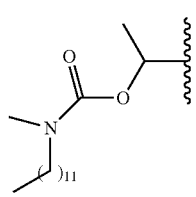
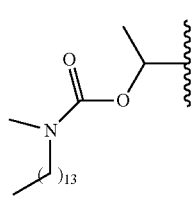
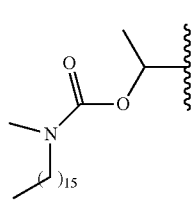
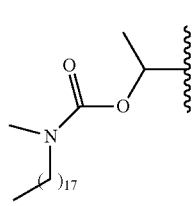
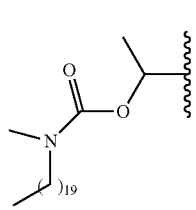
TABLE 1-continued
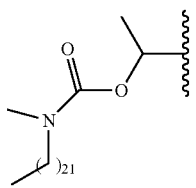
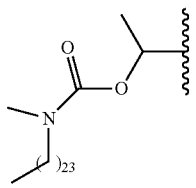
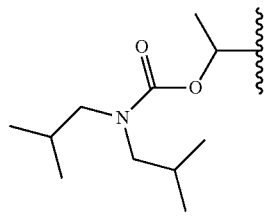 [SMILES: *C(C)OC(=O)N(CC(C)C)CC(C)C]
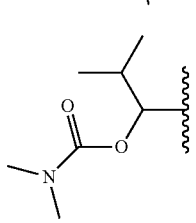
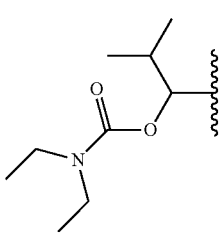 [SMILES: *C(OC(=O)N(CC)CC)C(C)C]
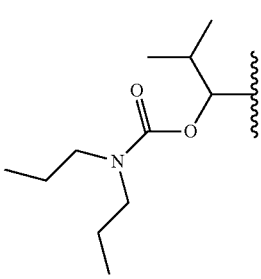 [SMILES: *C(OC(=O)N(CCC)CCC)C(C)C]
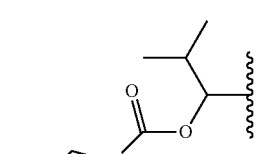

TABLE 1-continued
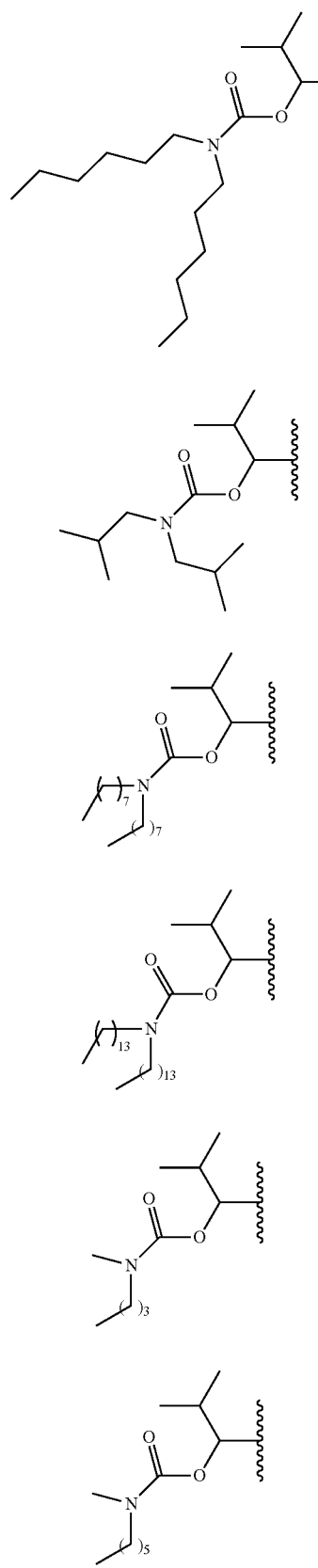
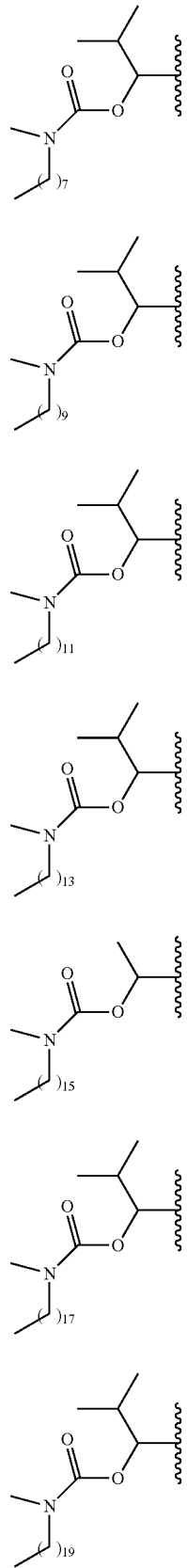

TABLE 1-continued
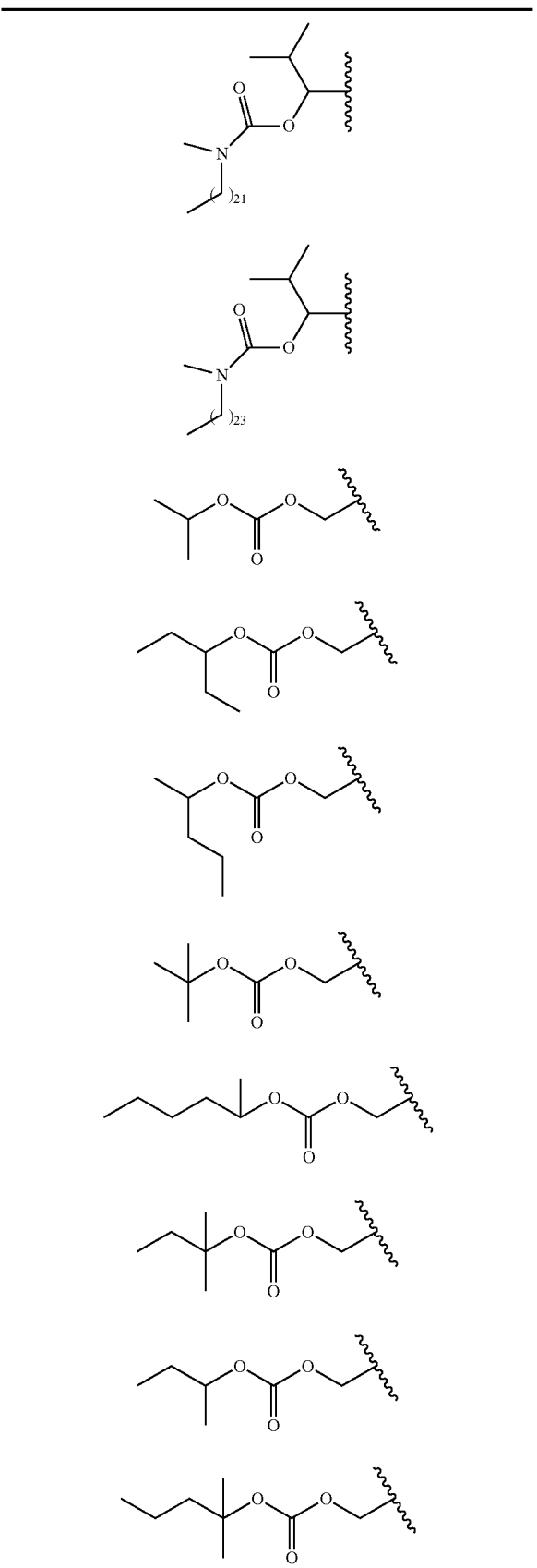
TABLE 1-continued
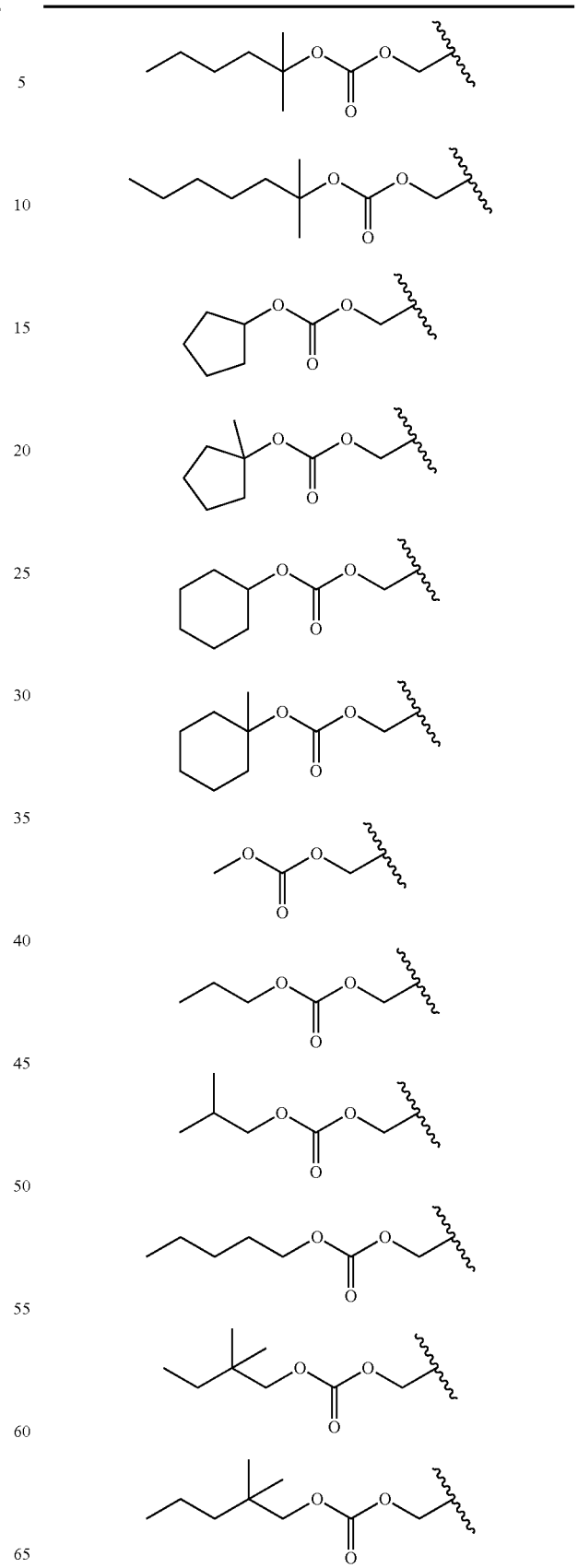

TABLE 1-continued
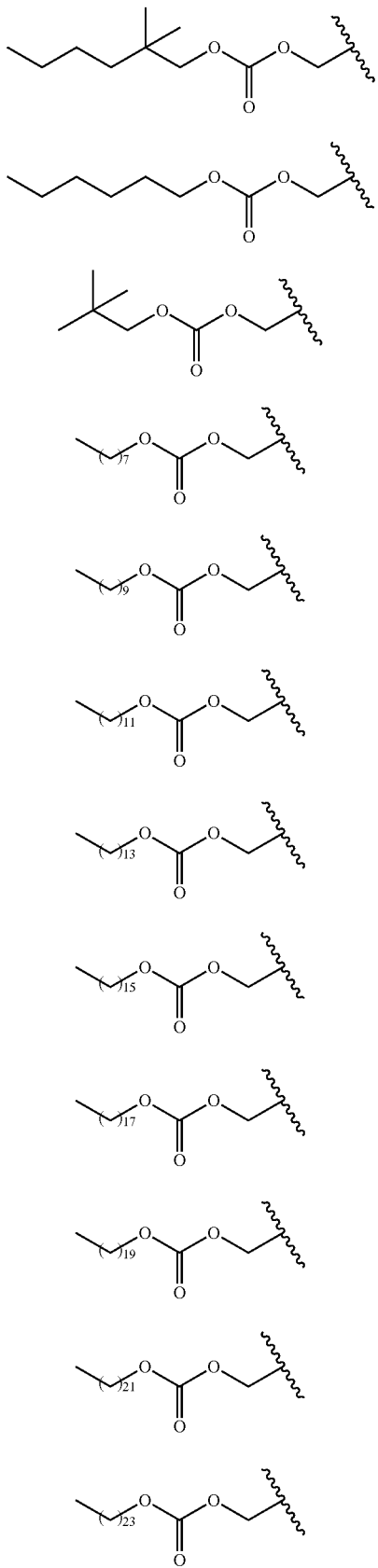
TABLE 1-continued
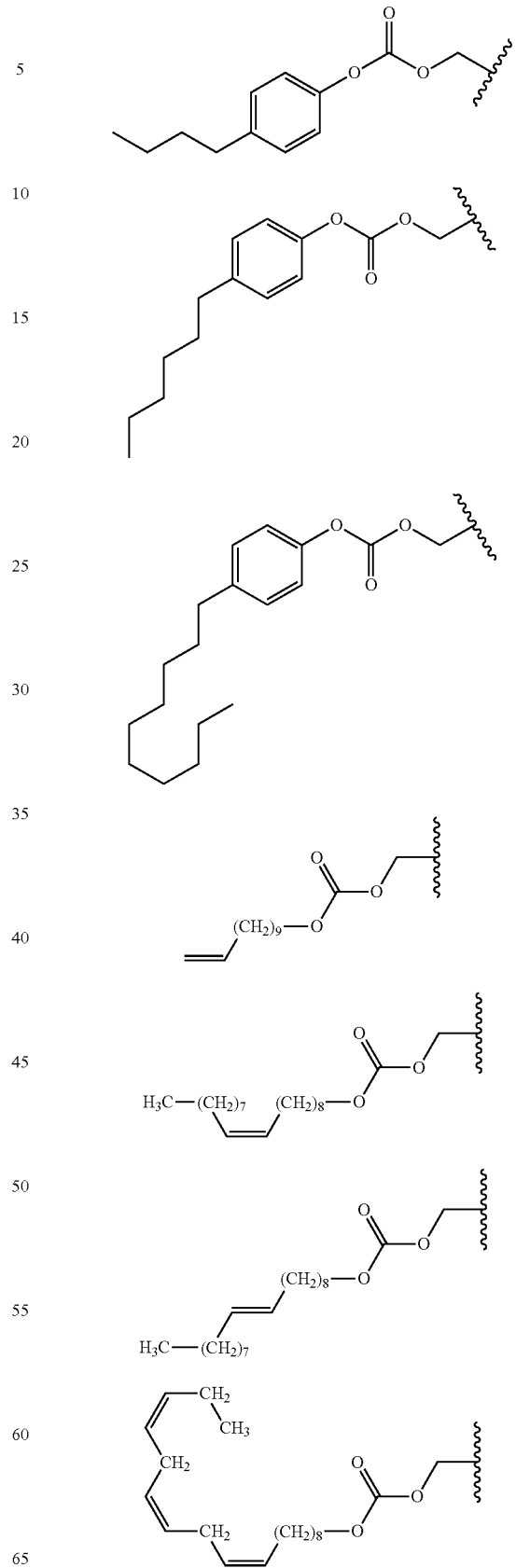

TABLE 1-continued

TABLE 1-continued
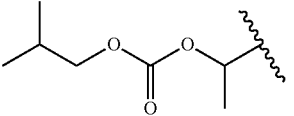 [SMILES: *C(C)OC(=O)OCC(C)C]
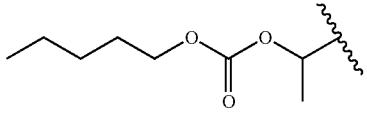 [SMILES: *C(C)OC(=O)OCCCCC]
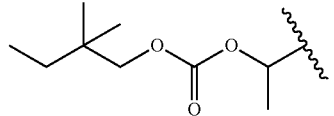 [SMILES: *C(C)OC(=O)OCC(C)(C)CC]
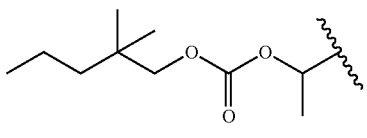 [SMILES: *C(C)OC(=O)OCC(C)(C)CCC]
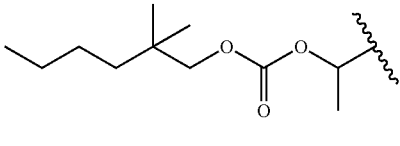 [SMILES: *C(C)OC(=O)OCC(C)(C)CCCC]
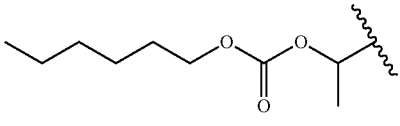 [SMILES: *C(C)OC(=O)OCCCCCC]
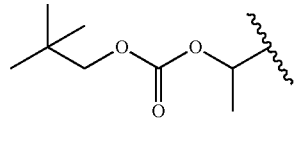 [SMILES: *C(C)OC(=O)OCC(C)(C)C]
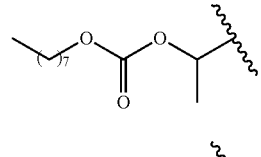
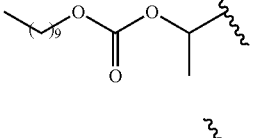
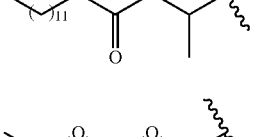
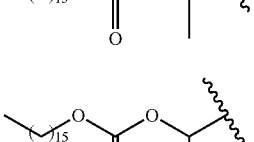
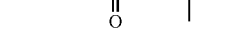
TABLE 1-continued
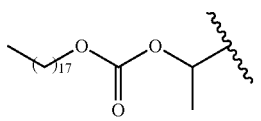
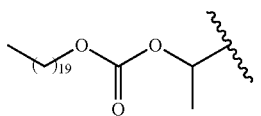
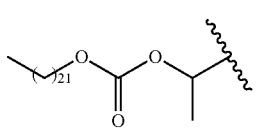
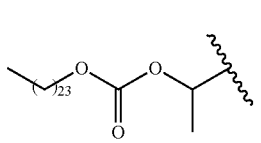
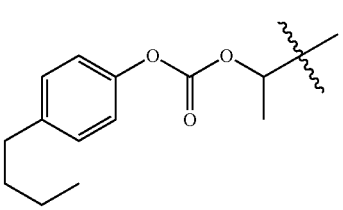 [SMILES: *C(C)OC(=O)Oc1ccc(CCCC)cc1]
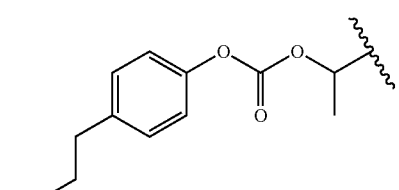
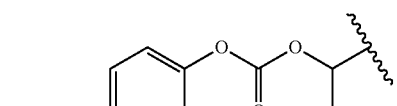
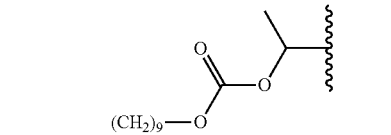

TABLE 1-continued
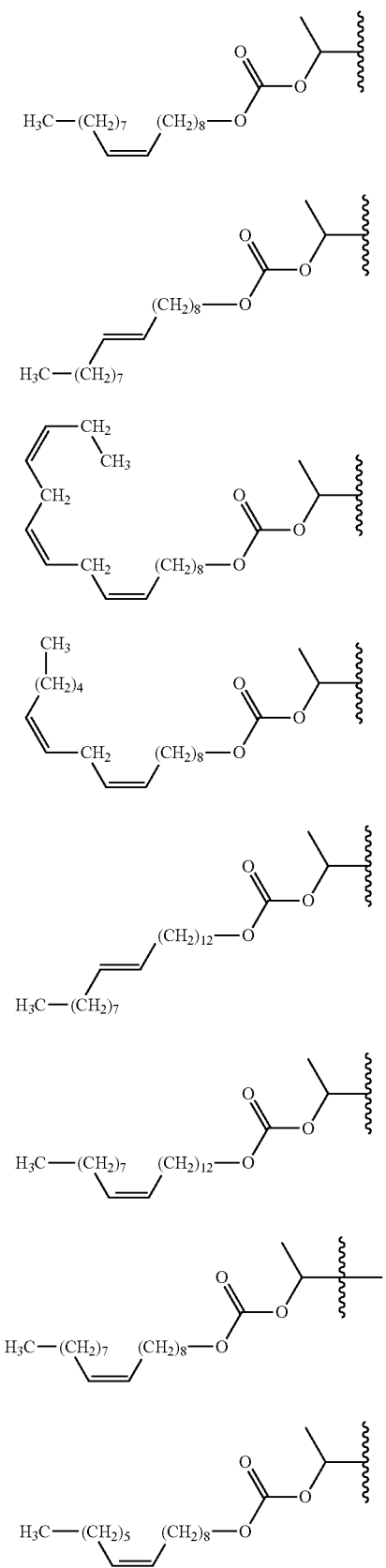
TABLE 1-continued
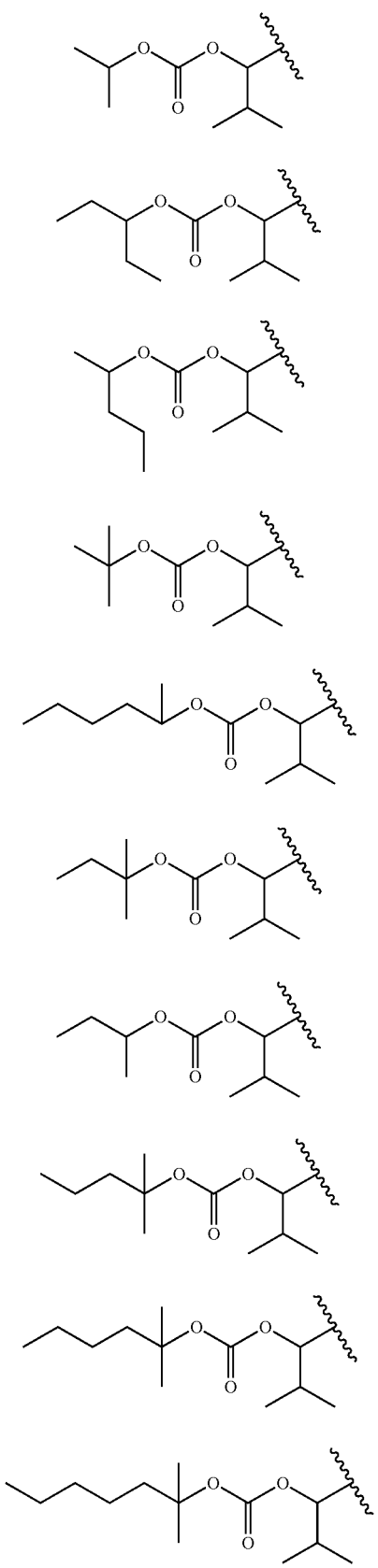

TABLE 1-continued
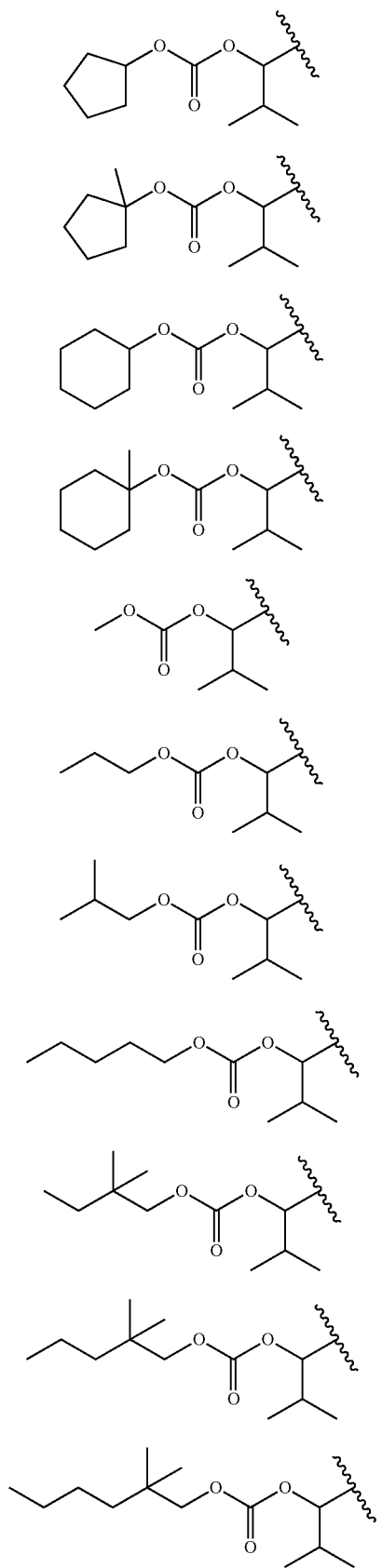
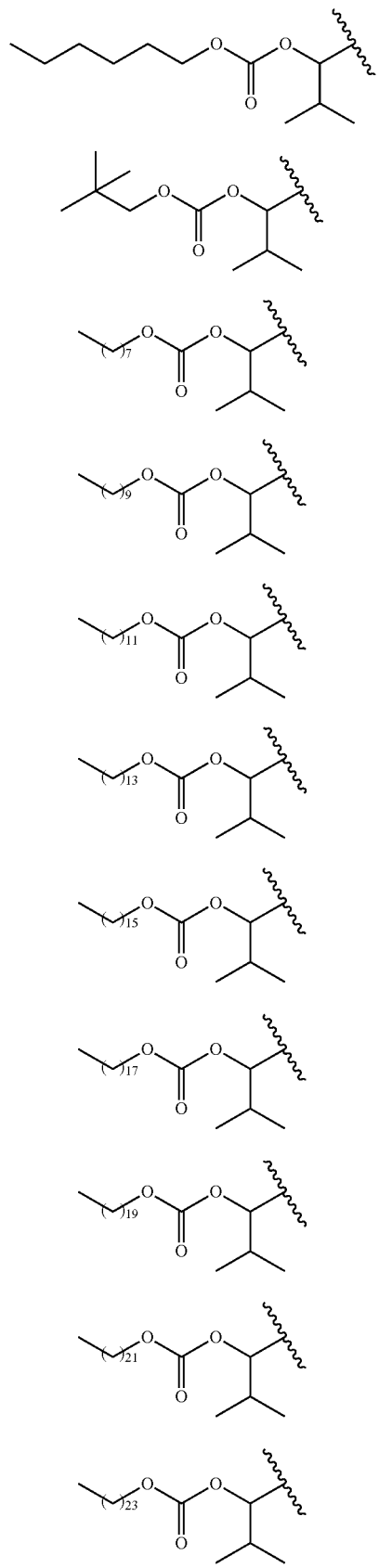

TABLE 1-continued
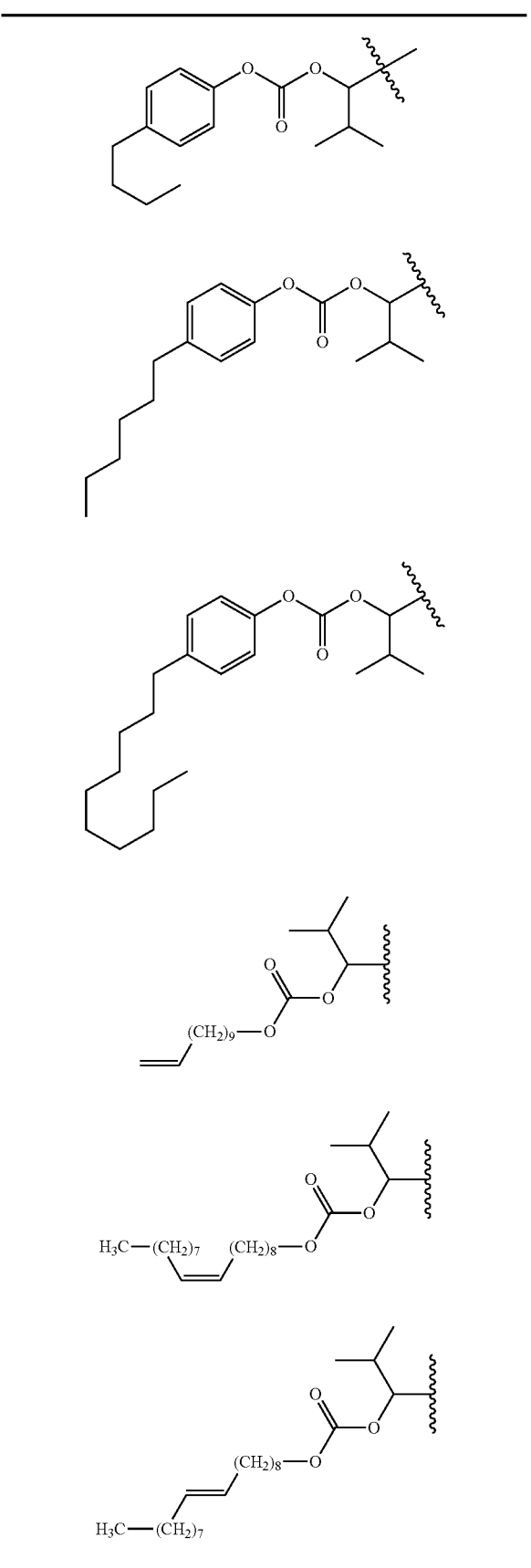
TABLE 1-continued
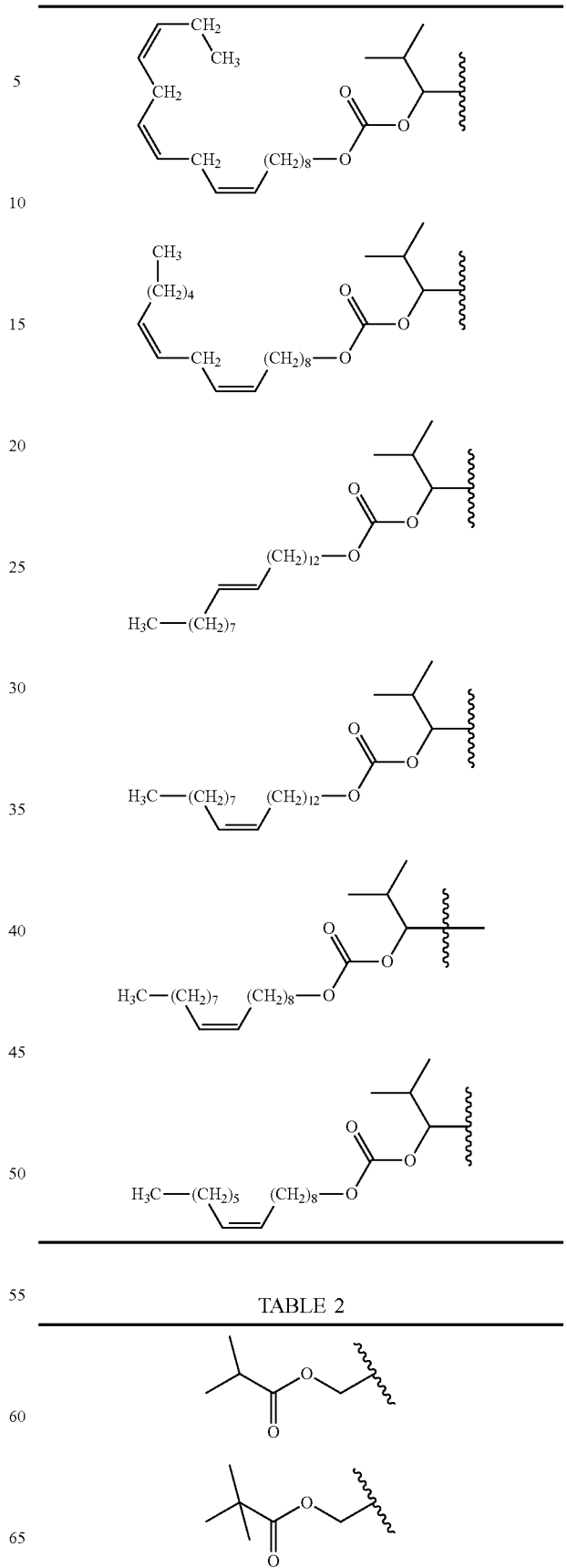
TABLE 2

TABLE 2-continued
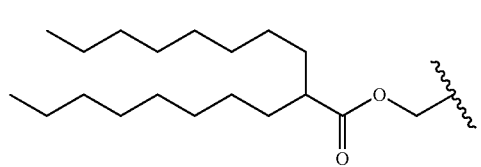 [SMILES: *COC(=O)C(CCCCCCCC)CCCCCCCC]
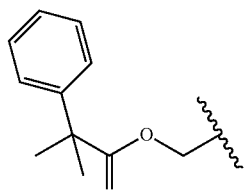
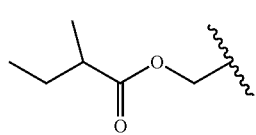 [SMILES: *COC(=O)C(C)CC]
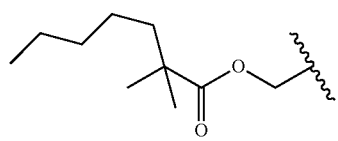 [SMILES: *COC(=O)C(C)(C)CCCCC]
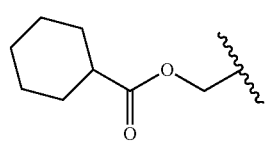
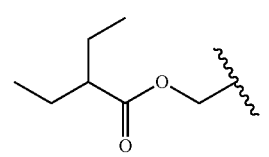 [SMILES: *COC(=O)C(CC)CC]
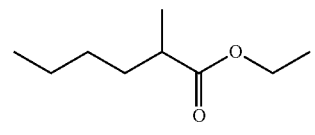
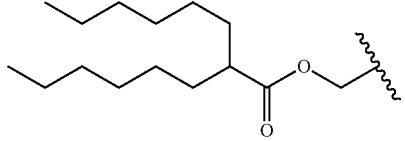 [SMILES: *COC(=O)C(CCCCCC)CCCCCC]
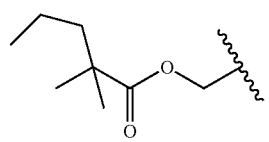 [SMILES: *COC(=O)C(C)(C)CCC]
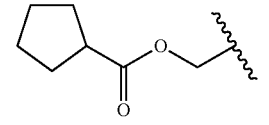 [SMILES: *COC(=O)C1CCCC1]
TABLE 2-continued
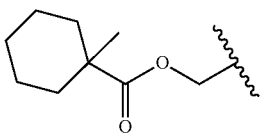 [SMILES: *COC(=O)C1(C)CCCCC1]
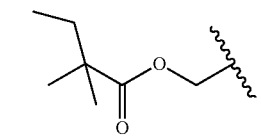 [SMILES: *COC(=O)C(C)(C)CC]
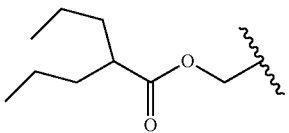 [SMILES: *COC(=O)C(CCC)CCC]
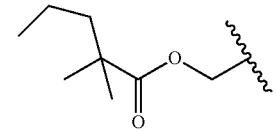 [SMILES: *COC(=O)C(C)(C)CCC]
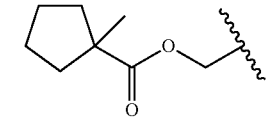 [SMILES: *COC(=O)C1(C)CCCC1]
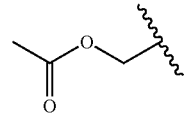 [SMILES: *COC(C)=O]
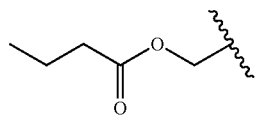 [SMILES: *COC(=O)CCC]
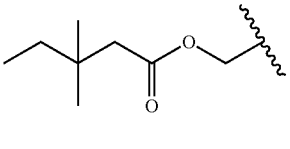 [SMILES: *COC(=O)CC(C)(C)CC]
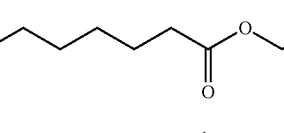
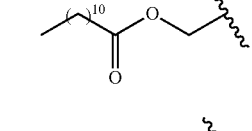
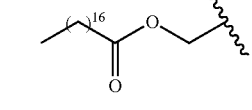

TABLE 2-continued
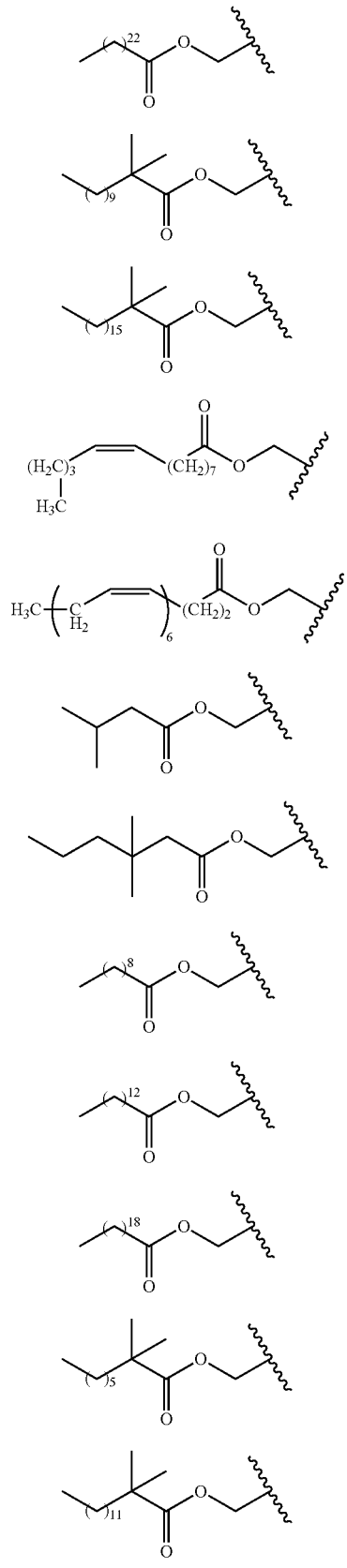
TABLE 2-continued
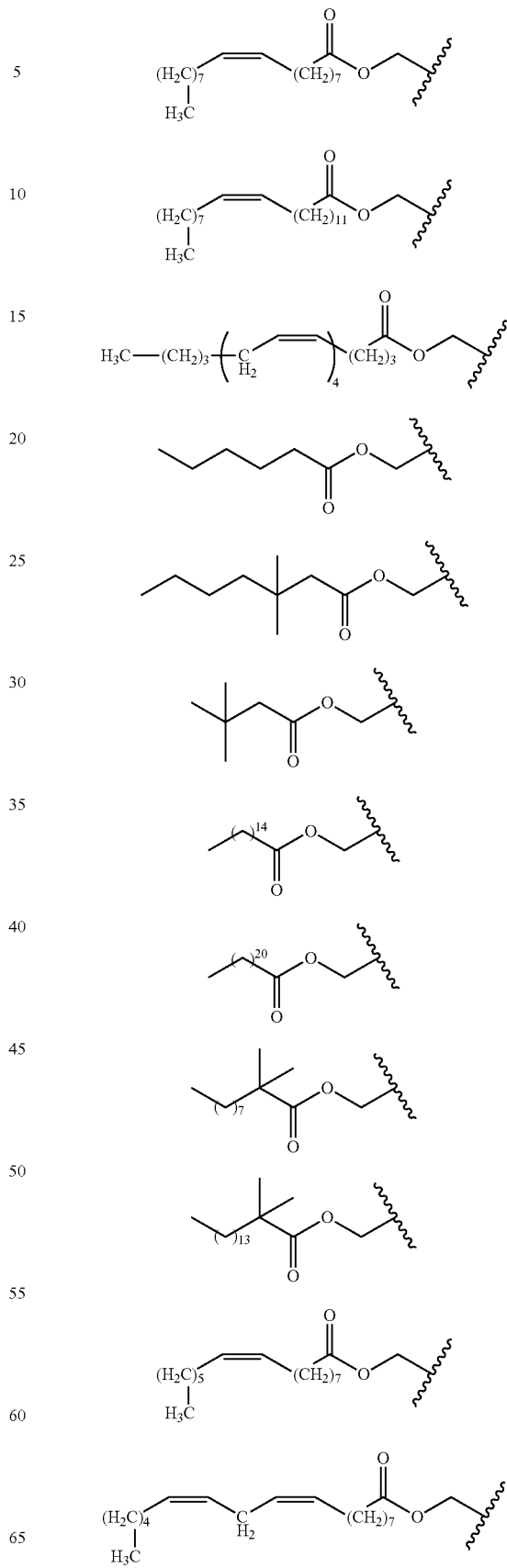

TABLE 2-continued
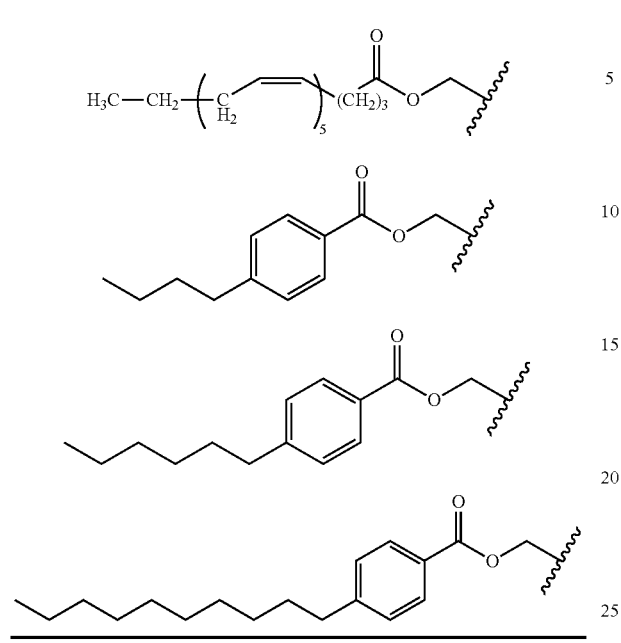
TABLE 3
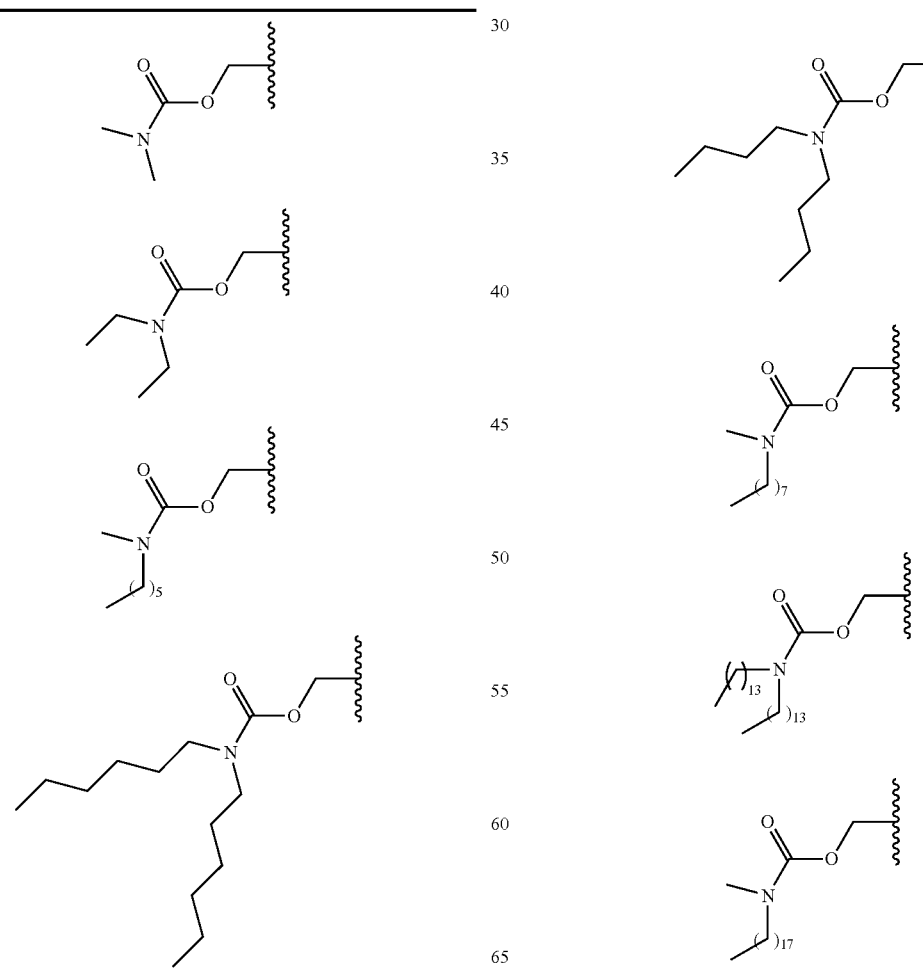
TABLE 3-continued
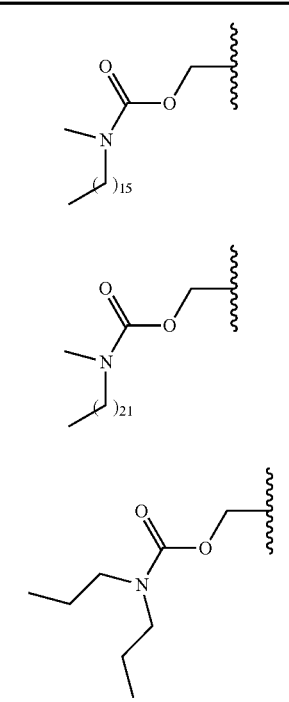

TABLE 3-continued
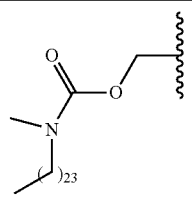
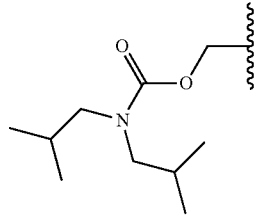
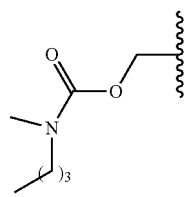
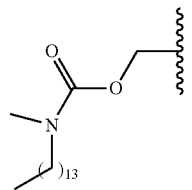
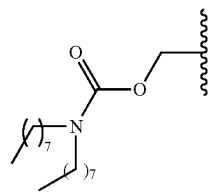
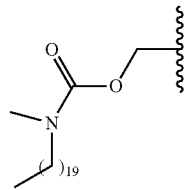
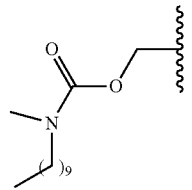
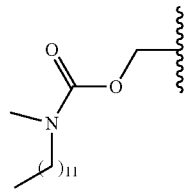
TABLE 3-continued
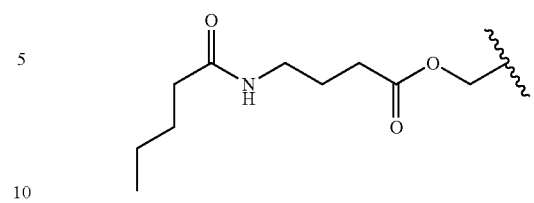
TABLE 4
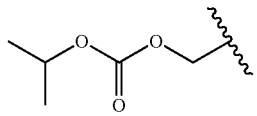 [SMILES: *COC(=O)OC(C)C]
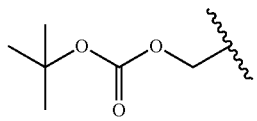 [SMILES: *COC(=O)OC(C)(C)C]
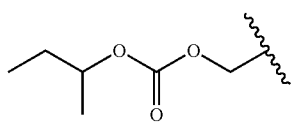 [SMILES: *COC(=O)OC(C)CC]
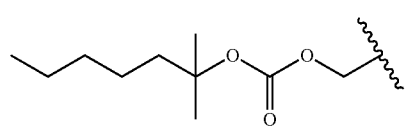 [SMILES: *COC(=O)OC(C)(C)CCCCC]
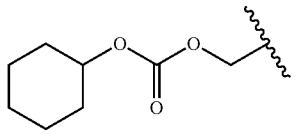 [SMILES: *COC(=O)OC1CCCCC1]
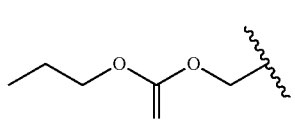
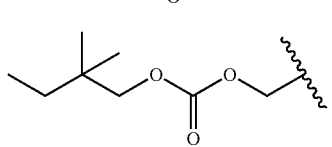
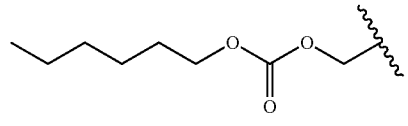 [SMILES: *COC(=O)OCCCCCC]
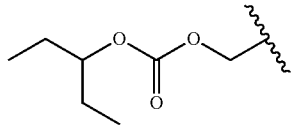 [SMILES: *COC(=O)OC(CC)CC]
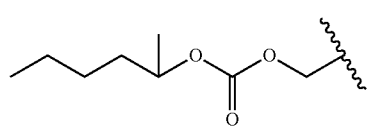 [SMILES: *COC(=O)OC(C)CCCC]

TABLE 4-continued
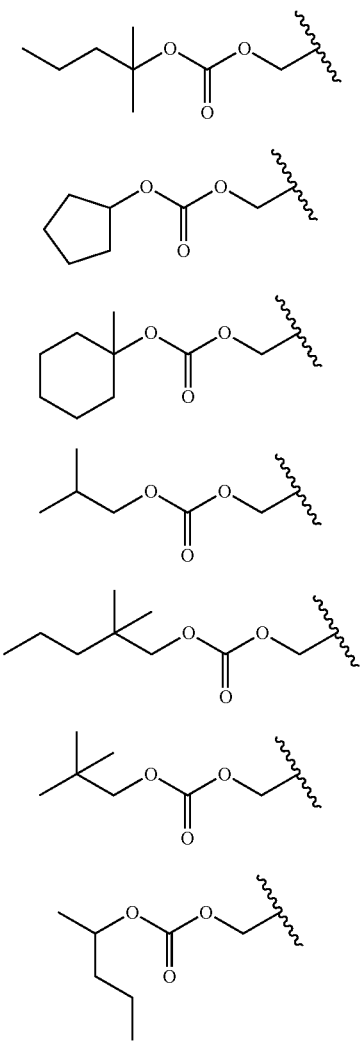
TABLE 4-continued
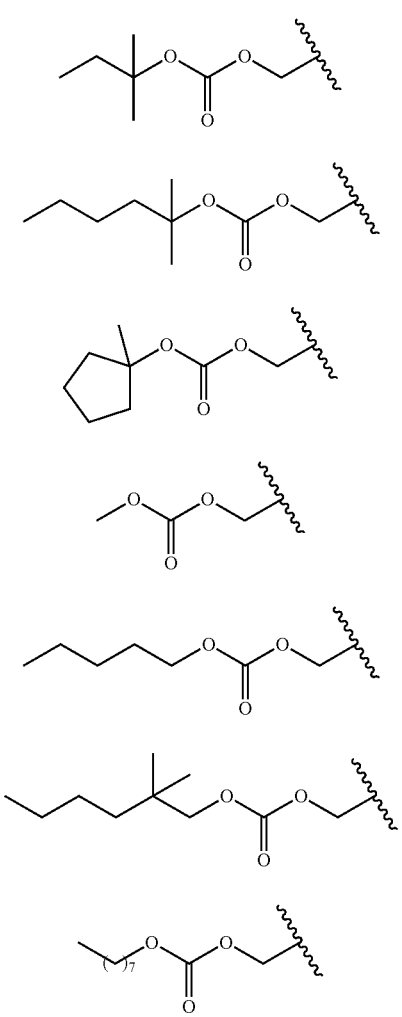
TABLE 5
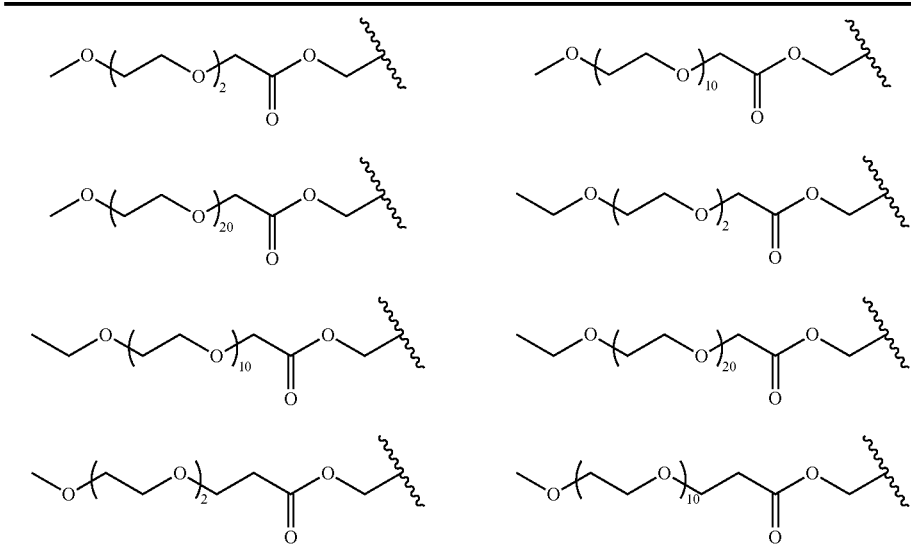

TABLE 5-continued
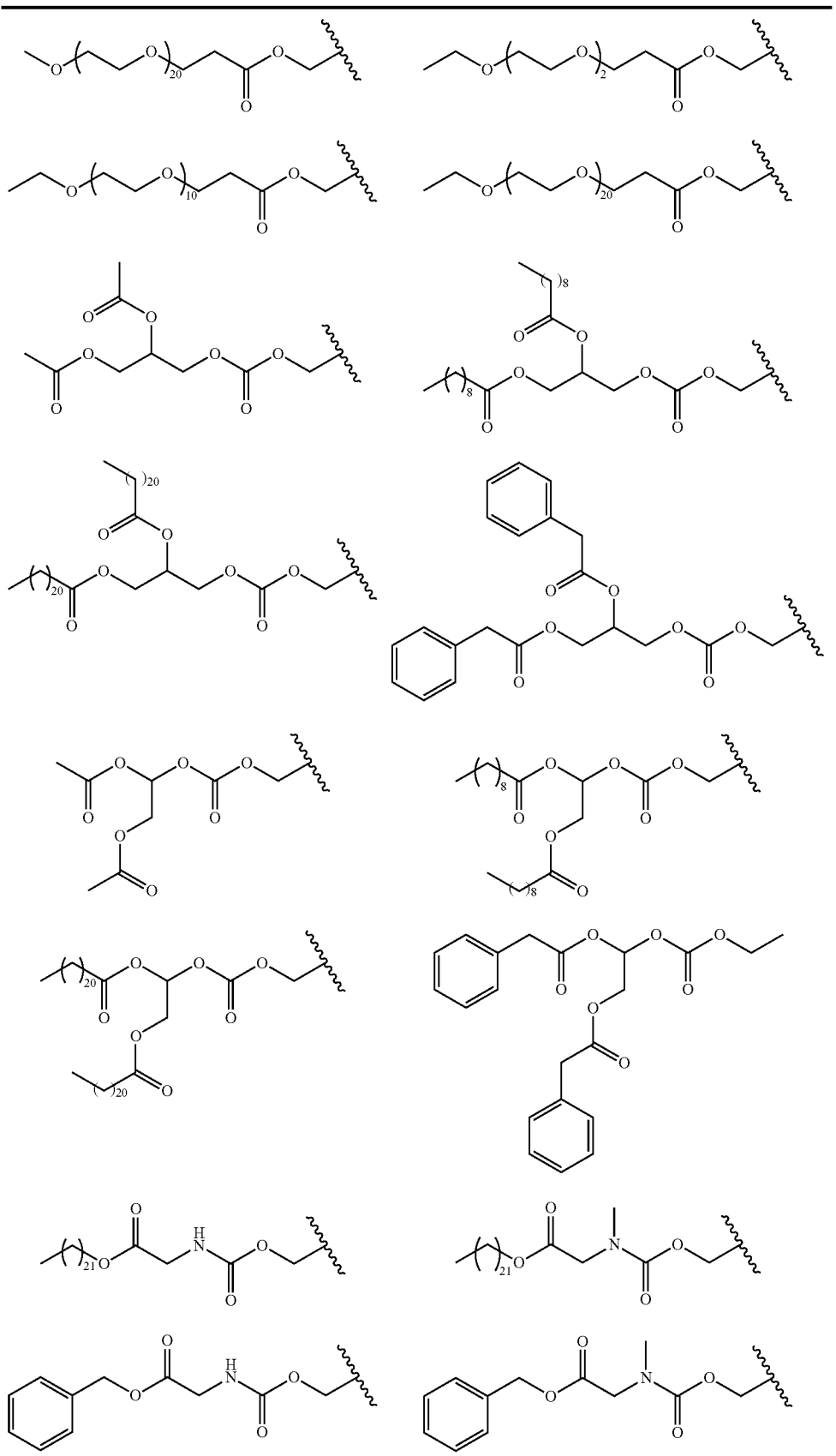

TABLE 5-continued
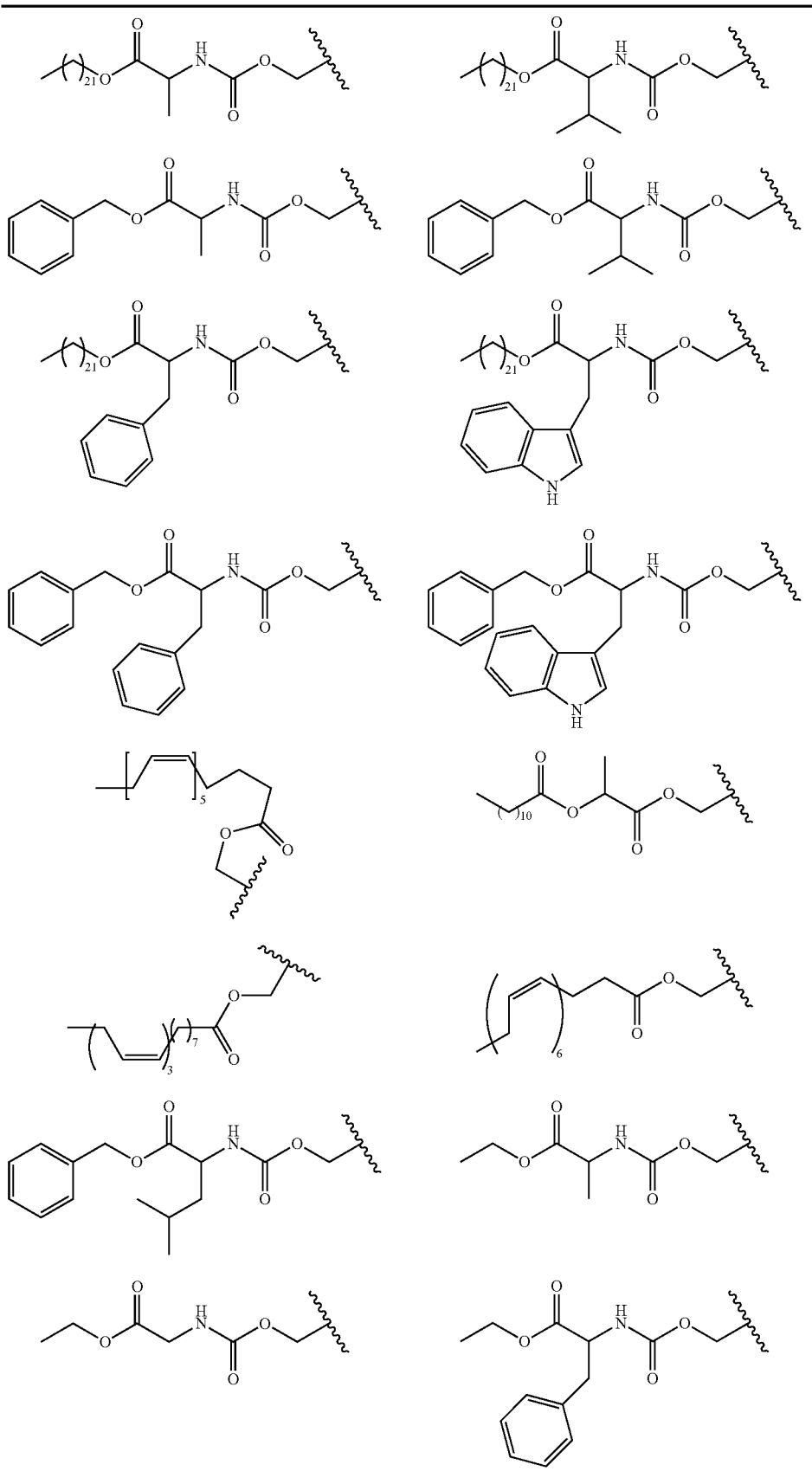

TABLE 5-continued

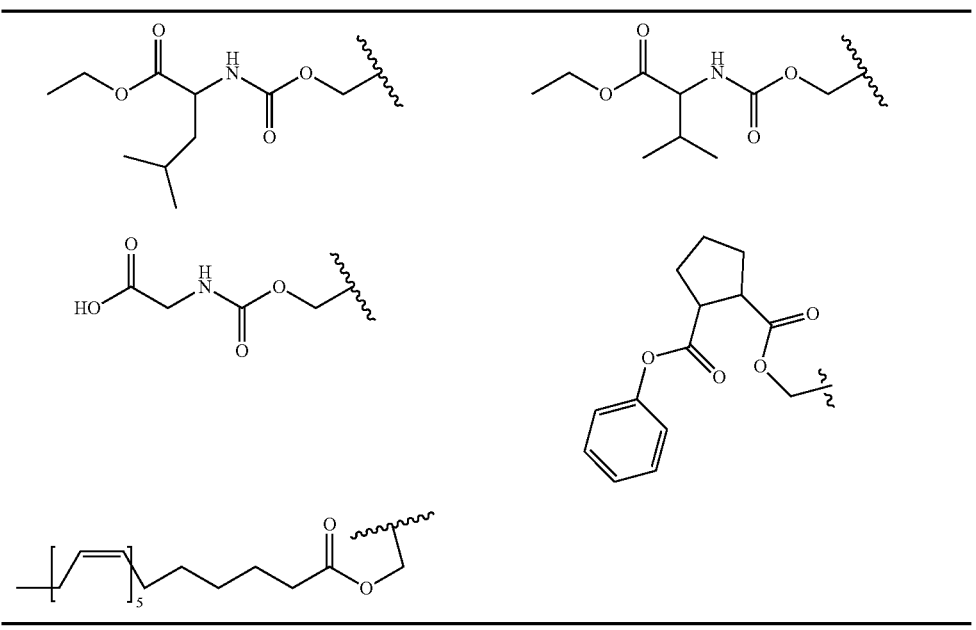

In another embodiment, the invention provides a prodrug compound of formula III having the structure of formula IV:

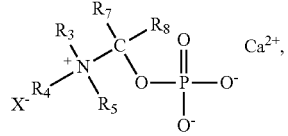

Formula IV wherein
$R_3$, $R_4$ and $R_5$, together with the nitrogen atom to which they are attached, form a tertiary amine-containing parent drug or a tertiary imine-containing parent drug; where $R_7$ and $R_8$ are each independently hydrogen or an aliphatic group and preferably $R_7$ and $R_8$ are each independently selected from:
  i) hydrogen;
  ii) branched or unbranched, substituted or unsubstituted $C_1$-$C_6$ alkyl;
  iii) branched or unbranched, substituted or unsubstituted $C_1$-$C_6$ alkenyl;
  iv) branched or unbranched, substituted or unsubstituted $C_1$-$C_6$ alkynyl; and $X^-$ is a pharmaceutically acceptable anion.

In one preferred embodiment, the invention provides a compound of formula V having the structure of formula V:

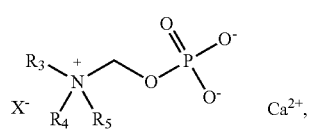

Formula V where $R_3$, $R_4$ and $R_5$ are as previously defined in formula IV.

In another embodiment, the invention provides a prodrug of compound of Formula III having the structure of Formula VI:

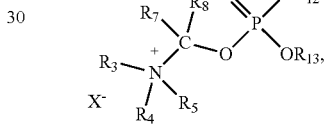

Formula VI wherein $R_3$, $R_4$ and $R_5$, together with the nitrogen atom to which they are attached, form a tertiary amine-containing parent drug or a tertiary imine-containing parent drug; where $R_7$ and $R_8$ are each independently hydrogen or an aliphatic group and preferably $R_7$ and $R_8$ are each independently selected from:

i) hydrogen;
  ii) branched or unbranched, substituted or unsubstituted $C_1$-$C_6$ alkyl;
  iii) branched or unbranched, substituted or unsubstituted $C_1$-$C_6$ alkenyl; and
  iv) branched or unbranched, substituted or unsubstituted $C_1$-$C_6$ alkynyl;

$R_{12}$ and $R_{13}$ are each independently hydrogen or an aliphatic group, provided that at least one of $R_{12}$ and $R_{13}$ is substituted or unsubstituted $C_7$-$C_{24}$-alkyl, substituted or unsubstituted $C_2$-$C_{24}$-alkenyl, substituted or unsubstituted $C_2$-$C_{24}$ alkynyl, and substituted or unsubstituted $C_3$-$C_{12}$ cycloalkyl and preferably at least one of $R_{12}$ and $R_{13}$ is substituted or unsubstituted $C_7$-$C_{24}$-alkyl such as a $C_8$-$C_{24}$ alkyl or a $C_9$-$C_{24}$ alkyl; and $X^-$ is a pharmaceutically acceptable anion.

In one embodiment, the invention provides a compound of Formula III having the structure of formula VII as represented by:

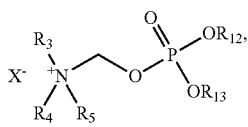

Formula VII where $R_3$, $R_4$ and $R_5$, $R_{12}$ and $R_{13}$ are as defined in Formula VI.

In another embodiment, the invention provides a prodrug compound of Formula III having the structure of formula VIII as represented by:

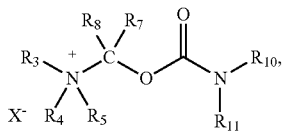

Formula VIII wherein
$R_3$, $R_4$ and $R_5$, together with the nitrogen atom to which they are attached, form a tertiary amine-containing parent drug or a tertiary imine-containing parent drug;
where $R_7$ and $R_8$ are each independently hydrogen or an aliphatic group and preferably $R_7$ and $R_8$ are each independently selected from:
i) hydrogen;
ii) branched or unbranched, substituted or unsubstituted $C_1$-$C_6$ alkyl;
iii) branched or unbranched, substituted or unsubstituted $C_1$-$C_6$ alkenyl; and
iv) branched or unbranched, substituted or unsubstituted $C_1$-$C_6$ alkynyl;
$R_{10}$ and $R_{11}$ are each independently hydrogen or an aliphatic group, provided that at least one of $R_{10}$ and $R_{11}$ is substituted or unsubstituted $C_1$-$C_{24}$-alkyl, substituted or unsubstituted $C_2$-$C_{24}$-alkenyl, substituted or unsubstituted $C_2$-$C_{24}$ alkynyl, substituted or unsubstituted $C_3$-$C_{12}$ cycloalkyl, substituted or unsubstituted aryl, substituted or unsubstituted heteroaryl or $R_{10}$ and $R_{11}$ when taken together with the nitrogen to which they are attached form a heterocycle. Preferably at least one of $R_{10}$ and $R_{11}$ is substituted or unsubstituted $C_5$-$C_{24}$-alkyl, $C_7$-$C_{24}$-alkyl, $C_8$-$C_{24}$-alkyl or $C_9$-$C_{24}$ alkyl; and
$X^-$ is a pharmaceutically acceptable anion.

In a preferred embodiment, the invention provides a compound of formula VIII having the structure of Formula IX:

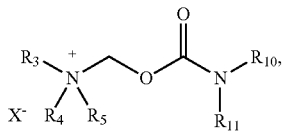

Formula IX where $R_3$, $R_4$ and $R_5$, $R_{10}$ and $R_{11}$ are as defined in Formula VIII.

In a preferred embodiment, the prodrug compounds of formulas IV-IX further comprises a biocompatible delivery system for delivering the prodrug wherein the system is capable of minimizing accelerated hydrolytic cleavage of the prodrug by minimizing exposure of the prodrug to water and/or pH conditions deviating from the physiological range of pH. Preferred delivery systems include biocompatible polymeric matrix delivery systems capable of minimizing diffusion of water into the matrix.

Other embodiments of the invention exploit the pH-independent aqueous solubility of the prodrugs of the invention. A key advantage of the prodrugs over their parent, tertiary amine-containing drugs, is that the prodrug solubility remains essentially unchanged between pH 3 and 8, while the solubility of the tertiary amine parent drugs commonly increases by more than 100-fold over this pH range. The extent of solubilization accompanying pH reduction across this range depends on drug base solubility, pKa of the conjugate acid and counter ions in the medium forming the ammonium salt. It is known in the art that biological tissues can become inflamed in response to injections, and that the pH of the inflamed tissue typically decreases from 7.1-7.4 down to pH 6.4 (See: *A Dominant Role of Acid pH in Inflammatory Excitation and Sensitization of Nociceptors in Rat Skin, in vitro*. Steen, K. H.; Steen, A. E.; Reeh, P. W. The Journal of Neuroscience, (1995), 15: pp. 3982-3989). Transiently pH in inflamed tissue can sometimes be as low as pH 4.7. Exercise alone can bring about a pH drop of about 0.5 units for up to 30 minutes (see: *Continuous intramuscular pH measurement during the recovery from brief maximal exercise in man*. Allsop P; Cheetham M; Brooks S; Hall G M; Williams C. European journal of applied physiology and occupational physiology (1990), 59(6), pp. 465-70). It has also been demonstrated that release of drug from sustained release formulations can become rapid with reduced pH from subcutaneous space (see: *Effect and interaction of pH and lidocaine on epinephrine absorption*. Ueda, Wasa; Hirakawa, Masahisa; Mori, Koreaki, Anesthesiology, (1988), 68(3), pp. 459-62), leading to a "burst" or "dumping" effect if the local pH drops at the injection site. It is hypothesized that this apparent failure of the formulations is caused by the high solubility of the drug at the lower pH.

Therefore, even if the solubility of the prodrugs is similar to that of the corresponding parent tertiary amine at pH 7, the pH-independent solubility profiles of the prodrugs mean that solubility is controlled by the formulation without concern over dose-dumping in response to injection site irritation or, more generally, by pH fluctuations caused by patient activities, therapeutic interventions or illness.

Sustained release drug formulations often contain higher amounts of drugs than immediate release formulations. Functionality and safety of a sustained release formulation are based on a reliable and controlled rate of drug release from the formulation over an extended period of time after administration. The drug release profile of a formulation often depends on the chemical environment of the sustained release formulation, for example, on pH, ionic strength, osmotic pressure and presence of solvents such as ethanol.

The relatively high amount of drug that is present in a sustained release formulation can, in some instances, harm a patient if the formulation releases the drug at a rate that is faster than the intended controlled release rate. If the formulation releases the drug at a rate that is slower than the intended controlled release rate, the therapeutic efficacy of the drug can be reduced.

In most cases, partial or total failure of a sustained release formulation results in a rapid release of the drug into the bloodstream. This rapid release is generally faster than the intended sustained release of the drug from the formulation, and is sometimes referred to as "dose dumping."

Dose dumping can create severe consequences for a patient, including permanent harm and even death. Examples of drugs that can be fatal if the therapeutically beneficial dose is exceeded, e.g., by dose dumping, include pain medications such as opioids, as well as other agents active in the central nervous system. In those situations where dose dumping may not be fatal, dose dumping may at least be responsible for the side effect of sedation or coma in the patient.

The present invention solves the problem of dose dumping and its associated side effects including, but not limited to, sedation or coma, in a sustained release formulation by providing prodrugs that maintain their reduced solubility and sustained release action in a manner which is independent of the pH of the environment in which the prodrug is administered. The pH-independent solubility of the prodrugs of the invention is an important feature for drugs that are administered both orally and by injection. During oral administration, the prodrugs of the invention are exposed to a variety of pH conditions including very low pHs in the stomach (e.g. pH 1-2) and then increased pH when crossing the intestinal walls into the bloodstream. During injection it has been observed that the pH at the injection site may also be lowered (e.g. below pH 6.0) (Poster #242 *Controlled Release Society* (CRS) Annual Meeting, Copenhagen, Denmark (July 2009); Steen K H, Steen A E, Reeh P W; A dominant role of acid pH in inflammatory excitation and sensitization of nociceptors in rat skin, in vitro. The Journal of Neuroscience (1995) 15: 3982-3989]). The pH of an injection site may be lowered for a short amount of time (1-2 hours), but the perturbation may be sufficient to substantially dissolve a basic drug having pH-dependent solubility. In accordance with the invention, the reduced solubility of the prodrugs of the invention remains independent of any change in pH. In one preferred embodiment the reduced solubility of the prodrugs of the invention remains independent over a pH range of about pH 4 to about pH 8. More preferably the reduced solubility of the prodrugs of the invention remains independent over a pH range of about pH 3 to about pH 9. Most preferably, the reduced solubility of the prodrugs of the invention remains essentially constant over a pH range of about pH 1.0 to about pH 10.

In addition, it is known that the stability of carboxyl ester linkages, such as those contemplated in the prodrugs of the invention, is dependent on pH with optimum stability occurring at around pH 4-5. If injection site pH fluctuates to a value lower than neutral pH of 7.4, then the stability of the prodrug is increased relative to its stability at neutral pH. This stability increase further reduces the risk of early release of active drug from the compound, and thus avoids dose dumping by way of accelerated chemical cleavage of the prodrug.

In one embodiment, the invention provides a method for pH-independent sustained delivery of a tertiary amine-containing parent drug to a patient comprising administering to the patient, a prodrug compound of the parent drug having the Formula III:

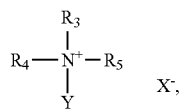

Formula III wherein $R_3$, $R_4$ and $R_5$, together with the nitrogen atom to which they are attached, form a tertiary amine-containing parent drug or a tertiary imine-containing parent drug;

Y is selected from:

a) $C(R_7R_8)OC(O)R_9$, where $R_7$ and $R_8$ are each independently hydrogen or an aliphatic group and preferably $R_7$ and $R_8$ are each independently selected from:
  i) hydrogen;
  ii) branched or unbranched, substituted or unsubstituted $C_1$-$C_6$ alkyl;
  iii) branched or unbranched, substituted or unsubstituted $C_2$-$C_6$ alkenyl; and
  iv) branched or unbranched, substituted or unsubstituted $C_2$-$C_6$ alkynyl;

$R_9$ is any aliphatic group that results in a prodrug having lower aqueous solubility at a reference pH (e.g. a pH wherein the parent drug is fully protonated such as pH 5) as compared to the aqueous solubility of the parent drug, at the same reference pH, and preferably, $R_9$ is selected from:
  i) branched or unbranched, substituted or unsubstituted $C_1$-$C_{24}$ alkyl;
  ii) branched or unbranched, substituted or unsubstituted $C_2$-$C_{24}$ alkenyl;
  iii) branched or unbranched, substituted or unsubstituted $C_2$-$C_{24}$ alkynyl;
  iv) substituted or unsubstituted $C_3$-$C_{12}$ cycloalkyl;
  v) aryl or substituted aryl; and
  vi) heteroaryl or substituted heteroaryl;

b) $C(R_7R_8)OC(O)OR_9$, where $R_7$, $R_8$ and $R_9$ are previously defined;

c) $C(R_7R_8)OC(O)N(R_{10}R_{11})$, where $R_7$, $R_8$ are previously defined; where $R_{10}$ and $R_{11}$ are each independently hydrogen or any aliphatic group that results in a prodrug having lower aqueous solubility at a reference pH (e.g. a pH at which the parent drug is fully protonated such as pH 5) as compared to the aqueous solubility of the parent drug, at the same reference pH, provided that, at least one of $R_{10}$ and $R_{11}$ is an aliphatic group that reduces the solubility of the parent drug in an aqueous solution at physiological pH, and preferably, $R_{10}$ and $R_{11}$ are each independently hydrogen or an aliphatic group, provided that at least one of $R_{10}$ and $R_{11}$ is substituted or unsubstituted $C_1$-$C_{24}$-alkyl, substituted or unsubstituted $C_2$-$C_{24}$-alkenyl, substituted or unsubstituted $C_2$-$C_{24}$ alkynyl, and substituted or unsubstituted $C_3$-$C_{12}$ cycloalkyl, substituted or unsubstituted aryl, substituted or unsubstituted heteroaryl or $R_{10}$ and $R_{11}$ when taken together with the nitrogen to which they are attached form a heterocycle;

d) $C(R_7R_8)OP(O_3)^{2-}MV$, wherein $R_7$ and $R_8$ are previously defined and M and V are each independently a monovalent cation or M and V together form a divalent cation;

e) $C(R_7R_8)OP(O)(OR_{12})(OR_{13})$, where $R_7$ and $R_8$ are previously defined; where $R_{12}$ and $R_{13}$ are each independently hydrogen or any aliphatic group that results in a prodrug having lower aqueous solubility at a reference pH (e.g. pH 5) as compared to the aqueous solubility of the parent drug, at the same reference pH, provided that at least one of $R_{12}$ and $R_{13}$ is an aliphatic group and preferably, $R_{12}$ and $R_{13}$ are each independently hydrogen or an aliphatic group, provided that at least one of $R_{12}$ and $R_{12}$ is substituted or unsubstituted $C_1$-$C_{24}$-alkyl, substituted or unsubstituted $C_2$-$C_{24}$-alkenyl, substituted or unsubstituted $C_2$-$C_{24}$ alkynyl, and substituted or unsubstituted $C_3$-$C_{12}$ cycloalkyl; and $X^-$ is a pharmaceutically acceptable anion; wherein the prodrug provides pH-independent sustained delivery of the tertiary amine-containing parent drug. In one preferred embodiment, the prodrug compound of formula III further comprises a biocompatible matrix for delivering the prodrug wherein the matrix is capable of minimizing diffusion of water into the matrix.

In a preferred embodiment, the invention provides a method for pH-independent sustained delivery of a tertiary amine-containing parent drug to a patient comprising administering to the patient, a prodrug compound of the parent drug having the Formula III:

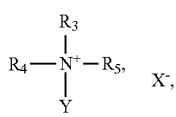

Formula III wherein Y is selected from the structures of Tables 1-4, Table 5 and most preferably selected from the structures of Table 2. In a preferred embodiment, the prodrug compound of formula III further comprises a biocompatible delivery system for delivering the prodrug wherein the system is capable of minimizing accelerated hydrolytic cleavage of the prodrug by minimizing exposure of the prodrug to water.

In another embodiment, the invention provides a method for producing a prodrug compound of a tertiary amine-containing parent drug comprising the step of reacting the tertiary amine of the parent drug of Formula IV:

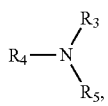

Formula IV wherein $R_3$, $R_4$ and $R_5$, together with the nitrogen atom to which they are attached, form the tertiary amine-containing parent drug compound, with a compound of Formula II:

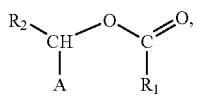

Formula II wherein A is a leaving group, and $R_1$ and $R_2$ are as defined for Formula I, thereby forming a prodrug having lower aqueous solubility at a reference pH (e.g. a pH at which the parent drug is fully protonated such as pH 5) as compared to the aqueous solubility of the parent drug, at the same reference pH and wherein the solubility of the prodrug is independent of pH. In one embodiment, the solubility is independent over the range of about pH 1.0 to about pH 10.

In another embodiment, the invention provides methods of reducing the side effect of sedation or coma in the patient as compared to the side effect of sedation or coma caused by the parent drug of formula IV (i.e. not as a prodrug of the invention) comprising administering to the patient, a prodrug compound of the parent drug having the Formula III:

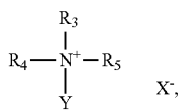

Formula III wherein Y is selected from the structures of Tables 1-4, Table 5 and most preferably selected from the structures of Table 2.

Pharmaceutical Compositions

The pharmaceutical compositions of the present invention comprise a therapeutically effective amount of a compound of the present invention formulated together with one or more pharmaceutically acceptable carriers or excipients.

As used herein, the term "pharmaceutically acceptable carrier or excipient" means a nontoxic, inert solid, semi-solid, gel or liquid filler, diluent, encapsulating material or formulation auxiliary of any type. Some examples of materials which can serve as pharmaceutically acceptable carriers are sugars such as lactose, glucose and sucrose; cyclodextrins such as alpha-(α), beta-(β) and gamma-(γ) cyclodextrins; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention may be administered orally, parenterally, by inhalation spray, topically, rectally, nasally, buccally, vaginally or via an implanted reservoir. In a preferred embodiment, administration is parenteral administration by injection.

The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, dimethylacetamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions, may be formulated according to the known art using suitable dispersing or wetting agents and suspending agents. The sterile injectable preparation may also be a sterile injectable suspension or emulsion, such as INTRALIPID®, LIPOSYN® OR OMEGAVEN®, or solution in a nontoxic parenterally acceptable diluent or solvent, for example, as a solution in 1,3-butanediol. INTRALIPID® is an intravenous fat emulsion containing 10-30% soybean oil, 1-10% egg yolk phospholipids, 1-10% glycerin and water. LIPOSYN® is also an intravenous fat emlusion containing 2-15% safflower oil, 2-15% soybean oil, 0.5-5% egg phosphatides 1-10% glycerin and water. Omegaven® is an emulsion for infusion containing about 5-25% fish oil, 0.5-10% egg phosphatides, 1-10% glycerin and water. Among the acceptable vehicles and solvents that may be employed are water, Ringer's solution, USP and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

Additional sustained release in accordance with the invention may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions that are compatible with body tissues.

In one preferred embodiment, the formulation provides a sustained release delivery system that is capable of minimizing the exposure of the prodrug to water. This can be accomplished by formulating the prodrug with a sustained release delivery system that is a polymeric matrix capable of minimizing the diffusion of water into the matrix. Suitable polymers comprising the matrix include polylactide (PLA) polymers and the lactide-co-glycolide (PLGA) co-polymers as described earlier. Other suitable polymers include tyrosinamide polymers (TyRx), as well as other biocompatible polymers.

Alternatively, the sustained release delivery system may comprise poly-anionic molecules or resins that are suitable for injection or oral delivery. Suitable polyanionic molecules include cyclodextrins and polysulfonates formulated to form a poorly soluble mass that minimizes exposure of the prodrug to water and from which the prodrug is slowly released.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or:
a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

For pulmonary delivery, a therapeutic composition of the invention is formulated and administered to the patient in solid or liquid particulate form by direct administration e.g., inhalation into the respiratory system. Solid or liquid particulate forms of the active compound prepared for practicing the present invention include particles of respirable size: that is, particles of a size sufficiently small to pass through the mouth and larynx upon inhalation and into the bronchi and alveoli of the lungs. Delivery of aerosolized therapeutics, particularly aerosolized antibiotics, is known in the art (see, for example U.S. Pat. No. 5,767,068 to VanDevanter et al., U.S. Pat. No. 5,508,269 to Smith et al., and WO 98/43650 by Montgomery, all of which are incorporated herein by reference). A discussion of pulmonary delivery of antibiotics is also found in U.S. Pat. No. 6,014,969, incorporated herein by reference.

By a "therapeutically effective amount" of a prodrug compound of the invention is meant an amount of the compound which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect).

In accordance with the invention, the therapeutically effective amount of a prodrug of the invention is typically based on the target therapeutic amount of the tertiary-amine containing parent drug. Information regarding dosing and frequency of dosing is readily available for many tertiary amine-containing parent drugs and the target therapeutic amount can be calculated for each prodrug of the invention. In accordance with the invention, the same dose of a prodrug of the invention provides a longer duration of therapeutic effect as compared to the parent drug. Thus if a single dose of the parent drug provides 12 hours of therapeutic effectiveness, a prodrug of that same parent drug in accordance with the invention that provides therapeutic effectiveness for greater than 12 hours will be considered to achieve a "sustained release".

The precise dose of a prodrug of the invention depends upon several factors including the nature and dose of the parent drug and the chemical characteristics of the prodrug moiety linked to the parent drug. The effective dose and dose frequency of a prodrug of the invention will be decided by clinical trials, and, ultimately, the attending physician within the scope of sound medical judgment. The specific therapeutically effective dose level and dose frequency for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

Definitions

Listed below are definitions of various terms used to describe this invention. These definitions apply to the terms as they are used throughout this specification and claims, unless otherwise limited in specific instances, either individually or as part of a larger group.

The term "aliphatic group" or "aliphatic" refers to a non-aromatic moiety that may be saturated (e.g. single bond) or contain one or more units of unsaturation, e.g., double and/or triple bonds. An aliphatic group may be straight chained, branched or cyclic, contain carbon, hydrogen or, optionally, one or more heteroatoms and may be substituted or unsubstituted. In addition to aliphatic hydrocarbon groups, aliphatic groups include, for example, polyalkoxyalkyls, such as polyalkylene glycols, polyamines, and polyimines, for example. Such aliphatic groups may be further substituted. It is understood that aliphatic groups may include alkyl, substituted alkyl, alkenyl, substituted alkenyl, alkynyl, substituted alkynyl, and substituted or unsubstituted cycloalkyl groups as described herein.

The term "acyl" refers to a carbonyl substituted with hydrogen, alkyl, partially saturated or fully saturated cycloalkyl, partially saturated or fully saturated heterocycle, aryl, or heteroaryl. For example, acyl includes groups such as ($C_1$-$C_6$) alkanoyl (e.g., formyl, acetyl, propionyl, butyryl, valeryl, caproyl, t-butylacetyl, etc.), ($C_3$-$C_6$)cycloalkylcarbonyl (e.g., cyclopropylcarbonyl, cyclobutylcarbonyl, cyclopentylcarbonyl, cyclohexylcarbonyl, etc.), heterocyclic carbonyl (e.g., pyrrolidinylcarbonyl, pyrrolid-2-one-5-carbonyl, piperidinylcarbonyl, piperazinylcarbonyl, tetrahydrofuranylcarbonyl, etc.), aroyl (e.g., benzoyl) and heteroaroyl (e.g., thiophenyl-2-carbonyl, thiophenyl-3-carbonyl, furanyl-2-carbonyl, furanyl-3-carbonyl, 1H-pyrroyl-2-carbonyl, 1H-pyrroyl-3-carbonyl, benzo[b]thiophenyl-2-carbonyl, etc.). In addition, the alkyl, cycloalkyl, heterocycle, aryl and heteroaryl portion of the acyl group may be any one of the groups described in the respective definitions. When indicated as being "optionally substituted", the acyl group may be unsubstituted or optionally substituted with one or more substituents (typically, one to three substituents) independently selected from the group of substituents listed below in the definition for "substituted" or the alkyl, cycloalkyl, heterocycle, aryl and heteroaryl portion of the acyl group may be substituted as described above in the preferred and more preferred list of substituents, respectively.

The term "alkyl" is intended to include both branched and straight chain, substituted or unsubstituted, saturated aliphatic hydrocarbon radicals/groups having the specified number of carbons. Preferred alkyl groups comprise about 1 to about 24 carbon atoms ("$C_1$-$C_{24}$"), preferably about 5 to about 24 carbons ("$C_5$-$C_{24}$") preferably about 7 to about 24 carbon atoms ("$C_7$-$C_{24}$"), preferably about 8 to about 24 carbon atoms ("$C_8$-$C_{24}$"), preferably about 9 to about 24 carbon atoms ("$C_9$-$C_{24}$"). Other preferred alkyl groups comprise at about 1 to about 8 carbon atoms ("$C_1$-$C_8$") such as about 1 to about 6 carbon atoms ("$C_1$-$C_6$"), or such as about 1 to about 3 carbon atoms ("$C_1$-$C_3$"). Examples of $C_1$-$C_6$ alkyl radicals include, but are not limited to, methyl, ethyl, propyl, isopropyl, n-butyl, tert-butyl, n-pentyl, neopentyl and n-hexyl radicals.

The term "alkenyl" refers to linear or branched radicals having at least one carbon-carbon double bond. Such radicals preferably contain from about two to about twenty-four carbon atoms ("$C_2$-$C_{24}$") preferably about 7 to about 24 carbon atoms ("$C_7$-$C_{24}$"), preferably about 8 to about 24 carbon atoms ("$C_8$-$C_{24}$"), and preferably about 9 to about 24 carbon atoms ("$C_9$-$C_{24}$"). Other preferred alkenyl radicals are "lower alkenyl" radicals having two to about ten carbon atoms ("$C_2$-$C_{10}$") such as ethenyl, allyl, propenyl, butenyl and 4-methylbutenyl. Preferred lower alkenyl radicals include 2 to about 6 carbon atoms ("$C_2$-$C_6$"). The terms "alkenyl", and "lower alkenyl", embrace radicals having "cis" and "trans" orientations, or alternatively, "E" and "Z" orientations.

The term "alkynyl" refers to linear or branched radicals having at least one carbon-carbon triple bond. Such radicals preferably contain from about two to about twenty-four carbon atoms ("$C_2$-$C_{24}$") preferably about 7 to about 24 carbon atoms ("$C_7$-$C_{24}$"), preferably about 8 to about 24 carbon atoms ("$C_8$-$C_{24}$"), and preferably about 9 to about 24 carbon atoms ("$C_9$-$C_{24}$"). Other preferred alkynyl radicals are "lower alkynyl" radicals having two to about ten carbon atoms such as propargyl, 1-propynyl, 2-propynyl, 1-butyne, 2-butynyl and 1-pentynyl. Preferred lower alkynyl radicals include 2 to about 6 carbon atoms ("$C_2$-$C_6$").

The term "cycloalkyl" refers to saturated carbocyclic radicals having three to about twelve carbon atoms ("$C_3$-$C_{12}$"). The term "cycloalkyl" embraces saturated carbocyclic radicals having three to about twelve carbon atoms. Examples of such radicals include cyclopropyl, cyclobutyl, cyclopentyl and cyclohexyl.

The term "cycloalkenyl" refers to partially unsaturated carbocyclic radicals having three to twelve carbon atoms. Cycloalkenyl radicals that are partially unsaturated carbocyclic radicals that contain two double bonds (that may or may not be conjugated) can be called "cycloalkyldienyl". More preferred cycloalkenyl radicals are "lower cycloalkenyl" radicals having four to about eight carbon atoms. Examples of such radicals include cyclobutenyl, cyclopentenyl and cyclohexenyl.

The term "alkylene," as used herein, refers to a divalent group derived from a straight chain or branched saturated hydrocarbon chain having the specified number of carbons atoms. Examples of alkylene groups include, but are not limited to, ethylene, propylene, butylene, 3-methyl-pentylene, and 5-ethyl-hexylene.

The term "alkenylene," as used herein, denotes a divalent group derived from a straight chain or branched hydrocarbon moiety containing the specified number of carbon atoms having at least one carbon-carbon double bond. Alkenylene groups include, but are not limited to, for example, ethenylene, 2-propenylene, 2-butenylene, 1-methyl-2-buten-1-ylene, and the like.

The term "alkynylene," as used herein, denotes a divalent group derived from a straight chain or branched hydrocarbon moiety containing the specified number of carbon atoms having at least one carbon-carbon triple bond. Representative alkynylene groups include, but are not limited to, for example, propynylene, 1-butynylene, 2-methyl-3-hexynylene, and the like.

The term "alkoxy" refers to linear or branched oxy-containing radicals each having alkyl portions of one to about twenty-four carbon atoms or, preferably, one to about twelve carbon atoms. More preferred alkoxy radicals are "lower alkoxy" radicals having one to about ten carbon atoms and more preferably having one to about eight carbon atoms. Examples of such radicals include methoxy, ethoxy, propoxy, butoxy and tert-butoxy.

The term "alkoxyalkyl" refers to alkyl radicals having one or more alkoxy radicals attached to the alkyl radical, that is, to form monoalkoxyalkyl and dialkoxyalkyl radicals.

The term "aryl", alone or in combination, means a carbocyclic aromatic system containing one, two or three rings wherein such rings may be attached together in a pendent manner or may be fused. The term "aryl" embraces aromatic radicals such as phenyl, naphthyl, tetrahydronaphthyl, indane and biphenyl.

The terms "heterocyclyl", "heterocycle", "heterocyclic" or "heterocyclo" refer to saturated, partially unsaturated and unsaturated heteroatom-containing ring-shaped radicals, which can also be called "heterocyclyl", "heterocycloalkenyl" and "heteroaryl" correspondingly, where the heteroatoms may be selected from nitrogen, sulfur and oxygen. Examples of saturated heterocyclyl radicals include saturated 3 to 6-membered heteromonocyclic group containing 1 to 4 nitrogen atoms (e.g. pyrrolidinyl, imidazolidinyl, piperidino, piperazinyl, etc.); saturated 3 to 6-membered heteromonocyclic group containing 1 to 2 oxygen atoms and 1 to 3 nitrogen atoms (e.g. morpholinyl, etc.); saturated 3 to 6-membered heteromonocyclic group containing 1 to 2 sulfur atoms and 1 to 3 nitrogen atoms (e.g., thiazolidinyl, etc.). Examples of partially unsaturated heterocyclyl radicals include dihydrothiophene, dihydropyran, dihydrofuran and dihydrothiazole. Heterocyclyl radicals may include tetravalent nitrogen, such as in tetrazolium and pyridinium radicals). The term "heterocycle" also embraces radicals where heterocyclyl radicals are fused with aryl or cycloalkyl radicals. Examples of such fused bicyclic radicals include benzofuran, benzothiophene, and the like.

The term "heteroaryl" refers to unsaturated aromatic heterocyclyl radicals. Examples of heteroaryl radicals include unsaturated 3 to 6 membered heteromonocyclic group containing 1 to 4 nitrogen atoms, for example, pyrrolyl, pyrrolinyl, imidazolyl, pyrazolyl, pyridyl, pyrimidyl, pyrazinyl, pyridazinyl, triazolyl (e.g., 4H-1,2,4-triazolyl, 1H-1,2,3-triazolyl, 2H-1,2,3-triazolyl, etc.) tetrazolyl (e.g. 1H-tetrazolyl, 2H-tetrazolyl, etc.), etc.; unsaturated condensed heterocyclyl group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl (e.g., tetrazolo[1,5-b]pyridazinyl, etc.), etc.; unsaturated 3 to 6-membered heteromonocyclic group containing an oxygen atom, for example, pyranyl, furyl, etc.; unsaturated 3 to 6-membered heteromonocyclic group containing a sulfur atom, for example, thienyl, etc.; unsaturated 3- to 6-membered heteromonocyclic group containing 1 to 2 oxygen atoms and 1 to 3 nitrogen atoms, for example, oxazolyl, isoxazolyl, oxadiazolyl (e.g., 1,2,4-oxadiazolyl, 1,3,4-oxadiazolyl, 1,2,5-oxadiazolyl, etc.) etc.; unsaturated condensed heterocyclyl group containing 1 to 2 oxygen atoms and 1 to 3 nitrogen atoms (e.g. benzothiazolyl, benzoxadiazolyl, etc.); unsaturated 3 to 6-membered heteromonocyclic group containing 1 to 2 sulfur atoms and 1 to 3 nitrogen atoms, for example, thiazolyl, thiadiazolyl (e.g., 1,2,4-thiadiazolyl, 1,3,4-thiadiazolyl, 1,2,5-thiadiazolyl, etc.) etc.; unsaturated condensed heterocyclyl group containing 1 to 2 sulfur atoms and 1 to 3 nitrogen atoms (e.g., benzothiazolyl, benzothiadiazolyl, etc.) and the like.

The term "heterocycloalkyl" refers to heterocyclo-substituted alkyl radicals. More preferred heterocycloalkyl radicals are "lower heterocycloalkyl" radicals having one to six carbon atoms in the heterocyclo radical.

The term "alkylthio" refers to radicals containing a linear or branched alkyl radical, of one to about ten carbon atoms attached to a divalent sulfur atom. Preferred alkylthio radicals have alkyl radicals of one to about twenty-four carbon atoms or, preferably, one to about twelve carbon atoms. More preferred alkylthio radicals have alkyl radicals which are "lower alkylthio" radicals having one to about ten carbon atoms. Most preferred are alkylthio radicals having lower alkyl radicals of one to about eight carbon atoms. Examples of such lower alkylthio radicals include methylthio, ethylthio, propylthio, butylthio and hexylthio.

The terms "aralkyl" or "arylalkyl" refer to aryl-substituted alkyl radicals such as benzyl, diphenylmethyl, triphenylmethyl, phenylethyl, and diphenylethyl.

The term "aryloxy" refers to aryl radicals attached through an oxygen atom to other radicals.

The terms "aralkoxy" or "arylalkoxy" refer to aralkyl radicals attached through an oxygen atom to other radicals.

The term "aminoalkyl" refers to alkyl radicals substituted with amino radicals. Preferred aminoalkyl radicals have alkyl radicals having about one to about twenty-four carbon atoms or, preferably, one to about twelve carbon atoms. More preferred aminoalkyl radicals are "lower aminoalkyl" that have alkyl radicals having one to about ten carbon atoms. Most preferred are aminoalkyl radicals having lower alkyl radicals having one to eight carbon atoms. Examples of such radicals include aminomethyl, aminoethyl, and the like.

The term "alkylamino" denotes amino groups which are substituted with one or two alkyl radicals. Preferred alkylamino radicals have alkyl radicals having about one to about twenty carbon atoms or, preferably, one to about twelve carbon atoms. More preferred alkylamino radicals are "lower alkylamino" that have alkyl radicals having one to about ten carbon atoms. Most preferred are alkylamino radicals having lower alkyl radicals having one to about eight carbon atoms. Suitable lower alkylamino may be monosubstituted N-alkylamino or disubstituted N,N-alkylamino, such as N-methylamino, N-ethylamino, N,N-dimethylamino, N,N-diethylamino or the like.

The term "substituted" refers to the replacement of one or more hydrogen radicals in a given structure with the radical of a specified substituent including, but not limited to: halo, alkyl, alkenyl, alkynyl, aryl, heterocyclyl, thiol, alkylthio, arylthio, alkylthioalkyl, arylthioalkyl, alkylsulfonyl, alkylsulfonylalkyl, arylsulfonylalkyl, alkoxy, aryloxy, aralkoxy, aminocarbonyl, alkylaminocarbonyl, arylaminocarbonyl, alkoxycarbonyl, aryloxycarbonyl, haloalkyl, amino, trifluoromethyl, cyano, nitro, alkylamino, arylamino, alkylaminoalkyl, arylaminoalkyl, aminoalkylamino, hydroxy, alkoxyalkyl, carboxyalkyl, alkoxycarbonylalkyl, aminocarbonylalkyl, acyl, acylamino, aralkoxycarbonyl, carboxylic acid, sulfonic acid, sulfonyl, phosphonic acid, aryl, heteroaryl, heterocyclic, and aliphatic. It is understood that the substituent may itself be further substituted.

For simplicity, chemical moieties that are defined and referred to throughout can be univalent chemical moieties (e.g., alkyl, aryl, etc.) or multivalent moieties under the appropriate structural circumstances clear to those skilled in the art. For example, an "alkyl" moiety can be referred to a monovalent radical (e.g. $CH_3$—$CH_2$—), or in other instances, a bivalent linking moiety can be "alkyl," in which case those skilled in the art will understand the alkyl to be a divalent radical (e.g., —$CH_2$—$CH_2$—), which is equivalent to the term "alkylene." Similarly, in circumstances in which divalent moieties are required and are stated as being "alkoxy", "alkylamino", "aryloxy", "alkylthio", "aryl", "heteroaryl", "heterocyclic", "alkyl" "alkenyl", "alkynyl", "aliphatic", or "cycloalkyl", those skilled in the art will understand that the terms alkoxy", "alkylamino", "aryloxy", "alkylthio", "aryl", "heteroaryl", "heterocyclic", "alkyl", "alkenyl", "alkynyl", "aliphatic", or "cycloalkyl" refer to the corresponding divalent moiety.

The terms "halogen" or "halo" as used herein, refers to an atom selected from fluorine, chlorine, bromine and iodine.

The terms "compound" "drug", and "prodrug" as used herein all include pharmaceutically acceptable salts, solvates, hydrates, polymorphs, co-crystals, enantiomers, diastereoisomers, tautomers, regioisomers, racemates and the like of the compounds, drugs and prodrugs having the formulas as set forth herein.

Substituents indicated as attached through variable points of attachments on a ring can be attached to any available position on the ring structure.

As used herein, the term "effective amount of the subject compounds," with respect to the subject method of treatment, refers to an amount of the subject compound which, when delivered as part of desired dose regimen, brings about management of the disease or disorder to clinically acceptable standards.

"Treatment" or "treating" refers to an approach for obtaining beneficial or desired clinical results in a patient. For purposes of this invention, beneficial or desired clinical results include, but are not limited to, one or more of the following: alleviation of symptoms, diminishment of extent of a disease, stabilization (i.e., not worsening) of a state of disease, preventing spread (i.e., metastasis) of disease, preventing occurrence or recurrence of disease, delay or slowing of disease progression, amelioration of the disease state, and remission (whether partial or total).

The following non-limiting examples are illustrative of the invention. The mechanism as shown in Scheme 1 for the prodrug synthesis based on tertiary amine-containing parent drugs are exemplified below.

EXAMPLES

Example 1

Risperidone (RSP)

There are several possible conversion routes for converting the prodrug back to the parent drug. One such conversion route is outlined below. In this route, risperidone would be released from a prodrug compound of the invention in two steps: 1. esterase cleavage of the labile bond; 2. Spontaneous release of formaldehyde under neutral and basic pH's. The scheme below shows the synthesis of such prodrugs with arrows pointing right and the expected cleavage with arrows pointing left:

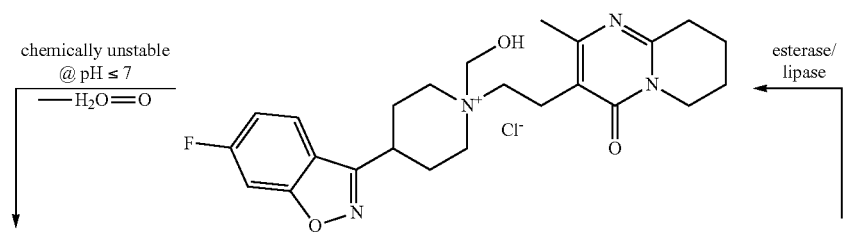

109

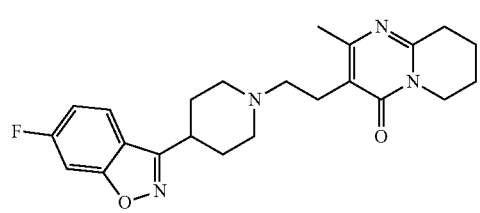

R = C1-C15 straight or branched aliphatic chain,
O—(C1-C16 aliphatic chain), NH—(C1-C16 aliphatic chain),
N—(C1-C16 aliphatic chain)$_2$
X = C, P

110

-continued

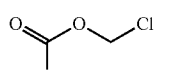
base,

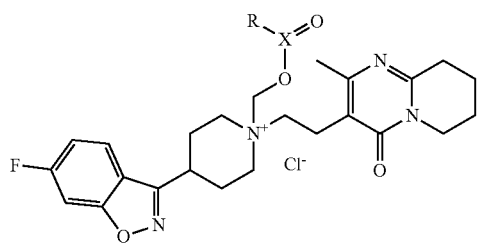

Quaternary ammonium chloride salt

General methodology for the preparation of paliperidone-, risperidone-, iloperidone-, perospirone-, and ziprasidone-related compounds can be found in the following publications: U.S. Pat. No. 5,158,952, U.S. Pat. No. 4,804,663, U.S. RE39198, US 2007/0254887 A1, U.S. Pat. No. 5,312,925.

General Reaction Procedures for Synthesis of Prodrugs (Referenced in Later Examples):

Compound RSP-44 (Risperidone Derivatized by Quaternary Amine Formaldehyde Stearate Iodide Prodrug Moiety)

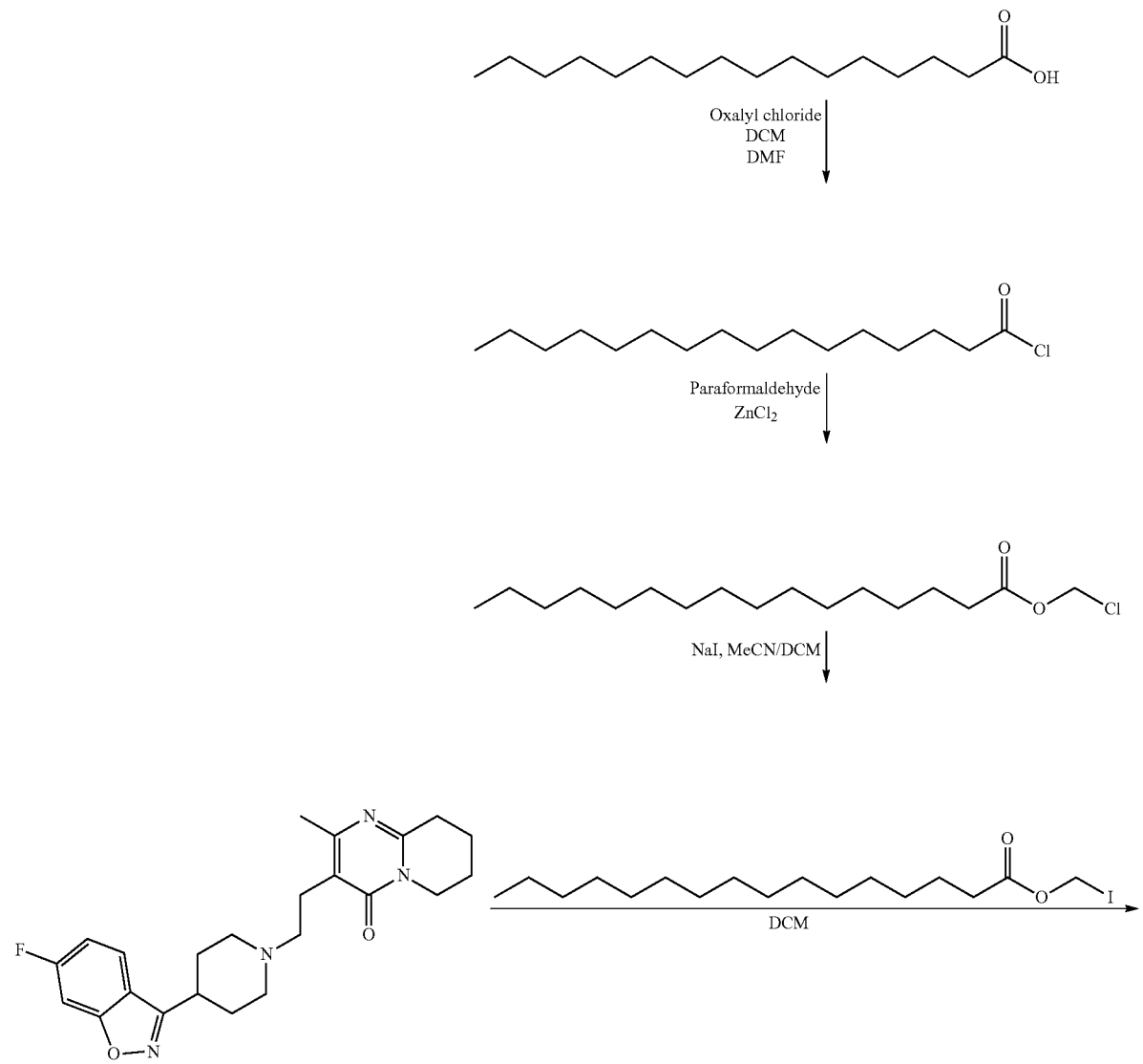

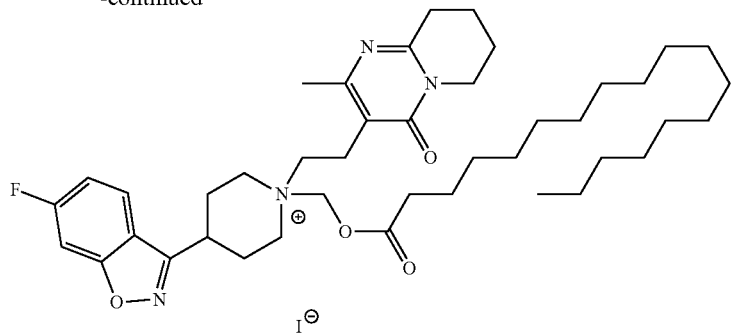

RSP-44

Step A—Formation of Acid Chloride

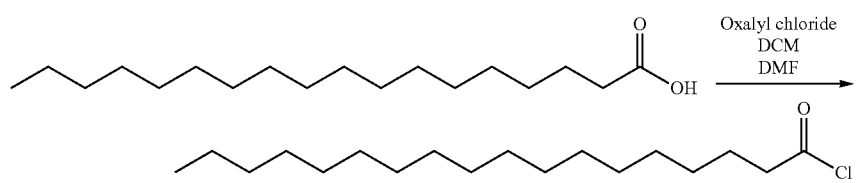

To a stirred suspension of stearic acid (20 g, 70.3 mmol) in dichloromethane (100 mL) was added oxalyl chloride (8.92 mL, 105.5 mmol). 1 drop dimethylformamide was added and the reaction stirred at room temperature for 3 hours. The solvent was removed in vacuo and the resulting product used in the next step without further purification. $^1$H-NMR (CDCl$_3$) δ 0.87 (3H, t), 1.20-1.40 (28H, m), 1.65-1.70 (2H, m), 2.87 (2H, t).

Step B—Formation of Chloromethyl Alkyl Ester

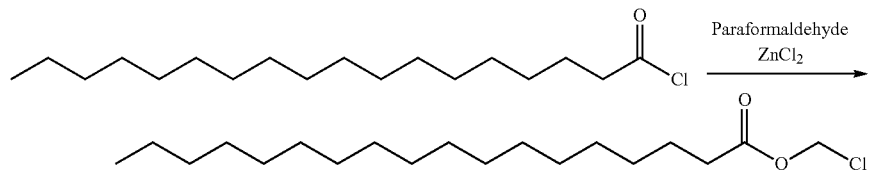

Paraformaldehyde (2.11 g, 70.3 mmol) and zinc chloride (258 mg) were added to the acid chloride prepared above and the reaction mixture was heated at 65° C. for 16 hours and then allowed to cool to room temperature. Dichloromethane (200 mL) and saturated aqueous NaHCO$_3$ (70 mL) were added. The aqueous emulsion was extracted with dichloromethane (2×50 mL) and the combined organic extracts washed with saturated aqueous NaHCO$_3$ (70 mL), brine (70 mL), and dried over MgSO$_4$. After filtration, the volatiles were removed and the residue purified by silica chromatography eluting with heptane to 12% DCM/heptane to give a yellow solid (12.64 g, 54% yield over two steps).

$^1$H-NMR (CDCl$_3$) δ 0.86 (3H, t), 1.20-1.40 (28H, m), 1.55-1.70 (2H, m), 2.37 (2H, t), 5.70 (2H, s).

Step C—Formation of Iodomethyl Alkyl Ester

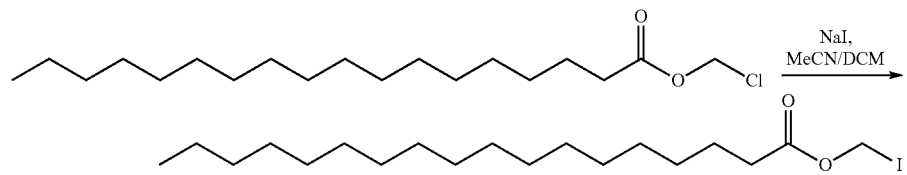

To a solution of the iodomethyl alkyl ester (12.64 g, 37.96 mmol) in acetonitrile (150 mL) and dichloromethane (75 mL) was added sodium iodide (17.07 g, 113.9 mmol). The flask was covered in tin foil to exclude light and stirred at room temperature for 70 hours and then at 25° C. for 24 hours. The reaction mixture was partitioned between dichloromethane (200 mL) and water (150 mL). The aqueous layer was extracted with dichloromethane (2×150 mL). The combined organics were washed with aq satd NaHCO$_3$ (200 mL), 5% aq sodium sulfite solution (200 mL) and brine (2×100 mL), then dried (MgSO$_4$) and concentrated to give the product as a yellow solid (14.53 g, 90% yield) which was not further purified. $^1$H-NMR (CDCl$_3$) δ 0.87 (3H, t), 1.20-1.35 (28H, m), 1.55-1.70 (2H, m), 2.32 (2H, t), 5.90 (2H, s).

Step D—Quaternization Reaction

Compound RSP-40

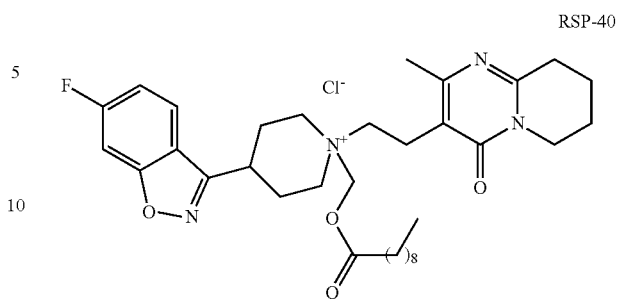

Using the general procedure described above starting from step B using decanoyl chloride. In step D, acetonitrile was used instead of dichloromethane and 3 equiv of iodomethyl decanoate was used. The iodide was converted to the

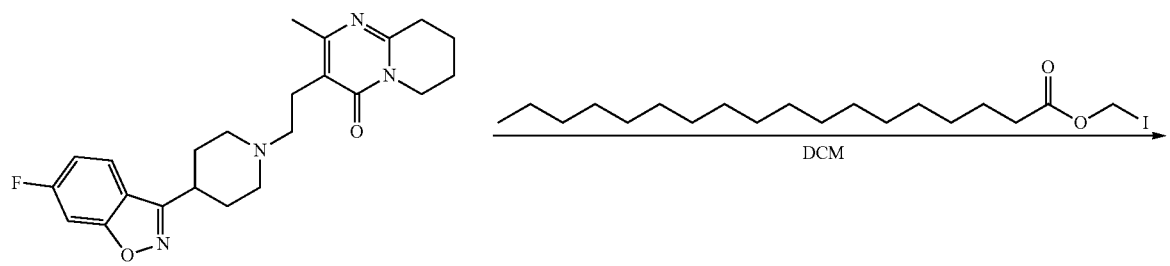

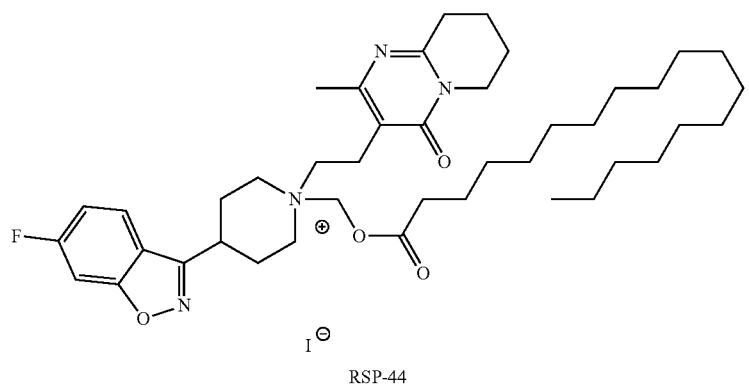

Risperidone (1.50 g, 3.65 mmol) and the iodomethyl alkyl ester (2.33 g, 5.48 mmol, 1.5 equiv) were stirred together in dichloromethane (30 mL) at room temperature overnight. The reaction mixture was concentrated and the residue triturated with diethyl ether to give RSP-44 (2.50 g) as an approximate 1:1 mix of two conformers. $^1$H-NMR (CDCl3) δ 7.95 (1H, dd), 7.84 (1H, dd), 7.22 (2H, 2×dd), 7.11 (2H, 2×t), 5.90 (2H, s), 5.61 (2H, s), 4.80-4.60 (4H, m), 4.35-4.20 (2H, m), 4.05-3.95 (2H, m), 3.95-3.70 (8H, m), 3.65-3.55 (2H, m), 3.05-2.85 (8H, m), 2.65-2.40 (13H, m), 2.40-2.25 (5H, m), 2.00-1.85 (8H, m), 1.70-1.60 (4H, m), 1.40-1.15 (56H, m), 0.87 (6H, 2×t).

corresponding chloride by passing through Dowex 1X8, 50-100 mesh, ion exchange resin eluting with MeOH followed by a diethyl ether trituration to give RSP-40 (3.99 g) as an approx 1:1 mixture of 2 conformers. $^1$H-NMR (CDCl$_3$) δ 7.91 (1H, dd), 7.81 (1H, dd), 7.23 (2H, 2×dd), 7.10 (2H, 2×t), 6.02 (2H, s), 5.67 (2H, s), 4.87 (2H, br t), 4.70 (2H, br t), 4.18-4.02 (4H, m), 3.89 (4H, dd), 3.82-3.69 (4H, m), 3.61-3.50 (2H, m), 3.08-2.87 (8H, m), 2.82-2.41 (11H, m), 2.32-2.22 (7H, m), 2.18-1.81 (8H, m), 1.73-1.58 (4H, m), 1.41-1.15 (24H, m), 0.86 (6H, 2×t).

Compound RSP-43

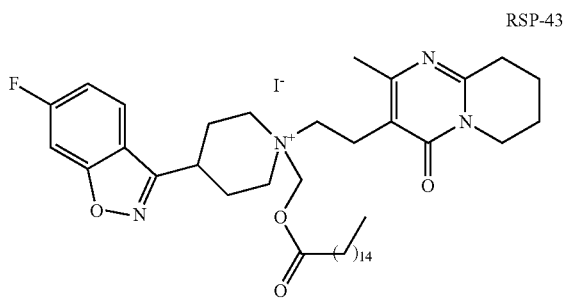

Using the general procedure described above starting from step B using palmitoyl chloride. In step D, 3 equiv of iodomethyl palmitate was used. After diethyl ether trituration RSP-43 (4.13 g) was obtained as an approx 1:1 mixture of 2 conformers. $^1$H-NMR (CDCl$_3$) δ 7.94 (1H, dd), 7.84 (1H, dd), 7.24 (2H, 2×dd), 7.11 (2H, 2×t), 5.89 (2H, s), 5.60 (2H, s), 4.77-4.63 (4H, m), 4.31-4.18 (2H, m), 4.05-4.02 (2H, m), 3.89 (4H, t), 3.78 (4H, br t), 3.62-3.57 (2H, m), 3.06-2.87 (8H, m), 2.64-2.48 (12H, m), 2.39-2.27 (6H, m), 1.99-1.88 (8H, m), 1.64-1.59 (4H, m), 1.39-1.18 (48H, m), 0.87 (6H, 2×t).

Compound RSP-42

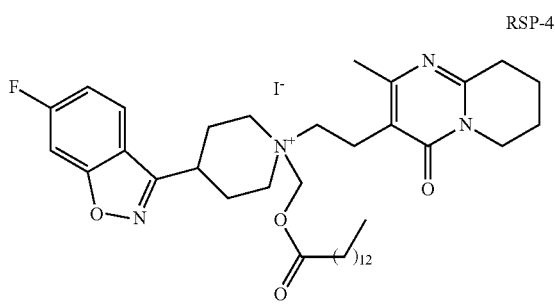

Using the general procedure described above starting from step B using myristoyl chloride. In step D, 3 equiv of iodomethyl myristate was used. RSP-42 (3.23 g) was obtained as an approximate 1:1 mix of two conformers. $^1$H-NMR (CDCl$_3$) δ 7.95 (1H, dd), 7.84 (1H, dd), 7.22 (2H, 2×dd), 7.11 (2H, 2×t), 5.89 (2H, s), 5.60 (2H, s), 4.80-4.60 (4H, m), 4.30-4.15 (2H, m), 4.05-3.95 (2H, m), 3.95-3.70 (8H, m), 3.60-3.55 (2H, m), 3.05-2.85 (8H, m), 2.65-2.40 (13H, m), 2.40-2.25 (5H, m), 2.00-1.85 (8H, m), 1.75-1.60 (4H, m), 1.40-1.15 (40H, m), 0.86 (6H, 2×t).

Compound RSP-41

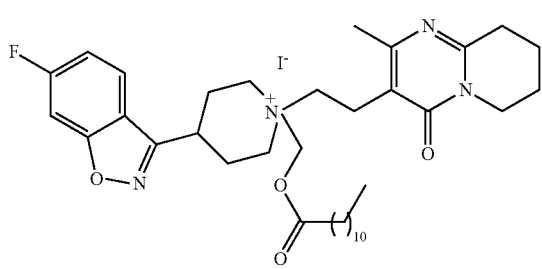

Using the general procedure described above starting from step B using lauroyl chloride. In step D, 3 equiv of iodomethyl laurate was used. After diethyl ether trituration RSP-41 (3.11 g) was obtained as an approx 1:1 mixture of 2 conformers. $^1$H-NMR (CDCl$_3$) δ 7.97 (1H, dd), 7.83 (1H, dd), 7.24 (2H, 2×dd), 7.11 (2H, 2×t), 5.89 (2H, s), 5.61 (2H, s), 4.72-4.58 (4H, m), 4.32-4.17 (2H, m), 4.06 (2H, br t), 3.92-3.72 (8H, m), 3.64-3.56 (2H, m), 3.06-2.87 (8H, m), 2.68-2.52 (12H, m), 2.39-2.28 (6H, m), 2.02-1.89 (8H, m), 1.68-1.61 (4H, m), 1.39-1.18 (32H, m), 0.87 (6H, 2×t).

Compound RSP-46

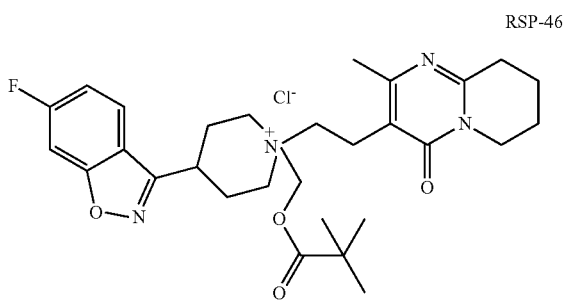

Using the general procedure described above starting from step C using chloromethyl pivalate. In step D, acetontirile was used instead of dichloromethane and 3 equiv of iodomethyl pivalate was used. The iodide was converted to the corresponding chloride by passing through Dowex 1X8, 50-100 mesh, ion exchange resin eluting with MeOH followed by a diethyl ether/THF trituration to give RSP-46 (2.91 g) as an approx 1:1 mixture of 2 conformers. $^1$H-NMR (d$^6$-MeOH) δ 7.99 (1H, dd), 7.91 (1H, dd), 7.45 (2H, 2×dd), 7.22 (2H, 2×t), 5.62 (2H, s), 5.55 (2H, s), 3.98-3.82 (8H, m), 3.78-3.52 (10H, m), 3.12-2.89 (8H, m), 2.62-2.33 (14H, m), 2.05-1.84 (8H, m), 1.35 (9H, s), 1.32 (9H, s).

Compound RSP-39

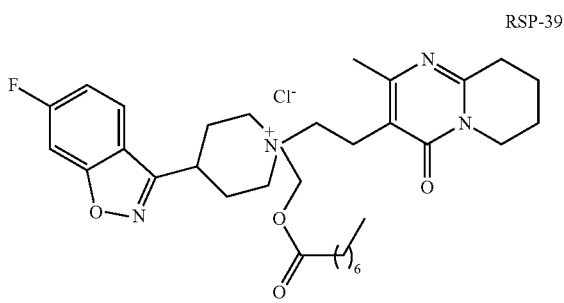

Using the general procedure described above starting from step B using octanoyl chloride. In step D, acetontirile was used instead of dichloromethane and 3 equiv of iodomethyl octanoate was used. The iodide was converted to the corresponding chloride by passing through Dowex 1X8, 50-100 mesh, ion exchange resin eluting with MeOH followed by an diethyl ether trituration. RSP-39 (2.017 g) was obtained as an approximate 1:1 mix of two conformers. $^1$H-NMR (CDCl3) δ 7.90 (1H, dd), 7.81 (1H, dd), 7.23 (2H, 2×dd), 7.10 (2H, 2×t), 6.01 (2H, s), 5.66 (2H, s), 4.95-4.65 (4H, m), 4.15-4.00 (4H, m), 3.95-3.80 (4H, m), 3.80-3.65 (4H, m), 3.60-3.50 (2H, m), 3.05-2.85 (8H, m), 2.65-2.40 (13H, m), 2.40-2.20 (5H, m), 2.05-1.75 (8H, m), 1.75-1.60 (4H, m), 1.40-1.20 (16H, m), 0.87 (6H, 2×t).

Compound RSP-47

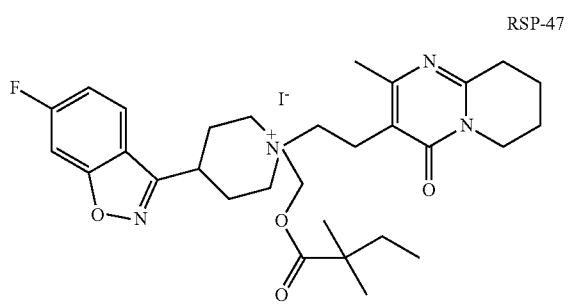

Using the general procedure described above starting from step B using 2,2-dimethylbutyryl chloride. In step D, 3 equiv of iodomethyl 2,2-dimethylbutyrate was used. RSP-47 (3.14 g) was obtained as an approximate 1:1 mix of two conformers. $^1$H-NMR (CDCl3) δ 7.95 (1H, dd), 7.84 (1H, dd), 7.23 (2H, 2×dd), 7.11 (2H, 2×t), 5.92 (2H, s), 5.64 (2H, s), 4.80-4.55 (4H, m), 4.30-4.15 (2H, m), 4.10-3.95 (2H, m), 3.95-3.65 (8H, m), 3.65-3.55 (2H, m), 3.10-2.85 (8H, m), 2.75-2.45 (9H, m), 2.40-2.25 (5H, m), 2.05-1.85 (8H, m), 1.75-1.55 (4H, m), 1.30-1.20 (12H, m), 0.90 (6H, 2×t).

Compound RSP-36

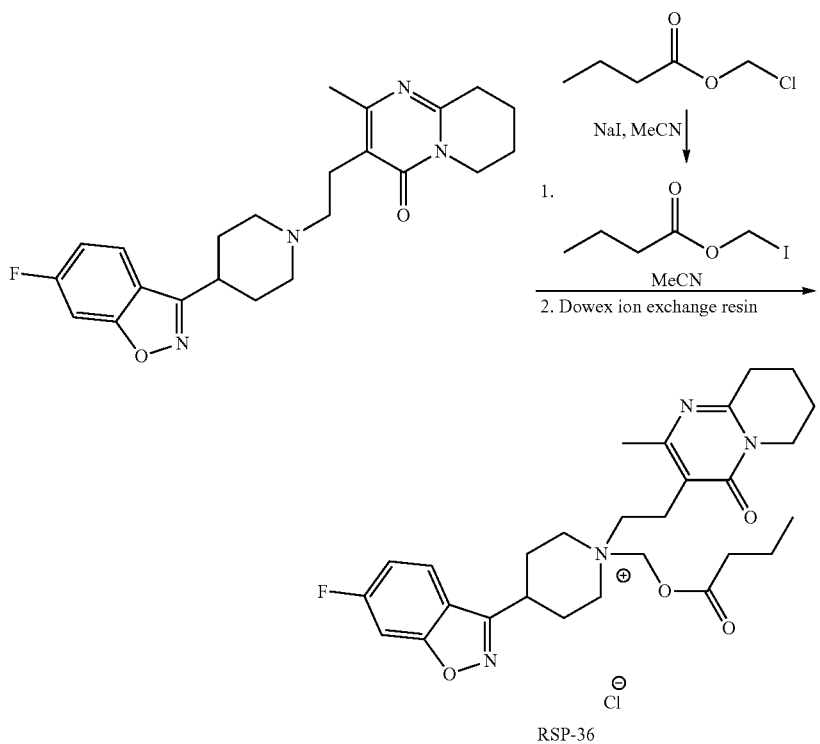

To a solution of chloromethyl butyrate (6.11 g, 44.7 mmol) in acetonitrile (60 mL) was added sodium iodide (20.12 g, 134.2 mmol). The flask was covered in tin foil and stirred overnight at room temperature. The reaction mixture was partitioned between dichloromethane (200 mL) and water (100 mL). The aqueous layer was extracted with dichloromethane (2×100 mL). The combined organics were washed with aq satd NaHCO$_3$ (100 mL), 5% aqueous sodium sulfite solution (100 mL) and brine (2×100 mL) then dried (MgSO$_4$) and concentrated to give iodomethyl butyrate (8.19 g, 80%). The iodide is used crude in the next reaction. $^1$H-NMR (CDCl$_3$) δ 5.89 (2H, s), 2.31 (2H, t), 1.67 (2H, sextet), 0.95 (3H, t).

Iodomethyl butyrate (12 g, 52.6 mmol) and risperidone (5.4 g, 13.2 mmol) were stirred together in acetonitrile (100 mL) at room temperature overnight (not all in solution). After stirring overnight the reaction was all completely dissolved and the reaction mixture concentrated to give a yellow oil, which was triturated with diethyl ether to remove aliphatic impurities. A pale yellow solid was obtained which was filtered and dried. The solid was a mixture of 2 conformers.

The solid was triturated twice with THF to give conformer A (2.73 g). This was then passed through Dowex 1X8, 50-100 mesh, ion exchange resin eluting with de-ionized water to give the chloride which was triturated with diethyl ether to give the chloride conformer A as a white solid (2.17 g). $^1$H-NMR (CDCl$_3$) δ 7.95 (1H, dd), 7.22 (1H, dd), 7.11 (1H, dt), 6.03 (2H, s), 4.79 (2H, br t), 4.09 (1H, br s), 3.90-3.78 (4H, m), 3.59-3.54 (2H, m), 2.98-2.88 (4H, m), 2.59-2.39 (4H, m), 2.33 (3H, s), 2.04-1.88 (6H, m), 1.70 (2H, sextet), 0.99 (3H, t).

The first THF liquors from the above triturations were concentrated and the residue dissolved in water (200 mL) and washed with ethyl acetate (250 ml). The water was concentrated to give a mixture of isomer A and B as a 1:3 mix. This was then triturated with chloroform to give an off white solid which was filtered and gave conformer B (1.29 g). This was then passed through Dowex 1X8, 50-100 mesh, ion exchange resin eluting with MeOH to give the chloride which was triturated with diethyl ether to give the chloride conformer B as an off white solid (707 mg). $^1$H-NMR (CDCl$_3$) δ 7.86 (1H, dd), 7.21 (1H, dd), 7.04 (1H, dt), 5.74 (2H, s), 4.40 (2H, br s), 4.12-3.91 (7H, m), 3.51-3.39 (2H, m), 3.21 (2H, br s), 2.81 (3H, s), 2.66 (2H, br d), 2.56 (2H, t), 2.39-2.18 (2H, m), 2.13-1.94 (4H, m) 1.71 (2H, sextet), 0.98 (3H, t).

Compound Rsp-162 (RSP—Quat Amine Formaldehyde Alpha Methyl Cyclohexylcarboxylate Iodide)

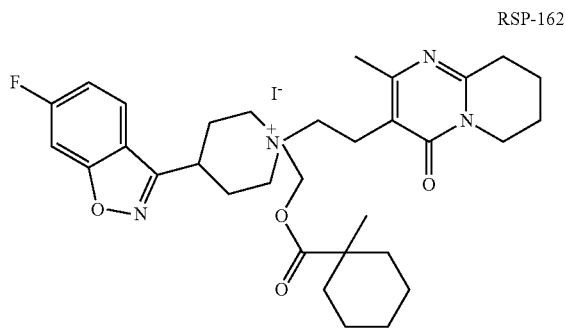

Made using the general procedure starting from 1-methyl cyclohexane carboxylic acid. After diethyl ether trituration RSP-162 (2.66 g) was obtained as an approx 1:1 mixture of 2 conformers.

$^1$H-NMR (300 MHz, CDCl$_3$) δ 7.94 (1H, dd), 7.83 (1H, dd), 7.25-7.22 (2H, m), 7.14-7.08 (2H, m), 5.93 (2H, s), 5.65 (2H, s), 4.79-4.54 (4H, m), 4.24-3.53 (16H, m), 3.11-2.89 (8H, m), 2.72-2.53 (8H, m), 2.41-2.27 (4H, m), 2.14-1.89 (12H, m), 1.69-1.27 (22H, m).

RSP-163 (RSP—Quat Amine Formaldehyde Isobutyrate Iodide)

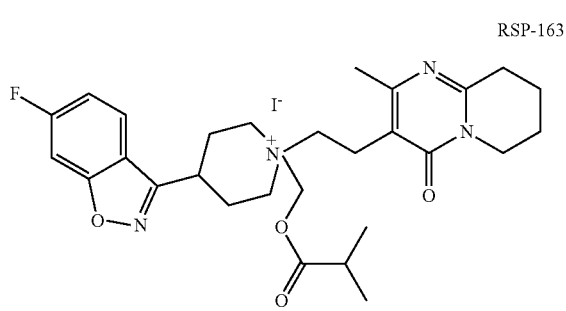

This compound was made using the general procedure starting from isobutyryl chloride. After dissolving in a minimum amount of THF followed by precipitation with diethyl ether RSP-163 (2.23 g) was obtained as an approx 1:1 mixture of 2 conformers.

$^1$H-NMR (300 MHz, CDCl$_3$) δ 7.93 (1H, dd), 7.83 (1H, dd), 7.25-7.22 (2H, m), 7.14-7.08 (2H, m), 5.90 (2H, s), 5.63 (2H, s), 4.75 (2H, br t), 4.65 (2H, br t), 4.33-4.19 (2H, m), 4.07-4.02 (2H, m), 3.89 (4H, dt), 3.82-3.71 (4H, m), 3.62-3.57 (2H, m), 3.07-3.02 (2H, m), 2.98-2.79 (8H, m), 2.68-2.63 (2H, m), 2.53-2.41 (6H, m), 2.39-2.28 (5H, m), 2.03-1.88 (8H, m), 1.27 (12H, 2×d).

RSP-49 (RSP—Quat Amine Formaldehyde Dimethyl Myristate Iodide)

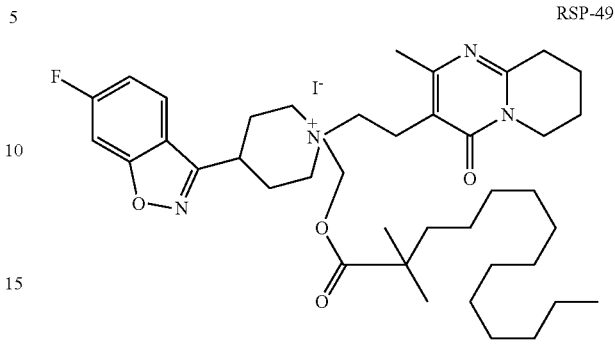

Synthesis of methyl 2,2-dimethyltetradecanoate

To a stirred solution of diisopropylamine (6.90 mL, 49.0 mmol) in THF (50 mL) under Ar (g) at −7° C. was added $^n$BuLi (2.3M in hexanes, 21.3 mL, 49.0 mmol) dropwise via a dropping funnel keeping the temperature between 0° C. and 5° C. The reaction was stirred at −7° C. for 30 min and then cooled to −78° C. Methyl isobutyrate (5.61 mL, 49.0 mmol) was added and the reaction stirred at −78° C. for 1.5 hours. 1-iodododecane (13.05 g, 44.1 mmol) in THF (10 mL) was added dropwise via a dropping funnel keeping the temperature below −70° C. A further 40 mL THF was added over 5 min to aid stirring. After complete addition the reaction was stirred at −78° C. for approx. 2 hours and then allowed to slowly warm to room temperature overnight.

The reaction was quenched with sat. aq. NH$_4$Cl (100 mL) and diluted with ethyl acetate (100 mL). The aqueous layer was extracted with ethyl acetate (2×50 mL) and the combined organics washed with brine (50 mL) and dried over MgSO$_4$. After filtration, the volatiles were removed. The reaction was repeated in a similar manner using 15.05 mL (131.27 mmol) of methyl isobutyrate. The two crude batches were combined and purified by silica chromatography eluting heptane to 50% DCM/heptane to give methyl 2,2-dimethyl myristate (31.7 g).

Synthesis of 2,2-dimethyltetradecanoic acid

To a stirred solution of methyl 2,2-dimethyltetradecanoate (31.7 g, 117.2 mmol) in ethanol (234 mL) was added 2M NaOH (117 mL, 234.4 mmol). The reaction was stirred at room temperature overnight. NaOH (4.69 g, 117 mmol) was added and the reaction heated at 50° C. for 24 hours. NaOH (4.69 g, 117 mmol) was added and the reaction heated to 100° C. for 4 hours and then cooled to room temperature. 140 mL 4M HCl was added to acidify. ethyl acetate (200 mL) was added and the layers separated. The aqueous was extracted with ethyl acetate (2×100 mL) and the combined organics concentrated in vacuo. The residue was partitioned between ethyl acetate (200 mL) and brine (100 mL). The organic layer was washed with brine (50 mL) and dried over MgSO$_4$. After filtration, the volatiles were removed to give 2,2-dimethyltetradecanoic acid (26.9 g).

RSP-49 was made using the general procedure starting from 2,2-dimethyltetradecanoic acid (synthesized as described above). After diethyl ether trituration RSP-49 (1.91 g) was obtained as an approx 1:1 mixture of 2 conformers.

¹H-NMR (300 MHz, CDCl₃) δ 7.94 (1H, dd), 7.84 (1H, dd), 7.24 (2H, 2×dd), 7.11 (2H, 2×t), 5.90 (2H, s), 5.62 (2H, s), 4.83-4.58 (4H, m), 4.36-4.19 (2H, m), 4.09-3.97 (2H, m), 3.97-3.65 (8H, m), 3.65-3.52 (2H, m), 3.12-2.83 (8H, m), 2.73-2.44 (9H, m), 2.44-2.23 (5H, m), 2.04-1.83 (8H, m), 1.67-1.52 (4H, m), 1.36-1.13 (52H, m), 0.87 (6H, 2×t).

RSP-164 (RSP—Quat Amine Formaldehyde 2-Propylpentanoate Iodide)

Made using the general procedure starting from 2,2-dimethylvaleric acid. After diethyl ether trituration RSP-165 (2.50 g) was obtained as an approx 1:1 mixture of 2 conformers. ¹H-NMR (300 MHz, CDCl₃) δ 7.93 (1H, dd), 7.83 (1H, dd), 7.27-7.20 (2H, m), 7.15-7.07 (2H, m), 5.90 (2H, s), 5.62 (2H, s), 4.80-4.62 (4H, m), 4.33-4.20 (2H, m), 4.08-4.00 (2H, m), 3.93-3.85 (4H, m), 3.81-3.65 (4H, m), 3.62-3.54 (2H, m), 3.08-2.85 (8H, m), 2.70-2.45 (9H, m), 2.39-2.27 (5H, m), 2.02-1.84 (8H, m), 1.62-1.52 (4H, m), 1.32-1.22 (16H, m), 0.91 (6H, 2×t).

RSP-166 (RSP—Quat Amine Formaldehyde Dimethyl Hexanoate Iodide)

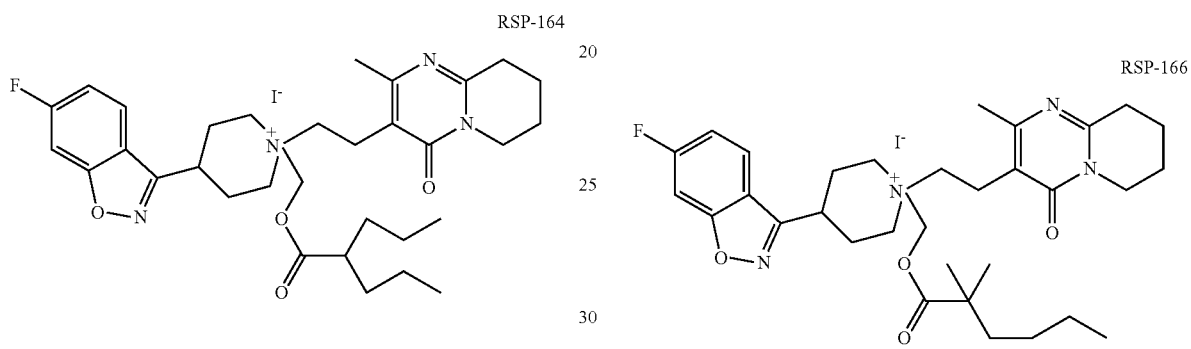

Made using the general procedure starting from 2,2-di-n-propylacetic acid. After diethyl ether trituration RSP-164 (2.75 g) was obtained as an approx 1:1 mixture of 2 conformers. ¹H-NMR (300 MHz, CDCl₃) δ 7.94 (1H, dd), 7.85 (1H, dd), 7.24 (2H, 2×dd), 7.11 (2H, 2×t), 5.92 (2H, s), 5.64 (2H, s), 4.78-4.57 (4H, m), 4.33-4.19 (2H, m), 4.07-3.97 (2H, m), 3.95-3.66 (8H, m), 3.66-3.55 (2H, m), 3.11-2.84 (8H, m), 2.71-2.44 (11H, m), 2.44-2.25 (5H, m), 2.04-1.83 (8H, m), 1.74-1.45 (8H, m), 1.40-1.23 (8H, m), 0.91 (12H, m).

RSP-165 (RSP—Quat Amine Formaldehyde Dimethyl Pentanoate Iodide)

This compound was made in a similar manner to RSP-49 from methyl isobutyrate and 1-iodobutane. After diethyl ether trituration RSP-166 (2.75 g) was obtained as an approx 1:1 mixture of 2 conformers. ¹H-NMR (300 MHz, CDCl₃) δ 7.94 (1H, dd), 7.84 (1H, dd), 7.28-7.21 (2H, m), 7.16-7.06 (2H, m), 5.91 (2H, s), 5.62 (2H, s), 4.82-4.59 (4H, m), 4.34-4.18 (2H, m), 4.09-3.97 (2H, m), 3.95-3.64 (8H, m), 3.64-3.53 (2H, m), 3.10-2.84 (8H, m), 2.72-2.45 (9H, m), 2.43-2.26 (5H, m), 2.04-1.83 (8H, m), 1.65-1.53 (4H, m), 1.37-1.12 (20H, m), 0.88 (6H, 2×t).

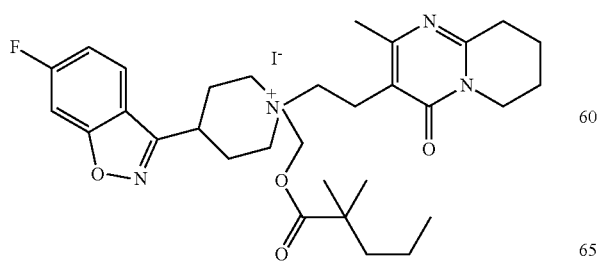

Example 2

Asenapine

There are several possible conversion routes for converting a prodrug of the invention back to the parent drug. One such conversion route for asenapine is outlined below. In this route, asenapine would be released from a prodrug compound of the invention in two steps: 1. esterase cleavage of the labile bond; 2. Spontaneous release of formaldehyde under neutral and basic pH's. The scheme below shows the synthesis of such prodrugs with arrows pointing right and the expected cleavage with arrows pointing left:

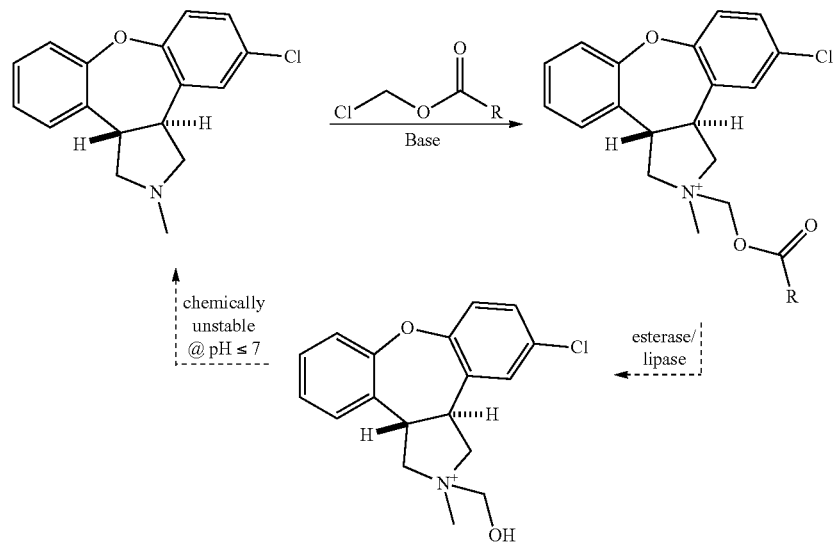

R = C1-C15 straight or branched aliphatic chain, O―(C1-C16aliphatic chain), NH―(C1-C16aliphatic chain), N―(C1-C16aliphatic chain)$_2$ General Reaction Procedures for Synthesis of Asenapine Prodrugs:

It is possible to separate the two enantiomers of Asenapine. Quaternization of a single enantiomer of Asenapine will provide two diastereomer products that can be either formulated and used as a mixture or separated and formulated and used as a single stereoisomer. Unless otherwise stated, the structural formula of a compound of Table A herein is intended to represent all enantiomers, racemates and diastereomers of that compound.

TABLE A

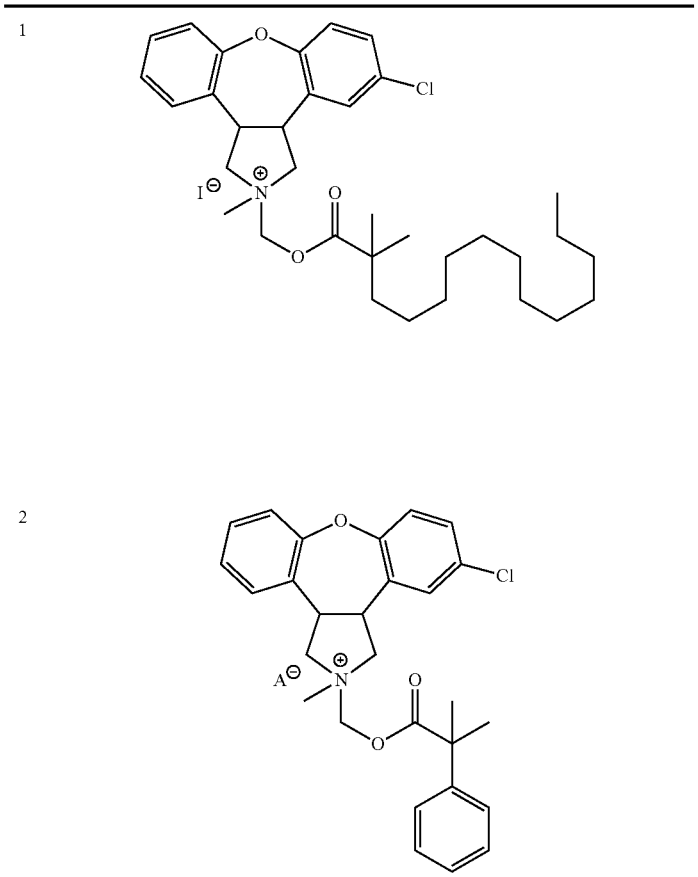

TABLE A-continued
| | |
|---|---|
| 3 | 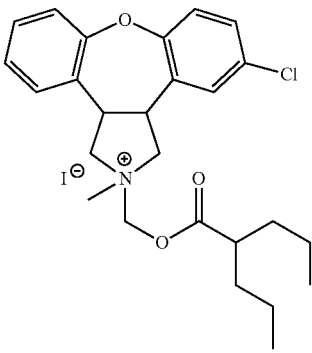 [SMILES: CCCC(CCC)C(=O)OC[N+]1(C)CC2c3ccccc3Oc3ccc(Cl)cc3C2C1 ; [I-]] |
| 4 | 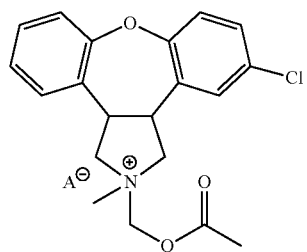 |
| 5 | 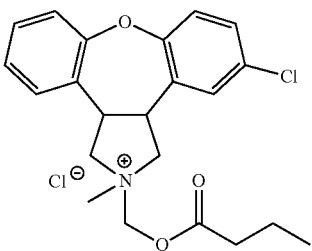 [SMILES: CCCC(=O)OC[N+]1(C)CC2c3ccccc3Oc3ccc(Cl)cc3C2C1 ; [Cl-]] |
| 6 | 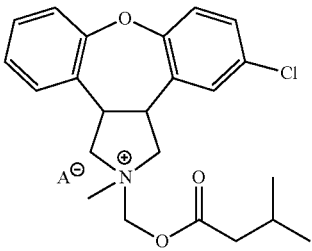 |
| 7 | 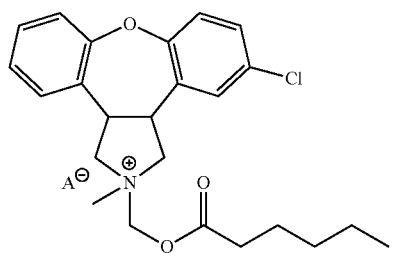 |

TABLE A-continued
8 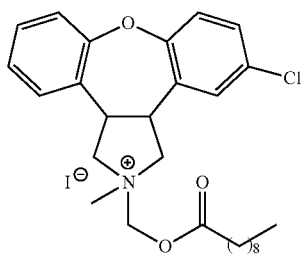
9 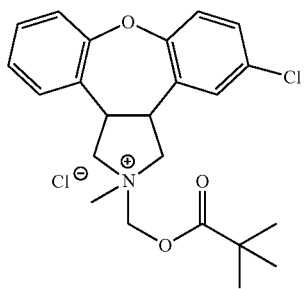 [SMILES: CC(C)(C)C(=O)OC[N+]1(C)CC2c3ccccc3Oc3ccc(Cl)cc3C2C1 ; [Cl-]]
10 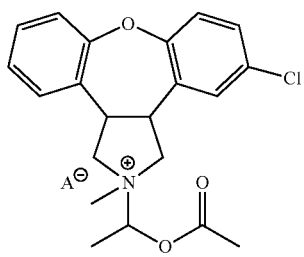
11 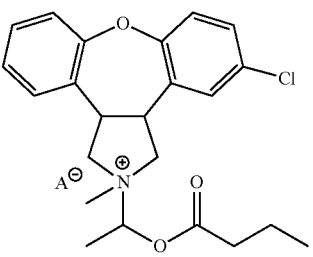
12 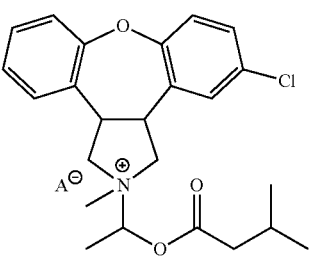
13 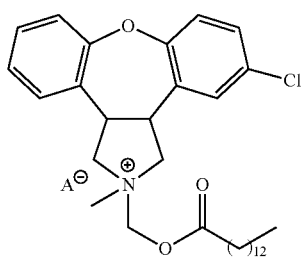

TABLE A-continued
14 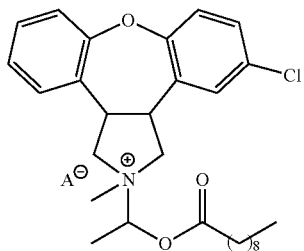
15 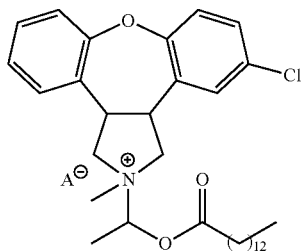
16 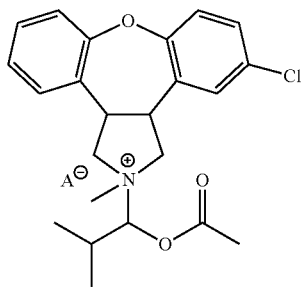
17 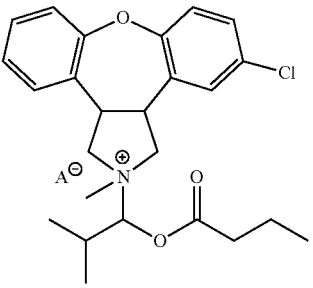
18 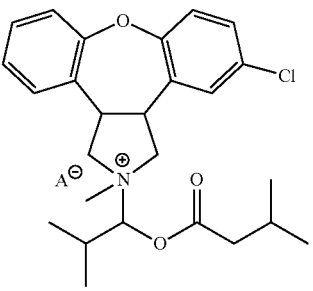

TABLE A-continued
19 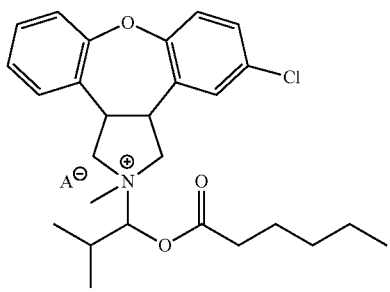
20 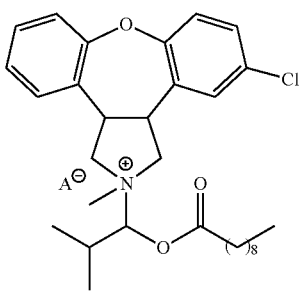
21 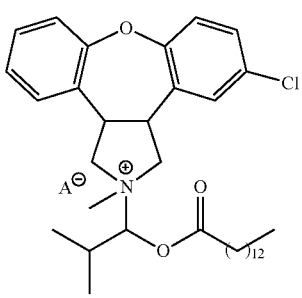
22 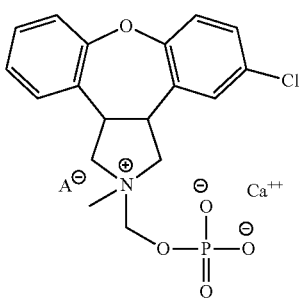
23 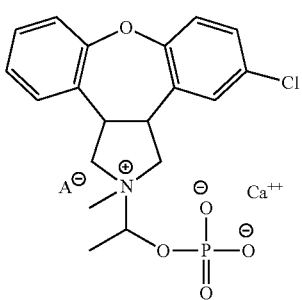

TABLE A-continued
| 24 | 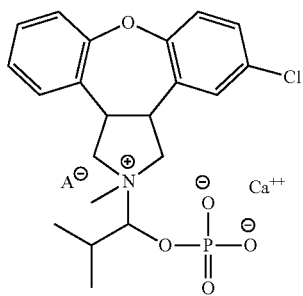 |
| --- | --- |
| 25 | 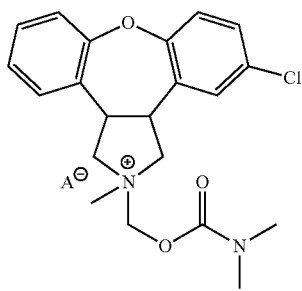 |
| 26 | 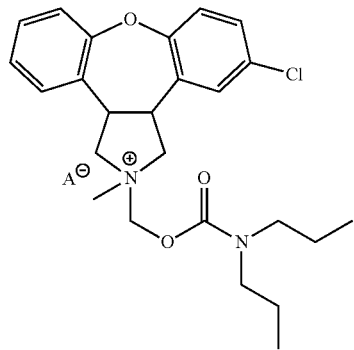 |
| 27 | 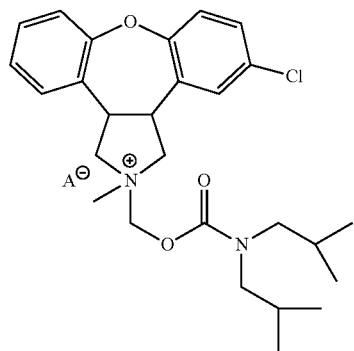 |

TABLE A-continued
| | |
|---|---|
| 28 | 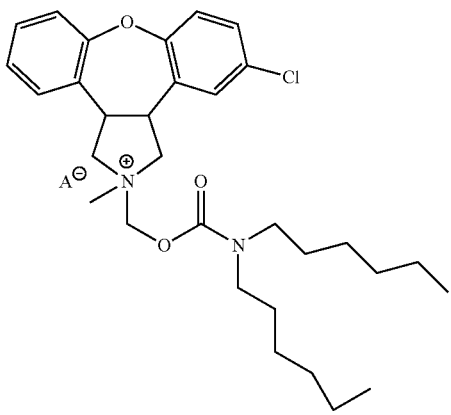 |
| 29 | 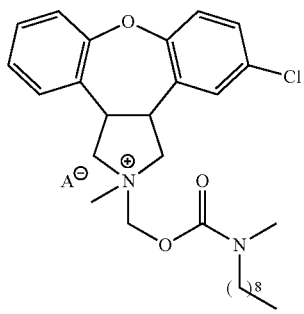 |
| 30 | 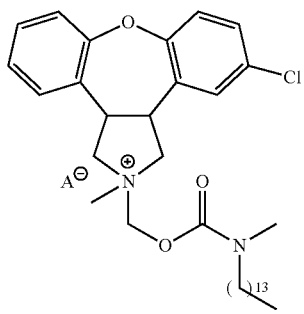 |
| 31 | 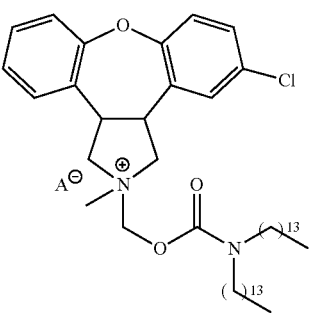 |

TABLE A-continued
32 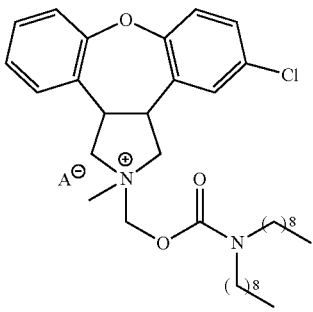
33 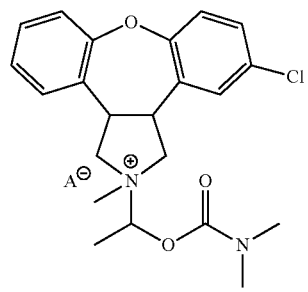
34 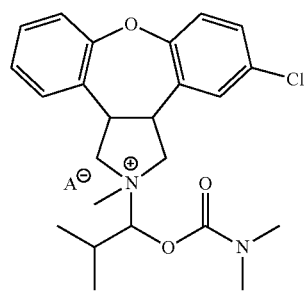
35 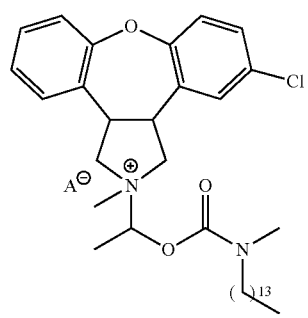
36 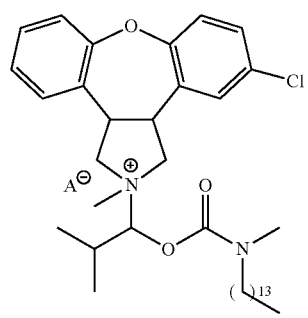

TABLE A-continued
| | |
|---|---|
| 37 | 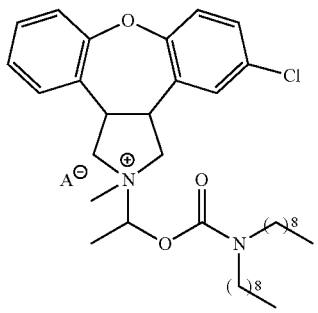 |
| 38 | 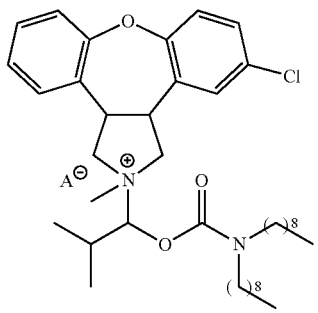 |
| 39 | 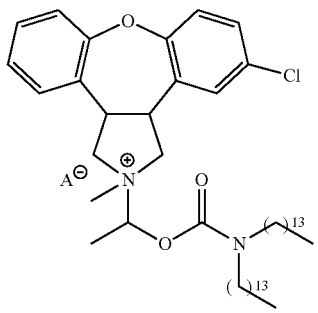 |
| 40 | 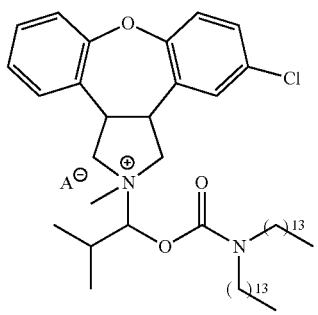 |
| 41 | 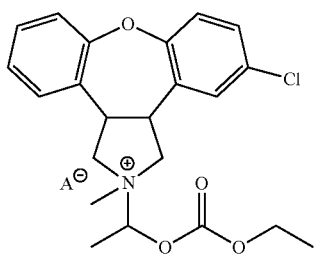 |

TABLE A-continued
42 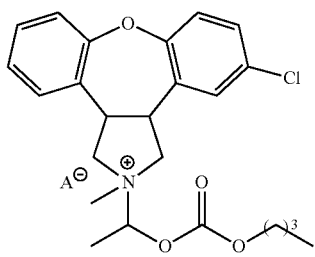
43 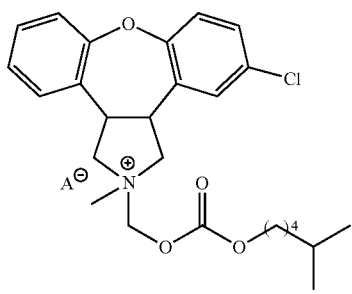
44 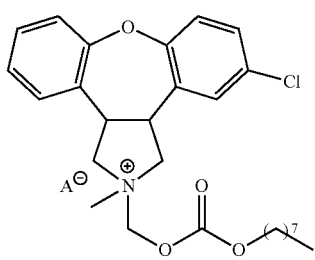
45 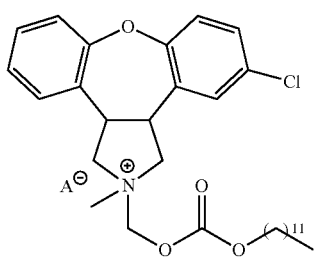
46 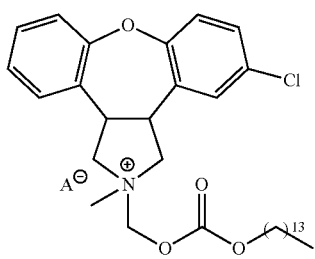
47 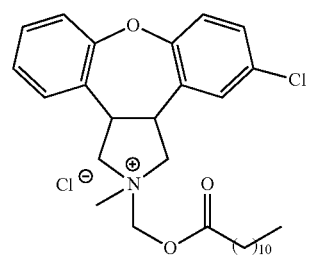

TABLE A-continued
48 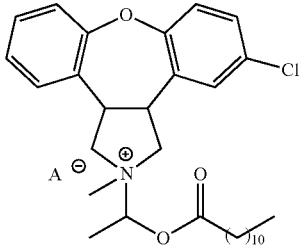
49 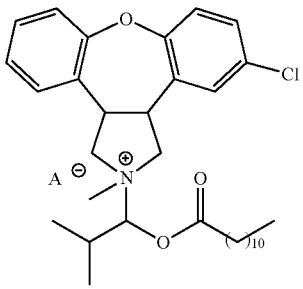
50 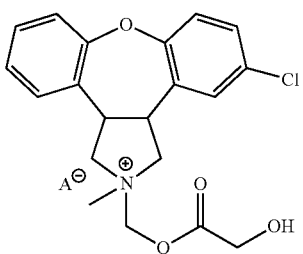
51 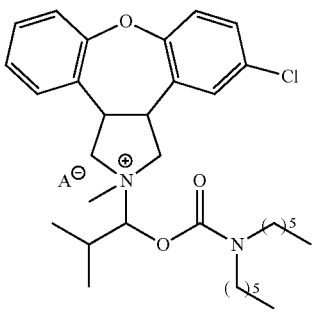
52 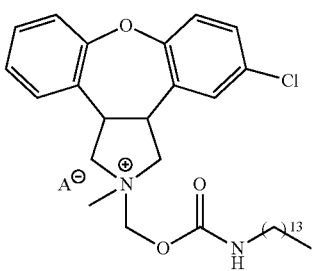

TABLE A-continued
53 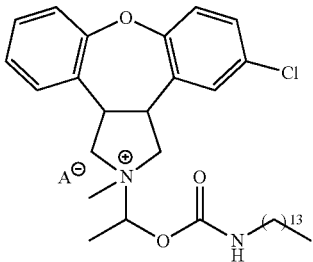
54 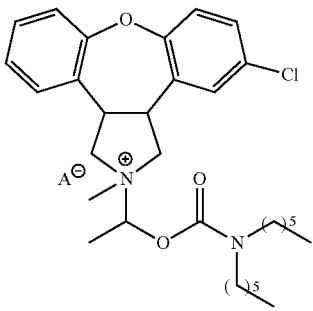
55 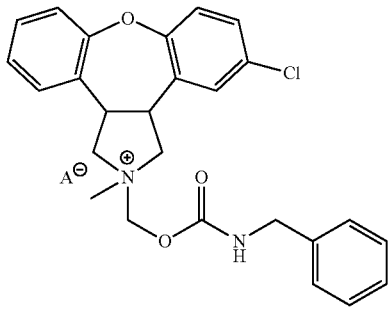
56 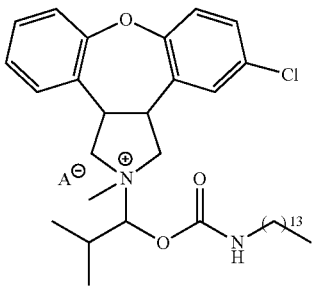
57 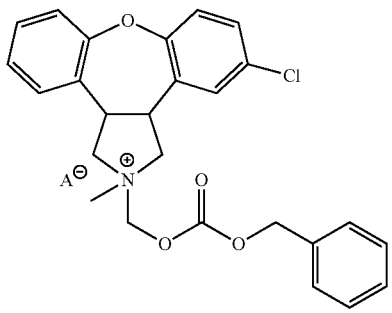

TABLE A-continued
58 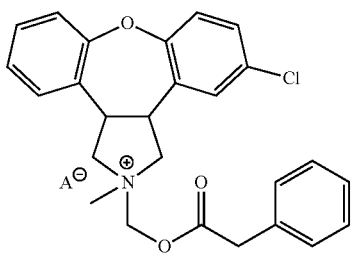
59 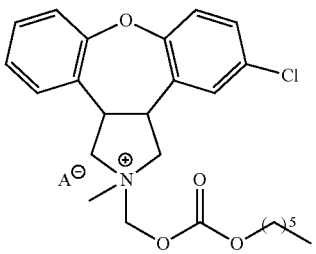
60 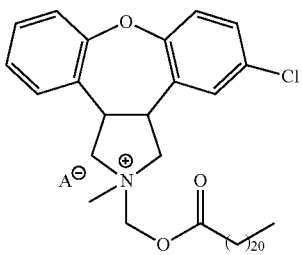
61 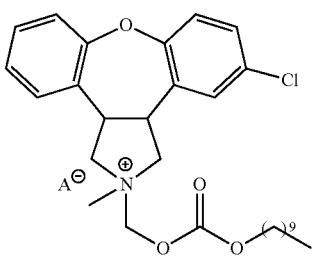
62 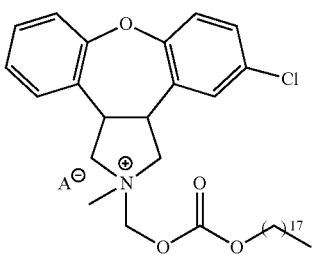
63 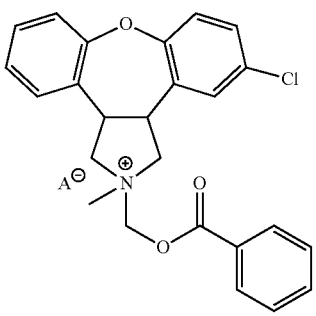

TABLE A-continued
64 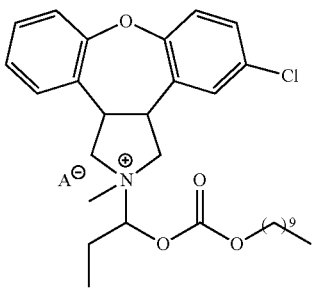
65 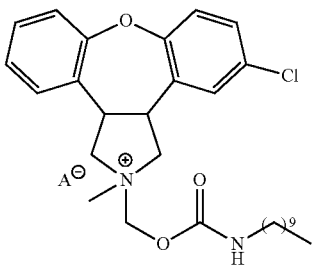
66 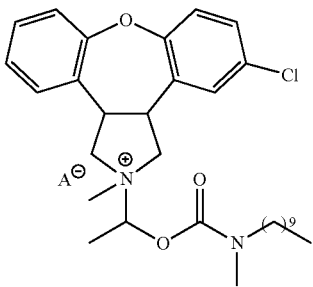
67 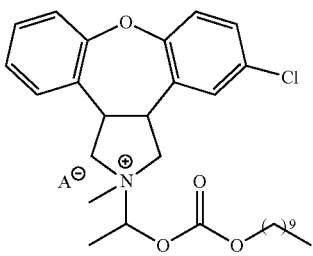
68 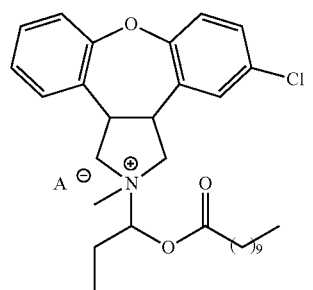

TABLE A-continued
69 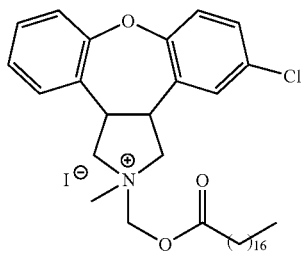
70 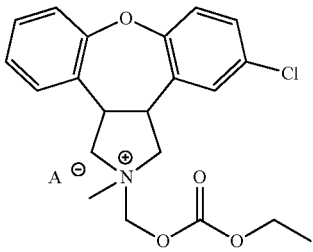
71 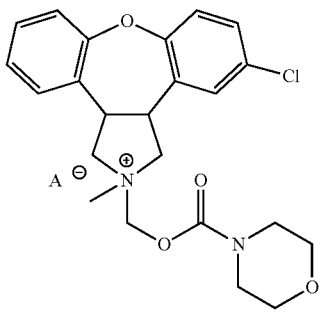
72 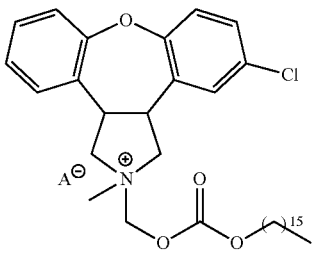
73 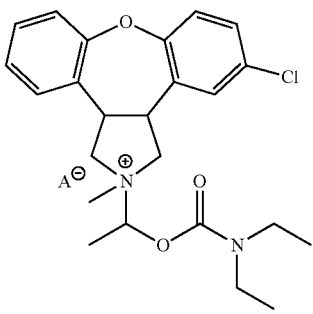

TABLE A-continued
| 74 | 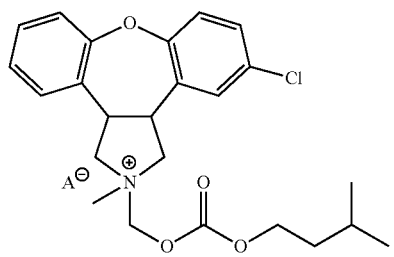 |
| --- | --- |
| 75 | 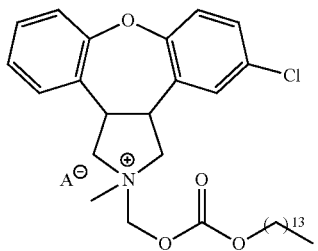 |
| 76 | 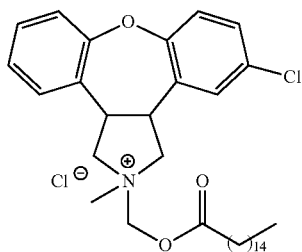 |
| 77 | 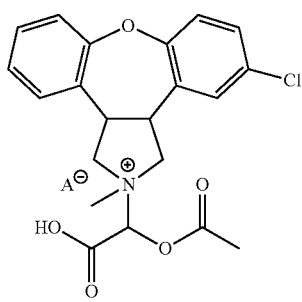 |
| 78 | 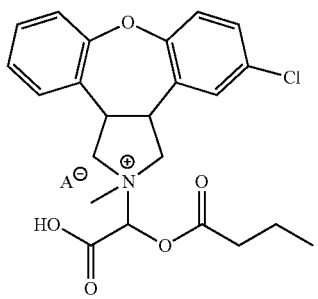 |
| 79 | 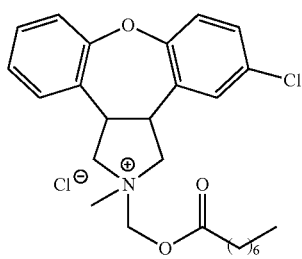 |

TABLE A-continued
80 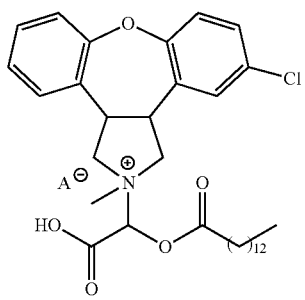
81 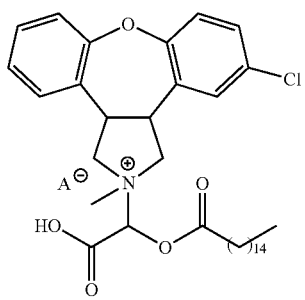
82 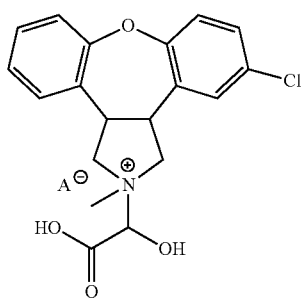
83 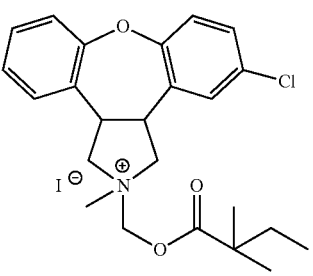 [SMILES: CCC(C)(C)C(=O)OC[N+]1(C)CC2c3ccccc3Oc3ccc(Cl)cc3C2C1 ; [I-]]
84 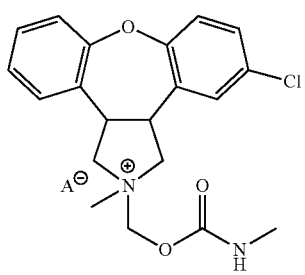

TABLE A-continued
| 85 | 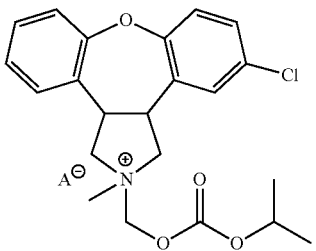 |
| 86 | 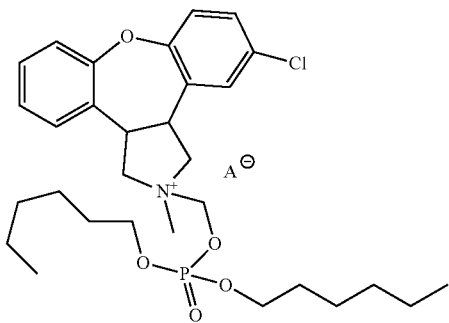 |
| 87 | 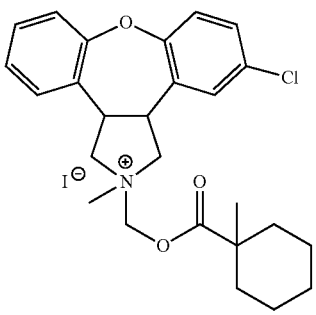 [SMILES: CC1(C(=O)OC[N+]2(C)CC3c4ccccc4Oc4ccc(Cl)cc4C3C2)CCCCC1 ; [I-]] |
| 88 | 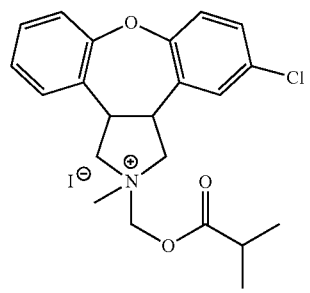 [SMILES: CC(C)C(=O)OC[N+]1(C)CC2c3ccccc3Oc3ccc(Cl)cc3C2C1 ; [I-]] |
| 89 | 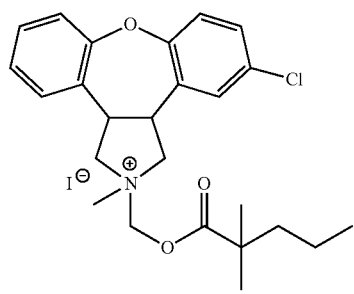 [SMILES: CCCC(C)(C)C(=O)OC[N+]1(C)CC2c3ccccc3Oc3ccc(Cl)cc3C2C1 ; [I-]] |

TABLE A-continued
90 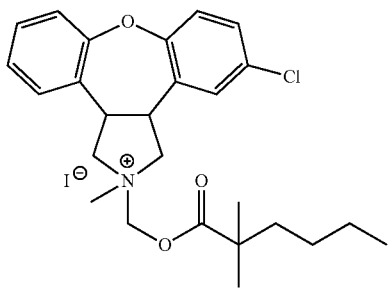 [SMILES: CCCCC(C)(C)C(=O)OC[N+]1(C)CC2c3ccccc3Oc3ccc(Cl)cc3C2C1 ; [I-]]
91 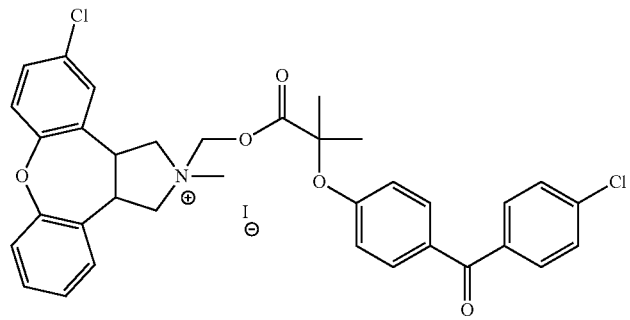 [SMILES: CC(C)(Oc1ccc(C(=O)c2ccc(Cl)cc2)cc1)C(=O)OC[N+]1(C)CC2c3ccccc3Oc3ccc(Cl)cc3C2C1 ; [I-]]
92 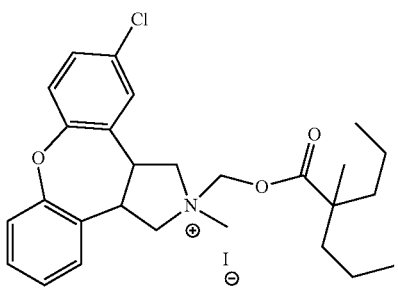 [SMILES: CCCC(C)(CCC)C(=O)OC[N+]1(C)CC2c3ccccc3Oc3ccc(Cl)cc3C2C1 ; [I-]]
93 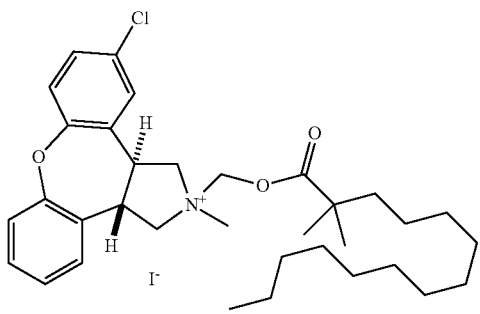 [SMILES: CCCCCCCCCCCCC(C)(C)C(=O)OC[N+]1(C)C[C@@H]2c3ccccc3Oc3ccc(Cl)cc3[C@H]2C1 ; [I-]]
94 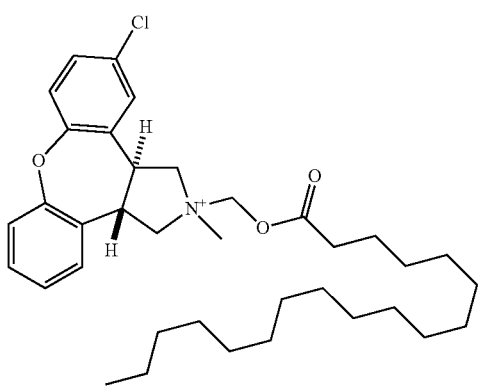 [SMILES: CCCCCCCCCCCCCCCCCC(=O)OC[N+]1(C)C[C@@H]2c3ccccc3Oc3ccc(Cl)cc3[C@H]2C1]

TABLE A-continued
95
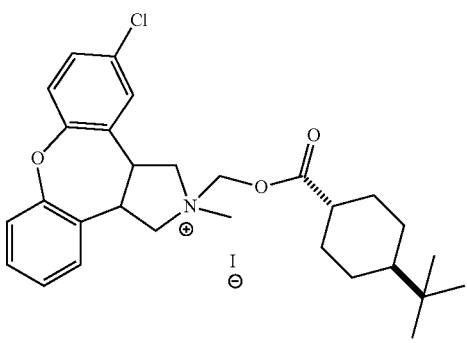
96
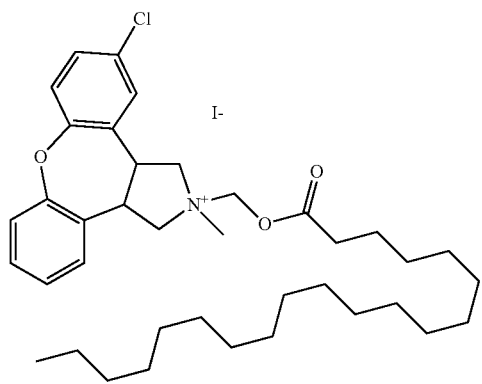 [SMILES: CCCCCCCCCCCCCCCCCCCC(=O)OC[N+]1(C)CC2c3ccccc3Oc3ccc(Cl)cc3C2C1 ; [I-]]
97
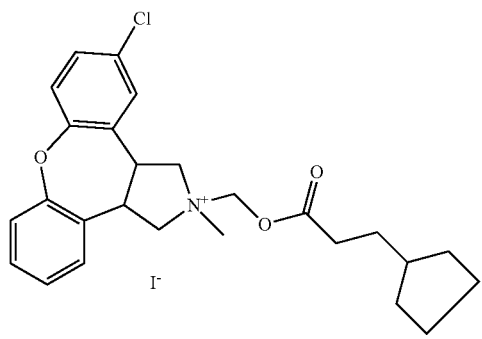 [SMILES: C[N+]1(COC(=O)CCC2CCCC2)CC2c3ccccc3Oc3ccc(Cl)cc3C2C1 ; [I-]]
98
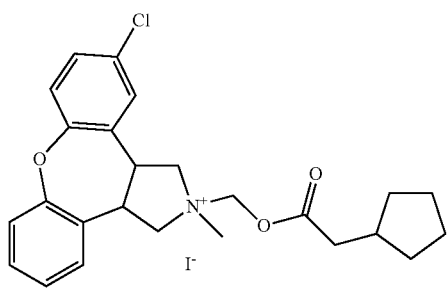 [SMILES: C[N+]1(COC(=O)CC2CCCC2)CC2c3ccccc3Oc3ccc(Cl)cc3C2C1 ; [I-]]

TABLE A-continued
99 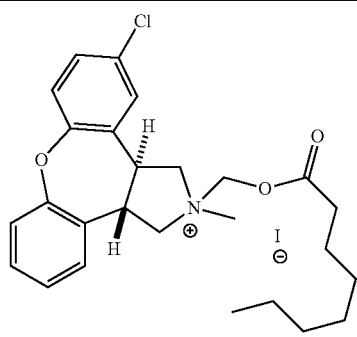
100 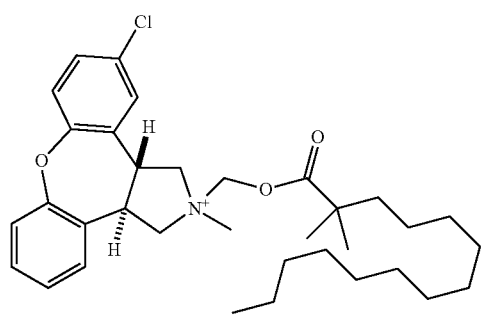 [SMILES: CCCCCCCCCCCCC(C)(C)C(=O)OC[N+]1(C)C[C@H]2c3ccccc3Oc3ccc(Cl)cc3[C@@H]2C1]
101 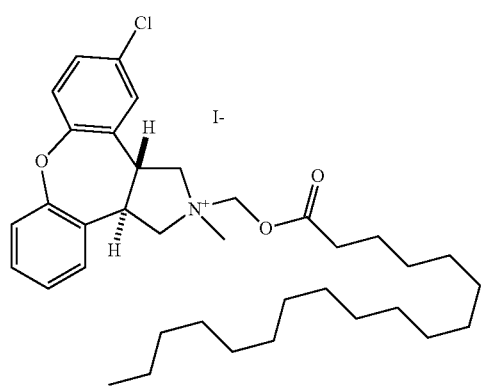 [SMILES: CCCCCCCCCCCCCCCCCC(=O)OC[N+]1(C)C[C@H]2c3ccccc3Oc3ccc(Cl)cc3[C@@H]2C1 ; [I-]]
102 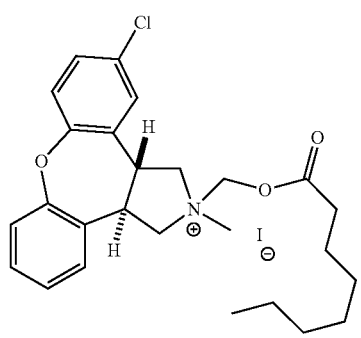 [SMILES: CCCCCCCC(=O)OC[N+]1(C)C[C@H]2c3ccccc3Oc3ccc(Cl)cc3[C@@H]2C1 ; [I-]]

TABLE A-continued
103 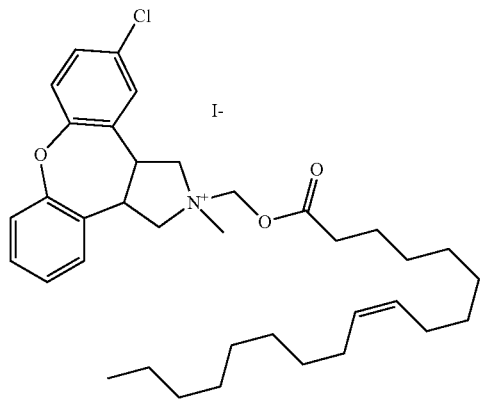 [SMILES: CCCCCCCC/C=C\CCCCCCCC(=O)OC[N+]1(C)CC2c3ccccc3Oc3ccc(Cl)cc3C2C1 ; [I-]]
104 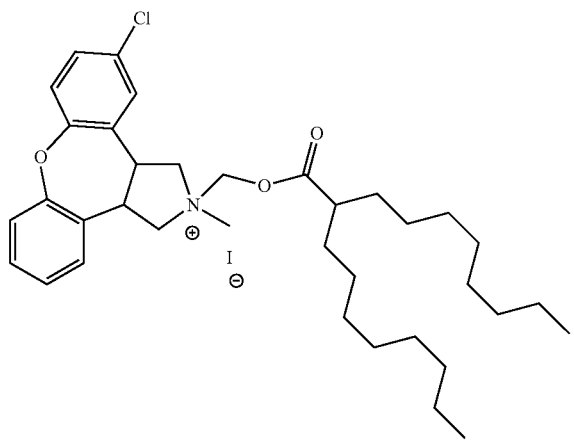
105 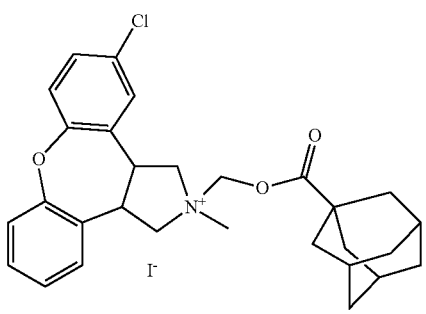 [SMILES: C[N+]1(COC(=O)C23CC4CC(CC(C4)C2)C3)CC2c3ccccc3Oc3ccc(Cl)cc3C2C1 ; [I-]]
106 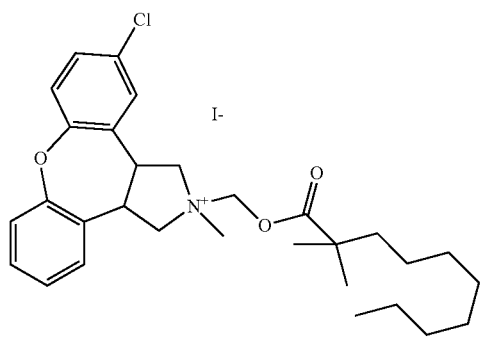 [SMILES: CCCCCCCCC(C)(C)C(=O)OC[N+]1(C)CC2c3ccccc3Oc3ccc(Cl)cc3C2C1 ; [I-]]

TABLE A-continued
107 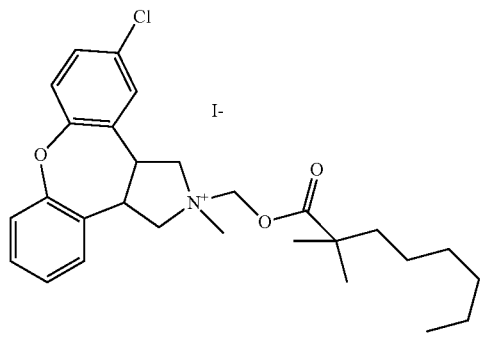 [SMILES: CCCCCCC(C)(C)C(=O)OC[N+]1(C)CC2c3ccccc3Oc3ccc(Cl)cc3C2C1 ; [I-]]
108 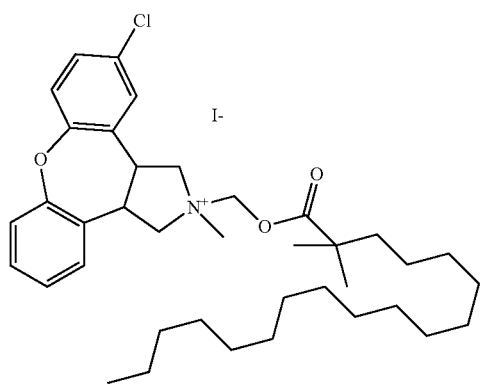 [SMILES: CCCCCCCCCCCCCCCCC(C)(C)C(=O)OC[N+]1(C)CC2c3ccccc3Oc3ccc(Cl)cc3C2C1 ; [I-]]
109 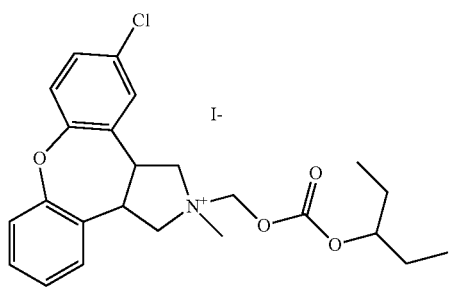 [SMILES: CCC(CC)OC(=O)OC[N+]1(C)CC2c3ccccc3Oc3ccc(Cl)cc3C2C1 ; [I-]]
110 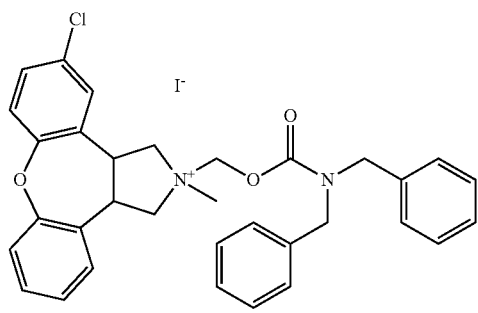 [SMILES: C[N+]1(COC(=O)N(Cc2ccccc2)Cc2ccccc2)CC2c3ccccc3Oc3ccc(Cl)cc3C2C1 ; [I-]]
111 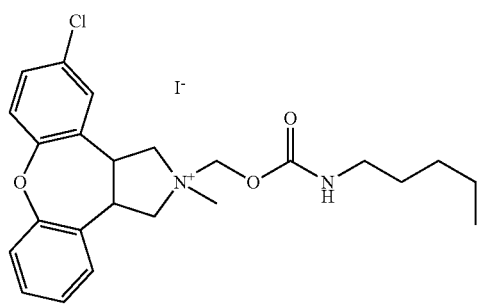 [SMILES: CCCCCNC(=O)OC[N+]1(C)CC2c3ccccc3Oc3ccc(Cl)cc3C2C1 ; [I-]]

TABLE A-continued
112 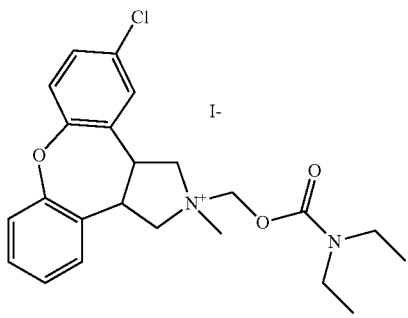 [SMILES: CCN(CC)C(=O)OC[N+]1(C)CC2c3ccccc3Oc3ccc(Cl)cc3C2C1 ; [I-]]
113 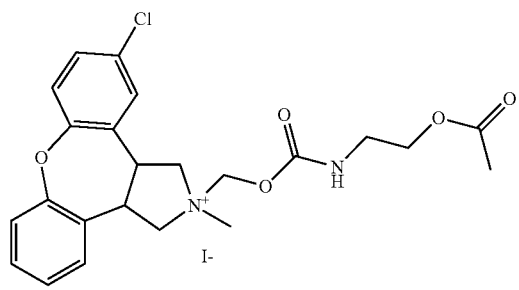 [SMILES: CC(=O)OCCNC(=O)OC[N+]1(C)CC2c3ccccc3Oc3ccc(Cl)cc3C2C1 ; [I-]]
114 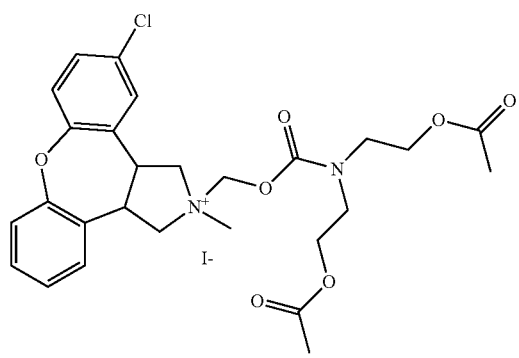 [SMILES: CC(=O)OCCN(CCOC(C)=O)C(=O)OC[N+]1(C)CC2c3ccccc3Oc3ccc(Cl)cc3C2C1 ; [I-]]
115 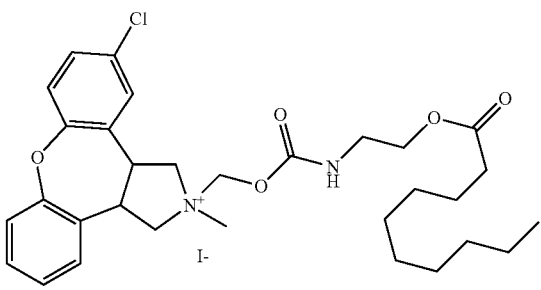 [SMILES: CCCCCCCCCC(=O)OCCNC(=O)OC[N+]1(C)CC2c3ccccc3Oc3ccc(Cl)cc3C2C1 ; [I-]]
116 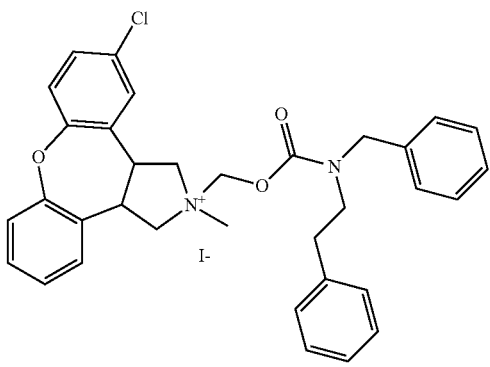 [SMILES: C[N+]1(COC(=O)N(CCc2ccccc2)Cc2ccccc2)CC2c3ccccc3Oc3ccc(Cl)cc3C2C1 ; [I-]]

Synthesis of Compound 69 (ASP stearate iodide)
5-chloro-2-methyl-2-((stearoyloxy)methyl)-2,3,3a,
12b-tetrahydro-1H-dibenzo[2,3:6,7]oxepino[4,5-c]
pyrrol-2-ium iodide General Reaction Procedure I Step A—Formation of Acid Chloride

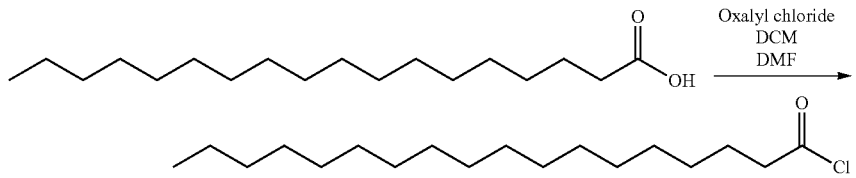

To a stirred suspension of stearic acid (20 g, 70.3 mmol) in dichloromethane (100 mL) was added oxalyl chloride (8.92 mL, 105.5 mmol). 1 drop dimethylformamide was added and the reaction stirred at 25° C. for 3 hours. The solvent was removed in vacuo and the resulting product used in the next step without further purification.

$^1$H-NMR (CDCl$_3$) δ 0.87 (3H, t), 1.20-1.40 (28H, m), 1.65-1.70 (2H, m), 2.87 (2H, t)

Step B—Formation of Chloromethyl Alkyl Ester

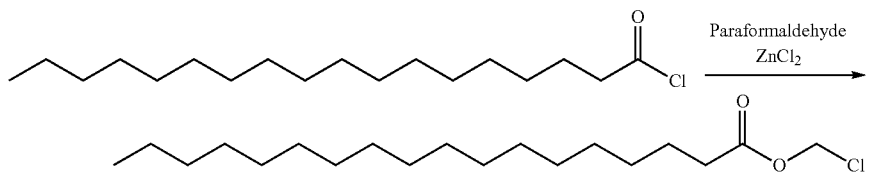

Paraformaldehyde (2.11 g, 70.3 mmol) and zinc chloride (258 mg) were added to the acid chloride prepared above and the reaction mixture was heated at 65° C. for 16 hours and then allowed to cool to 25° C. Dichloromethane (200 mL) and saturated aqueous NaHCO$_3$ (70 mL) were added. The aqueous emulsion was extracted with dichloromethane (2×50 mL) and the combined organic extracts washed with saturated aqueous NaHCO$_3$ (70 mL), brine (70 mL), and dried over MgSO$_4$. After filtration, the volatiles were removed and the residue purified by silica chromatography eluting with heptane to 12% dichloromethane (DCM) in heptane to give a yellow solid (12.64 g, 54% yield over two steps).

$^1$H-NMR (CDCl$_3$) δ 0.86 (3H, t), 1.20-1.40 (28H, m), 1.55-1.70 (2H, m), 2.37 (2H, t), 5.70 (2H, s).

Step C—Formation of Iodomethyl Stearate Ester

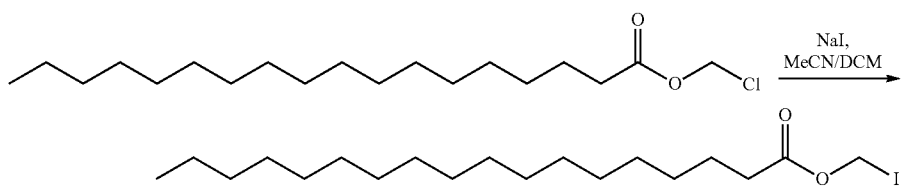

To a solution of the iodomethyl alkyl ester (12.64 g, 37.96 mmol) in acetonitrile (150 mL) and dichloromethane (75 mL) was added sodium iodide (17.07 g, 113.9 mmol). The flask was covered in tin foil to exclude light and stirred at 25° C. for 70 hours and then at 25° C. for 24 hours. The reaction mixture was partitioned between dichloromethane (200 mL) and water (150 mL). The aqueous layer was extracted with dichloromethane (2×150 mL). The combined organics were washed with saturated aqueous (aq) NaHCO$_3$ (200 mL), 5% aq sodium sulfite solution (200 mL) and brine (2×100 mL), then dried (MgSO$_4$) and concentrated to give the product as a yellow solid (14.53 g, 90% yield) which was not further purified. $^1$H-NMR (CDCl$_3$) δ 0.87 (3H, t), 1.20-1.35 (28H, m), 1.55-1.70 (2H, m), 2.32 (2H, t), 5.90 (2H, s).

Step D—Quaternisation Reaction

Asenapine (2 g, 4.85 mmol) and the iodomethyl stearate ester (3.55 g, 14.55 mmol) were stirred together in acetonitrile (50 mL) at 25° C. overnight. The reaction mixture was concentrated and the residue triturated with diethyl ether to give compound 69 (2.80 g, 81% yield).
$^1$H-NMR (CDCl$_3$) δ 7.30-7.10 (14H, m), 6.05-5.95 (4H, m), 4.90-4.55 (4H, m), 4.40-3.90 (8H, m), 3.85-3.80 (6H, m), 2.60-2.50 (4H, m), 1.65-1.55 (4H, m), 1.35-1.15 (56H, m), 0.85 (6H, 2×t).

Synthesis of compound 5 (ASP butyrate chloride) 2-((butyryloxy)methyl)-5-chloro-2-methyl-2,3,3a, 12b-tetrahydro-1H-dibenzo[2,3:6,7]oxepino[4,5-c] pyrrol-2-ium chloride The general procedure I described above was used for the synthesis of compound 5, starting from step B using butyroyl chloride. In step D, 3 equiv of iodomethyl butyrate was used. The iodide salt was converted to the corresponding chloride by passing through Dowex 1X8, 50-100 mesh, ion exchange resin eluting with methanol followed by a diethyl ether trituration then a ethyl acetate trituration to give compound 5 (1.44 g).
$^1$H-NMR (CDCl$_3$) δ 7.30-7.00 (14H, m), 6.17-6.11 (4H, m), 4.83-4.72 (2H, m), 4.63-4.53 (2H, m), 4.28-3.97 (7H, m), 3.95-3.83 (7H, m), 2.48 (4H, 2×t), 1.66 (4H, 2×sextet), 0.95 (6H, 2×t).

Synthesis of compound 47 (ASP laurate chloride) 5-chloro-2-((dodecanoyloxy)methyl)-2-methyl-2,3, 3a,12b-tetrahydro-1H-dibenzo[2,3:6,7]oxepino[4,5-c]pyrrol-2-ium chloride The general procedure I described above was used for the synthesis of compound 47, starting from step B using lauroyl chloride. In step D, 3 equiv of iodomethyl laurate was used. The iodide salt was converted to the corresponding chloride by passing through Dowex 1X8, 50-100 mesh, ion exchange resin eluting with dichloromethane. The exchange was then repeated followed by an diethyl ether trituration to give compound 47 (1.89 g).
$^1$H-NMR (CDCl$_3$) δ 7.29-7.09 (14H, m), 6.15-6.10 (4H, m), 4.81-4.73 (2H, m), 4.63-4.57 (2H, m), 4.31-3.83 (14H, m), 2.48 (4H, 2×t), 1.68-1.51 (4H, m), 1.29-1.18 (32H, m), 0.86 (6H, 2×t).

Synthesis of compound 76 (ASP palmitate chloride) 5-chloro-2-methyl-2-((palmitoyloxy)methyl)-2, 3,3a,12b-tetrahydro-1H-dibenzo[2,3:6,7]oxepino[4, 5-c]pyrrol-2-ium chloride The general procedure I described above was used for the synthesis of compound 76, starting from step B using palmitoyl chloride. In step D, 3 equiv of iodomethyl palmitate was used. The iodide salt was converted to the corresponding chloride by passing through Dowex 1X8, 50-100 mesh, ion exchange resin eluting with dichloromethane. The exchange was then repeated followed by an diethyl ether trituration to give compound 76 (2.05 g).
$^1$H-NMR (CDCl$_3$) δ 7.26-7.07 (14H, m), 6.17-6.12 (4H, m), 4.83-4.71 (2H, m), 4.64-4.52 (2H, m), 4.27-3.84 (14H, m), 2.49 (4H, 2×t), 1.64-1.58 (4H, m), 1.32-1.16 (48H, m), 0.87 (6H, 2×t).

Synthesis of compound 9 (ASP pivalate chloride) 5-chloro-2-methyl-2-((pivaloyloxy)methyl)-2,3,3a, 12b-tetrahydro-1H-dibenzo[2,3:6,7]oxepino[4,5-c] pyrrol-2-ium chloride The general procedure I described above was used for the synthesis of compound 9 starting from step C using chloromethyl pivalate. In step D, 3 equiv of iodomethyl pivalate was used. The iodide salt was converted to the corresponding chloride by passing through Dowex 1X8, 50-100 mesh, ion exchange resin eluting with methanol followed by an diethyl ether trituration to provide compound 9 (1.96 g)
$^1$H-NMR (CDCl$_3$) δ 7.30-7.05 (14H, m), 6.12-6.10 (4H, m), 4.75-4.55 (4H, m), 4.30-3.90 (8H, m), 3.87-3.85 (6H, m), 1.27 (18H, 2×s).

Synthesis of compound 79 (ASP octanoate chloride) 5-chloro-2-methyl-2-((octanoyloxy)methyl)-2, 3,3a,12b-tetrahydro-1H-dibenzo[2,3:6,7]oxepino[4, 5-c]pyrrol-2-ium chloride The general procedure I described above was used for the synthesis of compound 79 starting from step B using octanoyl chloride. In step D, 3 equiv of iodomethyl octanoate was used. The iodide salt was converted to the corresponding chloride by passing through Dowex 1X8, 50-100 mesh, ion exchange resin eluting with methanol followed by an diethyl ether trituration, to provide compound 79 (1.58 g).
$^1$H-NMR (CDCl$_3$) δ 7.30-7.00 (14H, m). 6.20-6.10 (4H, m), 4.85-4.55 (4H, m), 4.40-3.90 (8H, m), 3.90-3.80 (6H, m), 2.55-2.40 (4H, m), 1.70-1.50 (4H, m), 1.35-1.10 (16H, m) 0.85 (6H, 2×t).

Synthesis of compound 8 (ASP decanoate iodide) 5-chloro-2-((decanoyloxy)methyl)-2-methyl-2,3,3a, 12b-tetrahydro-1H-dibenzo[2,3:6,7]oxepino[4,5-c] pyrrol-2-ium iodide The general procedure I described above was used for the synthesis of compound 8 starting from step B using decanoyl chloride. In step D, 3 equiv of iodomethyl decanoate was used. After diethyl ether trituration compound 8 (3.04 g) was obtained.
$^1$H-NMR (CDCl$_3$) δ 7.31-7.10 (14H, m), 6.06-6.00 (4H, m), 4.89-4.76 (2H, m), 4.71-4.58 (2H, m), 4.37-3.83 (14H, m), 2.53 (4H, 2×t), 1.67-1.54 (4H, m), 1.34-1.14 (24H, m), 0.85 (6H, 2×t).

Synthesis of compound 83 (ASP dimethyl butyrate iodide) 5-chloro-2-(((2,2-dimethylbutanoyl)oxy) methyl)-2-methyl-2,3,3a,12b-tetrahydro-1H-dibenzo [2,3:6,7]oxepino[4,5-c]pyrrol-2-ium iodide The general procedure I described above was used for the synthesis of compound 83 starting from step B using 2,2-dimethylbutyryl chloride. In step D, 3 equiv of iodomethyl 2,2-dimethylbutyrate was used. After diethyl ether trituration compound 83(2.61 g) was obtained. $^1$H-NMR (CDCl$_3$) δ 7.30-7.10 (14H, m), 6.05-5.95 (4H, m), 4.80-4.60 (4H, m), 4.45-3.95 (8H, m), 3.90-3.80 (6H, m), 1.70-1.60 (4H, m), 1.23 (12H, 2×s), 0.85 (6H, 2×t).

Synthesis of compound 87 (ASP 2-methyl cyclohexyl carboxylate iodide) 5-chloro-2-methyl-2-(((1-methylcyclohexanecarbonyl)oxy)methyl)-2,3,3a,12b-tetrahydro-1H-dibenzo[2,3:6,7]oxepino[4,5-c]pyrrol-2-ium iodide Synthesized using the general procedure I starting from 1-methyl cyclohexane carboxylic acid. After diethyl ether trituration compound 87 (2.75 g) was obtained.

$^1$H-NMR (300 MHz, CDCl$_3$) δ 7.32-7.05 (14H, m), 6.00 (2H, s), 5.95 (2H, s), 4.76-4.52 (4H, m), 4.39-3.82 (12H, m), 2.04-2.00 (4H, m), 1.56-1.28 (23H, m).

Synthesis of compound 88 (ASP isobutyrate iodide) 5-chloro-2-((isobutyryloxy)methyl)-2-methyl-2,3,3a,12b-tetrahydro-1H-dibenzo[2,3:6,7]oxepino[4,5-c]pyrrol-2-ium iodide Synthesized using the general procedure I starting from isobutyryl chloride. After dissolving in a minimum amount of tetrahydrofuran followed by precipitation with diethyl ether compound 88 (2.23 g) was obtained. $^1$H-NMR (300 MHz, CDCl$_3$) δ 7.30-7.09 (14H, m), 6.03 (2H, s), 5.99 (2H, s), 4.85-4.54 (4H, m), 4.37-3.89 (8H, m), 3.48-3.82 (6H, 2×s), 2.83-2.72 (2H, m), 1.25 (12H, 2×d).

Synthesis of compound 1 (ASP Dimethyl myristate iodide) 5-chloro-2-(((2,2-dimethyltetradecanoyl)oxy)methyl)-2-methyl-2,3,3a,12b-tetrahydro-1H-dibenzo[2,3:6,7]oxepino[4,5-c]pyrrol-2-ium iodide Synthesis of methyl 2,2-dimethyltetradecanoate To a stirred solution of diisopropylamine (6.90 mL, 49.0 mmol) in tetrahydrofuran (50 mL) under Ar(g) at −7° C. was added ″BuLi (2.3M in hexanes, 21.3 mL, 49.0 mmol) dropwise via a dropping funnel keeping the temperature between 0° C. and 5° C. The reaction was stirred at −7° C. for 30 min and then cooled to −78° C. Methyl isobutyrate (5.61 mL, 49.0 mmol) was added and the reaction stirred at −78° C. for 1.5 hours. 1-Iodododecane (13.05 g, 44.1 mmol) in tetrahydrofuran (10 mL) was added dropwise via a dropping funnel keeping the temperature below −70° C. Further tetrahydrofuran (40 mL) was added over 5 min to aid stirring. After complete addition the reaction was stirred at −78° C. for approximately 2 hours and then allowed to slowly warm to 25° C. overnight.

The reaction was quenched with sat. aq. NH$_4$Cl (100 mL) and diluted with ethyl acetate (100 mL). The aqueous layer was extracted with ethyl acetate (2×50 mL) and the combined organics washed with brine (50 mL) and dried over MgSO$_4$. After filtration, the volatiles were removed. The reaction was repeated in a similar manner using methyl isobutyrate (15.05 mL, 131.27 mmol). The two crude batches were combined and purified by silica chromatography eluting heptane to 50% dichloromethane/heptane to give methyl 2,2-dimethyl myristate (31.7 g).

Synthesis of 2,2-dimethyltetradecanoic acid

To a stirred solution of methyl 2,2-dimethyltetradecanoate (31.7 g, 117.2 mmol) in ethanol (234 mL) was added 2M NaOH (117 mL, 234.4 mmol). The reaction was stirred at 25° C. overnight. NaOH (4.69 g, 117 mmol) was added and the reaction heated at 50° C. for 24 hours. NaOH (4.69 g, 117 mmol) was added and the reaction heated to 100° C. for 4 hours and then cooled to 25° C. 4M HCl (140 mL) was added to acidify. Ethyl acetate (200 mL) was added and the layers separated. The aqueous was extracted with ethyl acetate (2×100 mL) and the combined organics concentrated in vacuo. The residue was partitioned between ethyl acetate (200 mL) and brine (100 mL). The organic layer was washed with brine (50 mL) and dried over MgSO$_4$. After filtration, the volatiles were removed to give 2,2-dimethyltetradecanoic acid (26.9 g).

Compound 1 was prepared using the general procedure I starting from 2,2-dimethyltetradecanoic acid (synthesized as described above). After diethyl ether trituration compound 1 (1.07 g) was obtained.

$^1$H-NMR (300 MHz, CDCl$_3$) δ 7.32-7.05 (14H, m), 6.02-5.91 (4H, m), 4.78-4.59 (4H, m), 4.44-3.98 (8H, m), 3.92-3.84 (6H, m), 1.62-1.50 (4H, m), 1.34-1.11 (52H, m), 0.88 (6H, 2×t).

Synthesis of compound 3 (ASP 2-propyl pentanoate iodide) 5-chloro-2-methyl-2-(((2-propylpentanoyl)oxy)methyl)-2,3,3a,12b-tetrahydro-1H-dibenzo[2,3:6,7]oxepino[4,5-c]pyrrol-2-ium iodide Synthesized using the general procedure I starting from 2,2-di-n-propylacetic acid. After diethyl ether trituration compound 3 (2.46 g) was obtained.

$^1$H-NMR (300 MHz, CDCl$_3$) δ 7.33-7.05 (14H, m), 6.04-5.94 (4H, m), 4.78-4.54 (4H, m), 4.43-3.96 (8H, m), 3.93-3.84 (6H, m), 2.62-2.50 (2H, m), 1.72-1.43 (8H, m), 1.38-1.18 (8H, m), 0.93-0.83 (12H, m).

Synthesis of compound 89 (ASP dimethyl pentanoate iodide) 5-chloro-2-(((2,2-dimethylpentanoyl)oxy)methyl)-2-methyl-2,3,3a,12b-tetrahydro-1H-dibenzo[2,3:6,7]oxepino[4,5-c]pyrrol-2-ium iodide Synthesized using the general procedure I starting from 2,2-dimethylvaleric acid. After diethyl ether trituration compound 89 (2.58 g) was obtained. $^1$H-NMR (300 MHz, CDCl$_3$) δ 7.30-7.06 (14H, m), 6.02-5.94 (4H, m), 4.77-4.58 (4H, m), 4.41-4.30 (2H, m), 4.25-3.97 (6H, m), 3.90-3.84 (6H, m) 1.59-1.52 (4H, m), 1.29-1.18 (16H, m), 0.87 (6H, 2×t).

Synthesis of compound 90 (ASP dimethyl hexanoate iodide) 5-chloro-2-(((2,2-dimethylhexanoyl)oxy)methyl)-2-methyl-2,3,3a,12b-tetrahydro-1H-dibenzo[2,3:6,7]oxepino[4,5-c]pyrrol-2-ium iodide Synthesized in a similar manner to compound 1 from methyl isobutyrate and 1-iodobutane. After diethyl ether trituration compound 90 (2.50 g) was obtained.

$^1$H-NMR (300 MHz, CDCl$_3$) δ 7.32-7.06 (14H, m), 6.03-5.92 (4H, m), 4.78-4.57 (4H, m), 4.44-3.97 (8H, m), 3.94-3.83 (6H, m) 1.62-1.51 (4H, m), 1.34-1.10 (20H, m), 0.84 (6H, 2×t).

Synthesis of Compound 94—((+)-ASP-Stearate Iodide) 5-chloro-2-methyl-2-((stearoyloxy)methyl)-2,3,3a,12b-tetrahydro-1H-dibenzo[2,3:6,7]oxepino[4,5-c]pyrrol-2-ium Step D—Quaternisation Reaction This was synthesized employing general reaction procedure I starting from (+)-Asenapine (835 gm, 2.92 mmol) and stearic acid to give Compound 94 (1.98 g, 95%), which was obtained as an approx 1:1 mixture of 2 conformers. ¹H-NMR (300 MHz, CDCl₃) δ 7.31-7.08 (14H, m), 6.04-5.99 (4H, m), 4.84-3.88 (12H, m), 3.83-3.80 (6H, 2×s), 2.56-2.52 (4H, m), 1.71-1.56 (4H, m), 1.37-1.16 (56H, m), 0.88 (6H, 2×t).

Synthesis of Compound 101—((−)-ASP-Stearate Iodide) 5-chloro-2-methyl-2-((stearoyloxy)methyl)-2,3,3a,12b-tetrahydro-1H-dibenzo[2,3:6,7]oxepino [4,5-c]pyrrol-2-ium iodide This was synthesized employing general reaction procedure I starting from stearic acid and (−)-Asenapine. Compound 101 (1.92 g, 91%) was obtained as an approx 1:1 mixture of 2 conformers. ¹H-NMR (300 MHz, CDCl₃) δ 7.31-7.08 (14H, m), 6.05-6.00 (4H, m), 4.86-4.53 (4H, m), 4.39-3.85 (8H, m), 3.84-3.82 (6H, m), 2.57-2.49 (4H, m), 1.64-1.58 (4H, m), 1.31-1.15 (56H, m), 0.87 (6H, 2×t).

Synthesis of Compound 99—((+)-ASP-Octanoate Iodide) 5-chloro-2-methyl-2-((octanoyloxy)methyl)-2,3,3a,12b-tetrahydro-1H-dibenzo[2,3:6,7]oxepino [4,5-c]pyrrol-2-ium iodide This was synthesized employing general reaction procedure I starting from octanoyl chloride and (+)-Asenapine to give Compound 99 (1.55 g, 78%) as an approx 1:1 mixture of 2 conformers. ¹H-NMR (300 MHz, CDCl₃) δ 7.32-7.09 (14H, m), 6.04-6.01 (4H, m), 4.87-4.56 (4H, m), 4.38-3.82 (14H, m), 2.55-2.52 (4H, m), 1.76-1.59 (4H, m), 1.36-1.11 (16H, m), 0.85 (6H, 2×t).

Synthesis of Compound 102—((−)-ASP-Octanoate Iodide) 5-chloro-2-methyl-2-((octanoyloxy)methyl)-2,3,3a,12b-tetrahydro-1H-dibenzo[2,3:6,7]oxepino [4,5-c]pyrrol-2-ium iodide This was synthesized employing general reaction procedure I starting from octanoyl chloride and (−)-Asenapine. Compound 102 (1.34 g, 67%) was obtained as an approx 1:1 mixture of 2 conformers. ¹H-NMR (300 MHz, CDCl₃) δ 7.31-7.08 (14H, m), 6.05-5.98 (4H, m), 4.89-4.59 (4H, m), 4.40-3.82 (14H, m), 2.55-2.49 (4H, m), 1.64-1.60 (4H, m), 1.31-1.10 (16H, m), 0.85 (6H, 2×t).

Synthesis of Compound 95—(Asp Trans 4-Tbu-Cyclobutylcarboxylate Iodide) 2-(4(1,4-trans)-4-(tert-butyl)cyclohexanecarbonyl)oxy)methyl)-5-chloro-2-methyl-2,3,3a,12b-tetrahydro-1H-dibenzo [2,3:6,7]oxepino[4,5-c]pyrrol-2-ium iodide General Reaction Procedure II Chloromethyl ester of 4-trans-t-butyl cyclohexane carboxylic acid To a suspension of 4-trans-t-butyl cyclohexane carboxylic acid (5 g, 27.1 mmol) in water (50 mL) was added sodium carbonate (11.5 g, 108.5 mmol). After 20 minutes the reaction mixture was cooled to 0° C. the dichloromethane (100 mL) and chloromethyl chlorosulfate (3.6 mL, 35.3 mmol). The reaction was stirred at 0° C. for 1 hour then allowed to warm to 25° C. and stirred overnight. The reaction mixture was separated and the aqueous washed with dichloromethane (100 mL). The combined organics were dried (MgSO₄) and concentrated to give the crude product which was purified by filtering through silica eluting with 40% dichloromethane/heptane to give the product (4.91 g, 78%).

The product from this was then converted to the corresponding iodide using general reaction procedure I step C and the quaternization reaction was carried out using general reaction procedure I step D to give Compound 95 (2.71 g, 98%). ¹H-NMR (300 MHz, CDCl₃) δ 7.25-7.04 (14H, m), 6.01-5.97 (4H, m), 4.83-4.47 (2H, m), 4.31-4.04 (6H, m), 3.81-3.77 (6H, m), 2.49-2.35 (2H, m), 2.10-2.05 (4H, m), 1.88-1.85 (4H, m), 1.56 (8H, s), 1.51-1.41 (4H, m), 1.11-0.98 (6H, m), 0.84 (18H, s).

Synthesis of Compound 91—(ASP Fenofibrate Iodide) 5-chloro-2-(((2-(4-(4-chlorobenzoyl)phenoxy)-2-methylpropanoyl)oxy)methyl)-2-methyl-2,3,3a,12b-tetrahydro-1H-dibenzo[2,3:6,7]oxepino[4,5-c]pyrrol-2-ium iodide This was synthesized employing general reaction procedure II starting from 2-[4-(4-Chlorobenzoyl)-phenoxy]-2-methylpropionic acid. The solvent was removed from the quaternization reaction and the solid triturated with diethyl ether, filtered and dried under vacuum to give Compound 91 (2.03 g, 97%).

¹H-NMR (300 MHz, CDCl₃) δ 7.77-7.61 (8H, m), 7.48-7.38 (4H, m), 7.28-7.10 (8H, m), 7.08-6.78 (10H, m), 6.61-6.36 (4H, m), 4.75-4.59 (2H, m), 4.43-4.29 (2H, m), 4.14-3.94 (8H, m), 3.83-3.67 (6H, m), 1.79-1.72 (12H, m).

Synthesis of Compound 60—(ASP C22 Iodide) 5-chloro-2-((docosanoyloxy)methyl)-2-methyl-2,3,3a,12b-tetrahydro-1H-dibenzo[2,3:6,7]oxepino[4,5-c]pyrrol-2-ium This was synthesized employing general reaction procedure II starting from behenic acid to give Compound 60 (3.9 g 94%).

¹H-NMR (300 MHz, CDCl₃) δ 7.30-7.10 (7H, m), 6.02 (2H, d), 4.88-4.55 (2H, m), 4.39-3.88 (4H, m), 3.83 (3H, m), 2.57-2.48 (2H, m), 1.66-1.60 (2H, m), 1.32-1.20 (36H, m), 0.87 (3H, t).

Synthesis of Compound 97—(ASP Cypionate Iodide) 5-chloro-2-(((3-cyclopentylpropanoyl)oxy) methyl)-2-methyl-2,3,3a,12b-tetrahydro-1H-dibenzo [2,3:6,7]oxepino[4,5-c]pyrrol-2-ium iodide This was synthesized employing general reaction procedure II starting from 3-cyclopentylpropanoic acid to give Compound 97 (0.83 g 84%). ¹H-NMR (300 MHz, CDCl₃) δ 7.30-7.07 (7H, m), 6.05-5.99 (2H, m), 4.88-4.73 (1H, m), 4.70-4.55 (1H, m), 4.40-3.86 (4H, m), 3.83 (3H, m), 2.60-2.59 (2H, m), 1.78-1.42 (9H, m), 1.10-1.00 (2H, m).

Synthesis of Compound 98—(ASP Cyclopentyl Acetate Iodide) 5-chloro-2-((2-cyclopentylacetoxy) methyl)-2-methyl-2,3,3a,12b-tetrahydro-1H-dibenzo [2,3:6,7]oxepino[4,5-c]pyrrol-2-ium iodide This was synthesized employing general reaction procedure II starting from 2-cyclopentylacetic acid to give Compound 98 (0.84 g 87%). ¹H-NMR (300 MHz, CDCl₃) δ 7.31-7.08 (7H, m), 6.03-5.99 (2H, m), 4.86-4.54 (2H, m), 4.38-3.88 (4H, m), 3.83 (2H, m), 2.57-2.50 (2H, m), 2.28-2.16 (1H, m), 1.86-1.76 (2H, m), 1.67-1.44 (4H, m), 1.20-1.05 (2H, m).

Synthesis of Compound 103—(ASP Oleate Iodide) (Z)-5-chloro-2-methyl-2-((oleoyloxy)methyl)-2,3,3a, 12b-tetrahydro-1H-dibenzo[2,3:6,7]oxepino[4,5-c] pyrrol-2-ium iodide This was synthesized employing general reaction procedure II starting from oleic acid to give Compound 103 (1.69 g 49%).
$^1$H-NMR (300 MHz, CDCl$_3$) δ 7.29-7.07 (7H, m), 6.02-5.99 (2H, m), 5.38-5.25 (2H, m), 4.85-4.55 (2H, m), 4.37-4.25 (1H, m), 4.22-3.90 (3H, m), 3.83 (3H, m), 2.55-2.49 (2H, m), 2.03-1.95 (4H, m), 1.77-1.67 (2H, m), 1.33-1.20 (20H, m), 0.86 (3H, t).

Synthesis of Compound 105—(ASP Adamantate Iodide) 2-((((1s,3s)-adamantane-1-carbonyl)oxy) methyl)-5-chloro-2-methyl-2,3,3a,12b-tetrahydro-1H-dibenzo[2,3:6,7]oxepino[4,5-c]pyrrol-2-ium iodide This was synthesized employing general reaction procedure II starting from adamantane carboxylic acid to give Compound 105 (2.70 g, 85%). $^1$H-NMR (300 MHz, CDCl$_3$) δ 7.30-7.22 (5H, m), 7.22-7.17 (2H, m), 5.44-5.37 (2H, m), 4.50-4.45 (1H, m), 4.33-4.25 (1H, m), 4.25-3.86 (4H, m), 2.02-1.95 (3H, m), 1.95-1.88 (6H, m), 1.73-1.66 (6H, m).

Synthesis of Compound 6—(ASP Isovalerate Iodide) 5-chloro-2-methyl-2(((3-methylbutanoyl) oxy)methyl)-2,3,3a,12b-tetrahydro-1H-dibenzo[2,3: 6,7]oxepino[4,5-c]pyrrol-2-ium iodide This was synthesized employing general reaction procedure I starting from isovaleryl chloride to give Compound 6 (0.83 g, 92%) was obtained. $^1$H-NMR (300 MHz, CDCl$_3$) δ 7.32-7.09 (14H, m), 6.04-6.01 (4H, m), 4.87-4.56 (4H, m), 4.36-3.91 (8H, m), 3.85-3.83 (6H, 2×s), 2.44-2.42 (4H, m), 2.15-2.04 (2H, m), 0.97 (12H, 2×d).

Synthesis of Compound 104—(ASP Octyldecanoate Iodide) 5-chloro-2-methyl-2-(((2-octyldecanoyl)oxy) methyl)-2,3,3a,12b-tetrahydro-1H-dibenzo[2,3:6,7] oxepino[4,5-c]pyrrol-2-ium iodide General Reaction Procedure III Step A—Synthesis of Diethyl 2,2-Dioctylmalonate To a solution of diethylmalonate (20 g, 0.125 mol) in tetrahydrofuran (500 mL) was added octyl bromide (47 mL, 0.275 mol), followed by sodium hydride (60% in mineral oil, 11 g, 0.275 mol) over 1 h. The reaction mixture was stirred at 25° C. for 3 days. A second portion of sodium hydride (5 g, 0.125 mol) and octyl bromide (15 mL, 0.086) were added and the mixture heated at reflux for 5 hours. The reaction was cooled, carefully quenched with water and then diluted with 2M HCl. The reaction mixture was extracted with ethyl acetate, dried over MgSO$_4$ and evaporated. The residue was further purified by flash column chromatography eluting with 1:1 heptane/toluene to toluene gave diethyl 2,2-dioctylmalonate (41.4 g, 86%) as a pale yellow oil. $^1$H-NMR (300 MHz, CDCl$_3$) δ 3.98 (4H, q), 1.70-1.60 (4H, m), 1.15-0.88 (30H, m), 0.69 (6H, t).

Step B—Synthesis of 2-Octyldecanoic Acid

To diethyl 2,2-dioctylmalonate (41.4 g, 0.108 mol) was added industrial methylated spirit (50 mL), followed by a solution of KOH (40 g, 0.714 mol) in water (500 mL). The reaction mixture was heated at reflux for 20 hours, poured into ice/water and made acidic with 2M HCl. The mixture was then extracted with ethyl acetate and the organic phase dried over MgSO$_4$ before evaporation of the volatiles. The residue was then heated neat at 170° C. until gas evolution had ceased (~5 h) and on cooling 2-octyldecanoic acid (26.4 g, 86%) was obtained as a yellow solid. $^1$H-NMR (300 MHz, CDCl$_3$) δ2.40-2.26 (1H, m), 1.66-1.52 (2H, m), 1.51-1.39 (2H, m), 1.35-1.18 (24H, m), 0.87 (3H, t).

Step C—Synthesis of Chloromethyl 2-Octyldecanoate

To a mixture of 2-octyldecanoic acid (12.2 g, 42.9 mmol) and water (90 mL) was added Na$_2$CO$_3$ (17.7 g, 108 mmol), tetrabutylammonium hydrogensulfate (2.8 g, 8.2 mmol), dichloromethane (180 mL) and then chloromethyl chlorosulfate (5.5 mL, 54.3 mmol). The reaction mixture was stirred for 18 h and then diluted with water (300 mL) and dichloromethane (300 mL). The organic phase was separated, dried over MgSO$_4$ and evaporated. The residue was purified on silica eluting with heptane/dichloromethane (8:1) to give chloromethyl 2-octyldecanoate (12.0 g, 84%) as a colorless oil. $^1$H-NMR (300 MHz, CDCl$_3$) δ 5.72 (2H, s), 2.43-2.33 (1H, m), 1.67-1.52 (2H, m), 1.51-1.40 (2H, m), 1.33-1.18 (24H, m), 0.86 (3H, t).

The product from this was then converted to the corresponding iodide using general reaction procedure I step C and the quaternization reaction was carried out using general reaction procedure I step D to give Compound 104 (3.09 g, 100%). $^1$H-NMR (300 MHz, CDCl$_3$) δ 7.33-7.03 (14H, m), 6.02-5.93 (4H, m), 4.74-4.57 (4H, m), 4.34-4.28 (2H, m), 4.21-3.94 (4H, m), 3.90-3.87 (6H, 2×s), 2.54-2.48 (2H, m), 1.76-1.47 (8H, m), 1.31-1.12 (48H, m), 0.88-0.84 (12H, 2×t).

Synthesis of Compound 93—((+)-ASP-Dimethyl Myristate Iodide) 5-chloro-2-(((2,2-dimethyltetradecanoyl)oxy)methyl)-2-methyl-2,3,3a,12b-tetrahydro-1H-dibenzo[2,3:6,7]oxepino[4,5-c]pyrrol-2-ium iodide To a solution of 2,2-dimethyltetradecanoic acid, synthesized above, (3.5 g, 13.6 mmol) in water (35 mL) was added Na$_2$CO$_3$ (5.8 g, 54 mmol). After 20 minutes, the reaction was cooled to 0° C. and nBu$_4$NHSO$_4$ (0.93 g, 3 mmol), dichloromethane (75 mL) and chloromethyl chlorosulfate (1.8 mL, 17.7 mmol) was added. The reaction was allowed to warm to 25° C. and stirred overnight. The reaction mixture was separated and the aqueous extracted with dichloromethane (2×100 mL). The combined organics were dried (MgSO$_4$) and concentrated in vacuo. The product was purified by column chromatography eluting with heptane to 10% dichloromethane/heptane to give the product (5.0 g, 71%). $^1$H-NMR (CDCl$_3$) δ 7.01-6.89 (3H, m), 6.71-6.66 (1H, m), 6.37 (1H, s), 5.77 (2H, s), 5.40 (1H, s), 4.04-3.90 (2H, m), 3.84-3.67 (6H, m), 3.57 (3H, s), 2.31 (3H, s), 1.59-1.49 (2H, m), 1.31-1.10 (26H, m), 0.87 (3H, t).

The product from this was then converted to the corresponding iodide using general reaction procedure I step C and the quaternization reaction was carried out using general reaction procedure I step D with (+)-Asenapine to give Compound 93 (1.93 g, 81%) as an approx 1:1 mixture of 2 conformers. $^1$H-NMR (300 MHz, CDCl$_3$) δ 7.32-7.05 (14H, m), 6.01-5.94 (4H, m), 4.78-4.59 (4H, m), 4.44-3.98 (8H, m), 3.89-3.87 (6H, m), 1.59-1.50 (4H, m), 1.34-1.11 (52H, m), 0.87 (6H, 2×t).

Compound 100—((−)-ASP-Dimethyl Myristate Iodide) 5-chloro-2-(((2,2-dimethyltetradecanoyl)oxy)methyl)-2-methyl-2,3,3a,12b-tetrahydro-1H-dibenzo[2,3:6,7]oxepino[4,5-c]pyrrol-2-ium iodide This was synthesized employing general reaction procedure II starting from 2,2-dimethyltetradecanoic acid and (−)-Asenapine to give Compound 100 (1.97 g, 85%) was obtained as an approx 1:1 mixture of 2 conformers. $^1$H-NMR (300 MHz, CDCl$_3$) δ 7.32-7.07 (14H, m), 6.01-5.94 (4H, m), 4.73-4.58 (4H, m), 4.41-3.96 (8H, m), 3.89-3.86 (6H, m), 1.59-1.56 (4H, m), 1.31-1.11 (52H, m), 0.87 (6H, 2×t).

Compound 92—(2-Methyl-2Propyl Pentanoate Iodide) 5-chloro-2-methyl-2-(((2-methyl-2-propyl-pentanoyl)oxy)methyl)-2,3,3a,12b-tetrahydro-1H-dibenzo[2,3:6,7]oxepino[4,5-c]pyrrol-2-ium iodide This was synthesized employing general reaction procedure II starting from methyl 2-methylpentanoate to give Compound 92 (1.97 g, 85%). $^1$H-NMR (300 MHz, CDCl$_3$) δ 7.31-7.04 (8H, m), 6.00-5.88 (2H, m), 4.78-4.55 (2H, m), 4.43-4.30 (1H, m), 4.22-4.08 (2H, m), 4.07-3.95 (1H, m), 3.90 (3H, m), 1.68-1.54 (2H, m), 1.53-1.40 (2H, m), 1.38-1.05 (7H, m), 0.90-0.80 (6H, m).

Compound 59—(Hexyl Carbonate Iodide) 5-chloro-2-(((hexyloxy)carbonyl)oxy)methyl)-2-methyl-2,3,3a,12b-tetrahydro-1H-dibenzo[2,3:6,7]oxepino[4,5-c]pyrrol-2-ium iodide General Reaction Procedures IV To a solution of chloromethyl chloroformate (9.6 mL, 107.7 mmol) in dichloromethane (100 mL) at 0° C. was added a solution of 1-hexanol (10 g, 97.9 mmol) and pyridine (8.7 mL, 107.7 mmol) in dichloromethane (25 mL) dropwise over 3 hours (keeping the temp at approx 0° C.). The reaction was allowed to gradually warm to 25° C. overnight. 1 M HCl (50 ml) was added to the reaction mixture and separated. The organics were washed with 1M HCl (50 mL), water (100 mL), aq satd NaHCO$_3$ (2×100 mL), brine (100 mL) and dried (MgSO$_4$) to give hexyl chloromethyl carbonate (18.53 g, 97%).

The product from this was then converted to the corresponding iodide using general reaction procedure I step C and the quaternization reaction was carried out using general reaction procedure I step D. The quaternization reaction mixture was concentrated and the resulting residue dissolved in a minimum amount of chloroform and diethyl ether was added. A precipitate was formed which was filtered and dried to give Compound 59 (2.09 g, 80%). $^1$H-NMR (300 MHz, CDCl$_3$) δ 7.32-7.04 (14H, m), 6.13-6.04 (4H, m), 4.92-4.54 (4H, m), 4.39-4.03 (8H, m), 3.87-3.84 (6H, 2×s), 1.77-1.59 (8H, m), 1.41-1.18 (12H, m), 0.90-0.86 (6H, 2×t).

Compound 109—(3-Pentanol Carbonate) 5-chloro-2-methyl-2-(pentan-3-yloxy)carbonyl)oxy)methyl)-2,3,3a,12b-tetrahydro-1H-dibenzo[2,3:6,7]oxepino[4,5-c]pyrrol-2-ium iodide This was synthesized employing general reaction procedure IV starting from iodomethyl pentan-3-yl carbonate to give Compound 109 (3.20 g, 91%). $^1$H-NMR (300 MHz, CDCl$_3$) δ 7.32-7.08 (14H, m), 6.06-6.02 (4H, 2×s), 4.87-4.53 (6H, m), 4.41-3.92 (8H, m), 3.88-3.85 (6H, 2×s), 1.72-1.59 (8H, m), 0.92-0.88 (12H, m).

Compound 112—(Diethyl Carbamate) 5-chloro-2-(((diethylcarbamoyl)oxy)methyl)-2-methyl-2,3,3a,12b-tetrahydro-1H-dibenzo[2,3:6,7]oxepino[4,5-c]pyrrol-2-ium iodide This was synthesized via iodomethyl diethyl carbamate employing general procedure IV. The reaction final mixture concentrated and the resulting residue was dissolved in a minimum amount of dichloromethane and diethyl ether added. A precipitate formed which was filtered then dissolved in dichloromethane and washed with water. The dichloromethane layer was dried and concentrated then triturated with diethyl ether to give a solid which was filtered and dried to give Compound 112 (3.10 g, 91%). $^1$H-NMR (300 MHz, CDCl$_3$) δ 7.31-7.03 (14H, m), 5.93-5.90 (4H, m), 4.82-4.49 (4H, m), 4.38-3.99 (7H, m), 3.97-3.78 (7H, m), 3.40-3.31 (8H, m), 1.24-1.13 (12H, m).

Compound 110—(Dibenzyl Carbamate) 5-chloro-2-(((dibenzylcarbamoyl)oxy)methyl)-2-methyl-2,3,3a,12b-tetrahydro-1H-dibenzo[2,3:6,7]oxepino[4,5-c]pyrrol-2-ium iodide This was synthesized via iodomethyl dibenzyl carbamate employing general procedure IV. The reaction final mixture was concentrated and the resulting residue dissolved in a minimum amount of chloroform and diethyl ether was added. A precipitate was formed which was filtered and dried to give Compound 110 (3.21 g, >100%). $^1$H-NMR (300 MHz, CDCl$_3$) δ 7.64-6.83 (34H, m), 5.98-5.89 (4H, m), 4.66-3.65 (20H, m), 3.45-3.40 (6H, 2×s).

Compound 111—(Hexyl Carbamate) 5-chloro-2-(((hexylcarbamoyl)oxy)methyl)-2-methyl-2,3,3a,12b-tetrahydro-1H-dibenzo[2,3:6,7]oxepino[4,5-c]pyrrol-2-ium iodide This was synthesized via iodomethyl hexyl carbamate employing general procedure IV. At the end of the quaternization reaction RDC4560 was filtered off and the mother liqueur concentrated. The residue was triturated with diethyl ether, filtered and the resulting solids then combined to give Compound 111 (2.58 g, 86%). $^1$H-NMR (300 MHz, CDCl$_3$) δ 7.31-7.05 (7H, m), 6.54 (NH), 5.81 (2H, m), 4.78-4.65 (1H, m), 4.64-4.49 (1H, m), 4.33-4.21 (1H, m), 4.21-4.05 (2H, m), 4.01-3.78 (1H, m), 3.79 (3H, s), 3.18 (2H, q), 1.60-1.49 (2H, m), 1.33-1.19 (6H, m), 0.84 (3H, t).

Compound 113—(Ethanolamine Acetate) 2-((((2-acetoxyethyl)carbamoyl)oxy)methyl)-5-chloro-2-methyl-2,3,3a,12b-tetrahydro-1H-dibenzo[2,3:6,7]oxepino[4,5-c]pyrrol-2-ium iodide This was synthesized employing 2-((iodomethoxy)carbonylamino)ethyl acetate (made using general procedure IV) following general procedure I step D, to give Compound 113 (1.37 g, 91%). $^1$H-NMR (300 MHz, DMSO-d$_6$) δ 7.40-7.25 (5H, m), 5.45-5.35 (2H, m), 4.40-3.85 (8H, m), 3.35-3.25 (2H, m), 1.94 (3H, s).

Compound 114—(Bis-Ethanolamine Acetate) 2-(((bis(2-acetoxyethyl)carbamoyl)oxy)methyl)-5-chloro-2-methyl-2,3,3a,12b-tetrahydro-1H-dibenzo[2,3:6,7]oxepino[4,5-c]pyrrol-2-ium iodide This was synthesized employing 2,2'-((iodomethoxy)carbonylazanediyl)bis(ethane-2,1-diyl) diacetate (made using general procedure IV) following general procedure I step D, to give Compound 114 (1.63 g, 94%).

$^1$H-NMR (300 MHz, DMSO-$d_6$) δ 7.40-7.25 (5H, 7.20-7.16 (2H, m), 5.50-5.38 (2H, m), 4.52-4.45 (1H, m), 4.28-3.85 (10H, m), 3.59-3.66 (2H, m), 3.56-3.50 (2H, m), 1.99 (3H, s), 1.96 (3H, s).

Compound 116—(Benzyl-Phenethyl Carbamate) 2-(((benzyl(phenethyl)carbamoyl)oxy)methyl)-5-chloro-2-methyl-2,3,3a,12b-tetrahydro-1H-dibenzo[2,3:6,7]oxepino[4,5-c]pyrrol-2-ium iodide This was synthesized via iodomethyl benzyl(phenethyl)carbamate employing general procedure IV. The reaction mixture was concentrated and the resulting residue dissolved in a minimum amount of chloroform and diethyl ether was added. A precipitate was formed which was filtered and dried to give Compound 116 (1.79 g, 94%). $^1$H-NMR (300 MHz, CDCl$_3$) δ 7.34-6.79 (34H, m), 5.92-5.68 (4H, m), 4.62-3.39 (26H, m), 2.96-2.79 (4H, m).

Compound 115—(O-Decyl Ethanolamine Carbamate) 5-chloro-2-((((2-(decanoyloxy)ethyl)carbamoyl)oxy)methyl)-2-methyl-2,3,3a,12b-tetrahydro-1H-dibenzo[2,3:6,7]oxepino[4,5-c]pyrrol-2-ium iodide This was synthesized via 2-((iodomethoxy)carbonylamino)ethyl decanoate employing general procedure IV. At the end of the quaternization reaction diethyl ether was added to aid precipitation. Filtration and drying gave Compound 115 (0.78 g, 64%).

$^1$H-NMR (300 MHz, CDCl$_3$) δ 7.32-7.10 (7H, m), 7.00-6.92 (1H, m), 5.85 (2H, s), 4.80-4.69 (1H, m), 4.65-4.49 (1H, m), 4.32-4.07 (5H, m), 3.97-3.82 (1H, m), 3.78 (3H, s), 3.50-3.42 (3H, m), 2.31 (2H, t), 1.65-1.49 (2H, m), 1.33-1.16 (12H, m), 0.87 (3H, t).

Example 3

Amisulpride

There are several possible conversion routes for converting the prodrug back to the parent drug. One such conversion route is outlined below. In this route, amisulpride would be released from a prodrug compound of the invention in two steps: 1. esterase cleavage of the ester/carbonate/carbamate/phosphonate bond; 2. Spontaneous release of formaldehyde under neutral and basic pH's. The scheme below shows the synthesis of such amisulpride with arrows pointing right and the expected cleavage with arrows pointing left:

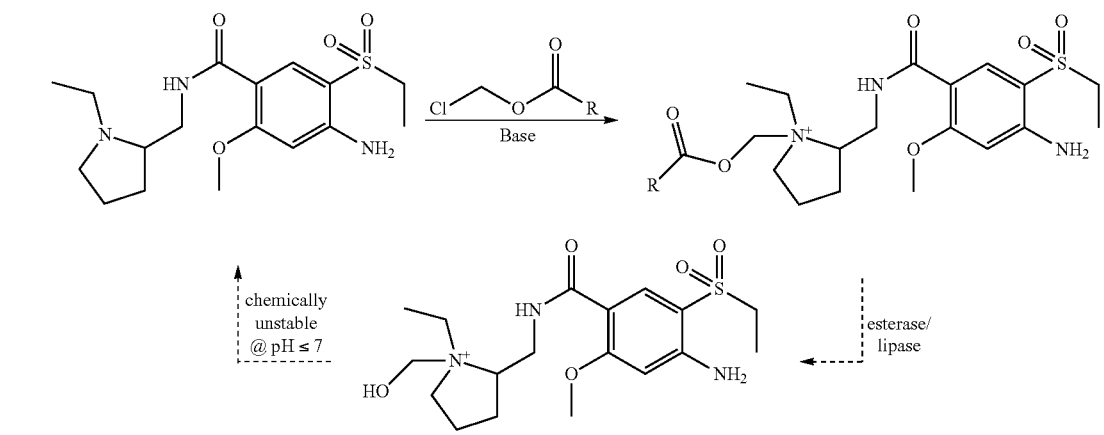

R = C1-C15 straight or branched aliphatic chain, O—(C1-C16 aliphatic chain), NH—(C1-C16 aliphatic chain), N—(C1-C16 aliphatic chain)$_2$

Example 4

Latrepirdine (Dimebon)

As discussed previously there are several possible conversion routes for converting the prodrug back to the parent drug. One such conversion route is outlined below. In this route, latrepirdine would be released from a prodrug compound of the invention in two steps: 1. esterase cleavage of the ester/carbonate/carbamate/phosphonate bond; 2. Spontaneous release of formaldehyde under neutral and basic pH's. The scheme below shows the synthesis of such latrepirdine derivatives with arrows pointing right and the expected cleavage with arrows pointing left:

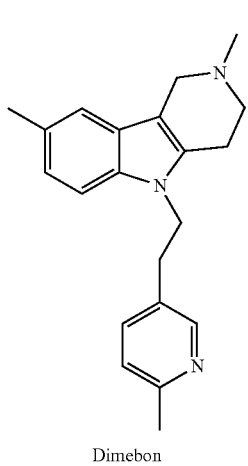

Dimebon

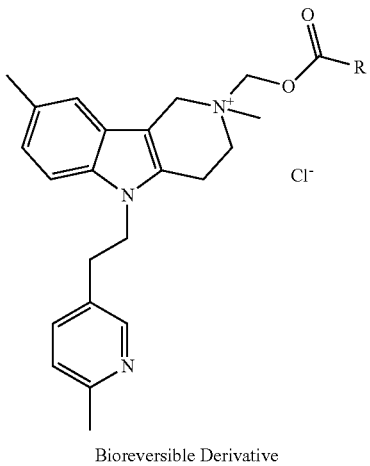

Bioreversible Derivative

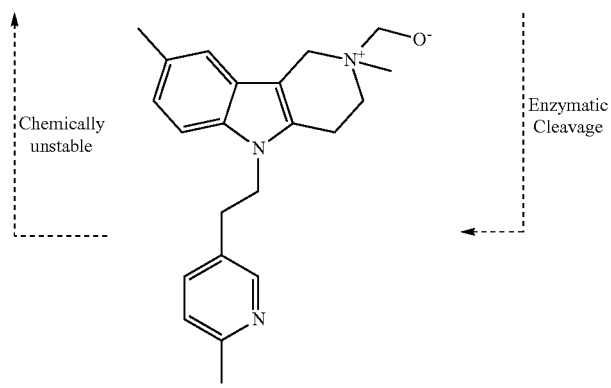

R = Aliphatic, O-Aliphatic, NH-Aliphatic, N(Aliphatic)2

Example 5

Olanzapine

The following example describes the synthesis of prodrug compounds of olanzapine having the following formulas as shown in Table 6. Unless otherwise stated, the structural formula of a compound herein is intend to represent all enantiomers, racemates and diastereomers of that compound.

Although the compounds are depicted in the table as salts with a particular counterion, these compounds are not limited to these particular salts. Although certain compounds of the invention can be conveniently prepared as the iodide salt, the iodide anion can be exchanged for another anion, as is known in the art. The compounds listed in the table can, therefore, be prepared as salts with any suitable anion or combination of anions, such as a pharmaceutically acceptable anion, including chloride, bromide, acetate, citrate, and phosphate. Similarly, Compound 56 is shown with an ammonium cation, but can be prepared with any suitable cation, preferably a pharmaceutically acceptable cation. Thus, the depiction of the compounds in the table is intended to include salts with any suitable counterion.

TABLE 6
| Olanzapine Compound # | Structure |
|---|---|
| 1 | 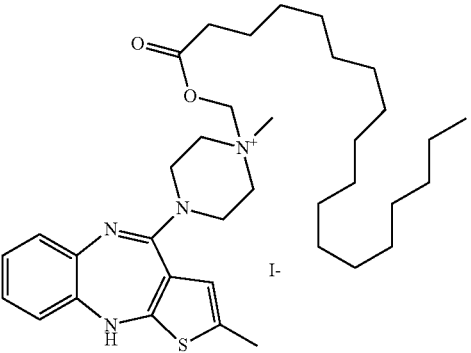 [SMILES: CCCCCCCCCCCCCCCCCC(=O)OC[N+]1(C)CCN(C2=Nc3ccccc3Nc3sc(C)cc32)CC1 ; [I-]] |
| 2 | 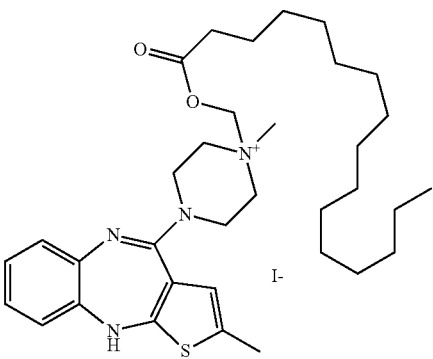 [SMILES: CCCCCCCCCCCCCCCC(=O)OC[N+]1(C)CCN(C2=Nc3ccccc3Nc3sc(C)cc32)CC1 ; [I-]] |
| 3 | 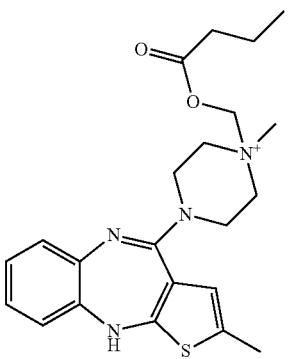 [SMILES: CCCC(=O)OC[N+]1(C)CCN(C2=Nc3ccccc3Nc3sc(C)cc32)CC1] |
| 4 | 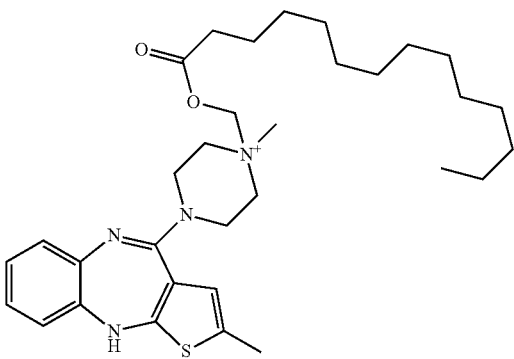 [SMILES: CCCCCCCCCCCCCC(=O)OC[N+]1(C)CCN(C2=Nc3ccccc3Nc3sc(C)cc32)CC1] |

TABLE 6-continued
| Olanzapine Compound # | Structure |
|---|---|
| 5 | 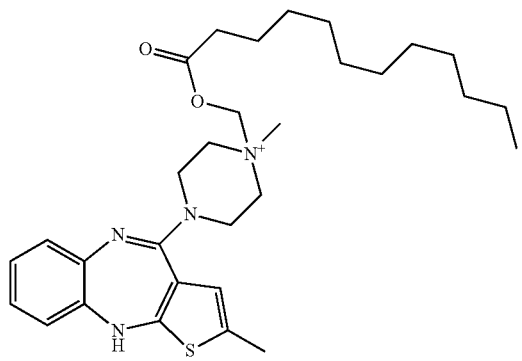 [SMILES: CCCCCCCCCCCC(=O)OC[N+]1(C)CCN(C2=Nc3ccccc3Nc3sc(C)cc32)CC1] |
| 6 | 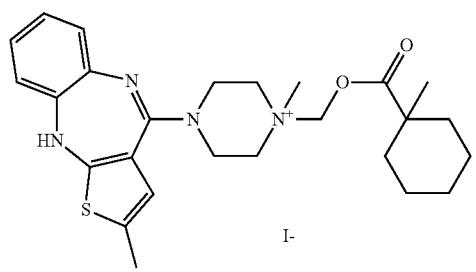 [SMILES: Cc1cc2c(s1)Nc1ccccc1N=C2N1CC[N+](C)(COC(=O)C2(C)CCCCC2)CC1 ; [I-]] |
| 7 | 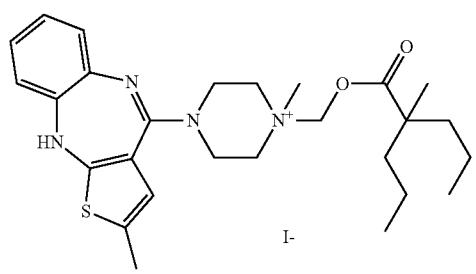 [SMILES: CCCC(C)(CCC)C(=O)OC[N+]1(C)CCN(C2=Nc3ccccc3Nc3sc(C)cc32)CC1 ; [I-]] |
| 8 | 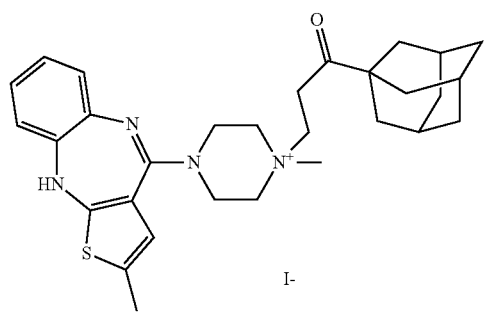 [SMILES: Cc1cc2c(s1)Nc1ccccc1N=C2N1CC[N+](C)(CCC(=O)C23CC4CC(CC(C4)C2)C3)CC1 ; [I-]] |
| 9 | 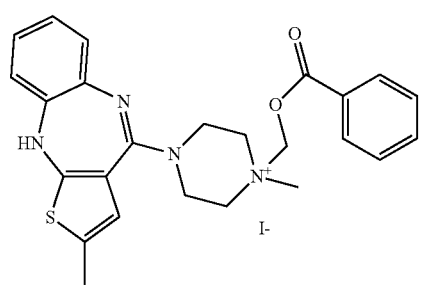 [SMILES: Cc1cc2c(s1)Nc1ccccc1N=C2N1CC[N+](C)(COC(=O)c2ccccc2)CC1 ; [I-]] |

TABLE 6-continued
| Olanzapine Compound # | Structure |
|---|---|
| 10 | 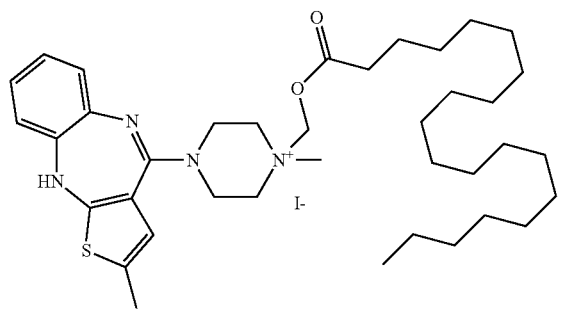 [SMILES: CCCCCCCCCCCCCCCCCCCC(=O)OC[N+]1(C)CCN(C2=Nc3ccccc3Nc3sc(C)cc32)CC1 ; [I-]] |
| 11 | 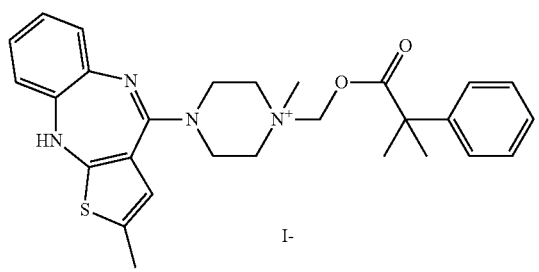 [SMILES: Cc1cc2c(s1)Nc1ccccc1N=C2N1CC[N+](C)(COC(=O)C(C)(C)c2ccccc2)CC1 ; [I-]] |
| 12 | 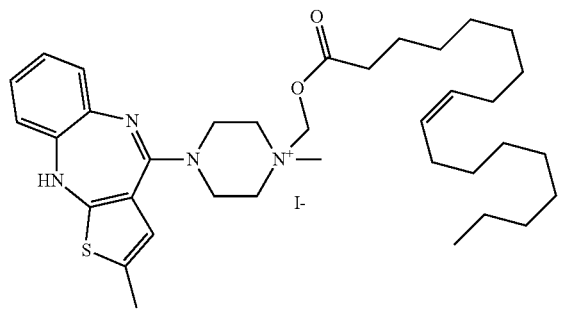 [SMILES: CCCCCCCC/C=C\CCCCCCCC(=O)OC[N+]1(C)CCN(C2=Nc3ccccc3Nc3sc(C)cc32)CC1 ; [I-]] |
| 13 | 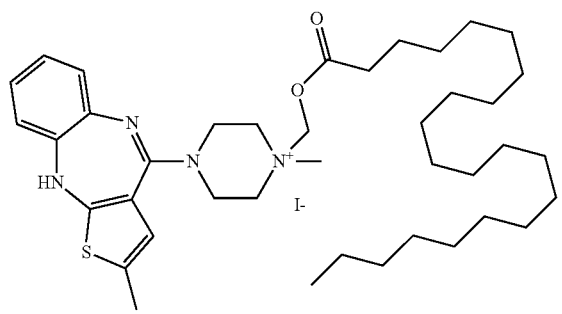 [SMILES: CCCCCCCCCCCCCCCCCCCCCC(=O)OC[N+]1(C)CCN(C2=Nc3ccccc3Nc3sc(C)cc32)CC1 ; [I-]] |
| 14 | 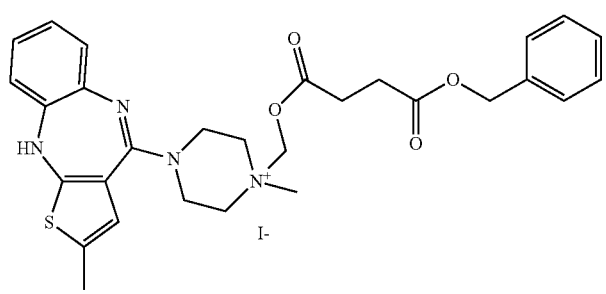 [SMILES: Cc1cc2c(s1)Nc1ccccc1N=C2N1CC[N+](C)(COC(=O)CCC(=O)OCc2ccccc2)CC1 ; [I-]] |

TABLE 6-continued

| Olanzapine Compound # | Structure |
|---|---|
| 15 | (structure with olanzapine core, N-methylated piperazinium with CH₂-O-C(=O)-CH(CH₃)-O-C(=O)-CH(CH₃)-O-C(=O)-phenyl substituent; I⁻ counterion) |
| 16 | (structure with olanzapine core, N-methylated piperazinium with CH₂-O-C(=O)-CH(CH₃)-O-C(=O)-phenyl substituent; I⁻ counterion) |
| 17 | (structure with olanzapine core, N-methylated piperazinium with CH₂-O-C(=O)-C(CH₃)(CH₂CH₃)CH₃ substituent) |
| 18 | (structure with olanzapine core, N-methylated piperazinium with CH₂-O-C(=O)-C(CH₃)₂-(long alkyl chain) substituent) |

| Olanzapine Compound # | Structure |
| --- | --- |
| 19 | 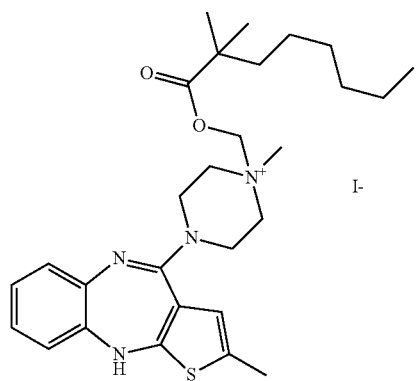 [SMILES: CCCCCCC(C)(C)C(=O)OC[N+]1(C)CCN(C2=Nc3ccccc3Nc3sc(C)cc32)CC1 ; [I-]] |
| 20 | 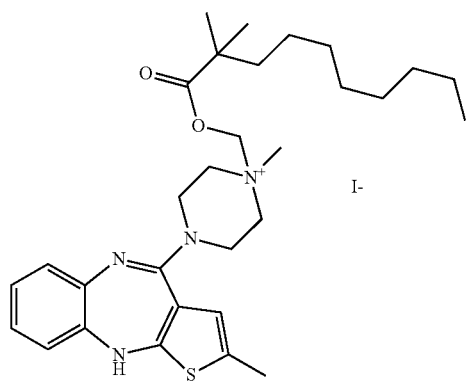 [SMILES: CCCCCCCCC(C)(C)C(=O)OC[N+]1(C)CCN(C2=Nc3ccccc3Nc3sc(C)cc32)CC1 ; [I-]] |
| 21 | 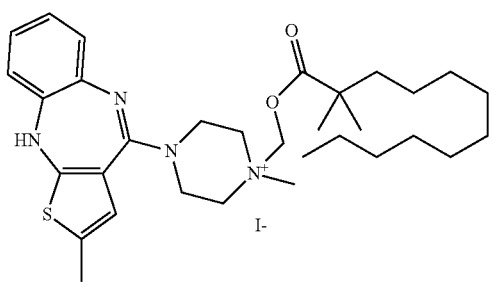 [SMILES: CCCCCCCCCCC(C)(C)C(=O)OC[N+]1(C)CCN(C2=Nc3ccccc3Nc3sc(C)cc32)CC1 ; [I-]] |
| 22 | 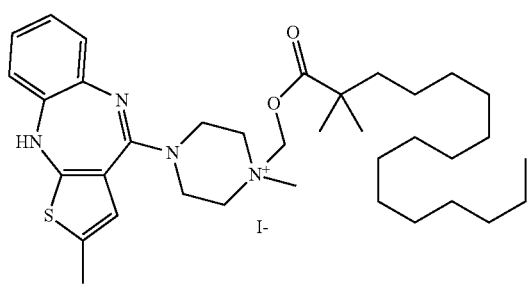 [SMILES: CCCCCCCCCCCCCCC(C)(C)C(=O)OC[N+]1(C)CCN(C2=Nc3ccccc3Nc3sc(C)cc32)CC1 ; [I-]] |

TABLE 6-continued
| Olanzapine Compound # | Structure |
|---|---|
| 23 | 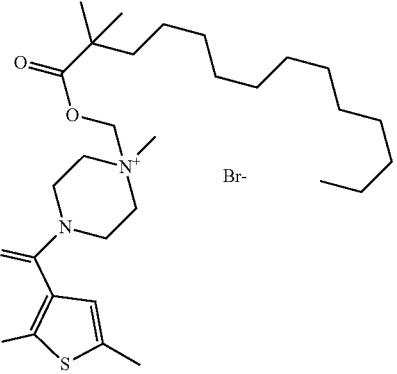 |
| 24 | 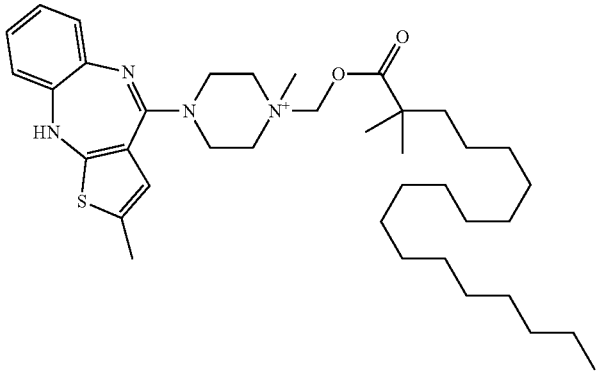 [SMILES: CCCCCCCCCCCCCCCCC(C)(C)C(=O)OC[N+]1(C)CCN(C2=Nc3ccccc3Nc3sc(C)cc32)CC1] |
| 25 | 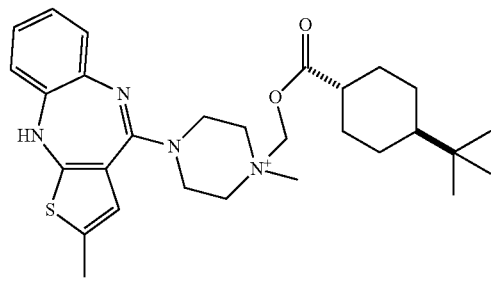 |
| 26 | 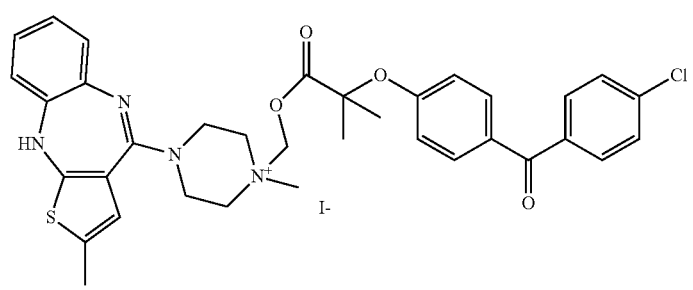 [SMILES: Cc1cc2c(s1)Nc1ccccc1N=C2N1CC[N+](C)(COC(=O)C(C)(C)Oc2ccc(C(=O)c3ccc(Cl)cc3)cc2)CC1 ; [I-]] |

TABLE 6-continued
| Olanzapine Compound # | Structure |
|---|---|
| 27 | 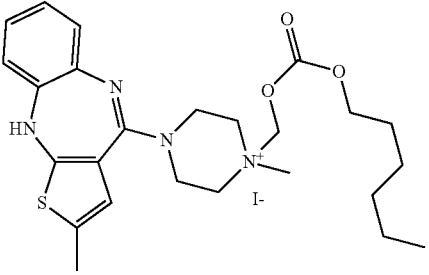 [SMILES: CCCCCCOC(=O)OC[N+]1(C)CCN(C2=Nc3ccccc3Nc3sc(C)cc32)CC1 ; [I-]] |
| 28 | 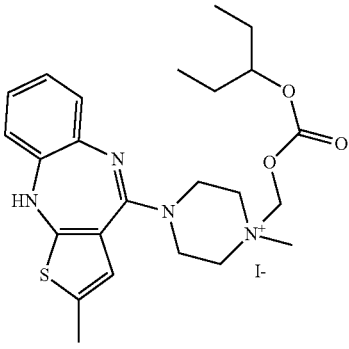 [SMILES: CCC(CC)OC(=O)OC[N+]1(C)CCN(C2=Nc3ccccc3Nc3sc(C)cc32)CC1 ; [I-]] |
| 29 | 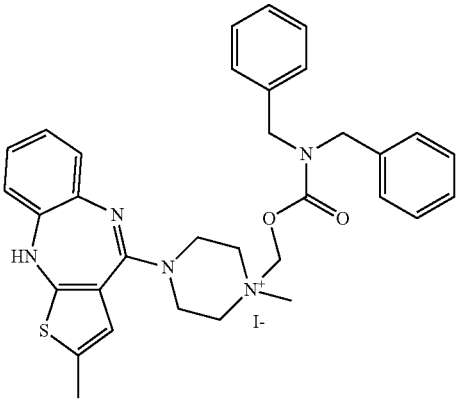 [SMILES: Cc1cc2c(s1)Nc1ccccc1N=C2N1CC[N+](C)(COC(=O)N(Cc2ccccc2)Cc2ccccc2)CC1 ; [I-]] |
| 30 | 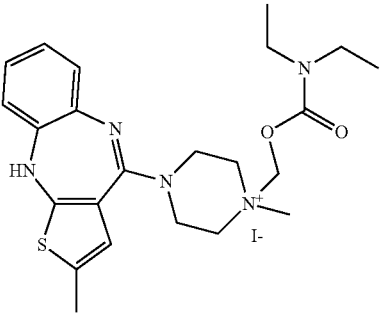 [SMILES: CCN(CC)C(=O)OC[N+]1(C)CCN(C2=Nc3ccccc3Nc3sc(C)cc32)CC1 ; [I-]] |

TABLE 6-continued
| Olanzapine Compound # | Structure |
|---|---|
| 31 | 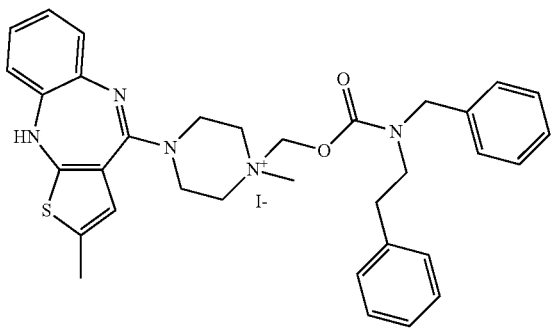 [SMILES: Cc1cc2c(s1)Nc1ccccc1N=C2N1CC[N+](C)(COC(=O)N(CCc2ccccc2)Cc2ccccc2)CC1 ; [I-]] |
| 32 | 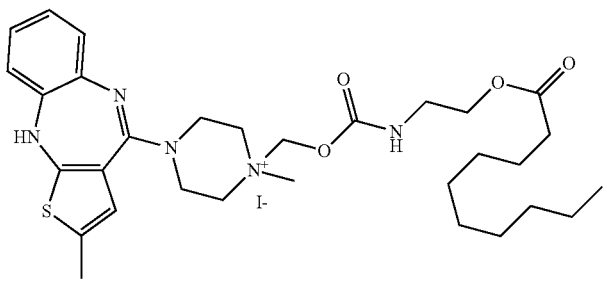 [SMILES: CCCCCCCCCC(=O)OCCNC(=O)OC[N+]1(C)CCN(C2=Nc3ccccc3Nc3sc(C)cc32)CC1 ; [I-]] |
| 33 | 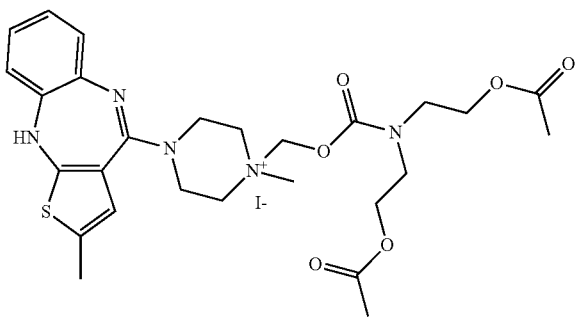 [SMILES: CC(=O)OCCN(CCOC(C)=O)C(=O)OC[N+]1(C)CCN(C2=Nc3ccccc3Nc3sc(C)cc32)CC1 ; [I-]] |
| 34 | 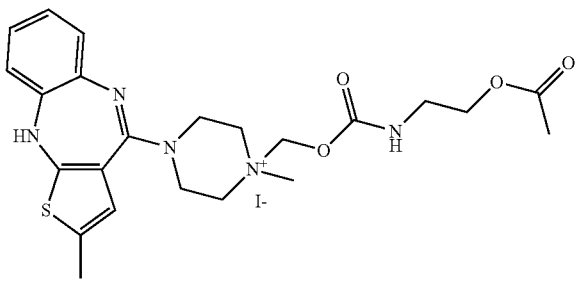 [SMILES: CC(=O)OCCNC(=O)OC[N+]1(C)CCN(C2=Nc3ccccc3Nc3sc(C)cc32)CC1 ; [I-]] |
| 35 | 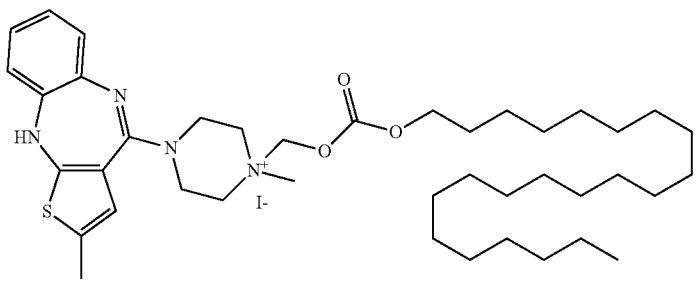 [SMILES: CCCCCCCCCCCCCCCCCCCCCCOC(=O)OC[N+]1(C)CCN(C2=Nc3ccccc3Nc3sc(C)cc32)CC1 ; [I-]] |

TABLE 6-continued

| Olanzapine Compound # | Structure |
|---|---|
| 36 | 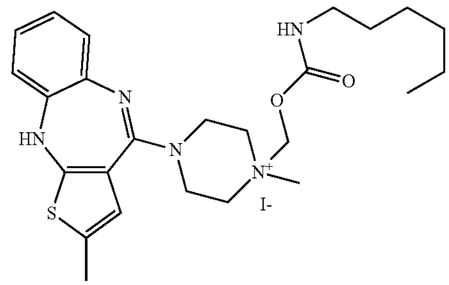 [SMILES: CCCCCCNC(=O)OC[N+]1(C)CCN(C2=Nc3ccccc3Nc3sc(C)cc32)CC1 ; [I-]] |
| 37 | 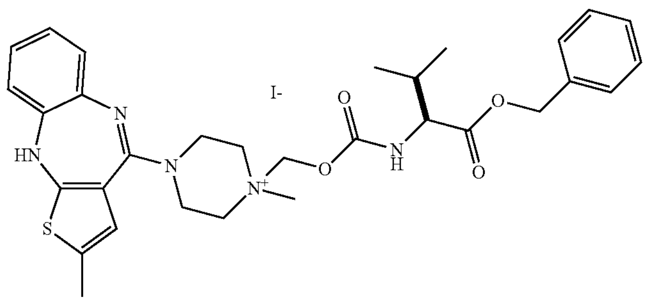 [SMILES: Cc1cc2c(s1)Nc1ccccc1N=C2N1CC[N+](C)(COC(=O)N[C@H](C(=O)OCc2ccccc2)C(C)C)CC1 ; [I-]] |
| 38 | 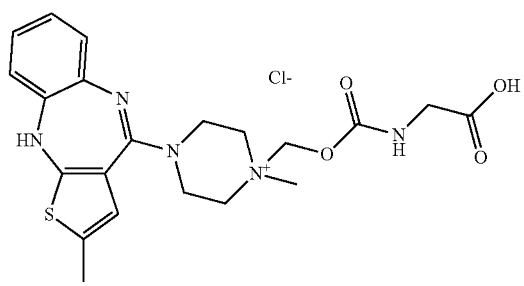 [SMILES: Cc1cc2c(s1)Nc1ccccc1N=C2N1CC[N+](C)(COC(=O)NCC(=O)O)CC1 ; [Cl-]] |
| 39 | 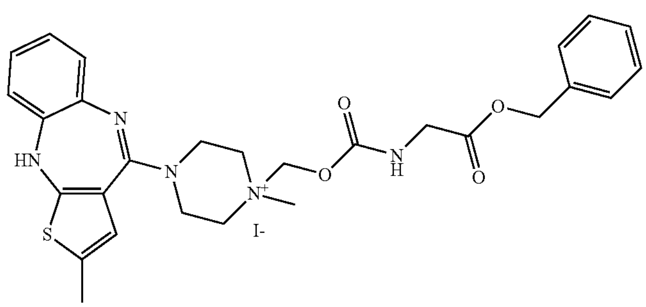 [SMILES: Cc1cc2c(s1)Nc1ccccc1N=C2N1CC[N+](C)(COC(=O)NCC(=O)OCc2ccccc2)CC1 ; [I-]] |
| 40 | 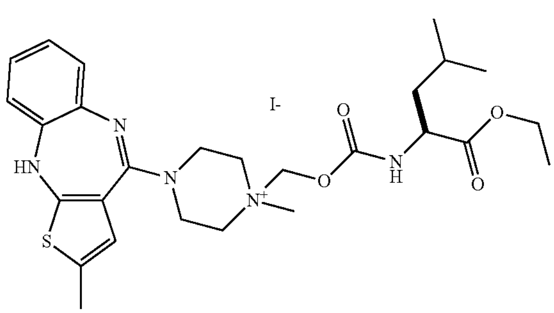 [SMILES: CCOC(=O)[C@H](CC(C)C)NC(=O)OC[N+]1(C)CCN(C2=Nc3ccccc3Nc3sc(C)cc32)CC1 ; [I-]] |

TABLE 6-continued
| Olanzapine Compound # | Structure |
|---|---|
| 41 | 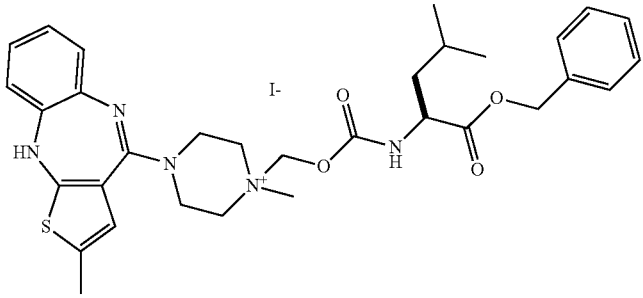 [SMILES: Cc1cc2c(s1)Nc1ccccc1N=C2N1CC[N+](C)(COC(=O)N[C@@H](CC(C)C)C(=O)OCc2ccccc2)CC1 ; [I-]] |
| 42 | 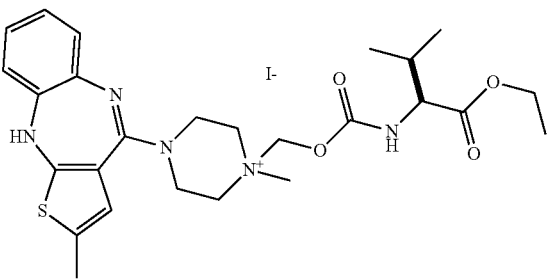 [SMILES: CCOC(=O)[C@@H](NC(=O)OC[N+]1(C)CCN(C2=Nc3ccccc3Nc3sc(C)cc32)CC1)C(C)C ; [I-]] |
| 43 | 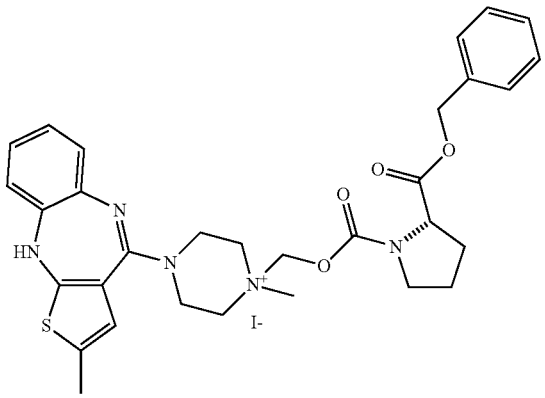 [SMILES: Cc1cc2c(s1)Nc1ccccc1N=C2N1CC[N+](C)(COC(=O)N2CCC[C@H]2C(=O)OCc2ccccc2)CC1 ; [I-]] |
| 44 | 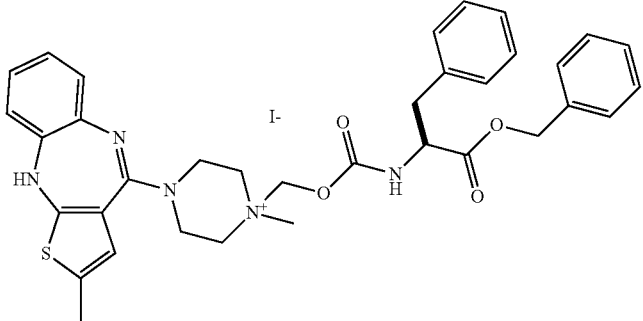 [SMILES: Cc1cc2c(s1)Nc1ccccc1N=C2N1CC[N+](C)(COC(=O)N[C@@H](Cc2ccccc2)C(=O)OCc2ccccc2)CC1 ; [I-]] |

TABLE 6-continued

| Olanzapine Compound # | Structure |
|---|---|
| 45 | 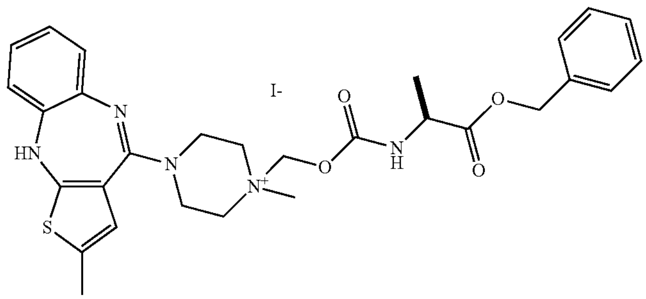 [SMILES: Cc1cc2c(s1)Nc1ccccc1N=C2N1CC[N+](C)(COC(=O)N[C@@H](C)C(=O)OCc2ccccc2)CC1 ; [I-]] |
| 46 | 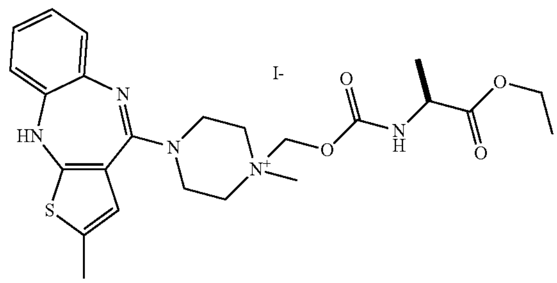 [SMILES: CCOC(=O)[C@H](C)NC(=O)OC[N+]1(C)CCN(C2=Nc3ccccc3Nc3sc(C)cc32)CC1 ; [I-]] |
| 47 | 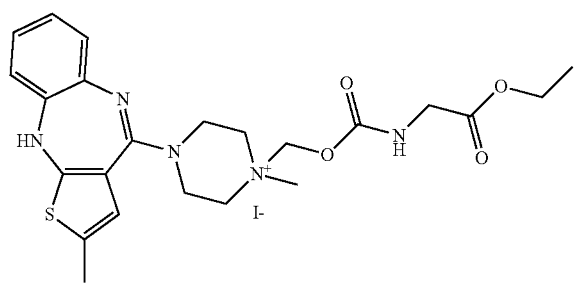 [SMILES: CCOC(=O)CNC(=O)OC[N+]1(C)CCN(C2=Nc3ccccc3Nc3sc(C)cc32)CC1 ; [I-]] |
| 48 | 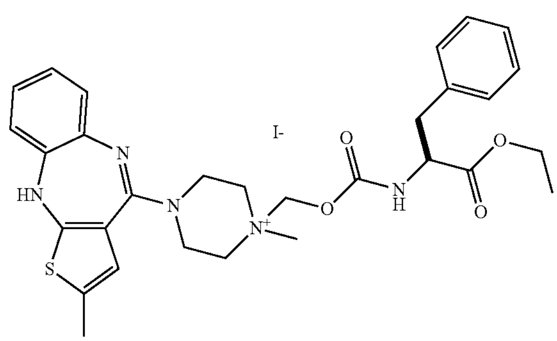 [SMILES: CCOC(=O)[C@H](Cc1ccccc1)NC(=O)OC[N+]1(C)CCN(C2=Nc3ccccc3Nc3sc(C)cc32)CC1 ; [I-]] |
| 49 | 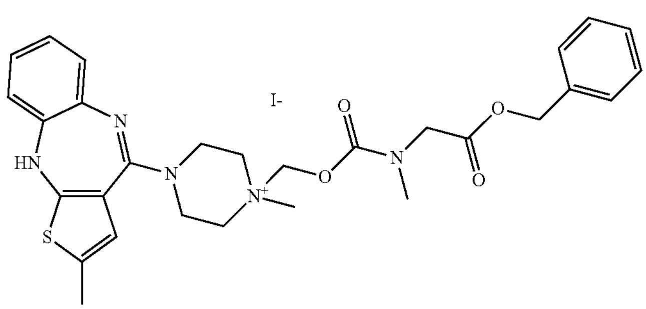 [SMILES: Cc1cc2c(s1)Nc1ccccc1N=C2N1CC[N+](C)(COC(=O)N(C)CC(=O)OCc2ccccc2)CC1 ; [I-]] |

TABLE 6-continued
| Olanzapine Compound # | Structure |
|---|---|
| 50 | 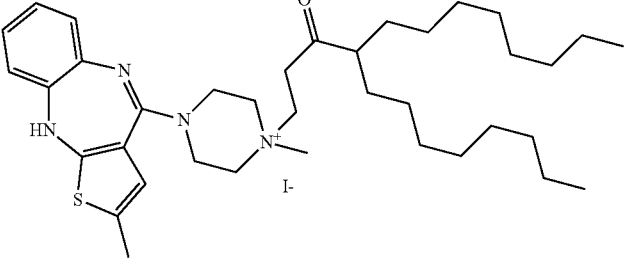 |
| 51 | 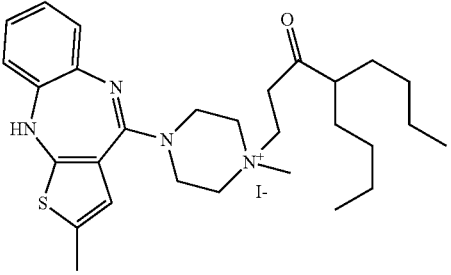 [SMILES: CCCCC(CCCC)C(=O)CC[N+]1(C)CCN(C2=Nc3ccccc3Nc3sc(C)cc32)CC1 ; [I-]] |
| 52 | 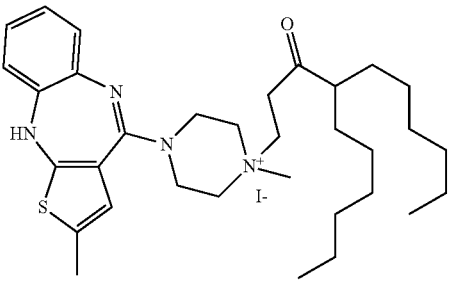 [SMILES: CCCCCCC(CCCCCC)C(=O)CC[N+]1(C)CCN(C2=Nc3ccccc3Nc3sc(C)cc32)CC1 ; [I-]] |
| 53 | 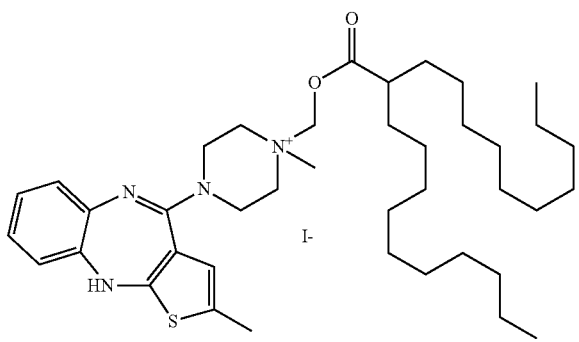 [SMILES: CCCCCCCCCCC(CCCCCCCCCC)C(=O)OC[N+]1(C)CCN(C2=Nc3ccccc3Nc3sc(C)cc32)CC1 ; [I-]] |

| Olanzapine Compound # | Structure |
| --- | --- |
| 54 | 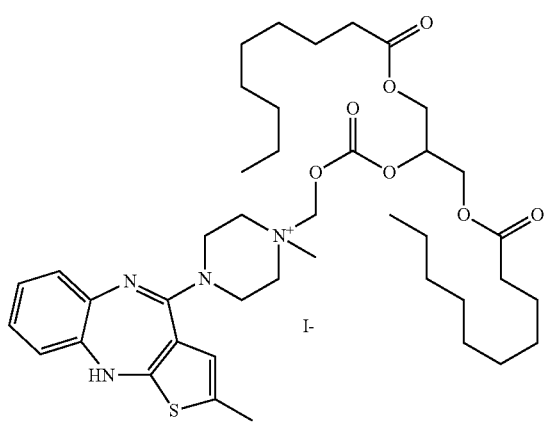 [SMILES: CCCCCCCCCC(=O)OCC(COC(=O)CCCCCCCC)OC(=O)OC[N+]1(C)CCN(C2=Nc3ccccc3Nc3sc(C)cc32)CC1 ; [I-]] |
| 55 | 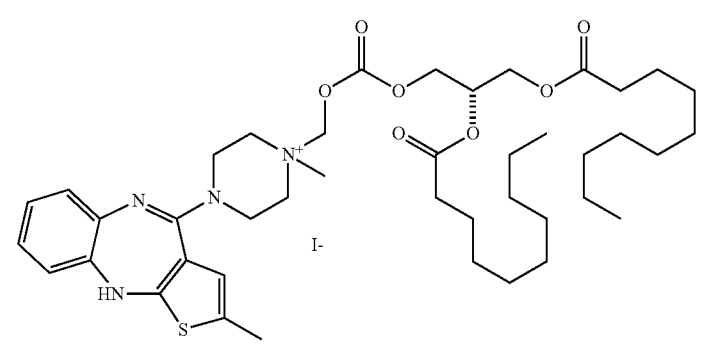 [SMILES: CCCCCCCCCC(=O)OC[C@@H](COC(=O)OC[N+]1(C)CCN(C2=Nc3ccccc3Nc3sc(C)cc32)CC1)OC(=O)CCCCCCCCC ; [I-]] |
| 56 | 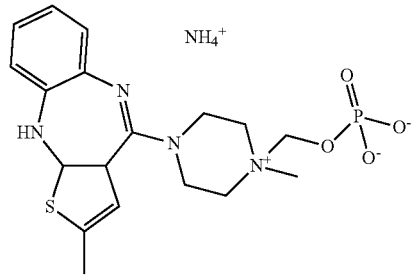 [SMILES: CC1=CC2C(N3CC[N+](C)(COP(=O)([O-])[O-])CC3)=Nc3ccccc3NC2S1 ; [NH4+]] |
| 57 | 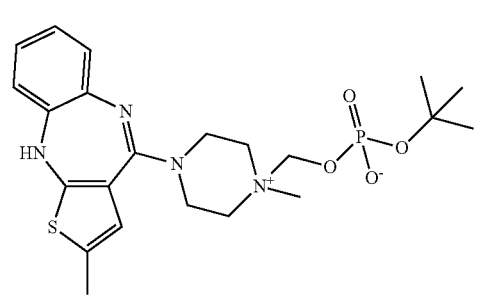 [SMILES: Cc1cc2c(s1)Nc1ccccc1N=C2N1CC[N+](C)(COP(=O)([O-])OC(C)(C)C)CC1] |

TABLE 6-continued
| Olanzapine Compound # | Structure |
|---|---|
| 58 | 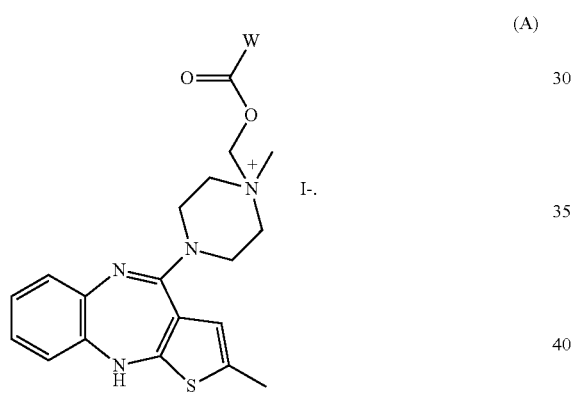 |
Synthesis of Olanzapine Prodrug Compounds
The following example describes the synthesis of prodrug compounds of olanzapine having the Formula A:
(A)
Compound 1 1-methyl-4-(2-methyl-10H-benzo[b]thieno[2,3-e][1,4]diazepin-4-yl)-1-((stearoyloxy)methyl)piperazin-1-ium iodide (Compound 1)
Quaternization Reaction
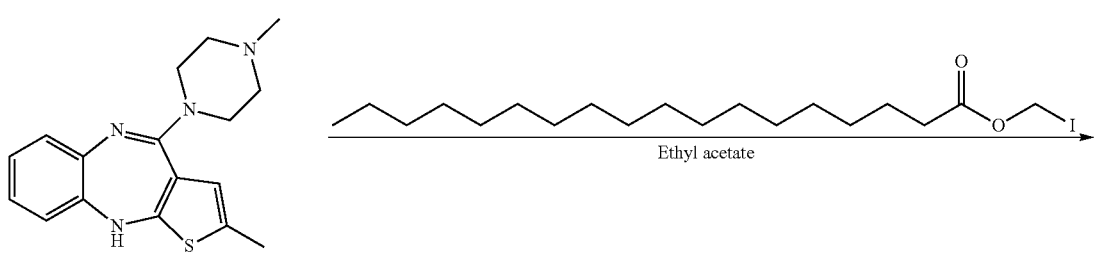

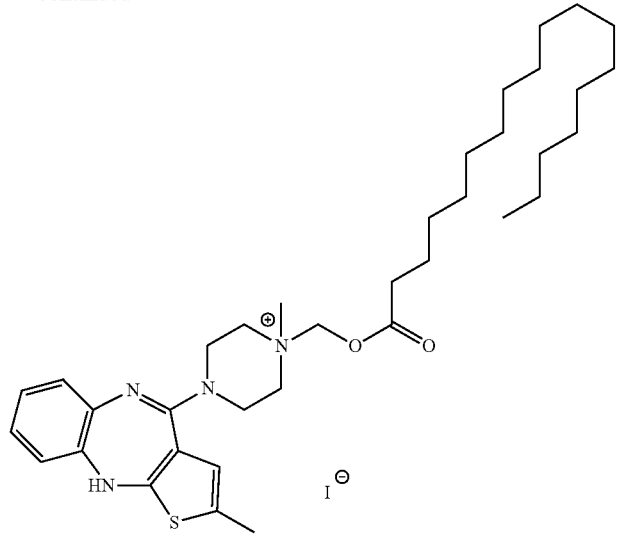

To a stirred solution of olanzapine (1 g, 3.20 mmol) in ethyl acetate (70 mL) was added a suspension of the iodomethyl stearate (1.426 g, 3.361 mmol) in ethyl acetate (30 mL) as is synthesized in Example 1. The resultant solution was stirred at room temperature overnight. The precipitate was collected by filtration, washed with ethyl acetate (3×10 mL), hexane (2×10 mL) and dried under vacuum to give Compound 1 (1.76 g) as a yellow solid. $^1$H-NMR (CDCl$_3$) δ 7.02-6.89 (3H, m), 6.72 (1H, d), 6.37 (1H, s), 5.80 (2H, s), 5.54 (1H, s), 4.02-3.90 (2H, m), 3.83-3.63 (6H, m), 3.53 (3H, s), 2.51 (2H, t), 2.31 (3H, s), 1.69-1.56 (2H, m), 1.31-1.22 (28H, m), 0.87 (3H, t).

Compounds 2-9 were synthesized according to the general method for Compound 1 using the appropriate acid (starting from step A of Example 1) or acid chloride (starting from Step B of Example 1) in place of stearic acid or stearyl chloride

Compound 2 1-methyl-4-(2-methyl-10H-benzo[b]thieno[2,3-e][1,4]diazepin-4-yl)-1-((palmitoyloxy)methyl)piperazin-1-ium iodide (Compound 2)

This compound was synthesized employing palmitoyl chloride. The product precipitated from the reaction mixture to give Compound 2 (1.23 g).

$^1$H-NMR (CDCl$_3$) δ 7.02-6.89 (3H, m), 6.67 (1H, dd), 6.35 (1H, s), 5.83 (2H, s), 5.32 (1H, s), 4.03-3.96 (2H, m), 3.79-3.71 (6H, m), 3.56 (3H, s), 2.52 (2H, t), 2.31 (3H, s), 1.64 (2H, t), 1.39-1.21 (24H, m), 0.87 (3H, t).

Compound 3 1-((butyryloxy)methyl)-1-methyl-4-(2-methyl-10H-benzo[b]thieno[2,3-e][1,4]diazepin-4-yl)piperazin-1-ium iodide (Compound 3)

This compound was synthesized employing butyryl chloride instead of stearyl chloride. The final precipitated from the reaction mixture to give Compound 3 (1.8 g).

$^1$H-NMR (d$_6$-DMSO) δ 6.77-6.88 (m, 3H), 6.65-6.69 (m, 1H), 6.37 (s, 1H), 5.42 (s, 2H), 3.78-3.89 (m, 2H), 3.45-3.60 (m, 6H), 3.16 (s, 3H), 2.51 (t, 2H), 2.25 (s, 3H), 1.57 (st, 2H), 0.89 (t, 3H).

Compound 4 1-methyl-4-(2-methyl-10H-benzo[b]thieno[2,3-e][1,4]diazepin-4-yl)-1-((tetradecanoyloxy)methyl)piperazin-1-ium iodide (Compound 4)

This compound was synthesized employing myristoyl chloride. The final product precipitated from the reaction mixture to give Compound 4 (2.83 g, 93%).

$^1$H-NMR (CDCl$_3$) δ 7.00-6.92 (3H, m), 6.73 (1H, d), 6.37 (1H, s), 5.80 (2H, s), 5.62 (NH), 4.01-3.93 (2H, m), 3.82-3.69 (6H, m), 3.53 (3H, s), 2.51 (2H, t), 2.31 (3H, s), 1.75-1.58 (2H, m), 1.32-1.20 (22H, m), 0.87 (3H, t).

Compound 5 1-((dodecanoyloxy)methyl)-1-methyl-4-(2-methyl-10H-benzo[b]thieno[2,3-e][1,4]diazepin-4-yl)piperazin-1-ium iodide (Compound 5)

This compound was synthesized employing lauroyl chloride. The final product precipitated from the reaction mixture to give Compound 5 (1.12 g, 67%).

$^1$H-NMR (300 MHz, d$_6$-DMSO) δ 7.73 (1H, s), 6.86-6.77 (3H, m), 6.69-6.65 91H, m), 6.37 (1H, s), 5.41 (2H, s), 3.85-3.76 (2H, m), 3.56-3.45 (6H, m), 3.16 (3H, s), 2.53 (2H, t), 2.25 (3H, s), 1.58-1.52 (2H, m), 1.29-1.18 (10H, m), 0.82 (3H, t).

Compound 6 1-methyl-4-(2-methyl-10H-benzo[b]thieno[2,3-e][1,4]diazepin-4-yl)-1-(((1-methylcyclohexanecarbonyl)oxy)methyl)piperazin-1-ium iodide (Compound 6)

This was compound was synthesized employing 1-methylcyclohexanecarbonyl chloride. The final product precipitated from the reaction mixture to give Compound 6 (2.56 g, 96%). $^1$H-NMR (CDCl$_3$) δ 7.00-6.90 (3H, m), 6.69 (1H, d), 6.37 (1H, s), 5.80 (2H, s), 5.47 (NH), 4.07-3.96 (2H, m), 3.83-3.72 (6H, m), 3.57 (3H, s), 2.31 (3H, s), 2.01-1.92 (2H, m), 1.78-1.50 (6H, m), 1.50-1.20 (9H, m).

Compound 7 1-Methyl-4-(2-methyl-10H-benzo[b]thieno[2,3-e][1,4]diazepin-4-yl)-1-4(2-methyl-2-propylpentanoyl)oxy)methyl)piperazin-1-ium iodide (Compound 7)

This compound was synthesized employing 2-methyl-2-propylpentanoic acid. The final product precipitated from the reaction mixture to give Compound 7 (2.12 g, 78%).
$^1$H-NMR (DMSO-d6) δ 6.88-6.69 (3H, m), 6.70-6.65 (1H, m), 6.34 (1H, s), 5.43 (2H, s), 3.90-3.80 (2H, m), 3.60-3.49 (6H, m), 3.18 (3H, s), 2.25 (3H, s), 1.59 (2H, dt), 1.43 (2H, dt), 1.30-1.05 (7H, m), 0.83 (6H, t).

Compound 8 1-((((3r,5r,7r)-Adamantane-1-carbonyl)oxy)methyl)-1-methyl-4-(2-methyl-10H-benzo[b]thieno[2,3-e][1,4]diazepin-4-yl)piperazin-1-ium iodide (Compound 8)

This compound was synthesized employing 1-adamantane carboxylic acid. The final product precipitated from the reaction mixture to give Compound 8 (2.12 g, 78%).
$^1$H-NMR (300 MHz, d$_6$-DMSO) δ 7.75 (NH), 6.88-6.78 (3H, m), 6.68-6.65 (1H, m), 6.35 (2H, s), 3.90-3.78 (2H, m), 3.60-3.42 (6H, m), 3.18 (3H, s), 2.25 (3H, s), 1.97-1.90 (3H, m), 1.90-1.85 (6H, m), 1.68-1.58 (6H, m).

Compound 9 1-((Benzoyloxy)methyl)-1-methyl-4-(2-methyl-10H-benzo[b]thieno[2,3-e][1,4]diazepin-4-yl)piperazin-1-ium iodide (Compound 9)

This compound was synthesized employing benzoyl chloride. The final product precipitated from the reaction mixture to give Compound 9 (2.97 g, 85%).
$^1$H-NMR (300 MHz, d$_6$-DMSO) δ 8.12 (2H, d), 7.75 (2H, t), 7.57 (2H, t), 6.87-6.76 (3H, m), 6.71-6.64 (1H, m), 6.40 (1H, s), 5.66 (2H, s), 3.92-3.83 (2H, m), 3.76-3.51 (6H, m), 3.30 (3H, s), 2.26 (3H, s).

Compound 10 1-((eicosanoyloxy)methyl)-1-methyl-4-(2-methyl-10H-benzo[b]thieno[2,3-e][1,4]diazepin-4-yl)piperazin-1-ium iodide (Compound 10)

To a suspension of arachidic acid (8 g, 25.6 mmol) in water (80 mL) was added Na$_2$CO$_3$ (10.9 g, 102.4 mmol). After 20 minutes, the reaction was cooled to 0° C. and nBu$_4$NHSO$_4$ (1.74 g, 5.12 mmol), dichloromethane (160 mL) and chloromethyl chlorosulfate (3.4 mL, 33.3 mmol) were added. The reaction was allowed to warm to 25° C. and stirred overnight. The reaction mixture was separated and the aqueous extracted with dichloromethane (2×200 mL). The combined organics were dried (MgSO$_4$) and concentrated in vacuo. The product was purified by column chromatography eluting with heptane to 10% dichloromethane/heptane to give the product (6.54 g, 71%).
The iodomethyl ester formation and quaternization reactions were then carried out as described in steps C and D from the synthesis of Compound 1 using arachidoyl chloride instead of stearoyl chloride. The final product precipitated from the reaction mixture to give Compound 10 (2.77 g, 87%).
$^1$H-NMR (300 MHz, CDCl$_3$) δ 7.01-6.89 (3H, m), 6.70 (1H, d), 6.37 (1H, s), 5.81 (2H, s), 5.48 (1H, s), 4.03-3.91 (2H, m), 3.79-3.70 (6H, m), 3.54 (3H, s), 2.51 (2H, t), 2.31 (3H, s), 1.69-1.61 (2H, m), 1.35-1.19 (35H, m), 0.87 (3H, t). Compounds 11-18 were prepared using the general method described for the preparation of Compound 10 employing the appropriate acid or acid chloride.

Compound 11 1-Methyl-4-(2-methyl-10H-benzo[b]thieno[2,3-e][1,4]diazepin-4-yl)-1-(((2-methyl-2-phenylpropanoyl)oxy)methyl)piperazin-1-ium iodide (Compound 11)

This compound was synthesized employing 2-methyl-2-phenylpropanoic acid. The product precipitated from the reaction to give Compound 11 (2.29 g, 66%).
$^1$H-NMR (300 MHz, d$_6$-DMSO) δ 7.74 (NH), 7.42-7.31 (4H, m), 7.30-7.22 (1H, m), 7.88-7.78 (3H, m), 6.70-6.65 (1H, m), 6.31 (1H, s), 5.42 (2H, s), 3.80-3.72 (2H, m), 3.54-3.30 (6H, m), 3.01 (3H, s), 2.26 (3H, s), 1.60 (6H, s).

Compound 12 (Z)-1-Methyl-4-(2-methyl-10H-benzo[b]thieno[2,3-e][1,4]diazepin-4-yl)-1-((oleoyloxy)methyl)piperazin-1-ium iodide (Compound 12)

This compound was synthesized employing oleic acid. The final product precipitated from the reaction to give Compound 12 (2.28 g, 65%).
$^1$H-NMR (300 MHz, CDCl$_3$) δ 7.00-6.90 (3H, m), 6.71-6.66 (1H, m), 6.36 (1H, s), 5.82 (2H, s), 5.45-5.30 (3H, m), 4.04-3.93 (2H, m), 3.80-3.68 (6H, m), 3.54 (3H, s), 2.52 (2H, t), 2.31 (3H, s), 2.05-1.95 (4H, m), 1.69-1.58 (2H, m), 1.35-1.20 (12H, m), 0.87 (3H, t).

Compound 13 1-((docosanoyloxy)methyl)-1-methyl-4-(2-methyl-10H-benzo[b]thieno[2,3-e][1,4]diazepin-4-yl)piperazin-1-ium iodide (Compound 13)

This compound was synthesized employing docosanoic acid. The product precipitated from the reaction to give Compound 13 (4.21 g, 84%).
$^1$H-NMR (300 MHz, CDCl$_3$) δ 7.00-6.92 (3H, m), 6.71-6.66 (1H, m), 6.36 (1H, s), 5.82 (2H, s), 5.43 (NH), 4.01-3.93 (2H, m), 3.82-3.68 (6H, m), 3.54 (3H, s), 2.51 (2H, t), 2.31 (3H, s), 1.67-1.60 (2H, m), 1.32-1.22 (36H, m), 0.87 (3H, t).

Compound 14 1-(((4-(benzyloxy)-4-oxobutanoyl)oxy)methyl)-1-methyl-4-(2-methyl-10H-benzo[b]thieno[2,3-e][1,4]diazepin-4-yl)piperazin-1-ium iodide (Compound 14)

Synthesis of 4-(benzyloxy)-4-oxobutanoic acid

Succinic anhydride (7 g, 70.0 mmol) and benzyl alcohol (8.7 mL, 83.9 mmol) were combined in dichloromethane (350 mL) at 0° C. and DMAP (0.85 g, 7.0 mmol) was added portionwise. The reaction was allowed to gradually warm to 25° C. and stirred for 4 days. The reaction mixture was washed with 1M HCl (3×200 mL) then water (300 mL). The organic phases were then extracted with aq saturated NaHCO3 (3×300 mL). This was then acidified with conc HCl until pH 1 resulting in a solid precipitating which was filtered then dissolved in dichloromethane. The dichloromethane was dried (MgSO$_4$) and concentrated in vacuo to give 4-(benzyloxy)-4-oxobutanoic acid (10.36 g, 71%).
$^1$H-NMR (300 MHz, CDCl$_3$) δ 7.41-7.29 (5H, m), 5.15 (2H, s), 2.74-2.63 (4H, m).
Compound 14 was synthesized employing 4-(benzyloxy)-4-oxobutanoic acid. The product precipitated from the reaction to give Compound 14 (1.80 g, 85%).
$^1$H-NMR (300 MHz, CDCl$_3$) δ 7.39-7.27 (5H, m), 7.02-6.95 (3H, m), 6.72 (1H, d), 6.38 (1H, s), 5.89 (2H, s), 5.12 (2H, s), 4.02-3.64 (8H, m), 3.40 (3H, s), 2.79 (4H, s), 2.32 (3H, s).

Compound 15 1-((((S)-2-(((S)-2-(benzoyloxy)propanoyl)oxy)propanoyl)oxy)methyl)-1-methyl-4-(2-methyl-10H-benzo[b]thieno[2,3-e][1,4]diazepin-4-yl)piperazin-1-ium iodide (Compound 15)

This compound was synthesized employing (S)-1-(S)-1-(1-oxopropan-2-yloxy)-1-oxopropan-2-yl benzoic acid. The final product precipitated from the reaction to give Compound 15 (0.28 g, 15%). $^1$H-NMR (300 MHz, CDCl$_3$) δ 8.04 (2H, d), 8.60 (1H, t), 7.45 (2H, t), 6.93-7.08 (3H, m), 6.75-6.80 (m, 1H), 6.43 (1H, s), 6.01 (1H, d), 5.90 (1H, d), 5.28 (1H, q), 5.06 (1H, q), 3.95-4.15 (4H, m), 3.70-3.95 (4H, m), 3.47 (3H, s), 3.08 (NH), 2.26 (3H, s), 1.69 (3H, d), 1.61 (3H, d).

Compound 16 (S)-1-(((2-(benzoyloxy)propanoyl) oxy)methyl)-1-methyl-4-(2-methyl-10H-benzo[b] thieno[2,3-e][1,4]diazepin-4-yl)piperazin-1-ium iodide (Compound 16)

This compound was synthesized employing (S)-1-(1-oxopropan-2-yl)benzoic acid. The final product precipitated from the reaction to give Compound 16 (0.9 g, 36%). $^1$H-NMR (300 MHz, CDCl$_3$) δ 8.03 (2H, d), 7.62 (1H, t), 7.47 (2H, t), 6.91-7.05 (3H, m), 6.79 (1H, d), 6.40 (1H, s), 6.01 (2H, dd), 5.15 (1H, q), 3.72-4.05 (8H, m), 3.46 (3H, s), 2.30 (3H, s), 1.72 (3H, d).

Compound 17 1-(((2,2-Dimethylbutanoyl)oxy) methyl)-1-methyl-4-(2-methyl-10H-benzo[b]thieno [2,3-e][1,4]diazepin-4-yl)piperazin-1-ium iodide (Compound 17)

This compound was synthesized employing 2,2-dimethylbutyryl chloride. The product precipitated from the reaction mixture to give Compound 17 (2.27 g).
$^1$H-NMR (CDCl$_3$) δ 7.02-6.93 (3H, m), 6.67 (1H, d), 6.35 (1H, s), 5.81 (2H, s), 5.27 (1H, s), 4.03-3.95 (2H, m), 3.83-3.72 (6H, m), 3.58 (3H, s), 2.32 (3H, s), 1.65-1.61 (2H, m), 1.21 (9H, s), 0.83 (3H, t).

Compound 18 1-(((2,2-dimethyltetradecanoyl)oxy) methyl)-1-methyl-4-(2-methyl-10H-benzo[b]thieno [2,3-e][1,4]diazepin-4-yl)piperazin-1-ium iodide (Compound 18)

A. Synthesis of methyl 2,2-dimethyltetradecanoate

To a stirred solution of diisopropylamine (6.90 mL, 49.0 mmol) in THF (50 mL) under Ar (g) at −7° C. was added n-BuLi (2.3M in hexanes, 21.3 mL, 49.0 mmol) dropwise via a dropping funnel keeping the temp. between 0° C. and 5° C. The reaction was stirred at −7° C. for 30 mins. And then cooled to −78° C. Methyl isobutyrate (5.61 mL, 49.0 mmol) was added and the reaction stirred at −78° C. for 1.5 hours. 1-iodododecane (13.05 g, 44.1 mmol) in THF (10 mL) was added dropwise via a dropping funnel keeping the temperature below −70° C. A further 40 mL THF was added over mins. to aid stirring. After complete addition the reaction was stirred at −78° C. for approx. 2 hours and then allowed to slowly warm to room temp. overnight. The reaction was quenched with sat. aq. NH$_4$Cl (100 mL) and diluted with ethyl acetate (100 mL). The aqueous layer was extracted with ethyl acetate (2×50 mL) and the combined organics washed with brine (50 mL) and dried over MgSO$_4$. After filtration, the volatiles were removed. The reaction was repeated in a similar manner using 15.05 mL (131.27 mmol) of methyl isobutyrate. The two crude batches were combined and purified by silica chromatography eluting heptane to 50% DCM/heptane to give methyl 2,2-dimethyl myristate (31.7 g).

B. Synthesis of 2,2-dimethyltetradecanoic acid

To a stirred solution of methyl 2,2-dimethyltetradecanoate (31.7 g, 117.2 mmol) in ethanol (234 mL) was added 2M NaOH (117 mL, 234.4 mmol). The reaction was stirred at room temperature overnight. NaOH (4.69 g, 117 mmol) was added and the reaction heated at 50° C. for 24 hours. NaOH (4.69 g, 117 mmol) was added and the reaction heated to 100° C. for 4 hours and then cooled to room temperature. 140 mL 4M HCl was added to acidify. ethyl acetate (200 mL) was added and the layers separated. The aqueous was extracted with ethyl acetate (2×100 mL) and the combined organics concentrated in vacuo. The residue was partitioned between ethyl acetate (200 mL) and brine (100 mL). The organic layer was washed with brine (50 mL) and dried over MgSO$_4$. After filtration, the volatiles were removed to give 2,2-dimethyltetradecanoic acid (26.9 g).

C. Synthesis of Compound 18

This compound was synthesized employing the general procedure of Compound 10 employing 2,2-dimethyltetradecanoic acid. The final product precipitated from the reaction mixture to give Compound 18 (1.84 g). $^1$H-NMR (CDCl$_3$) δ 7.01-6.89 (3H, m), 6.71-6.66 (1H, m), 6.37 (1H, s), 5.77 (2H, s), 5.40 (1H, s), 4.04-3.90 (2H, m), 3.84-3.67 (6H, m), 3.57 (3H, s), 2.31 (3H, s), 1.59-1.49 (2H, m), 1.31-1.10 (26H, m), 0.87 (3H, t).
Olanzapine Compounds 19-24 were prepared using the general method of Compound 18, using the appropriate iodoalkane in place of 1-iodododecane.

Compound 19 1-(((2,2-dimethyloctanoyl)oxy) methyl)-1-methyl-4-(2-methyl-10H-benzo[b]thieno [2,3-e][1,4]diazepin-4-yl)piperazin-1-ium iodide (Compound 19)

This compound was synthesized via 2,2-dimethyloctanoic acid. The final product precipitated from the reaction mixture to give Compound 19 (2.5 g, 83%).
$^1$H-NMR (DMSO-d$_6$) δ 7.74 (NH), 6.88-6.76 (3H, m), 6.70-6.63 (1H, m), 6.35 (1H, s), 5.42 (2H, s), 3.90-3.75 (2H, m), 3.60-3.44 (6H, m), 3.17 (3H, s), 2.25 (3H, s), 1.54-1.46 (2H, m), 1.28-1.10 (14H, m), 0.81 (3H, t).

Compound 20 1-(((2,2-dimethyldecanoyl)oxy) methyl)-1-methyl-4-(2-methyl-10H-benzo[b]thieno [2,3-e][1,4]diazepin-4-yl)piperazin-1-ium iodide (Compound 20)

This compound was synthesized via 2,2-dimethyldecanoic acid. The final product precipitated from the reaction mixture to give Compound 20 (2.8 g, 90%).
$^1$H-NMR (DMSO-d$_6$) δ 7.74 (NH), 6.88-6.75 (3H, m), 6.70-6.63 (1H, m), 6.35 (s, 1H), 5.42 (s, 2H), 3.89-3.78 (2H, m), 3.60-3.45 (6H, m), 3.18 (3H, s), 2.25 (s, 3H), 1.56-1.48 (2H, m), 1.29-1.11 (16H, m), 0.81 (3H, t).

Compound 21 1-(((2,2-dimethyldodecanoyl)oxy) methyl)-1-methyl-4-(2-methyl-10H-benzo[b]thieno [2,3-e][1,4]diazepin-4-yl)piperazin-1-ium iodide (Compound 21)

This compound was synthesized via 2,2-dimethyldodecanoic acid. The final product precipitated from the reaction mixture to give Compound 21 (1.5 g, 69%).
$^1$H-NMR (CDCl$_3$) δ 7.00-6.90 (3H, m), 6.71-6.66 (1H, m), 6.37 (1H, s), 5.77 (2H, s), 5.40 (1H, s), 4.05-3.90 (2H, m), 3.80-3.67 (6H, m), 3.57 (3H, s), 2.31 (3H, s), 1.58-1.50 (2H, m), 1.30-1.10 (16H, m), 0.87 (3H, t).

Compound 22 1-(((2,2-dimethylhexadecanoyl)oxy)
methyl)-1-methyl-4-(2-methyl-10H-benzo[b]thieno
[2,3-e][1,4]diazepin-4-yl)piperazin-1-ium iodide
(Compound 22)

This compound was synthesized via 2,2-dimethylhexadecanoic acid. The final product precipitated from the reaction mixture to give Compound 22 (1.92 g, 82%).
$^1$H-NMR (CDCl$_3$) δ 7.00-6.90 (3H, m), 6.67-6.62 (1H, m), 6.34 (1H, s), 5.80 (2H, s), 5.22 (NH), 4.02-3.95 (2H, m), 3.81-3.70 (6H, m), 3.57 (3H, s), 2.31 (3H, s), 1.52-1.60 (2H, m), 1.30-1.13 (30H, m), 0.87 (3H, t).

Compound 23 1-(((2,2-dimethyltetradecanoyl)oxy)
methyl)-1-methyl-4-(2-methyl-10H-benzo[b]thieno
[2,3-e][1,4]diazepin-4-yl)piperazin-1-ium bromide
(Compound 23)

This compound was synthesized via 2,2-dimethyloctadecanoic acid. NaI was replaced with NaBr. The final product precipitated from the reaction mixture to give Compound 23 (1.28 g, 59%).
$^1$H-NMR (CDCl$_3$) δ 7.02-6.90 (3H, m), 6.63 (1H, d), 6.30 (1H, s), 5.89 (2H, s), 5.21 (NH), 4.03-3.95 (2H, m), 3.85-3.68 (6H, m), 3.58 (3H, s), 2.31 (3H, s), 1.60-1.52 (2H, m), 1.32-1.14 (26H, m), 0.87 (3H, t).

Compound 24—1-(((2,2-dimethyloctadecanoyl)oxy)
methyl)-1-methyl-4-(2-methyl-10H-benzo[b]thieno
[2,3-e][1,4]diazepin-4-yl)piperazin-1-ium iodide
(Compound 24)

This compound was synthesized via 2,2-dimethyloctadecanoic acid. The final product precipitated from the reaction mixture to give Compound 24 (2.91 g, 92%).
$^1$H-NMR (CDCl$_3$) δ 7.00-6.92 (3H, m), 6.71-6.66 (1H, m), 6.36 (1H, s), 5.78 (2H, s), 5.44 (NH), 4.06-3.95 (2H, m), 3.81-3.70 (6H, m), 3.55 (3H, s), 2.31 (3H, s), 1.58-1.50 (2H, m), 1.30-1.12 (34H, m), 0.87 (3H, t).

Compound 25 1-((((1r,4r)-4-(tert-butyl)cyclohexanecarbonyl)oxy)methyl)-1-methyl-4-(2-methyl-10H-benzo[b]thieno[2,3-e][1,4]diazepin-4-yl)piperazin-1-ium iodide (Compound 25)

This compound was synthesized via the general method of Compound 10 using 4-tert-butylcyclohexanecarboxylic acid. The final product precipitated from the reaction mixture to give Compound 25 (2.81 g, 84%). $^1$H-NMR (300 MHz, CDCl$_3$) δ 7.01-6.89 (3H, m), 6.94 (1H, d), 6.32 (1H, s), 5.84 (2H, s), 5.12 (1H, s), 4.05-3.99 (2H, m), 3.75-3.66 (6H, m), 3.58 (3H, s), 02.41-2.33 (1H, m), 2.32 (3H, s), 2.07-2.01 (2H, m), 1.78-1.72 (2H, m), 1.43-1.33 (2H, m), 1.03-0.92 (3H, m), 0.81 (9H, s).

Compound 26 1-(((2-(4-(4-chlorobenzoyl)phenoxy)-
2-methylpropanoyl)oxy)methyl)-1-methyl-4-(2-
methyl-10H-benzo[b]thieno[2,3-e][1,4]diazepin-4-
yl)piperazin-1-ium iodide (Compound 26)

This compound was prepared using the general method of Compound 10 employing 2-[4-(4-Chlorobenzoyl)-phenoxy]-2-methylpropionic acid. The quaternization reaction was conducted in cyclopropyl methyl ether. The final product precipitated from the reaction and was purified by dissolution in a minimum amount of dichloromethane followed by precipitation with ethyl acetate to give Compound 26 (2.08 g, 57%). $^1$H-NMR (300 MHz, CDCl$_3$) δ 7.78 (2H, d), 7.71 (2H, d), 7.01-6.89 (5H, m), 6.81-6.62 (1H, m), 6.33 (1H, s), 6.04 (2H, s), 5.39 (1H, br s), 4.06-3.92 (2H, m), 3.79-3.59 (6H, m), 3.44 (3H, s), 2.29 (3H, s), 1.74 (6H, s).

Compound 27 1-((((Hexyloxy)carbonyl)oxy)
methyl)-1-methyl-4-(2-methyl-10H-benzo[b]thieno
[2,3-e][1,4]diazepin-4-yl)piperazin-1-ium iodide
(Compound 27)

To a solution of chloromethyl chloroformate (9.6 mL, 107.7 mmol) in dichloromethane (100 mL) at 0° C. was added a solution of 1-hexanol (10 g, 97.9 mmol) and pyridine (8.7 mL, 107.7 mmol) in dichloromethane (25 mL) dropwise over 3 hours (keeping the temp at approx 0° C.). The reaction was allowed to gradually warm to 25° C. overnight. 1 M HCl (50 ml) was added to the reaction mixture and separated. The organics were washed with 1M HCl (50 mL), water (100 mL), aq satd NaHCO$_3$ (2×100 mL), brine (100 mL) and dried (MgSO$_4$) to give hexyl chloromethyl carbonate (18.53 g, 97%).
Compound 27 was prepared via steps C and D (General Procedures, Example 1) of the general method of Compound 1 using hexyl chloromethyl carbonate. The product precipitated from the reaction and was re-triturated by dissolving in a minimum amount of dichloromethane and precipitated with diethyl ether to give Compound 28 (2.13 g, 86%).
$^1$H-NMR (300 MHz, CDCl$_3$) δ 7.04-6.92 (3H, m), 6.66 (1H, d), 6.37 (1H, s), 5.92 (2H, s), 5.29 (1H, s), 4.25 (2H, t), 4.08-3.94 (2H, m), 3.88-3.69 (6H, m), 3.56 (3H, s), 2.32 (3H, s), 1.77-1.51 (4H, m), 1.43-1.26 (4H, m), 0.90 (3H, t).
Olanzapine Compounds 28-49 were prepared using the general method of Compound 27 using the appropriate carbonate or carbamate in place of hexyl chloromethyl carbonate.

Compound 28 1-Methyl-4-(2-methyl-10H-benzo[b]
thieno[2,3-e][1,4]diazepin-4-yl)-1-((((pentan-3-
yloxy)carbonyl)oxy)methyl)piperazin-1-ium iodide
(Compound 28)

This compound was synthesized via iodomethyl pentan-3-yl carbonate. The final product precipitated from the reaction mixture to give Compound 28 (2.93 g, 87%).
$^1$H-NMR (300 MHz, d$_6$-DMSO) δ 7.73 (1H, s), 6.85-6.78 (3H, m), 6.69-6.64 (1H, m), 6.37 (1H, s), 5.45 (2H, s), 4.64-4.56 (1H, m), 3.88-3.79 (2H, m), 3.56-3.48 (6H, m), 3.18 (3H, s), 2.25 (3H, s), 1.69-1.53 (4H, m), 0.85 (6H, t).

Compound 29 1-(((dibenzylcarbamoyl)oxy)methyl)-
1-methyl-4-(2-methyl-10H-benzo[b]thieno[2,3-e][1,
4]diazepin-4-yl)piperazin-1-ium iodide (Compound
29)

This compound was synthesized via iodomethyl dibenzyl carbamate. The product precipitated from the reaction and was purified by trituration with diethyl ether/dichloromethane, 1:2 to give Compound 29 (2.29 g, 79%).
$^1$H-NMR (300 MHz, d$_6$-DMSO) δ 7.73 (1H, s), 7.38-7.22 (8H, m), 6.87-6.78 (4H, m), 6.68-6.64 (1H, m), 6.34 (1H, s), 5.44 (2H, s), 4.53 (4H, s), 3.81-3.75 (2H, m), 3.53-3.31 (6H, m), 2.99 (3H, s), 2.26 (3H, s).

Compound 30 1-(((Diethylcarbamoyl)oxy)methyl)-
1-methyl-4-(2-methyl-10H-benzo[b]thieno[2,3-e][1,
4]diazepin-4-yl)piperazin-1-ium iodide (Compound
30)

This compound was synthesized via iodomethyl diethyl carbamate. The final product precipitated from the reaction mixture to give Compound 30 (3.10 g, 95%).

¹H-NMR (300 MHz, d₆-DMSO) δ 7.73 (1H, s), 6.86-6.79 (2H, m), 6.69-6.61 (1H, m), 6.37 (1H, s), 5.39 (2H, s), 3.61-3.46 (6H, m), 3.29-3.21 (4H, m), 3.14 (3H, s), 2.25 (3H, s), 1.14-1.01 (6H, m).

Compound 31 1-(((Benzyl(phenethyl)carbamoyl)oxy)methyl)-1-methyl-4-(2-methyl-10H-benzo[b]thieno[2,3-e][1,4]diazepin-4-yl)piperazin-1-ium iodide (Compound 31)

This compound was synthesized via iodomethyl benzyl (phenethyl)carbamate. The final product precipitated from the reaction mixture to give Compound 31 (2.04 g, 93%) as a 1:1 mixture of diastereoisomers. ¹H-NMR (300 MHz, CDCl₃) δ 7.39-7.11 (20H, m), 7.04-6.88 (6H, m), 6.69 (1H, d), 6.61 (1H, d), 6.30 (2H, d), 5.77 (2H, s), 5.69 (2H, s), 5.37 (1H, s), 5.16 (1H, s), 4.53 (2H, s), 4.43 (2H, s), 3.97-3.33 (20H, m), 3.13 (3H, s), 3.03 (3H, s), 2.90 (2H, t), 2.79 (2H, t), 2.31 (6H, s).

Compound 32 1-((((2-(Decanoyloxy)ethyl)carbamoyl)oxy)methyl)-1-methyl-4-(2-methyl-10H-benzo[b]thieno[2,3-e][1,4]diazepin-4-yl)piperazin-1-ium iodide (Compound 32)

This compound was synthesized via 2-((iodomethoxy)carbonylamino)ethyl decanoate. The final product precipitated from the reaction mixture and was re-triturated from diethyl ether to give Compound 32 (0.79 g, 63%). ¹H-NMR (400 MHz, CDCl₃) δ 7.01-6.90 (3H, m), 6.71 (1H, d), 6.33 (1H, s), 5.64 (2H, s), 5.52 (NH), 4.18 (2H, dd), 4.00-3.92 (2H, m), 3.71-3.62 (6H, m), 3.51 (3H, s), 3.42 (2H, dd), 2.36-2.29 (5H, m), 1.62-1.52 (2H, m), 1.31-1.18 (m, 12H), 0.86 (3H, t).

Compound 33 1-(((bis(2-acetoxyethyl)carbamoyl)oxy)methyl)-1-methyl-4-(2-methyl-10H-benzo[b]thieno[2,3-e][1,4]diazepin-4-yl)piperazin-1-ium iodide (Compound 33)

This compound was synthesized via 2,2'-((iodomethoxy)carbonylazanediyl)bis(ethane-2,1-diyl)diacetate. The final product precipitated from the reaction mixture to give Compound 33 (1.46 g, 89%).
¹H-NMR (300 MHz, DMSO-d₆) δ 7.74 (NH), 6.86-6.77 (3H, m), 6.70-6.65 (1H, m), 6.38 (1H, s), 5.41 (2H, s), 4.08-4.01 (4H, m), 4.87-4.79 (2H, m), 4.61-4.46 (10H, m), 3.17 (3H, s), 2.25 (3H, s), 2.00 (3H, s), 1.96 (3H, s).

Compound 34 1-((((2-Acetoxyethyl)carbamoyl)oxy)methyl)-1-methyl-4-(2-methyl-10H-benzo[b]thieno[2,3-e][1,4]diazepin-4-yl)piperazin-1-ium iodide (Compound 34)

This compound was synthesized via 2-((iodomethoxy)carbonylamino)ethyl acetate. The final product precipitated from the reaction mixture to give Compound 34 (1.40 g, 97%). ¹H-NMR (300 MHz, DMSO-d₆) δ 8.11 (NH, t), 7.73 (NH, s), 6.88-6.78 (3H, m), 6.70-6.64 (1H, m), 6.38 (1H, s), 5.38 (2H, s), 4.05 (2H, t), 3.85-3.78 (2H, m), 3.58-3.40 (6H, m), 3.29 (2H, t), 3.12 (3H, s), 2.25 (3H, s), 1.98 (3H, s).

Compound 35 1-((((Docosyloxy)carbonyl)oxy)methyl)-1-methyl-4-(2-methyl-10H-benzo[b]thieno[2,3-e][1,4]diazepin-4-yl)piperazin-1-ium iodide (Compound 35)

This compound was synthesized via 1-(((docosyloxy)carbonyl)oxy)methyl iodide. The final product precipitated from the reaction mixture to give Compound 35 (2.56 g, 65%). ¹H-NMR (300 MHz, CDCl₃) δ 6.91-7.01 (3H, m), 6.65 (1H, d), 6.37 (1H, s), 5.91 (2H, s), 5.29 (NH), 4.25 (2H, t), 3.95-4.03 (2H, m), 3.81-3.89 (4H, m), 3.68-3.71 (2H, m), 3.56 (3H, s), 2.32 (3H, s), 1.65-1.71 (2H, m), 1.20-1.38 (36H, m), 0.87 (3H, t).

Compound 36 1-(((Hexylcarbamoyl)oxy)methyl)-1-methyl-4-(2-methyl-10H-benzo[b]thieno[2,3-e][1,4]diazepin-4-yl)piperazin-1-ium iodide (Compound 36)

This compound was synthesized via iodomethyl hexylcarbamate with CHCl₃/diethyl ether as solvent for the quaternization reaction. The final product precipitated from the reaction mixture to give Compound 36 (1.85 g, 65%).
¹H-NMR (300 MHz, CDCl₃) δ 7.02-6.90 (3H, m), 6.72-6.60 (2H, m), 6.33 (1H, s), 5.63 (2H, s), 5.41 (NH), 4.02-3.90 (2H, m), 6.78-6.63 (6H, m), 3.52 (3H, s), 3.16 (2H, q), 2.32 (3H, s), 1.57-1.50 (2H, m), 1.32-1.20 (6H, m), 0.87 (3H, t).

Compound 37 (S)-1-((((1-(benzyloxy)-3-methyl-1-oxobutan-2-yl)carbamoyl)oxy)methyl)-1-methyl-4-(2-methyl-10H-enzo[b]thieno[2,3-e][1,4]diazepin-4-yl)piperazin-1-ium iodide (Compound 37)

This compound was synthesized via (S)-benzyl 2-((iodomethoxy)carbonylamino)-3-methylbutanoate. The quaternization reaction was carried out in ethy acetate using (S)-benzyl 2-((iodomethoxy)carbonylamino)-3-methylbutanoate and after 4 hours the solvent was decanted from the reaction. The remaining gummy solid was purified by dissolving in a minimum amount of dichloromethane and adding to 10% ethyl acetate/diethyl ether to give Compound 37 (1.47 g, 45%). ¹H-NMR (300 MHz, CDCl₃) δ 7.36-7.28 (5H, m), 6.98-6.91 (4H, m), 6.70 (2H, dd), 6.38 (1H, s), 5.72 (2H, s), 5.16 (2H, dd), 4.24-4.19 (1H, m), 4.01-3.84 (2H, m), 3.76-3.53 (6H, m), 3.51 (3H, s), 2.28 (3H, s), 1.27-1.21 (1H, m), 0.96 (6H, t).

Compound 38 1-(((((carboxymethyl)carbamoyl)oxy)methyl)-1-methyl-4-(2-methyl-10H-benzo[b]thieno[2,3-e][1,4]diazepin-4-yl)piperazin-1-ium chloride (Compound 38)

This compound was synthesized via tert-butyl 2-((iodomethoxy)carbonylamino)acetate. The quaternization reaction was carried out in ethyl acetate, and after 4 hours the reaction mixture was filtered and dried to give Compound 38 as the iodide salt (300 mg, 60%). ¹H-NMR (300 MHz, CDCl₃) δ 7.30 (NH), 7.01-6.93 (3H, m), 6.82-6.76 (1H, m), 6.37 (1H, s), 5.68 (2H, s), 4.03-3.90 (2H, m), 3.88-3.62 (8H, m), 3.48 (3H, s), 2.31 (3H, s), 1.45 (9H, s).

To a solution of 1-((2-tert-butoxy-2-oxoethylcarbamoyloxy)methyl)-1-methyl-4-(2-methyl-10H-benzo[b]thieno[2,3-e][1,4]diazepin-4-yl)piperazin-1-ium iodide (250 mg, 0.40 mmol) in dichloromethane (20 mL) was added 2M HCl/diethyl ether (20 mL), a solid began to precipitate instantly. The reaction was stirred for 30 minutes then the reaction mixture left to settle. The solvent was then decanted and further 10 mL dichloromethane was added and the remaining solid triturated. The solvent was decanted and the remaining solid dried under a stream of argon gas. The solid was then purified by dissolving in a minimum amount of DMF (~2 mL) and then adding dichloromethane (~30 mL). A solid precipitated and the solvent decanted. The remaining solid was then triturated a further 3 times with dichloromethane. The remaining solid was then suspended in dichloromethane and dried using a Genevac (after each 24 hour period the solid was re-suspended in dichloromethane) for 3 days to remove the last of the DMF to give Compound 38 as the chloride salt. (208 mg, 23%, contains 5% olanzapine and 1.5% DMF). $^1$H-NMR (300 MHz, d$_6$-DMSO) δ 8.38 (1H, t), 7.92 (2H, s), 7.31-6.88 (4H, m), 6.59 (1H, br s), 5.45 (2H, s), 4.29-2.96 (13H, m), 2.29 (3H, s).

Compound 39 1-((((2-(Benzyloxy)-2-oxoethyl)carbamoyl)oxy)methyl)-1-methyl-4-(2-methyl-10H-benzo[b]thieno[2,3-e][1,4]diazepin-4-yl)piperazin-1-ium iodide (Compound 39)

This compound was synthesized via benzyl 2-((iodomethoxy)carbonylamino)acetate. The product precipitated from the reaction and was further purified by dissolving in industrial methylated spirits and dichloromethane (3:1) and precipitating with diethyl ether to give Compound 39 (2.15 g, 69%).
$^1$H-NMR (400 MHz, CDCl$_3$) δ 8.46 (1H, m), 7.73 (1H, s), 7.33 (5H, m), 6.81 (2H, m), 6.67 (1H, m), 6.37 (1H, s), 5.41 (2H, s), 5.13 (2H, s), 3.94 (2H, d), 3.78 (2H, m), 3.30-3.53 (6H, m), 3.11 (3H, s), 2.46 (1H, s), 2.25 (3H, s).

Compound 40 (S)-1-((((1-(ethoxy)-4-methyl-1-oxopentan-2-yl)carbamoyl)oxy)methyl)-1-methyl-4-(2-methyl-10H-benzo[b]thieno[2,3-e][1,4]diazepin-4-yl)piperazin-1-ium iodide (Compound 40)

This compound was synthesized via (S)-ethyl 2-((iodomethoxy)carbonylamino)-4-methylpentanoate. The product precipitated from the reaction and was further purified by dissolving in the minimum volume of dichloromethane followed by precipitation with diethyl ether to give Compound 40 (1.89 g, 60%). $^1$H-NMR (300 MHz, CDCl$_3$) δ 6.98 (3H, m), 6.84 (1H, d), 6.69 (1H, d), 6.35 (1H, s), 5.75 (2H, s), 5.41 (1H, s), 4.15-4.31 (3H, m), 3.96 (2H, m), 3.72 (6H, m), 3.55 (3H, s), 2.31 (3H, s), 1.60-1.81 (3H, m), 1.27 (3H, t), 0.94 (6H, t).

Compound 41 (S)-1-((((1-(benzyloxy)-4-methyl-1-oxopentan-2-yl)carbamoyl)oxy)methyl)-1-methyl-4-(2-methyl-10H-benzo[b]thieno[2,3-e][1,4]diazepin-4-yl)piperazin-1-ium iodide (Compound 41)

This compound was synthesized via (S)-benzyl 2-((iodomethoxy)carbonylamino)-4-methylpentanoate. The product precipitated from the reaction mixture upon completion by the addition of diethyl ether and was further purified by dissolving in the minimum volume of dichloromethane and precipitating with diethyl ether/ethyl acetate (1:1) to give Compound 41 (0.81 g, 61%).
$^1$H-NMR (300 MHz, CDCl$_3$) δ 7.38 (5H, m), 6.91-7.05 (4H, m), 6.69 (1H, d), 6.36 (1H, s), 5.70 (2H, s), 5.46 (1H, br s), 5.14 (2H, s), 4.32 (1H, m), 3.89 (2H, m), 3.56-3.78 (6H, m), 3.47 (3H, s), 2.31 (3H, s), 1.63-1.87 (3H, m), 0.91 (6H, m).

Compound 42 (S)-1-((((1-ethoxy-3-methyl-1-oxobutan-2-yl)carbamoyl)oxy)methyl)-1-methyl-4-(2-methyl-10H-benzo[b]thieno[2,3-e][1,4]diazepin-4-yl)piperazin-1-ium iodide (Compound 42)

This compound was synthesized via (S)-ethyl 2-((iodomethoxy)carbonylamino)-3-methylbutanoate. The product precipitated from the reaction mixture and was further purified by dissolving in the minimum volume of dichloromethane and precipitating with dietyl ether/ethyl acetate (8:2) to give Compound 42 (1.56 g, 50%).
$^1$H-NMR (300 MHz, CDCl$_3$) δ 6.98 (3H, m), 6.73 (1H, d), 6.47 (1H, d), 6.38 (1H, s), 5.75 (2H, m), 5.61 (1H, br s), 4.21 (3H, m), 3.98 (2H, m), 3.64-3.85 (6H, m), 3.55 (3H, s), 2.23-2.18 (4H, m), 1.28 (3H, t), 0.98 (6H, t).

Compound 43 (S)-1-(((2-((benzyloxy)carbonyl)pyrrolidine-1-carbonyl)oxy)methyl)-1-methyl-4-(2-methyl-10H-benzo[b]thieno[2,3-e][1,4]diazepin-4-yl)piperazin-1-ium iodide (Compound 43)

This compound was synthesized via (S)-2-benzyl 1-iodomethylpyrrolidine-1,2-dicarboxylate The product precipitated from the reaction and was further purified by dissolving in the minimum volume of dichloromethane/acetonitrile (1:1) and precipitating with ethyl acetate to give Compound 43 (0.78 g, 59%). The product exists as a mixture of conformers (3:1) by $^1$H-NMR. $^1$H-NMR (300 MHz, CDCl$_3$) δ 7.39 (5H, m), 6.97 (3H, m), 6.65 (1H, t), 6.31 (1H, s), 5.96 (1H, d), 5.67 (1H, d), 5.19 (3H, m), 4.58 (0.75H, dd), 4.44 (0.25H, dd), 3.27-4.04 (10.75H, m), 2.98 (2.25H, s), 2.31-2.38 (4H, m), 1.80-2.23 (3H, m).

Compound 44 (S)-1-((((1-(benzyloxy)-1-oxo-3-phenylpropan-2-yl)carbamoyl)oxy)methyl)-1-methyl-4-(2-methyl-10H-benzo[b]thieno[2,3-e][1,4]diazepin-4-yl)piperazin-1-ium iodide (Compound 44)

This compound was synthesized via (S)-benzyl 2-((iodomethoxy)carbonylamino)-3-phenylpropanoate employing general procedure IV and the product precipitated from the reaction. This was further purified by dissolving in the minimum volume of dichloromethane/acetonitrile (1:1) and precipitating with ethyl acetate/diethyl ether to give Compound 44 (0.43 g, 20%). $^1$H-NMR (300 MHz, DMSO-d6) δ 8.63 (NH, d), 7.75 (NH, bs), 7.15-7.38 (10H, m), 6.80-6.93 (3H, m), 6.65-6.75 (1H, m), 5.28-5.39 (2H, m), 5.13 (2H, s), 4.40-4.50 (1H, m), 3.40-3.80 (6H, m), 3.16 (1H, dd), 3.01 (3H, s), 2.83-2.93 (1H, m), 2.27 (3H, s).

Compound 45 (S)-1-((((1-(benzyloxy)-1-oxopropan-2-yl)carbamoyl)oxy)methyl)-1-methyl-4-(2-methyl-10H-benzo[b]thieno[2,3-e][1,4]diazepin-4-yl)piperazin-1-ium iodide (Compound 45)

This compound was synthesized via (S)-benzyl 2-((iodomethoxy)carbonylamino)propanoate. The product precipitated from the reaction and was further purified by dissolving in the minimum volume of dichloromethane and precipitating with ethyl acetate/diethyl ether to give Compound 45 (1.75 g, 59%).
$^1$H-NMR (300 MHz, DMSO-d6) δ 8.53 (NH, d), 7.74 (NH, s), 7.30-7.36 (5H, m), 6.79-6.89 (3H, m), 6.65-6.70 (1H, m), 6.37 (1H, s), 5.35-5.43 (2H, m), 5.13 (2H, s), 4.16-4.23 (1H, m), 3.72-3.83 (2H, m), 3.35-3.55 (6H, m), 3.10 (3H, s), 2.23 (3H, s), 1.34 (3H, d).

Compound 46 (S)-1-((((1-(ethoxy)-1-oxopropan-2-yl)carbamoyl)oxy)methyl)-1-methyl-4-(2-methyl-10H-benzo[b]thieno[2,3-e][1,4]diazepin-4-yl)piperazin-1-ium iodide (Compound 46)

This compound was synthesized via (S)-ethyl 2-((iodomethoxy)carbonylamino)propanoate. The product precipitated from the reaction and was further purified by dissolving in the minimum volume of dichloromethane and precipitating with ethyl acetatec/diethyl ether to give Compound 46 (1.33 g, 48%).

$^1$H-NMR (300 MHz, DMSO-$d_6$) δ 8.49 (NH, d), 7.74 (1H, s), 6.79-6.86 (3H, m), 6.65-6.70 (1H, m), 6.37 (1H, s), 5.39-5.42 (2H, m), 4.10 (2H, q), 3.75-3.90 (2H, m), 3.40-3.60 (6H, m), 3.13 (3H, s), 2.26 (3H, s), 1.31 (3H, d), 1.16 (3H, t).

Compound 47 1-((((2-ethoxy-2-oxoethyl)carbamoyl)oxy)methyl)-1-methyl-4-(2-methyl-10H-benzo[b]thieno[2,3-e][1,4]diazepin-4-yl)piperazin-1-ium iodide (Compound 47)

This compound was synthesized via ethyl 2-((iodomethoxy)carbonylamino)acetate. The product precipitated from the reaction and was further purified by dissolving in the minimum volume of acetonitrile and precipitating with diethyl ether to give Compound 47 (1.62 g, 56%). $^1$H-NMR (300 MHz, DMSO-$d_6$) δ 8.43 (NH, t), 7.74 (NH, s), 6.79-6.89 (3H, m), 6.65-6.71 (1H, m), 6.38 (2H, s), 4.10 (2H, q), 7.78-7.89 (4H, m), 3.42-3.60 (6H, m), 3.13 (3H, s), 2.25 (3H, s), 1.17 (3H, t).

Compound 48 (S)-1-((((1-ethoxy-1-oxo-3-phenylpropan-2-yl)carbamoyl)oxy)methyl)-1-methyl-4-(2-methyl-10H-benzo[b]thieno[2,3-e][1,4]diazepin-4-yl)piperazin-1-ium iodide (Compound 48)

This compound was synthesized via (S)-ethyl 2-((iodomethoxy)carbonylamino)-3-phenylpropanoate. The product precipitated from the reaction and was further purified by dissolving in the minimum volume of acetonitrile and precipitating with ethyl acetate to give Compound 48 (1.73 g, 52%). $^1$H-NMR (300 MHz, DMSO-$d_6$) δ 8.57 (NH, d), 7.75 (NH, 1H), 7.20-7.28 (4H, m), 7.13-7.20 (1H, m), 7.80-7.88 (3H, m), 6.65-7.00 (1H, m), 6.36 (1H, s), 5.28-5.38 (2H, m), 4.31-4.40 (1H, m), 4.09 (2H, q), 3.65-3.83 (2H, m), 3.25-3.55 (6H, m), 3.12 (1H, dd), 3.02 (3H, s), 2.88 (1H, dd), 2.27 (3H, s), 1.13 (3H, t).

Compound 49 1-(4(2-(benzyloxy)-2-oxoethyl)(methyl)carbamoyl)oxy)methyl)-1-methyl-4-(2-methyl-10H-benzo[b]thieno[2,3-e][1,4]diazepin-4-yl)piperazin-1-ium iodide (Compound 49)

This compound was synthesized via benzyl 2-(((iodomethoxy)carbonyl)(methyl)amino)acetate. The product precipitated from the reaction to give Compound 49 (0.28 g, 50%).

$^1$H-NMR (300 MHz, CDCl$_3$) δ 7.42-7.31 (5H, m), 7.03-6.90 (3H, m), 6.72-6.66 (1H, m), 6.33 (1H, s), 5.86 (2H, s), 5.17 (2H, s), 4.09 (2H, s), 4.00-3.85 (2H, m), 3.78-3.45 (6H, m), 3.05 (3H, s), 2.31 (3H, s).

Compound 50 1-methyl-4-(2-methyl-10H-benzo[b]thieno[2,3-e][1,4]diazepin-4-yl)-1-(((2-octyldecanoyl)oxy)methyl)piperazin-1-ium iodide (Compound 50)

Step A—Synthesis of Diethyl 2,2-dioctylmalonate

To a solution of diethylmalonate (20 g, 0.125 mol) in tetrahydrofuran (500 mL) was added octyl bromide (47 mL, 0.275 mol), followed by sodium hydride (60% in mineral oil, 11 g, 0.275 mol) over 1 h. The reaction mixture was stirred at 25° C. for 3 days. A second portion of sodium hydride (5 g, 0.125 mol) and octyl bromide (15 mL, 0.086) were added and the mixture heated at reflux for 5 h. The reaction was cooled, carefully quenched with water and then diluted with 2M HCl. The reaction mixture was extracted with ethyl acetate, dried over MgSO$_4$ and evaporated. The residue was further purified by flash column chromatography eluting with 1:1 heptane/toluene to toluene to give diethyl 2,2-dioctylmalonate (41.4 g, 86%) as a pale yellow oil.

$^1$H-NMR (300 MHz, CDCl$_3$) δ 3.98 (4H, q), 1.70-1.60 (4H, m), 1.15-0.88 (30H, m), 0.69 (6H, t).

Step B—Synthesis of 2-Octyldecanoic acid

To diethyl 2,2-dioctylmalonate (41.4 g, 0.108 mol) was added industrial methylated spirit (50 mL), followed by a solution of KOH (40 g, 0.714 mol) in water (500 mL). The reaction mixture was heated at reflux for 20 h, poured into ice/water and made acidic with 2M HCl. The mixture was then extracted with ethyl acetate and the organic phase dried over MgSO$_4$ before evaporation of the volatiles. The residue was then heated neat at 170° C. until gas evolution had ceased (~5 h) and on cooling 2-octyldecanoic acid (26.4 g, 86%) was obtained as a yellow solid.

$^1$H-NMR (300 MHz, CDCl$_3$) δ2.40-2.26 (1H, m), 1.66-1.52 (2H, m), 1.51-1.39 (2H, m), 1.35-1.18 (24H, m), 0.87 (3H, t).

Step C—Synthesis of Chloromethyl 2-octyldecanoate

To a mixture of 2-octyldecanoic acid (12.2 g, 42.9 mmol) and water (90 mL) was added Na$_2$CO$_3$ (17.7 g, 108 mmol), tetrabutylammonium hydrogensulfate (2.8 g, 8.2 mmol), dichloromethane (180 mL) and then chloromethyl chlorosulfate (5.5 mL, 54.3 mmol). The reaction mixture was stirred for 18 h and then diluted with water (300 mL) and dichloromethane (300 mL). The organic phase was separated, dried over MgSO$_4$ and evaporated. The residue was purified on silica eluting with heptane/dichloromethane (8:1) to give chloromethyl 2-octyldecanoate (12.0 g, 84%) as a colorless oil. $^1$H-NMR (300 MHz, CDCl$_3$) δ 5.72 (2H, s), 2.43-2.33 (1H, m), 1.67-1.52 (2H, m), 1.51-1.40 (2H, m), 1.33-1.18 (24H, m), 0.86 (3H, t).

Step D—Synthesis of Iodomethyl 2-octyldecanoate

A mixture of chloromethyl 2-octyldecanoate (12.0 g, 0.036 mol), sodium iodide (27 g, 0.18 mol) and acetonitrile (300 mL) was stirred for 48 h. The reaction was concentrated, diluted with water (250 mL) and extracted with ethyl acetate (250 mL). The organic phase was washed with water (200 mL), dried over MgSO$_4$ and evaporated to give iodomethyl 2-octyldecanoate (13.5 g, 88%) as a light brown oil.

$^1$H-NMR (300 MHz, CDCl$_3$) δ 5.91 (2H, s), 2.35-2.29 (1H, m), 1.64-1.52 (2H, m), 1.50-1.38 (2H, m), 1.30-1.18 (24H, m), 0.87 (3H, t).

Step E—Synthesis of Compound 50

To a solution of olanzapine (5.0 g, 0.016 mol) in ethyl acetate (150 mL) was added iodomethyl 2-octyldecanoate (7.13 g, 0.016 mol) and the mixture stirred for 20 h. The reaction mixture was then filtered, washed with ethyl acetate and dried under vacuum at 40° C. to give Compound 50 (10.2 g, 87%) as a yellow solid.

¹H-NMR (300 MHz, CDCl₃) δ 6.99-6.89 (3H, m), 6.82-6.78 (1H, m), 6.38 (1H, s), 5.78 (2H, s), 5.47 (NH), 3.99-3.87 (2H, m), 3.82-3.70 (6H, m), 3.55 (3H, s), 2.50 (1H, q), 2.30 (3H, s), 1.68-1.42 (4H, m), 1.31-1.18 (24H, m), 0.87 (3H, t).

Compound 51 1-(((2-butylhexanoyl)oxy)methyl)-1-methyl-4-(2-methyl-10H-benzo[b]thieno[2,3-e][1,4]diazepin-4-yl)piperazin-1-ium iodide (Compound 51)

This compound was synthesized according to the general method of Compound 50 via iodomethyl 2-butylhexanoate. The product precipitated from the reaction to give Compound 51 (1.44 g, 72%). ¹H-NMR (300 MHz, CDCl₃) δ 6.96 (3H, m), 6.66 (1H, d), 6.36 (1H, s), 5.81 (2H, s), 5.30 (1H, s), 3.98 (2H, m), 3.78 (6H, m), 3.56 (3H, s), 2.50 (1H, m), 2.31 (3H, s), 1.49-1.72 (4H, m), 1.27-1.35 (8H, m), 0.87 (6H, t).

Compound 52 1-(((2-hexyloctanoyl)oxy)methyl)-1-methyl-4-(2-methyl-10H-benzo[b]thieno[2,3-e][1,4]diazepin-4-yl)piperazin-1-ium iodide (Compound 52)

This compound was synthesized according to the general method of Compound 50 via iodomethyl 2-hexyloctanoate. The product precipitated from the reaction to give Compound 52 (1.31 g, 75%). ¹H-NMR (300 MHz, CDCl₃) δ 6.97 (3H, m), 6.63 (1H, d), 6.35 (1H, s), 5.84 (2H, s), 5.18 (1H, s), 3.97 (2H, m), 3.79 (6H, m), 3.56 (3H, s), 2.52 (1H, m), 2.32 (3H, s), 1.60 (4H, m), 1.25 (16H, m), 0.88 (6H, t).

Compound 53 1-(((2-decyldodecanoyl)oxy)methyl)-1-methyl-4-(2-methyl-10H-benzo[b]thieno[2,3-e][1,4]diazepin-4-yl)piperazin-1-ium iodide (Compound 53)

This compound was synthesized according to the general method of Compound 51 via iodomethyl 2-decyldodecanoate. The product precipitated from the reaction to give Compound 53 (2.33 g, 61%). ¹H-NMR (300 MHz, DMSO-d6) δ 7.73 (NH, s), 6.78-6.85 (3H, m), 6.65-6.70 (1H, m), 5.44 (2H, s), 3.79-3.88 (2H, m), 3.48-3.60 (6H, m), 3.18 (3H, s), 2.49-2.55 (1H, m), 2.25 (3H, s), 1.40-1.61 (4H, m), 1.12-1.28 (32H, m), 0.81 (6H, t).

Compound 54 1-(((((1,3-bis(decanoyloxy)propan-2-yl)oxy)carbonyl)oxy)methyl)-1-methyl-4-(2-methyl-10H-benzo[b]thieno[2,3-e][1,4]diazepin-4-yl)piperazin-1-ium iodide (Compound 54)

Synthesis of 2-Hydroxypropane-1,3-diyl bis(decanoate)

To a solution of glycerol (2.5 g, 27.14 mmol) in pyridine (50 mL) was added decanoyl chloride (10.6 mL, 51.57 mmol) at 0° C. The reaction was allowed to warm to 25° C. overnight. The reaction was quenched with MeOH (3 mL) before diluting with 2M HCl (50 mL). The reaction was extracted with ethyl acetate (150 mL). The organics were washed with 2M HCl (2×30 mL), brine (30 mL), dried over MgSO₄ and concentrated. A portion of the crude material (2.2 g) was purified by column chromatography eluting with heptane to 40% ethyl acetate in heptane to give 2-hydroxypropane-1,3-diyl bis(decanoate) (1.19 g, 10%).

¹H-NMR (400 MHz, CDCl₃) δ 4.14 (5H, m), 2.43 (1H, s), 2.34 (4H, t), 1.52-1.68 (4H, m), 1.27 (24H, m), 0.87 (6H, t).

Synthesis of 2-((Chloromethoxy)carbonyloxy)propane-1,3-diyl bis(decanoate)

To a solution of 2-hydroxypropane-1,3-diyl bis(decanoate) (1.19 g, 2.97 mmol) in dichloromethane (20 mL) was added pyridine (0.72 mL, 8.91 mmol). The reaction was cooled to 0° C. and chloromethyl chloroformate (0.29 mL, 3.26 mmol) was added slowly. The reaction was allowed to warm to 25° C. after 30 minutes and left overnight. The reaction was incomplete so a catalytic amount of dimethylaminopyridine was added with a further equivalent of chloromethyl chloroformate (0.26 mL, 2.97 mmol) and the reaction left for 24 hours. The reaction was quenched with aqueous sodium hydrogen carbonate solution (20 mL) and extracted with dichloromethane (3×20 mL). The organic phases were washed with aqueous sodium hydrogen carbonate solution (20 mL), 2M HCl (20 mL), brine, dried over MgSO₄ and concentrated. The material was purified by column chromatography and eluted with heptane to 20% ethyl acetate/heptane to give 2-((chloromethoxy)carbonyloxy)propane-1,3-diyl bis(decanoate) (0.543 g, 37%). The product contains 15% of isomer 3-((chloromethoxy)carbonyloxy)propane-1,2-diylbis(decanoate). This could not be removed by chromatography and was carried through to the final product. This was then converted to 2-((iodomethoxy)carbonyloxy)propane-1,3-diylbis(decanoate) using the general method of Compound 1, step C. ¹H-NMR (300 MHz, CDCl₃) δ 5.73 (2H, s), 5.18 (1H, m), 4.36 (2H, dd), 4.18 (2H, dd), 2.32 (4H, t), 1.56-1.62 (4H, m), 1.25 (24H, m), 0.87 (6H, t).

To a solution of olanzapine (0.22 g, 0.70 mmol) in a mixture of ethyl acetate (5 mL) and diethyl ether (2 mL) was added 2-((iodomethoxy)carbonyloxy)propane-1,3-diyl bis(decanoate) (0.45 g, 0.77 mmol). The reaction was stirred at 25° C. for 2 days before addition of a further 0.1 equivalents of 2-((iodomethoxy)carbonyloxy)propane-1,3-diyl bis(decanoate) (0.033 g) to the reaction. The reaction was left for a further 6 days before the product was isolated by filtration. The product was washed with diethyl ether and dried under vacuum to give Compound 54 (0.179 g, 30%). Contains 5% of Compound 55 by ¹H NMR. ¹H-NMR (300 MHz, CDCl₃) δ 6.97 (3H, m), 6.65 (1H, d), 6.36 (1H, s), 6.01 (2H, s), 5.24 (1H, s), 5.01 (1H, m), 4.57 (2H, dd), 4.10 (2H, dd), 3.71-4.07 (8H, m), 3.53 (3H, s), 2.34 (7H, m), 1.59 (4H, m), 1.25 (24H, m), 0.86 (6H, t).

Compound 55 (S)-1-(((((2,3-bis(decanoyloxy)propoxy)carbonyl)oxy)methyl)-1-methyl-4-(2-methyl-10H-benzo[b]thieno[2,3-e][1,4]diazepin-4-yl)piperazin-1-ium iodide (Compound 55)

Synthesis of (S)-4-(benzyloxymethyl)-2,2-dimethyl-1,3-dioxolane

To a suspension of sodium hydride (4.54 g, 113.5 mmol) in THF (100 mL) and DMF (20 mL) at 0° C. was added a solution of (S)-(+)-2,3-O-isopropylideneglycerol (10 g, 75.7 mmol) in THF (10 mL) and DMF (10 mL) dropwise over 30 minutes. Stirring ceased after addition therefore a further 50 mL THF and 10 mL DMF was added. After 1 hour, benzyl bromide (10 mL, 83.2 mmol) was added dropwise over 10 minutes. The reaction was then warmed to 25° C. After 4 hours the reaction was quenched with aq satd NH₄Cl (100 mL) and extracted with ethyl acetate (2×100 mL). The combined organic phases were washed with water (5×100 mL) then brine (100 mL) then dried (MgSO$_4$) and concentrated to give (S)-4-(benzyloxymethyl)-2,2-dimethyl-1,3-dioxolane (23.6 g) which was used with out further purification. $^1$H-NMR (300 MHz, CDCl$_3$) δ 7.43-7.26 (5H, m), 4.57 (2H, dd), 4.35-4.27 (1H, m), 4.09-4.01 (1H, m), 3.76-3.69 (1H, m), 3.55 (1H, dd), 3.45 (1H, dd), 1.42 (3H, s), 1.36 (3H, s).

Synthesis of I-3-(benzyloxy)propane-1,2-diol (S)-4-(benzyloxymethyl)-2,2-dimethyl-1,3-dioxolane (23.6 g, 106.2 mmol) was stirred in MeOH (100 mL) and 2 M HCl (50 mL) and heated to a gentle reflux. After 4 hours the reaction was cooled to 25° C. then aq satd NaHCO$_3$ was added until pH 7. This was then extracted with dichloromethane (3×250 mL). The combined organic phases were dried (MgSO$_4$) and concentrated. The crude product was purified using silica column chromatography eluting with dichloromethane to 10% MeOH/dichloromethane to give I-3-(benzyloxy)propane-1,2-diol (7.81 g, 57%). $^1$H-NMR (300 MHz, CDCl$_3$) δ 7.38-7.26 (5H, m), 4.53 (2H, s), 3.93-3.86 (1H, m), 3.73-3.51 (4H, m), 2.04 (2H, br s).

Synthesis of (S)-3-(benzyloxy)propane-1,2-diylbis(decanoate)

To a solution of (S)-1-(benzyloxy)ethane-1,2-diol (2.6 g, 14.3 mmol) in dichloromethane (50 mL) at 0° C. was added pyridine (2.9 mL, 35.7 mmol) and decanoyl chloride (6.8 mL, 32.8 mmol). The reaction was gradually warmed to 25° C. and stirred for 5 days. The reaction was quenched with water (50 mL) then separated. The aqueous was extracted with dichloromethane (50 mL). The combined organic phases were washed with water (100 mL), 1 M HCl (2×75 mL) and water (100 mL) then dried (MgSO$_4$) and concentrated. The crude product was purified by silica column chromatography eluting with heptane to 5% ethyl acetate/heptane to give (S)-3-(benzyloxy)propane-1,2-diyl bis(decanoate) (6.81 g, 97%). $^1$H-NMR (300 MHz, CDCl$_3$) δ 7.39-7.26 (5H, m), 5.31-5.21 (1H, m), 4.53 (2H, dd), 4.34 (1H, dd), 4.18 (1H, dd), 3.58 (2H, d), 2.37-2.25 (4H, m), 1.64-1.56 (4H, m), 1.37-1.16 (24H, m), 0.87 (6H, t).

Synthesis of (S)-3-hydroxypropane-1,2-diylbis(decanoate)

To a solution of (S)-3-(benzyloxy)propane-1,2-diylbis(decanoate) (5.75 g, 11.7 mmol) in ethyl acetate (10 mL) and MeOH (10 mL) was added 20% Pd(OH)$_2$ (0.5 g). The reaction was then stirred at 25° C. under 1 atm of H$_2$ gas overnight then filtered through celite eluting with ethyl acetate. The organic phase was concentrated and the crude product purified by silica column chromatography eluting with heptane to 20% ethyl acetate/heptane to give (S)-3-hydroxypropane-1,2-diylbis(decanoate) (5.25 g). The product contained impurities but was taken onto the next step without further purification.
$^1$H-NMR (300 MHz, CDCl$_3$) δ 5.11-5.05 (1H, m), 4.27 (2H, ddd), 3.73 (2H, d), 2.39-2.29 (4H, m), 1.69-1.51 (4H, m), 1.38-1.14 (24H, m), 0.87 (6H, t).

Synthesis of I-3-((chloromethoxy)carbonyloxy)propane-1,2-diylbis(decanoate)

To a solution of (S)-3-hydroxypropane-1,2-diyl bis(decanoate) (5.1 g, 12.7 mmol) in dichloromethane (100 mL) was added pyridine (3.09 mL, 38.2 mmol). The reaction was cooled to 0° C. and chloromethyl chloroformate (1.24 mL, 14.0 mmol) was added slowly. The reaction was allowed to warm to 25° C. after 30 minutes. After two hours the reaction was incomplete so a further equivalent of chloromethyl chloroformate (1.13 mL, 12.7 mmol) was added and the reaction left for a further three hours. The reaction was quenched with aqueous sodium hydrogen carbonate solution (50 mL) and extracted with dichloromethane (100 mL). The organic phases were washed with aqueous sodium hydrogen carbonate solution (2×30 mL), brine (30 mL), dried over MgSO$_4$ and concentrated. The product was purified by column chromatography, eluting with heptane to 20% ethyl acetate/heptane to give I-3-((chloromethoxy)carbonyloxy)propane-1,2-diylbis(decanoate) (5.35 g, 85%). This was then converted to I-3-((iodomethoxy)carbonyloxy)propane-1,2-diyl bis(decanoate) using the method of Compound 1, step C. $^1$H-NMR (400 MHz, CDCl$_3$) δ 5.71 (2H, m), 5.27 (1H, m), 4.43 (1H, dd), 4.30 (2H, m), 4.14 (1H, dd), 2.30 (4H, m), 1.60 (4H, m), 1.27 (24H, m), 0.86 (6H, t).

To a solution of olanzapine (0.49 g, 1.57 mmol) in a mixture of ethyl acetate (10 mL) and diethyl ether (5 mL) was added I-3-((iodomethoxy)carbonyloxy)propane-1,2-diylbis(decanoate) (0.12 g, 2.03 mmol). The reaction was stirred at 25° C. for 6 days before the product was isolated by filtration. The product was washed with diethyl ether and dried under vacuum to give Compound 55 (0.673 g, 51%). $^1$H-NMR (300 MHz, CDCl$_3$) δ 6.97 (3H, m), 6.67 (1H, s), 6.37 (1H, s), 6.03 (1H, d), 5.93 (1H, d), 5.33 (2H, m), 4.51 (1H, dd), 4.13-4.31 (3H, m), 3.68-4.11 (8H, m), 3.55 (3H, s), 2.33 (7H, m), 1.57 (4H, m), 1.25 (24H, m), 0.87 (6H, t).

Compound 57 (via Compound 56)

Ammonium (1-methyl-4-(2-methyl-10H-benzo[b]thieno[2,3-e][1,4]diazepin-4-yl)piperazin-1-ium-1-yl)methyl phosphate (Compound 56) and tert-butyl((1-methyl-4-(2-methyl-10H-benzo[b]thieno[2,3-e][1,4]diazepin-4-yl)piperazin-1-ium-1-yl)methyl)phosphate (Compound 57)

To an ice cold solution of di-tert-butyl phosphate (7.84 g, 40.37 mmol) and KHCO$_3$ (2.42 g, 24.17 mmol) in H$_2$O (35 mL), was added KmnO$_4$ (4.46 g, 28.22 mmol) in three portions. The reaction was allowed to warm to 25° C. and stir for 30 minutes. To the reaction was added charcoal (0.6 g) and the reaction was heated to 60° C. for 15 minutes. The reaction was allowed to cool before filtering through a pad of celite. The celite was washed with H$_2$O (×3) before the filtrates were combined, stirred with charcoal (1 g) and heated to 60° C. for a further 20 minutes. The reaction was allowed to cool and filtered through a pad of celite. The filtrate was cooled to 0° C. and acidified with conc. HCl (7 mL). The resulting precipitate was isolated by filtration, washed with ice cold H$_2$O and dissolved in acetone (100 mL). To this was added 10% solution of NMe$_4$OH (4.38 g in 43 mL of H$_2$O) at 0° C. The resulting solution was concentrated under vacuum to give tetramethylammonium di-tert-butyl phosphate as a brown oil (6 g).

To a solution of tetramethylammonium di-tert-butyl phosphate (3.6 g, 12.74 mmol) in dimethoxyethane (70 mL) at reflux was added chloroiodomethane (10.2 mL, 140.09 mmol). The reaction was heated for 1.5 hours before allowing to cool to 25° C. The reaction was filtered and the filtrate concentrated under vacuum. The product was purified by column chromatography, eluted 0 to 30% ethyl acetate in heptane to give di-tert-butyl chloromethyl phosphate (1.24 g, 38%). $^1$H-NMR (300 MHz, CDCl$_3$) δ 5.63 (2H, d), 1.48 (18H, s).

To a solution of olanzapine (0.710 g, 2.27 mmol) in acetonitrile (40 mL) was added sodium iodide (0.613 g, 4.09 mmol) followed by di-tert-butyl chloromethyl phosphate (0.823 g, 3.18 mmol). The flask was wrapped in tin foil to eliminate light and the reaction was stirred at 25° C. for 3 days. The reaction was concentrated to remove the volatiles before diluting with dichloromethane (30 mL) and washing with $H_2O$ (3×15 mL). The organic phases were passed through a phase separation cartridge and concentrated under vacuum. The resulting oil was stirred in diethyl ether overnight to give 1-((di-tert-butoxyphosphoryloxy)methyl)-1-methyl-4-(2-methyl-10H-benzo[b]thieno[2,3-e][1,4]diazepin-4-yl)piperazin-1-ium iodide as a fine yellow powder (1.105 g). Upon attempted purification by trituration, deprotection occurred leading to the isolation of Compound 56 (0.60 g) as a yellow solid. m/z 479 [M-I$^-$].

To Compound 56 (0.383 g, 0.71 mmol) was added trifluoroacetic acid (6 mL). The reaction was stirred at 25° C. for 1.5 hours. To the reaction was added an excess of diethyl ether which resulted in the precipitation of the product. This was filtered and basified via the slow addition of $NaHCO_3$ solution before purifying under basic preparative HPLC conditions to give Compound 57 (0.227 g, 72%) as a yellow solid. $^1$H-NMR (300 MHz, $CD_3OD$) δ 6.86-6.91 (3H, m), 6.64 (1H, m), 6.42 (1H, s), 4.93 (2H, d), 3.92 (2H, m), 3.64 (4H, m), 3.42 (2H, m), 3.15 (3H, s), 2.30 (3H, s).

Compound 58 (S)-1-((((1-(docosyloxy)-1-oxopropan-2-yl)carbamoyl)oxy)methyl)-1-methyl-4-(2-methyl-10H-benzo[b]thieno[2,3-e][1,4]diazepin-4-yl)piperazin-1-ium iodide (Compound 58)

Synthesis of (S)-docosyl
2-(tert-butoxycarbonylamino)propanoate

To a solution of N-Boc-L-alanine (2.5 g, 13.21 mmol) in THF (130 mL) was added 1,1'-carbonyldiimidazole (2.14 g, 13.21 mmol) portionwise. The reaction was heated to 40° C. for 4 hours. To the reaction was added docosanol (4.3 g, 13.21 mmol) and N,N'-dimethylaminopyridine (0.80 g, 6.60 mmol). The reaction was heated at 40° C. overnight before heating to reflux for 20 hours. The reaction was allowed to cool before quenching with saturated $NaHCO_3$ solution (100 mL) and extracting with ethyl acetate (3×80 mL). The organic phases were combined, washed with brine (50 mL), dried over $MgSO_4$ and concentrated. The residue was taken up in ethyl acetate and upon standing docosanol precipitated from the solution. This was filtered off and the filtrate concentrated. The material was purified by column chromatography eluting with 0 to 10% ethyl acetate in toluene to give (S)-docosyl 2-(tert-butoxycarbonylamino)propanoate (5.64 g, 86%). $^1$H-NMR (300 MHz, $CDCl_3$) δ 5.05 (1H, br s), 4.31 (1H, m), 4.11 (2H, m), 1.63 (2H, m), 1.44 (9H, s), 1.37 (3H, d), 1.24 (38H, m), 0.87 (3H, t).

Synthesis of (S)-docosyl
2-((chloromethoxy)carbonylamino)propanoate

To (S)-docosyl 2-(tert-butoxycarbonylamino)propanoate (5.60 g, 11.25 mmol) was added trifluoroacetic acid (5 mL). The reaction was stirred at room temperature overnight before removing the volatiles under vacuum to give (S)-1-(docosyloxy)-1-oxopropan-2-aminium 2,2,2-trifluoroacetate (4.55 g, 79%).

To a suspension of (S)-1-(docosyloxy)-1-oxopropan-2-aminium 2,2,2-trifluoroacetate (4.35 g, 8.50 mmol) in dichloromethane (70 mL) at 0° C. was added chloromethylchloroformate (1.51 mL, 17.00 mmol) dropwise, followed by the dropwise addition of pyridine (2.06 mL, 25.5 mmol). The reaction was allowed to warm to room temperature over 2 hours before stirring at 25° C. overnight. The reaction was quenched with saturated $NaHCO_3$ solution (60 mL) and extracted with dichloromethane (3×50 mL). The organic phases were combined, washed with 2M HCl (50 mL), water (50 mL), brine (50 mL) and dried over $MgSO_4$ before concentrating under vacuum. A portion was purified by column chromatography eluting with 40 to 60% dichloromethane in heptane to give (S)-docosyl 2-((chloromethoxy)carbonylamino)propanoate (0.269 g) as a colourless solid.

$^1$H-NMR (400 MHz, $CDCl_3$) δ 5.76 (1H, d), 5.71 (1H, d), 5.51 (1H, m), 4.38 (1H, m), 4.13 (2H, t), 1.64 (2H, t), 1.44 (3H, d), 1.24 (38H, m), 0.86 (3H, t).

Synthesis of (S)-docosyl
2-((iodomethoxy)carbonylamino)propanoate

To a suspension of (S)-docosyl 2-((chloromethoxy)carbonylamino)propanoate (0.269 g, 0.55 mmol) in a mixture of acetonitrile (10 mL) and dichloromethane (10 mL) was added sodium iodide (0.247 g, 1.65 mmol). The reaction was wrapped in tin foil to exclude light and the reaction stirred at 25° C. for 7 days. The reaction was concentrated to remove the volatiles. To the residue was added $H_2O$ (30 mL) and the product was extracted with dichloromethane (3×15 mL). The organic phases were washed with 5% aq sodium sulfite solution (20 mL), water (20 mL), dried over $MgSO_4$ and concentrated to give (S)-docosyl 2-((iodomethoxy)carbonylamino)propanoate (0.320 g, 100%) as a white solid. The product was used in the next reaction without further purification.

$^1$H-NMR (300 MHz, $CDCl_3$) δ 5.98 (1H, d), 5.94 (1H, d), 5.46 (1H, m), 4.37 (1H, m), 4.14 (2H, t), 1.60 (2H, m), 1.43 (3H, d), 1.24 (38H, m), 0.87 (3H, t).

To a solution of Olanzapine (0.14 g, 0.45 mmol) in ethyl acetate (50 mL) was added a solution of (S)-docosyl 2-((iodomethoxy)carbonylamino)propanoate (0.319 g, 0.54 mmol) in dichloromethane (10 mL). The reaction was stirred overnight at 25° C. The product precipitated from solution and was isolated by decanting off the liquors. The residue was triturated with diethyl ether to give Compound 58 as a yellow solid (0.270 g, 67%).

$^1$H-NMR (300 MHz, $CDCl_3$) δ 6.96-7.12 (3H, m), 6.83 (1H, m), 6.46 (1H, s), 5.69 (2H, s), 4.27 (1H, m), 3.71-4.19 (10H, m), 3.51 (3H, s), 2.31 (3H, s), 1.62 (2H, m), 1.51 (3H, d), 1.24 (38H, m), 0.87 (3H, t).

Chloride Salt of Compound of Compound 18

1-(((2,2-dimethyltetradecanoyl)oxy)methyl)-1-methyl-4-(2-methyl-10H-benzo[b]thieno[2,3-e][1,4]diazepin-4-yl)piperazin-1-ium chloride General Procedure for Conversion from the Iodide Salt to the Chloride The olanzapine prodrug chloride salts were prepared from the corresponding iodide by ion exchange on a polymeric macroreticular resin containing quaternary ammonium groups. As an example, 1-(((2,2-dimethyltetradecanoyl)oxy)methyl)-1-methyl-4-(2-methyl-10H-benzo[b]thieno[2,3-e][1,4]diazepin-4-yl)piperazin-1-ium chloride was obtained by the following procedure: 8 g of Amberlyst A-26 (hydroxide form) were loaded as a suspension in methanol on a glass column and 1% HCl in methanol (50 mL) were passed to obtain the chloride form of the resin. The column was washed with methanol (50 mL), and then a methanol solution of 1-(((2,2-dimethyltetradecanoyl)oxy)methyl)-1-methyl-4-(2-methyl-10H-benzo[b]thieno[2,3-e][1,4]diazepin-4-yl)piperazin-1-ium iodide (Compound 18, 181.9 mg in 10 mL of methanol) was passed through the column and eluted with additional methanol (50 mL). The yellow fractions (~50 mL) were combined and dried under nitrogen flow at room temperature. The solid was suspended in 2-PrOH (10% solid load) with vortexing and sonication. The suspension was stirred at room temperature for 48 hours and filtered. The collected solid was left to dry under vacuum at room temperature to provide the 1-(((2,2-dimethyltetradecanoyl)oxy)methyl)-1-methyl-4-(2-methyl-10H-benzo[b]thieno[2,3-e][1,4]diazepin-4-yl)piperazin-1-ium chloride salt characterized by the endotherm peak in the DSC at 195° C.

Chloride Salt of Compound 19

1-(((2,2-dimethyloctanoyl)oxy)methyl)-1-methyl-4-(2-methyl-10H-benzo[b]thieno[2,3-e][1,4]diazepin-4-yl)piperazin-1-ium chloride This compound was prepared according to the general method of conversion of the iodide salt to the chloride as described for Compound 18 via 1-(((2,2-dimethyloctanoyl)oxy)methyl)-1-methyl-4-(2-methyl-10H-benzo[b]thieno[2,3-e][1,4]diazepin-4-yl)piperazin-1-ium iodide (Compound 19) to give 1(((2,2-dimethyloctanoyl)oxy)methyl)-1-methyl-4-(2-methyl-10H-benzo[b]thieno[2,3-e][1,4]diazepin-4-yl)piperazin-1-ium chloride (endotherm peak in the DSC at 201° C.).

Chloride Salt of Compound 20

1-(((2,2-dimethyldecanoyl)oxy)methyl)-1-methyl-4-(2-methyl-10H-benzo[b]thieno[2,3-e][1,4]diazepin-4-yl)piperazin-1-ium chloride This compound was prepared according to the general method of conversion of the iodide salt to the chloride as described for Compound 18 via 1-(((2,2-dimethyldecanoyl)oxy)methyl)-1-methyl-4-(2-methyl-10H-benzo[b]thieno[2,3-e][1,4]diazepin-4-yl)piperazin-1-ium iodide (Compound 20) to give 1-(((2,2-dimethyldecanoyl)oxy)methyl)-1-methyl-4-(2-methyl-10H-benzo[b]thieno[2,3-e][1,4]diazepin-4-yl)piperazin-1-ium chloride (endotherm peak in the DSC at 198° C.).

Chloride Salt of Compound 21

1-(((2,2-dimethyldodecanoyl)oxy)methyl)-1-methyl-4-(2-methyl-10H-benzo[b]thieno[2,3-e][1,4]diazepin-4-yl)piperazin-1-ium chloride This compound was prepared according to the general method of conversion of the iodide salt to the chloride as described for Compound 18 via (((2,2-dimethyldodecanoyl)oxy)methyl)-1-methyl-4-(2-methyl-10H-benzo[b]thieno[2,3-e][1,4]diazepin-4-yl)piperazin-1-ium iodide (Compound 21) to give 1-(((2,2-dimethyldodecanoyl)oxy)methyl)-1-methyl-4-(2-methyl-10H-benzo[b]thieno[2,3-e][1,4]diazepin-4-yl)piperazin-1-ium chloride (endotherm peak in the DSC at 199° C.).

Chloride Salt of Compound 22 1-(((2,2-dimethylhexadecanoyl)oxy)methyl)-1-methyl-4-(2-methyl-10H-benzo[b]thieno[2,3-e][1,4]diazepin-4-yl)piperazin-1-ium chloride This compound was prepared according to the general method of the general method of conversion of the iodide salt to the chloride as described for Compound 18 via 14(2,2-dimethylhexadecanoyl)oxy)methyl)-1-methyl-4-(2-methyl-10H-benzo[b]thieno[2,3-e][1,4]diazepin-4-yl)piperazin-1-ium iodide (Compound 22) to give 1-(((2,2-dimethylhexadecanoyl)oxy)methyl)-1-methyl-4-(2-methyl-10H-benzo[b]thieno[2,3-e][1,4]diazepin-4-yl)piperazin-1-ium chloride (endotherm peak in the DSC at 192° C.).

Chloride Salt of Compound 2 1-methyl-4-(2-methyl-10H-benzo[b]thieno[2,3-e][1,4]diazepin-4-yl)-1-((palmitoyloxy)methyl)piperazin-1-ium chloride This compound was prepared according to the general method of conversion of the iodide salt to the chloride as described for Compound 18 via 1-methyl-4-(2-methyl-10H-benzo[b]thieno[2,3-e][1,4]diazepin-4-yl)-1-((palmitoyloxy)methyl)piperazin-1-ium iodide (Compound 2) to give 1-methyl-4-(2-methyl-10H-benzo[b]thieno[2,3-e][1,4]diazepin-4-yl)-1-((palmitoyloxy)methyl)piperazin-1-ium chloride (endotherm peak in the DSC at 185° C.).

Chloride Salt of Compound 1

1-(((stearoyl)oxy)methyl)-1-methyl-4-(2-methyl-10H-benzo[b]thieno[2,3-e][1,4]diazepin-4-yl)piperazin-1-ium chloride This compound was prepared according to the general method of conversion of the iodide salt to the chloride as described for Compound 18 via 1-(((stearoyl)oxy)methyl)-1-methyl-4-(2-methyl-10H-benzo[b]thieno[2,3-e][1,4]diazepin-4-yl)piperazin-1-ium iodide (Compound 1) to give 1-(((stearoyl)oxy)methyl)-1-methyl-4-(2-methyl-10H-benzo[b]thieno[2,3-e][1,4]diazepin-4-yl)piperazin-1-ium chloride (endotherm peak in the DSC at 185° C.).

Chloride Salt of Compound 3 1-((butyryloxy)methyl)-1-methyl-4-(2-methyl-10H-benzo[b]thieno[2,3-e][1,4]diazepin-4-yl)piperazin-1-ium chloride This compound was prepared according to the general method of conversion of the iodide salt to the chloride as described for Compound 18 via 1-((butyryloxy)methyl)-1-methyl-4-(2-methyl-10H-benzo[b]thieno[2,3-e][1,4]diazepin-4-yl)piperazin-1-ium iodide (Compound 3) to give 1-((butyryloxy)methyl)-1-methyl-4-(2-methyl-10H-benzo[b]thieno[2,3-e][1,4]diazepin-4-yl)piperazin-1-ium chloride (endotherm peak in the DSC at 222° C.).

Chloride Salt of Compound 4 1-methyl-4-(2-methyl-10H-benzo[b]thieno[2,3-e][1,4]diazepin-4-yl)-1-((tetradecanoyloxy)methyl)piperazin-1-ium chloride This compound was prepared according to the general method of conversion of the iodide salt to the chloride as described for Compound 18 via 1-methyl-4-(2-methyl-10H-benzo[b]thieno[2,3-e][1,4]diazepin-4-yl)-1-((tetradecanoyloxy)methyl)piperazin-1-ium iodide (Compound 4) to give 1-methyl-4-(2-methyl-10H-benzo[b]thieno[2,3-e][1,4]diazepin-4-yl)-1-((tetradecanoyloxy)methyl)piperazin-1-ium chloride (endotherm peak in the DSC at 191° C.).

Chloride Salt of Compound 5 1-((dodecanoyloxy)methyl)-1-methyl-4-(2-methyl-10H-benzo[b]thieno[2,3-e][1,4]diazepin-4-yl)piperazin-1-ium chloride This compound was prepared according to the general method of conversion of the iodide salt to the chloride as described for Compound 18 via 1-((dodecanoyloxy)methyl)-1-methyl-4-(2-methyl-10H-benzo[b]thieno[2,3-e][1,4]diazepin-4-yl)piperazin-1-ium iodide (Compound 5) to give 1-((dodecanoyloxy)methyl)-1-methyl-4-(2-methyl-10H-benzo[b]thieno[2,3-e][1,4]diazepin-4-yl)piperazin-1-ium chloride (endotherm peak in the DSC at 180° C.).

Example 6

Solution Stability of Asenapine Prodrugs as a Function of pH

The asenapine derived prodrugs were prepared at approximately 300 ug/mL in buffers with acetonitrile (see table of buffers below). The initial ratio of prodrug/parent was measured using a freshly prepared solution in unbuffered water. Acetonitrile was titrated into all samples as needed to ensure the complete dissolution of the compounds. The amount of acetonitrile varied depending on the solubility of each compound (see Note 1). 1.5 mL of each stability sample was transferred into a HPLC vial and the vials were maintained at 25° C. in the temperature controlled sample compartment of the HPLC. Each sample was assayed by HPLC after 1, 4, 10, and 24 hours for prodrug and asenapine content (see Note 2).

The fraction of prodrug remaining at each time point was calculated as

Fraction Prodrug=(HPLC Area of Prodrug)/(HPLC area of prodrug+asenapine)(see Note 3).

The loss of prodrug was then fit to the equation for first order decay:

Fraction Prodrug=(Initial Fraction prodrug)$*e^{-kt}$ where t=time (in hours) and k is the rate constant for decay. Finally, the half-lives were calculated as:

$t_{1/2}=0.693/k$

Table of Buffers: All buffers were 0.01M.

| | Buffering Agents | | | | |
|---|---|---|---|---|---|
| | $H_3PO_4$/ $NaH_2PO_4$ | Citric Acid/ Sodium Citrate | $NaH_2PO_4$/ $Na_2HPO_4$ | $NaH_2PO_4$/ $Na_2HPO_4$ | Glycine/ NaOH |
| pH (measured) | 2.11 | 5.08 | 5.95 | 6.95 | 9.01 |

Figure 2:
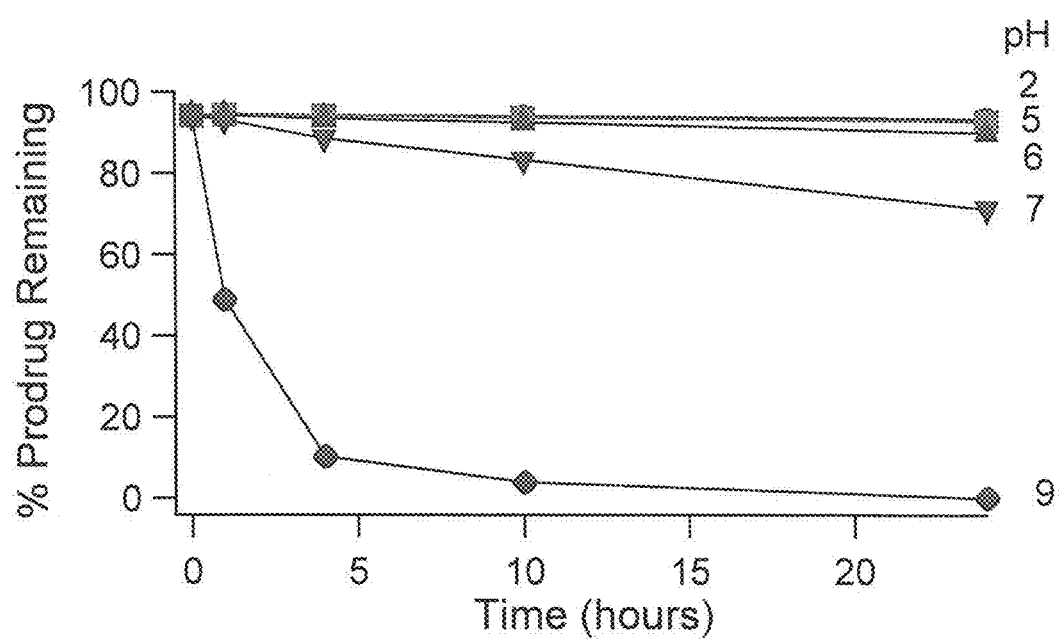
FIG. 2: Solution stability of asenapine pivalate prodrug as a function of pH.

The results are shown in FIGS. 1 and 2. As shown in the figures, asenapine pivalate (FIG. 2) is more stable than the asenapine octanoate (FIG. 1).

Note 1: The acetonitrile concentration is not expected to have a large impact on the degradation rate since the rate follows first order decay with respect to compound (ie, the rate constant is independent of the concentration). The absolute concentration of prodrug does not need to be known since the data are fit as a fraction of prodrug relative to total prodrug+asenapine.

Note 2: A duplicate sample of the pivalate prodrug of asenapine at pH 7 was injected at more frequent time points (initial+0.5, 1, 2, 4, 8, 12, and 24 hours) to ensure that the 5-point curve (includes initial time point+1, 4, 10, and 24 hours)) adequately represents the degradation rate; the two curves were virtually identical.

Note 3: Since HPLC area percents without conversion factors are used in the calculation instead of actual concentration values, the "Fraction Prodrug" is an estimate, and the reported half-lives are also estimated based on the area under the curve. However, the trends/conclusion for degradation vs. pH are indisputable. The rank-order of stability for two different prodrugs will also be correct though the relative rates of degradation between any two compounds may differ from those predicted here.

Example 7

Pharmacokinetic Evaluation of Asenapine and Asenapine Prodrugs in Rats

Animals: 18 Male Sprague-Dawley rats (Charles River Laboratories, Wilmington, Mass.) were used in the study. Three groups of 6 rats were used and are referred to in this study as Groups A, B and C. Rats were approximately 350-375 g at time of arrival. Rats are housed 2 per cage with ad libitum chow and water. Environmental conditions in the housing room: 64-67° F., 30% to 70% relative humidity, and 12:12-h light: dark cycle. All experiments were approved by the institutional animal care and use committee.

Test Compounds: The following formulations of Asenapine parent drug and prodrug compounds of the invention were used in the study.

| Study Group | Formulation | Lot # | Dose mg/rat | Dose volume (mL)/route | Dosing Vehicle |
|---|---|---|---|---|---|
| A | Asenapine: Maleic Acid (1:1 molar ratio) | 200-00381-201B | 10 | 0.3/IM | 1% HPMC in PBS saline with 0.2% Tween pH 6.0 |
| B | Asenapine Palmitate Chloride (Cpd ASN-76) | 200-00381-200A | 10 | 0.3/IM | 1% HPMC in PBS saline with 0.2% Tween pH 6.0 |

-continued

| Study Group | Formulation | Lot # | Dose mg/rat | Dose volume (mL)/route | Dosing Vehicle |
|---|---|---|---|---|---|
| C | Asenapine Dimethyl butyrate Iodide (Cpd ASN-83) | 200-00381-200B | 10 | 0.3/IM | 1% HPMC in PBS saline with 0.2% Tween pH 6.0 |

Pharmacokinetics study: Rats were dosed IM by means of a 23 gauge, 1 in. needle with 1 cc syringe 0.3 mL suspension was withdrawn from the vial containing the test compound. The rat was injected in the muscles of the hind limb after anesthesia with isoflurane. Blood samples were collected via a lateral tail vein after brief anesthesia with Isoflurane. A 27 1/2 G needle and 1 cc syringe without an anticoagulant was used for the blood collection. Approximately 350 µL of whole blood was collected at each sampling time point of 6 hours, 24 hours and 2, 5, 7, 9, 12, 14, 21, 28, 35 days after administration. Once collected, whole blood was immediately transferred to tubes containing K2 EDTA, inverted 10-15 times and immediately placed on ice. The tubes were centrifuged for 2 minutes at >14,000 g's (11500 RPMs using Eppendorf Centrifuge 5417C, F45-30-11 rotor) at room temperature to separate plasma. Plasma samples were transferred to labeled plain tubes (MICROTAINER®; MFG# BD5962) and stored frozen at <−70° C.

Data Analysis:

Drug concentrations in plasma samples were analyzed by liquid chromatography-mass spectroscopy using appropriate parameters for each compound. Half-life, volume of distribution, clearance, maximal concentration, and AUC were calculated by using WinNonlin version 5.2 software (Pharsight, St. Louis, Mo.).

Figure 3:
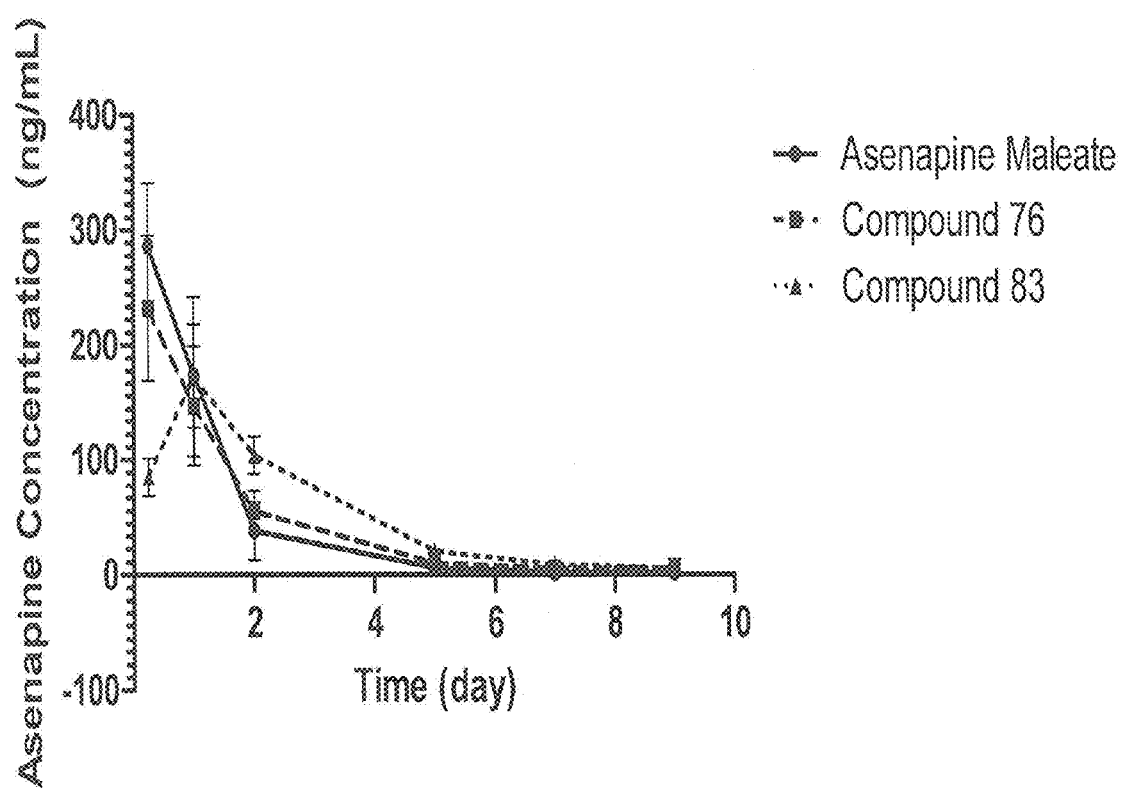
FIG. 3: Pharmacokinetic analysis of asenapine:maleate, asenapine palmitate chloride; and asenapine (α,α)-dimethyl butyrate iodide.

Results:

The results are shown in FIG. 3. As is seen in FIG. 3, the Cmax of, the Asenapine released from an injection of the asenapine dimethyl butyrate prodrug (Compound 83 in the FIG. 3, also referred to herein as ASN-83), was lower than the Cmax of the parent Asenapine formulation as well as lower than that of the Asenapine palmitate prodrug (Compound 76 in FIG. 3, also referred to herein as ASN-76). It should be noted that the first sampled time point on the graph is 6 hours and therefore it is likely that the Cmax for Asenapine and Asenapine palmitate was earlier than 6 hours. The Asenapine dimethyl butyrate prodrug provides asenapine pharmacokinetics with a longer duration in the animals and a more gradual decrease in plasma concentration over all the time points sampled as compared to either Asenapine, or Asenapine palmitate prodrug.

Example 8

Pharmacodynamic Studies Using an Amphetamine-Induced Locomotion Model

Introduction:

Prodrugs of the invention useful in the treatment of schizophrenia and bipolar disorder are expected to show predictive validity in rodent models of hyperlocomotion. D-Amphetamine-induced locomotion is postulated to mimic the dopaminergic hyperactivity which forms the basis for the "dopamine hypothesis" of schizophrenia. The AMPH-induced hyperactivity model provides a simple, initial screen of antipsychotic compound efficacy. See, Fell et al., Journal of Pharmacology and Experimental Therapeutics, (2008) 326:209-217. Amphetamine induced hyperactivity is used to screen various doses of prodrug formulations administered either orally or by injection. For the purposes of this Example, prodrugs of antipsychotics will be tested to measure pharmacodynamic efficacy in an acute hyperlocomotion paradigm. The hypothesis of the study is that administration of aripiprazole prodrug formulations, which result in plasma concentrations of ~100-200 ng/ml, will produce a significant attenuation of AMPH-induced locomotion.

General behavior and activity can be measured in experimental animals (typically rats and mice) in order to assess psychomotor stimulant properties, anxiogenic/anxiolytic or sedative properties of a drug. As such, open-field studies can provide insight into the behavioral effects of test compounds. Certain prodrugs of the present invention are useful in the treatment of schizophrenia and bipolar disorder including but not limited to, amisulpride, aripiprazole, asenapine, cariprazine, dehydroaripiprazole, latrepirdine, iloperidone, olanzapine, paliperidone, risperidone, and ziprasidone. Such prodrugs of the invention show predictive validity in rodent models of hyperlocomotion. D-Amphetamine-induced locomotion is postulated to mimic the dopaminergic hyperactivity which forms the basis for the "dopamine hypothesis" of schizophrenia. Likewise, glutamate NMDA receptor antagonist (MK-801, PCP, etc.) induced locomotion is postulated to mimic the NMDA hypoactivity hypothesis of schizophrenia (Fell et al., supra). These tests of drug-induced hyperactivity provide simple, initial screens of antipsychotic compound efficacy. Amphetamine induced hyperactivity will be used to screen various prodrugs of administered orally or by injection in oil solutions, to measure pharmacodynamic efficacy. The results of the D-AMPH induced locomotion done in this study will be compared to the historical results of subcutaneous (S.C.) parent drug administration on D-AMPH. The hypothesis of the study is that administration of prodrugs of parent drugs (injection PO), which results in efficacious concentrations at locomotor testing, will display efficacy in in vivo measures of antipsychotic efficacy.

Materials: Experimental Animals:

12, Sprague Dawley rats are purchased from Charles River Laboratory. The rats are approximately 90 days old, and weighed in the range of 350-275 grams upon receipt from the supplier. One rat is placed in each cage and allowed to acclimate for about 1 week. The rats are provided with food and water ad libitum.

Dosing Solution of D-Amphetamine (D-AMPH):

D-AMPH is purchased from Sigma Aldrich. D-amphetamine HCl (obtained from Sigma Aldrich) is prepared in 0.9% saline to a concentration of 1.5 mg/ml. Salt form correction is not used in accordance with historical literature. D-Amphetamine (DAMPH) was given I.P. per body weight at a dose of 1 ml/kg (=1.5 mg/kg). DAMPH is prepared fresh from solid form 30 min. prior to each test period.

Dosing Solutions of Prodrug Derivatives of Antipsychotic Parent Drugs:

Dosing solutions comprise any number of suitable excipients for PO injection including but not limited to, i) oil emulsion in water with any combination of diphosphotidylcholine (DPPC), glycerol and NaOH, ii) aqueous suspensions including crystalline suspensions in any combination of hydroxypropylmethyl cellulose (HPMC) glycerol, phosphate buffered saline (PBS) and polysorbate (e.g. Tween 20).

Behavior Box:

The behavior chambers are purchased from Med Associates, Inc. of St. Albans, Vt., Model ENV-515. Software for measuring animal movement is provided with the behavior chamber by the supplier.

Methods:

The animals are acclimated for one week prior to commencing experimentation. The animals are initially acclimated to the behavior box for about 15 minutes before they are removed from the box and administered a prodrug compound of the invention, at concentrations which produce target therapeutic levels for the drug approximately 1 hour after administration. After an additional 15 minutes the animals are placed back in the behavior box for an additional 30 minute drug-baseline test session. The mice are then administered by IP injection, D-AMPH (1.5 mg/kg) followed by a 60 minute experimental behavioral measurement period. The parameters that are measured include a) total distance measured (primary measure), b) total number of ambulatory moves (second measure), c) total number of vertical moves (secondary measure) and d) time spent immobile (secondary measure.

Blood Sampling:

Tail vein blood is taken on experiment days immediately following locomotor activity measurements (2-hours post-prodrug administration) and again the following day at time-points corresponding to 22 hours post-prodrug administration. Blood samples are collected via a lateral tail vein after anesthesia with Isoflurane. A 27 1/2 G syringe without an anticoagulant is used for the blood collection, and the whole blood is transferred to pre-chilled (wet ice) tubes containing K2 EDTA. 0.5 ml of blood per animal is collected per time point. The tubes are inverted 15-20 times and immediately returned to the wet ice until being centrifuged for 2 minutes>14,000 g to separate plasma. The plasma samples that are prepared in this manner are transferred to labeled plain tubes (MICROTAINER®; MFG# BD5962) and stored frozen at <−70° C.

Behavioral Data Acquisition:

Behavioral data is captured electronically by the software package associated with the behavior chambers. Data is transformed and analyzed via GraphPad PRISM® 5 software (GraphPad Software, Inc., La Jolla, Calif.). The data is analyzed using a 2-way repeated measures ANOVA.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

Example 9

Apomorphine (APO)

Preparation of apomorphine diacetate (APO diacetate)(S)-6-methyl-5,6,6a,7-tetrahydro-4H-dibenzo[de,g]quinoline-10,11-diyl diacetate

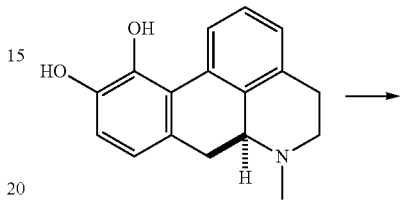

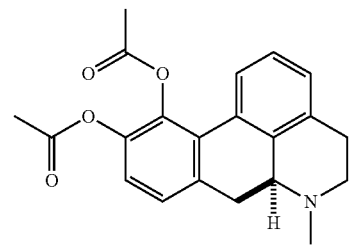

APO diacetate

To a mixture of apomorphine hydrochloride (9.0 g, 29.7 mmol) and dichloromethane (150 mL) at 5° C. was added triethylamine (13.6 mL, 97.8 mmol), followed by acetyl chloride (5.3 mL, 74.3 mmol) over 10 min. The reaction mixture was stirred for 1 h and then warmed to 25° C. After a further 3 h the reaction was quenched with methanol (5 mL) and then diluted with dichloromethane (100 mL). The reaction mixture was washed with saturated NaHCO$_3$, dried over MgSO$_4$ and evaporated. The residue was further purified by silica chromatography eluting with ethyl acetate to 97:3 ethyl acetate/methanol. The product containing fractions were evaporated and triturated with heptane to give RDC 3915 as a pale green solid (10.3 g, 99%). $^1$H-NMR (300 MHz, CDCl$_3$) δ 7.74 (1H, d), 7.22-7.18 (2H, m), 7.08 (2H, t), 3.25-3.11 (3H, m), 3.03 (1H, dd), 2.75 (1H, dd), 2.60-2.47 (5H, m), 2.31 (3H, s), 2.27 (3H, s).

Quaternisation Procedures

APO-1 (APO diacetate dimethyl myristate) (6aS)-10,11-diacetoxy-6-(((2,2-dimethyltetradecanoyl)oxy)methyl)-6-methyl-5,6,6a,7-tetrahydro-4H-dibenzo[de,g]quinolin-6-ium General Procedure I

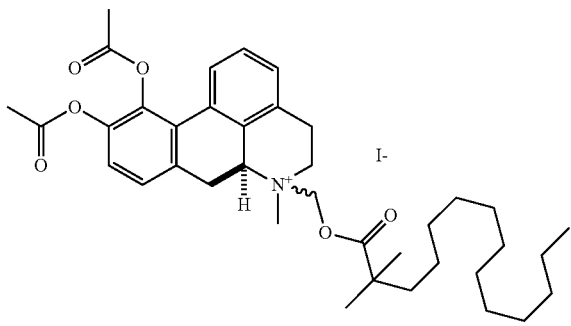

Quaternisation Reaction

To a solution of RDC 3915 (1.6 g, 4.55 mmol) in diethyl ether (80 mL) was added iodomethyl 2,2-dimethyltetradecanoate (2.16 g, 5.46 mmol) as prepared in Example 1. The reaction was stirred at 25° C. The reaction had partially precipitated from solution so dichloromethane (20 mL) was added to fully solubilize the reaction. After a further 4 days at 25° C., the reaction was complete. The reaction mixture was concentrated to a minimum volume and heptane was added (100 mL). The product precipitated from the solution as a gum which was stirred in heptane overnight. The heptane was removed under vacuum to give a solid. This was triturated in heptane overnight to give APO-1 (3.083 g, 90%) as a pale green solid. The product is a 1:1 ratio of diastereoisomers by $^1$H-NMR analysis. $^1$H-NMR (CDCl$_3$) δ 7.91 (2H, t), 7.52 (1H, d), 7.44 (2H, m), 7.31 (2H, m), 7.23 (1H, m), 7.16 (2H, d), 6.09 (2H, s), 5.56 (1H, d), 5.45 (1H, d), 5.02 (2H, m), 4.26 (3H, m), 3.96 (1H, dd), 3.85 (3H, s), 3.51-3.70 (3H, m), 3.49 (3H, s), 3.22 (3H, m), 2.94 (2H, m), 2.31 (3H, s), 2.28 (3H, s), 2.25 (6H, s), 1.55 (4H, m), 1.14-1.24 (52H, m), 0.87 (6H, t).

Synthesis of APO-2 (APO diacetate dimethyl decanoate) (6aS)-10,11-diacetoxy-6-(((2,2-dimethyldecanoyl)oxy)methyl)-6-methyl-5,6,6a,7-tetrahydro-4H-dibenzo[de,g]quinolin-6-ium iodide

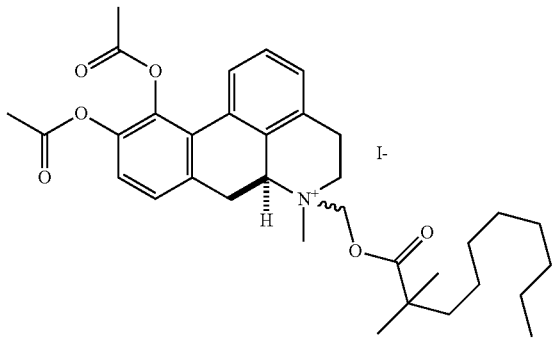

APO-2 was synthesized from 1-iodooctane following general procedure I. At the end of the quaternization reaction the mixture was concentrated to a minimum volume and heptane was added (100 mL). The product precipitated from the solution as a gum which was stirred in heptane overnight to give APO-2 (3.079 g, 78%) as a pale green solid. The product is a 1:1 ratio of diastereoisomers by $^1$H-NMR analysis.

$^1$H-NMR (CDCl$_3$) δ 7.91 (2H, t), 7.57 (1H, d), 7.43 (2H, m), 7.35 (1H, d), 7.24-7.28 (2H, m), 7.17 (1H, d), 7.14 (1H, d), 6.09 (2H, s), 5.54 (1H, d), 5.44 (1H, d), 5.06 (1H, d), 4.95 (1H, m), 4.19-4.40 (3H, m), 4.02 (1H, dd), 3.86 (3H, s), 3.49-3.70 (3H, m), 3.48 (3H, s), 3.22 (3H, m), 2.93 (2H, t), 2.31 (3H, s), 2.24-2.29 (9H, m), 1.56 (4H, m), 1.02-1.36 (36H, m), 0.87 (6H, m).

APO-3 (APO diacetate palmitate) (6aS)-10,11-diacetoxy-6-methyl-6-((palmitoyloxy)methyl)-5,6,6a,7-tetrahydro-4H-dibenzo[de,g]quinolin-6-ium iodide

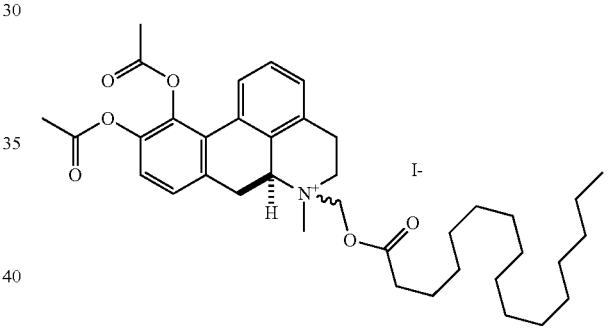

APO-3 was synthesized from 1-iodooctane following general procedure I. At the end of the quaternization reaction the mixture was concentrated to a minimum volume and heptane was added (100 mL). The product precipitated from the solution as a gum which was stirred in heptane overnight. The heptane was removed under vacuum to give a solid. This was triturated in heptane overnight to give APO-3 (2.867 g, 84%) as a pale green solid. The product is a 1:1 ratio of diastereoisomers by $^1$H-NMR analysis.

$^1$H-NMR (CDCl$_3$) δ 7.93 (1H, d), 7.90 (1H, d), 7.55 (1H, d), 7.36-7.46 (3H, m), 7.25 (2H, m), 7.15 (2H, m), 6.15 (1H, d), 6.08 (1H, d), 5.56 (1H, d), 5.39 (1H, d), 4.85-5.01 (2H, m), 4.36-4.52 (2H, m), 3.94-4.16 (2H, m), 3.82 (3H, s), 3.60 (3H, m), 3.47 (3H, s), 3.12-3.41 (3H, m), 2.95 (2H, t), 2.58 (2H, q), 2.50 (2H, t), 2.32 (3H, s), 2.27 (6H, s), 2.25 (3H, s), 1.61 (4H, m), 1.24 (48H, m), 0.87 (6H, t).

Example 10

Loperamide (LOP)

Quaternisation Reaction Procedures-Straight Chains

LOP-1 and LOP-2 (LOP Decanoate) (1,4 trans)-4-(4-chlorophenyl)-1-((decanoyloxy)methyl)-1-(4-(dimethylamino)-4-oxo-3,3-diphenylbutyl)-4-hydroxypiperidin-1-ium iodide and (1,4 syn)-4-(4-chlorophenyl)-1-((decanoyloxy)methyl)-1-(4-(dimethylamino)-4-oxo-3,3-diphenylbutyl)-4-hydroxypiperidin-1-ium iodide

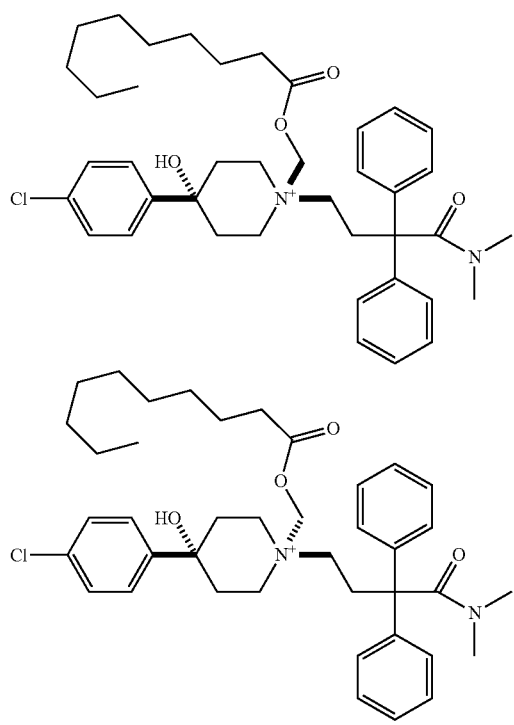

General Procedure I

Step A—Formation of Chloromethyl Alkyl Ester

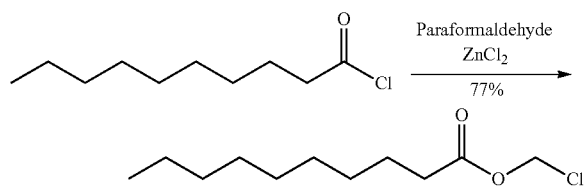

Decanoyl chloride (15 g, 78.7 mmol), paraformaldehyde (2.36 g, 78.7 mmol) and zinc chloride (200 mg) were combined and the reaction mixture heated to 65° C. overnight. The reaction was cooled to 25° C. then partitioned between dichloromethane (200 mL) and aq NaHCO$_3$ (100 mL, 50% of a saturated solution). The organics were again washed with NaHCO$_3$ (100 mL), then water (50 mL) and dried (MgSO$_4$) and concentrated to give the crude product. This was purified by column chromatography eluting with dichloromethane to give chloromethyl decanoate (13.3 g, 77%) as a pale yellow oil.

$^1$H-NMR (CDCl$_3$) δ 5.70 (2H, s), 2.38 (2H, t), 1.70-1.55 (2H, m), 1.38-1.15 (12H, m), 0.87 (3H, t).

Step B—Formation of Iodomethyl Alkyl Ester

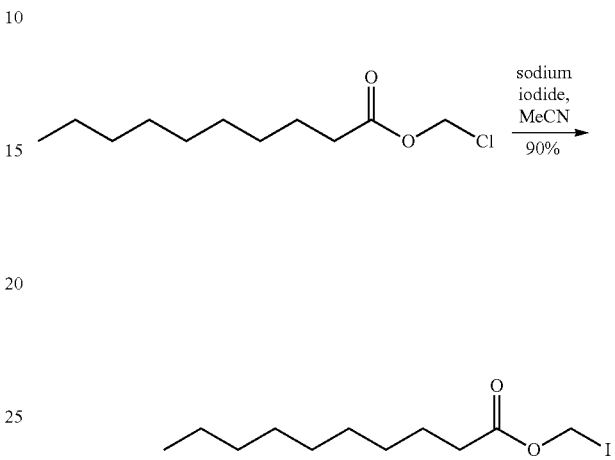

To a solution of the chloromethyl alkyl ester (8 g, 36.2 mmol) in acetonitrile (80 mL) was added sodium iodide (16.3 g, 108.7 mmol). The flask was covered in tin foil to exclude light and stirred at 25° C. overnight. The reaction mixture was partitioned between dichloromethane (200 mL) and water (150 mL). The aqueous layer was extracted with dichloromethane (2×150 mL). The combined organics were washed with aq satd NaHCO$_3$ (200 mL), 5% aq sodium sulfite solution (200 mL) and brine (2×100 mL), then dried (MgSO$_4$) and concentrated to give iodomethyl decanoate (11.3 g, 90%) as a yellow oil which was not purified any further. $^1$H-NMR (CDCl$_3$) δ 5.90 (2H, s), 2.32 (2H, t), 1.68-1.58 (2H, m), 1.38-1.18 (12H, m), 0.87 (3H, t).

Step C—Quaternisation Reaction

To a solution of Loperamide (2.0 g, 4.19 mmol) in ethylacetate (60 mL) was added iodomethyl decanoate (1.44 g, 4.61 mmol). The reaction was stirred at room temperature overnight. The product was isolated by filtration and purified by dissolving in the minimum volume of dichloromethane/methanol followed by addition of ethylacetate (200 mL) to give LOP-1 as a colourless solid (1.097 g, 33%). The product was a single conformer by $^1$H-NMR. The other conformer was isolated through concentration of the filtrate. The residue was purified by dissolving in the minimum volume of dichloromethane/methanol followed by addition of ethylacetate (200 mL) to give LOP-2 as a colourless solid (0.917 g, 28%).

$^1$H-NMR (CDCl$_3$) batch 46631 δ 7.27-7.49 (14H, m), 5.41 (2H, s), 4.94 (1H, s), 3.94 (2H, t), 3.39 (2H, d), 3.05 (2H, m), 2.97 (3H, s), 2.66 (2H, m), 2.44 (2H, t), 2.29 (3H, s), 2.26 (4H, m), 1.62 (2H, m), 1.28 (12H, m), 0.88 (3H, t).

$^1$H-NMR (CDCl$_3$) batch 46633 δ 7.27-7.52 (14H, m), 5.35 (2H, s), 4.35 (2H, m), 3.23 (4H, m), 2.99 (3H, s), 2.50 (4H, m), 2.29 (3H, s), 1.88-2.17 (4H, m), 1.67 (2H, m), 1.28 (12H, m), 0.88 (3H, t).

LOP-3 (LOP Laurate) 4-(4-chlorophenyl)-1-(4-(dimethylamino)-4-oxo-3,3-diphenylbutyl)-4-hydroxy-1-((dodecanoyloxy)methyl)piperidin-1-ium

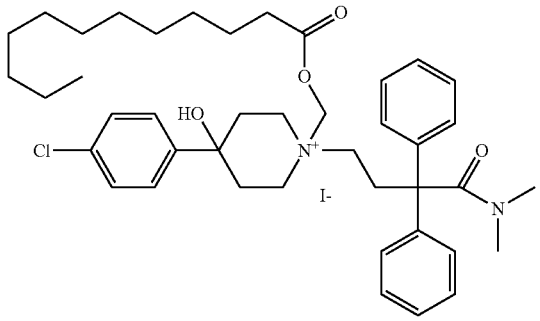 [SMILES: CCCCCCCCCCCC(=O)OC[N+]1(CCC(C(=O)N(C)C)(c2ccccc2)c2ccccc2)CCC(O)(c2ccc(Cl)cc2)CC1 ; [I-]]

The quaternization was carried out in ethylacetate using iodomethyl laurate (made from lauroyl chloride using general procedure I) and left for 4 days. The reaction mixture was concentrated and the residue dissolved in a minimum amount of dichloromethane and added to diethyl ether to give LOP-3 (2.14 g, 83%). The product was isolated as an approx 1:1 mixture of conformer by $^1$H-NMR.

$^1$H-NMR (CDCl$_3$) δ 7.52-7.19 (28H, m), 5.52 (2H, s), 5.33 (2H, s), 4.69 (1H, s), 4.37 (1H, s), 4.43 (2H, br t), 3.81 (2H, br t), 3.48 (2H, d), 3.29-3.11 (4H, m), 2.99 (3H, s), 2.92 (3H, s), 2.73-2.62 (2H, m), 2.50-2.07 (15H, m), 1.89 (2H, br t), 1.73 (3H, s), 1.68-1.54 (4H, m), 1.38-1.18 (32H, m), 0.87 (6H, t).

LOP-4 (LOP Palmitate) 4-(4-chlorophenyl)-1-(4-(dimethylamino)-4-oxo-3,3-diphenylbutyl)-4-hydroxy-1-((palmitoyloxy)methyl)piperidin-1-ium

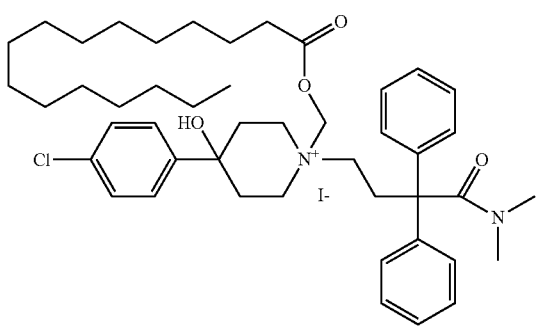 [SMILES: CCCCCCCCCCCCCCCC(=O)OC[N+]1(CCC(C(=O)N(C)C)(c2ccccc2)c2ccccc2)CCC(O)(c2ccc(Cl)cc2)CC1 ; [I-]]

The quaternization was carried out in ethylacetate with iodomethyl palmitate (synthesized from palmitoyl chloride using general procedure I). The reaction was stirred at 25° C. for 3 days before the solvent was removed in vacuo. The residue was dissolved in the minimum volume of dichloromethane and was precipitated with diethyl ether (200 mL) to give LOP-4 as a colourless solid (2.07 g, 75%). The product was isolated as an approx 1:1 mixture of conformers by $^1$H-NMR. $^1$H-NMR (300 MHz, CDCl$_3$) δ 7.26-7.52 (28H, m), 5.49 (2H, s), 5.34 (2H, s), 4.66 (1H, s), 4.26 (2H, t), 4.15 (1H, s), 3.87 (2H, m), 3.46 (2H, d), 3.21 (2H, m), 3.04 (2H, m), 2.99 (3H, s), 2.96 (3H, s), 2.69 (2H, m), 2.40-2.52 (6H, m), 2.29 (10H, m), 2.11 (2H, d), 1.93 (2H, t), 1.65 (4H, m), 1.25 (48H, m), 0.87 (6H, t).

LOP-5 (LOP Butyrate) 1-((butyryloxy)methyl)-4-(4-chlorophenyl)-1-(4-(dimethylamino)-4-oxo-3,3-diphenylbutyl)-4-hydroxypiperidin-1-ium iodide

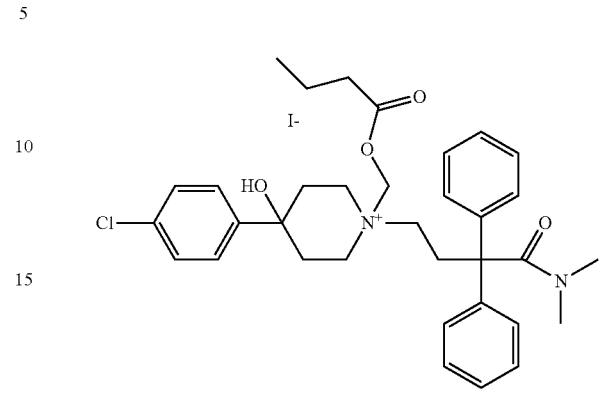

The quarternization was carried out in ethylacetate using iodomethyl butyrate (synthesized from chloromethyl butyrate using general procedure I, from step B) and the product precipitated from the reaction. The reaction was stirred at 25° C. for 6 days before the product was isolated by filtration. The product was purified by dissolving in the minimum volume of dichloromethane/methanol and followed by the addition of diethyl ether (200 mL) to give LOP-5 as a colourless solid (2.21 g, 75%). The product was isolated as an approx 1:1 ratio of conformers by $^1$H-NMR.

$^1$H-NMR (300 MHz, CDCl$_3$) δ 7.26-7.52 (28H, m), 5.46 (2H, s), 5.34 (2H, s), 4.62 (1H, s), 4.33 (2H, t), 3.90 (2H, m), 3.42 (2H, d), 3.20 (3H, m), 3.05 (2H, m), 3.00 (3H, s), 2.96 (3H, s), 2.71 (2H, m), 2.39-2.52 (6H, m), 2.27-2.29 (12H, m), 1.88-2.13 (4H, t), 1.58-1.76 (4H, m), 0.97 (6H, 2×t).

LOP GEM Dimethyl Quats

LOP-6 (Dimethyl Butyrate) 4-(4-chlorophenyl)-1-(4-(dimethylamino)-4-oxo-3,3-diphenylbutyl)-1-(((2,2-dimethylbutanoyl)oxy)methyl)-4-hydroxypiperidin-1-ium iodide

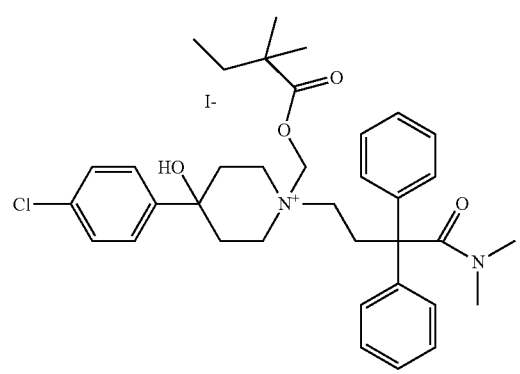 [SMILES: CCC(C)(C)C(=O)OC[N+]1(CCC(C(=O)N(C)C)(c2ccccc2)c2ccccc2)CCC(O)(c2ccc(Cl)cc2)CC1 ; [I-]]

The quaternization was carried out in ethyl acetate using iodomethyl 2,2-dimethylbutanoate (synthesized from 2,2-dimethylbutyryl chloride using general procedure I) and the product precipitated from the reaction. The reaction was stirred at 25° C. for 6 days before the product was isolated by filtration. The product was purified by dissolving in the minimum volume of dichloromethane/methanol followed by the addition of ethyl acetate (200 mL) to give LOP-6 as a colourless solid (1.97 g, 64%). The product is a 7:10 ratio of conformers by $^1$H-NMR. $^1$H-NMR (CDCl$_3$) δ 7.25-7.52 (14H, m), 5.45 (0.8H, s), 5.29 (1.2H, s), 4.24 (1.2H, t), 3.99 (0.8H, m), 3.42 (0.8H, d), 3.22 (2.4H, m), 2.96-3.09 (3.8H, m), 2.76 (0.8H, m), 2.53 (1.2H, m), 2.29 (5H, m), 1.88-2.19 (2H, m), 1.59 (2H, m), 1.23 (3.6H, s), 1.15 (2.4H, s), 0.83 (3H, m).

LOP-7 (Dimethylmyristate) 4-(4-chlorophenyl)-1-(4-(dimethylamino)-4-oxo-3,3-diphenylbutyl)-1-(((2,2-dimethyltetradecanoyl)oxy)methyl)-4-hydroxypiperidin-1-ium iodide

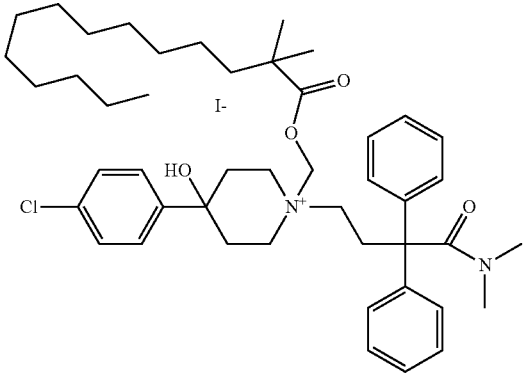 [SMILES: CCCCCCCCCCCCC(C)(C)C(=O)OC[N+]1(CCC(C(=O)N(C)C)(c2ccccc2)c2ccccc2)CCC(O)(c2ccc(Cl)cc2)CC1 ; [I-]]

General Procedure II

Step A—Synthesis of methyl 2,2-dimethyltetradecanoate

To a stirred solution of diisopropylamine (6.90 mL, 49.0 mmol) in THF (50 mL) under Ar (g) at −7° C. was added n-BuLi (2.3M in hexanes, 21.3 mL, 49.0 mmol) dropwise via a dropping funnel keeping the temp. between 0° C. and 5° C. The reaction was stirred at −7° C. for 30 mins. And then cooled to −78° C. Methyl isobutyrate (5.61 mL, 49.0 mmol) was added and the reaction stirred at −78° C. for 1.5 hours. 1-Iodododecane (13.05 g, 44.1 mmol) in THF (10 mL) was added dropwise via a dropping funnel keeping the temperature below −70° C. A further 40 mL THF was added over 5 minutes to aid stirring. After complete addition the reaction was stirred at −78° C. for approx. 2 hours and then allowed to slowly warm to 25° C. overnight.

The reaction was quenched with sat. aq. NH$_4$Cl (100 mL) and diluted with ethyl acetate (100 mL). The aqueous was extracted with ethyl acetate (2×50 mL) and the combined organics washed with brine (50 mL) and dried over MgSO$_4$. After filtration, the volatiles were removed. The reaction was repeated in a similar manner using 15.05 mL (131.27 mmol) of methyl isobutyrate. The two crude batches were combined and purified by silica chromatography eluting heptane to 50% dichloromethane/heptane to give methyl 2,2-dimethyl myristate (31.7 g). $^1$H-NMR (300 MHz, CDCl$_3$) δ 3.65 (3H, s), 1.52-1.45 (2H, m), 1.32-1.18 (20H, m), 1.15 (6H, s), 0.86 (6H, s).

Step B—Synthesis of 2,2-dimethyltetradecanoic acid

To a stirred solution of methyl 2,2-dimethyltetradecanoate (31.7 g, 117.2 mmol) in ethanol (234 mL) was added 2M NaOH (117 mL, 234.4 mmol). The reaction was stirred at 25° C. overnight. NaOH (4.69 g, 117 mmol) was added and the reaction heated at 50° C. for 24 hours. NaOH (4.69 g, 117 mmol) was added and the reaction heated to 100° C. for 4 hours and then cooled to 25° C. 140 mL 4M HCl was added to acidify. ethyl acetate (200 mL) was added and the layers separated. The aqueous was extracted with ethyl acetate (2×100 mL) and the combined organics concentrated in vacuo. The residue was partitioned between ethyl acetate (200 mL) and brine (100 mL). The organic layer was washed with brine (50 mL) and dried over MgSO$_4$. After filtration, the volatiles were removed to give 2,2-dimethyltetradecanoic acid (26.9 g).

$^1$H-NMR (300 MHz, CDCl$_3$) δ 1.55-1.48 (2H, m), 1.30-1.20 (20H, m), 1.18 (6H, s), 0.87 (3H, t).

Step C—Synthesis of chloromethyl 2,2-dimethyltetradecanoate

To a suspension of 2,2-dimethyltetradecanoic acid (14.3 g, 55.8 mmol) in water (100 mL) was added sodium hydrogen carbonate (23.6 g, 223.1 mmol) at 25° C. After stirring for 15 minutes, the reaction was cooled to 0° C. and chloromethyl chlorosulfate (7.3 mL, 72.5 mmol), nBu$_4$NHSO$_4$ (3.79 g, 11.1 mmol) and dichloromethane (200 mL) were added. After stirring at 0° C. for 1 hour, the reaction was allowed to warm to 25° C. and stirred overnight. The reaction mixture was separated and the aqueous layer washed with dichloromethane (2×100 mL). The combined organic layers were dried over MgSO$_4$ and concentrated. The residue was purified by column chromatography eluting with 40% dichlormethane/heptane to give chloromethyl 2,2-dimethyltetradecanoate (14.47 g, 85%). $^1$H-NMR (300 MHz, CDCl$_3$) δ 5.71 (2H, s), 1.55-1.48 (2H, m), 1.31-1.19 (20H, m), 1.19 (6H, s), 0.87 (3H, t).

The iodomethyl alkyl ester was then made as described in general procedure I step B. The quaternization was carried out following general procedure step C in ethylacetate with iodomethyl 2,2-dimethyltetradecanoate. The reaction was stirred at 25° C. for 4 days before the volatiles were removed under vacuum. The residue was purified by dissolving in the minimum volume of dichloromethane before the addition of diethyl ether (300 mL) to give a very fine solid. The product was isolated by filtering through celite to remove the mother liquors before the product was washed off the celite with dichloromethane. Concentration under vacuum gave a solid which was triturated with diethyl ether to give LOP-7 as a colourless solid (1.4 g, 38%). $^1$H-NMR (CDCl$_3$) δ 7.27-7.51 (14H, m), 5.28 (2H, s), 4.63 (1H, s), 4.18 (2H, t), 3.23 (4H, m), 3.00 (3H, s), 2.52 (2H, m), 2.28 (3H, s), 2.20 (2H, d), 1.93 (2H, t), 1.54 (2H, m), 1.24 (26H, m), 0.86 (3H, t).

LOP-8 (LOP Dimethyl Laurate) 4-(4-chlorophenyl)-1-(4-(dimethylamino)-4-oxo-3,3-diphenylbutyl)-1-(((2,2-dimethyldodecanoyl)oxy)methyl)-4-hydroxypiperidin-1-ium iodide

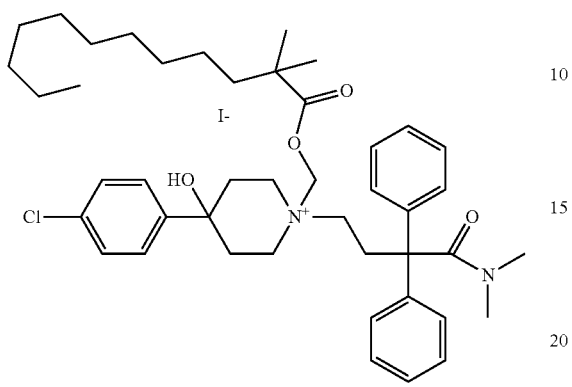

The quaternization was carried out in ethylacetate with iodomethyl 2,2-dimethyldodecanoate (synthesized from 1-iododecane using general procedure II). The reaction was stirred at 25° C. for 3 days before the solvent was concentrated. The residue was dissolved in the minimum volume of dichloromethane and precipitated with diethyl ether (200 mL) to give LOP-8 as a colourless solid (0.941 g, 35%). The product was isolated as a single conformer by $^1$H-NMR.

$^1$H-NMR (CDCl$_3$) δ 7.32-7.51 (14H, m), 5.28 (2H, s), 4.66 (1H, s), 4.17 (2H, t), 3.23 (4H, t), 3.00 (3H, s), 2.51 (2H, m), 2.29 (3H, s), 2.19 (2H, m), 1.93 (2H, t), 1.52 (2H, m), 1.24 (26H, m), 0.86 (3H, t).

LOP-9 (LOP Dimethyl Palmitate) 4-(4-chlorophenyl)-1-(4-(dimethylamino)-4-oxo-3,3-diphenylbutyl)-1-(((2,2-dimethylpalmitoyl)oxy)methyl)-4-hydroxypiperidin-1-ium iodide

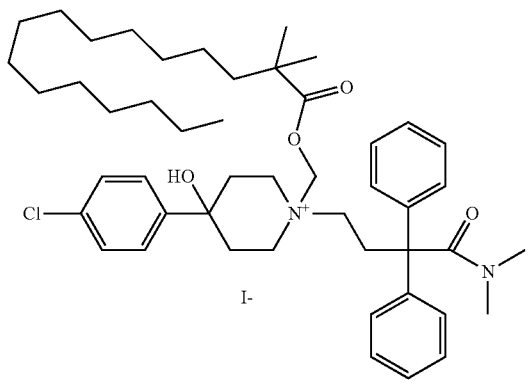 [SMILES: CCCCCCCCCCCCCCC(C)(C)C(=O)OC[N+]1(CCC(C(=O)N(C)C)(c2ccccc2)c2ccccc2)CCC(O)(c2ccc(Cl)cc2)CC1 ; [I-]]

The quaternization was carried out in ethylacetate with iodomethyl 2,2-dimethylhexadecanoate (synthesized from 1-iodotetradecane using general procedure II). The reaction was stirred at 25° C. for 3 days before the solvent was removed in vacuo. The residue was dissolved in the minimum volume of dichloromethane and was precipitated with diethyl ether (200 mL) to give LOP-9 as a colourless solid (1.185 g, 42%). The product was isolated as a single conformer by $^1$H-NMR. $^1$H-NMR (CDCl$_3$) δ 7.35-7.53 (12H, m), 7.31 (2H, s), 5.28 (2H, s), 4.67 (1H, s), 4.16 (2H, t), 3.24 (4H, m), 3.00 (3H, s), 2.51 (2H, m), 2.29 (3H, s), 2.19 (2H, d), 1.92 (2H, t), 1.53 (2H, m), 1.24 (30H, m), 0.87 (3H, t).

LOP-10 (LOP Isopentyl Carbonate Quat) 4-(4-chlorophenyl)-1-(4-(dimethylamino)-4-oxo-3,3-diphenylbutyl)-4-hydroxy-1-((((pentan-3-yloxy)carbonyl)oxy)methyl)piperidin-1-ium iodide

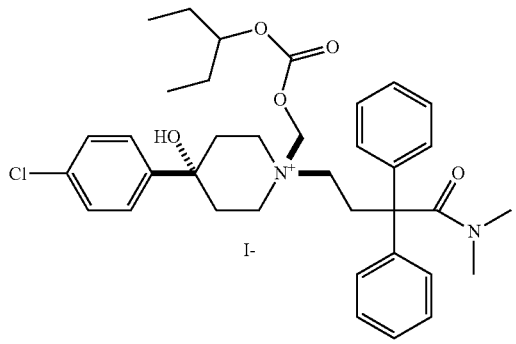

To a solution of chloromethylchloroformate (6 g, 46.5 mmol) in heptane at 0° C. was added 3-pentanol (4.9 mL, 45.3 mmol), followed by pyridine (7.5 mL, 92.7 mmol) over 15 min. The reaction mixture was stirred for 30 min and then allowed to self warm to 25° C. After 5 h the reaction mixture was washed with 1M HCl and then saturated NaHCO$_3$. The organic phase was dried over MgSO$_4$ filtered and evaporated. The residue was further purified by silica chromatography eluting with 8:1 heptane/ethyl acetate to give chloromethyl pentan-3-yl carbonate (7.4 g, 90%). $^1$H-NMR (CDCl$_3$) δ 5.72 (2H, s), 4.66 (1H, dt), 1.70-1.57 (4H, m), 0.92 (6H, t).

The iodomethyl alkyl ester was then made as described in general procedure I step B. The quaternization was conducted in ethyl acetate using iodomethyl pentan-3-yl carbonate. The product precipitated from the reaction and was isolated by filtration after 16 hours at 25° C. The product was purified by dissolving in the minimum volume of dichloromethane/methanol followed by the addition of ethylacetate (300 mL) and diethyl ether (200 mL) to give LOP-10 as a colourless solid (0.472 g, 15%). The product exists as a single conformer by $^1$H-NMR. $^1$H-NMR (CDCl$_3$) δ 7.28-7.49 (14H, m), 5.45 (2H, s), 4.65 (1H, m), 3.97 (2H, m), 3.42 (2H, d), 3.11 (2H, m), 2.98 (3H, s), 2.73 (2H, m), 2.27 (7H, m), 1.67 (4H, m), 0.92 (6H, t).

Example 11

Citalopram

CIT-1 (stearate) 3-(5-cyano-1-(4-fluorophenyl)-1,3-dihydroisobenzofuran-1-yl)-N,N-dimethyl-N-((stearoyloxy)methyl)propan-1-aminium iodide

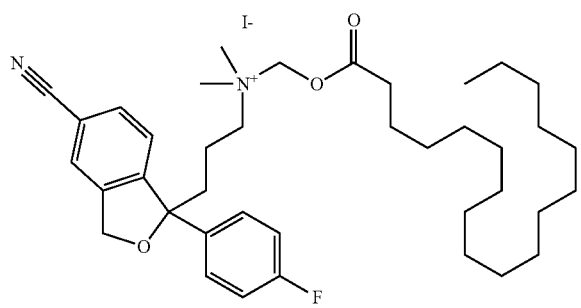 [SMILES: CCCCCCCCCCCCCCCCCC(=O)OC[N+](C)(C)CCCC1(c2ccc(F)cc2)OCc2cc(C#N)ccc21 ; [I-]]

General Reaction Procedure I

Step A—Formation of Acid Chloride

To a stirred suspension of stearic acid (20 g, 70.3 mmol) in dichloromethane (100 mL) was added oxalyl chloride (8.92 mL, 105.5 mmol). 1 drop dimethylformamide was added and the reaction stirred at 25° C. for 3 hours. The solvent was removed in vacuo and the resulting product used in the next step without further purification. $^1$H-NMR (CDCl$_3$) δ 2.87 (2H, t), 1.65-1.70 (2H, m), 1.20-1.40 (28H, m), 0.87 (3H, t).

Step B—Formation of Chloromethyl Alkyl Ester

Paraformaldehyde (2.11 g, 70.3 mmol) and zinc chloride (258 mg) were added to the acid chloride prepared above and the reaction mixture was heated at 65° C. for 16 hours and then allowed to cool to 25° C. Dichloromethane (200 mL) and saturated aqueous NaHCO$_3$ (70 mL) were added. The aqueous emulsion was extracted with dichloromethane (2×50 mL) and the combined organic extracts washed with saturated aqueous NaHCO$_3$ (70 mL), brine (70 mL), and dried over MgSO$_4$. After filtration, the volatiles were removed and the residue purified by silica chromatography eluting with heptane to 12% DCM/heptane to give a yellow solid (12.64 g, 54% yield over two steps). $^1$H-NMR (CDCl$_3$) δ 5.70 (2H, s), 2.37 (2H, t), 1.55-1.70 (2H, m), 1.20-1.40 (28H, m) 0.86 (3H, t).

Step C—Formation of Iodomethyl Alkyl Ester

To a solution of the chloromethyl alkyl ester (12.64 g, 37.96 mmol) in acetonitrile (150 mL) and dichloromethane (75 mL) was added sodium iodide (17.07 g, 113.9 mmol). The flask was covered in tin foil to exclude light and stirred at 25° C. for 70 hours and then at 25° C. for 24 hours. The reaction mixture was partitioned between dichloromethane (200 mL) and water (150 mL). The aqueous layer was extracted with dichloromethane (2×150 mL). The combined organics were washed with aq satd NaHCO$_3$ (200 mL), 5% aq sodium sulfite solution (200 mL) and brine (2×100 mL), then dried (MgSO$_4$) and concentrated to give the product as a yellow solid (14.53 g, 90% yield) which was not further purified. $^1$H-NMR (CDCl$_3$) δ 5.90 (2H, s), 2.32 (2H, t), 1.55-1.70 (2H, m), 1.20-1.35 (28H, m), 0.87 (3H, t).

Step D—Quaternisation of Citalopram to Give RDC9354-07

To a stirred solution of Citalopram (1 g, 3.083 mmol) in ethyl acetate (10 mL) was added iodomethyl stearate (1.96 g, 4.624 mmol) as a suspension in ethyl acetate (15 mL). A further 25 mL ethyl acetate was added and the reaction stirred in the dark at 25° C. over the weekend. The precipitate solid was collected by filtration, washed with ethyl acetate (3×10 mL) and dried to give CIT-1 (1.66 g, 72%). $^1$H-NMR (300 MHz, CDCl$_3$) δ 7.66-7.57 (2H, m), 7.52-7.43 (3H, m), 7.08-6.99 (2H, m), 5.40 (2H, s), 5.28 (1H, d), 5.14 (1H, d), 4.01-3.88 (1H, m), 3.85-3.72 (1H, m), 3.26 (6H, s), 2.48 (2H, t), 2.43-2.19 (2H, m), 1.82-1.55 (4H, m), 1.36-1.17 (28H, m), 0.87 (3H, t).

CIT-2-(Dimethyl Myristate) 3-(5-cyano-1-(4-fluorophenyl)-1,3-dihydroisobenzofuran-1-yl)-N-4(2,2-dimethyltetradecanoyl)oxy)methyl)-N,N-dimethyl-propan-1-aminium iodide

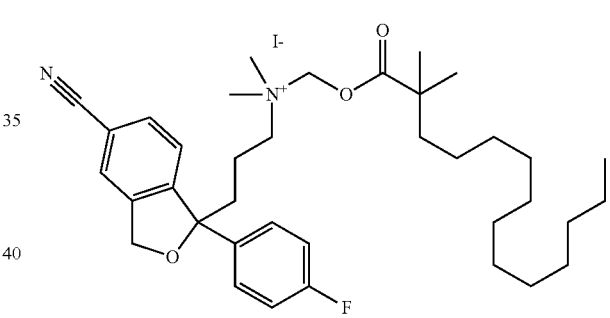

Step A Synthesis of methyl 2,2-dimethyltetradecanoate

To a stirred solution of diisopropylamine (6.90 mL, 49.0 mmol) in THF (50 mL) under argon (g) at −7° C. was added n-BuLi (2.3M in hexanes, 21.3 mL, 49.0 mmol) dropwise via a dropping funnel keeping the temperature between 0° C. and 5° C. The reaction was stirred at −7° C. for 30 mins. And then cooled to −78° C. Methyl isobutyrate (5.61 mL, 49.0 mmol) was added and the reaction stirred at −78° C. for 1.5 hours. 1-iodododecane (13.05 g, 44.1 mmol) in THF (10 mL) was added dropwise via a dropping funnel keeping the temperature below −70° C. A further 40 mL THF was added over 5 mins. To aid stirring. After complete addition the reaction was stirred at −78° C. for approx. 2 hours and then allowed to slowly warm to 25° C. overnight. The reaction was quenched with sat. aq. NH$_4$Cl (100 mL) and diluted with ethyl acetate (100 mL). The aqueous phase was extracted with ethyl acetate (2×50 mL) and the combined organics were washed with brine (50 mL) and dried over MgSO$_4$. After filtration, the volatiles were removed. The reaction was repeated in a similar manner using 15.05 mL (131.27 mmol) of methyl isobutyrate. The two crude batches were combined and purified by silica chromatography eluting heptane to 50% dichloromethane/heptane to give methyl 2,2-dimethyl myristate (31.7 g). $^1$H-NMR (300 MHz, CDCl$_3$) δ 3.65 (3H, s), 1.52-1.45 (2H, m), 1.32-1.18 (20H, m), 1.15 (6H, s), 0.86 (6H, s).

Step B—Synthesis of 2,2-dimethyltetradecanoic acid

To a stirred solution of methyl 2,2-dimethyltetradecanoate (31.7 g, 117.2 mmol) in ethanol (234 mL) was added 2M NaOH (117 mL, 234.4 mmol). The reaction was stirred at room temperature overnight. NaOH (4.69 g, 117 mmol) was added and the reaction heated at 50° C. for 24 hours. NaOH (4.69 g, 117 mmol) was added and the reaction heated to 100° C. for 4 hours and then cooled to 25° C. 140 mL 4M HCl was added to acidify. Ethyl acetate (200 mL) was added and the layers separated. The aqueous was extracted with ethyl acetate (2×100 mL) and the combined organics concentrated in vacuo. The residue was partitioned between ethyl acetate (200 mL) and brine (100 mL). The organic layer was washed with brine (50 mL) and dried over MgSO$_4$. After filtration, the volatiles were removed to give 2,2-dimethyltetradecanoic acid (26.9 g). $^1$H-NMR (300 MHz, CDCl$_3$) δ 1.55-1.48 (2H, m), 1.30-1.20 (20H, m), 1.18 (6H, s), 0.87 (3H, t).

Step C—Synthesis of chloromethyl 2,2-dimethyltetradecanoate

To a solution of 2,2-dimethyltetradecanoic acid (3.5 g, 13.6 mmol) in water (35 mL) was added Na$_2$CO$_3$ (5.8 g, 54 mmol). After 20 minutes, the reaction was cooled to 0° C. and nBu$_4$NHSO$_4$ (0.93 g, 3 mmol), dichloromethane (75 mL) and chloromethyl chlorosulfate (1.8 mL, 17.7 mmol) was added. The reaction was allowed to warm to 25° C. and stirred overnight. The reaction mixture was separated and the aqueous extracted with dichloromethane (2×100 mL). The combined organics were dried (MgSO$_4$) and concentrated in vacuo. The product was purified by column chromatography eluting with heptane to 10% dichloromethane/heptane to give chloromethyl 2,2-dimethyltetradecanoate (5.0 g, 71%). $^1$H-NMR (300 MHz, CDCl$_3$) δ 5.71 (2H, s), 1.55-1.48 (2H, m), 1.31-1.19 (20H, m), 1.19 (6H, s), 0.87 (3H, t).

CIT-2 was synthesized employing chloromethyl 2,2-dimethyltetradecanoate following general procedure I steps C and D described above. The final reaction mixture was concentrated to give an oil which was triturated with diethyl ether (×2) then dissolved in a minimum amount of DCM and added to diethyl ether. An oil formed and the solvent decanted. The remaining oil was then dried under vacuum to give CIT-2 (2.31 g, 70%). $^1$H-NMR (300 MHz, CDCl$_3$) δ 7.65-7.59 (2H, m), 7.51-7.44 (3H, m), 7.04 (2H, t), 5.36 (2H, s), 5.21 (2H, dd), 4.07-3.98 (1H, m), 3.88-3.79 (1H, m), 3.26 (6H, s), 2.41-2.19 (2H, m), 1.81-1.66 (2H, m), 1.55-1.50 (2H, m), 1.31-1.13 (26H, m), 0.87 (3H, t).

CIT-3-(CIT Octyldecanoate) 3-(5-cyano-1-(4-fluorophenyl)-1,3-dihydroisobenzofuran-1-yl)-N,N-dimethyl-N-4(2-octyldecanoyl)oxy)methyl)propan-1-aminium iodide

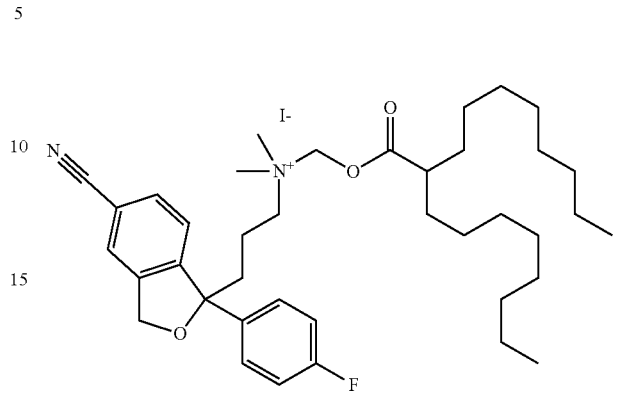

Step A—Synthesis of Diethyl 2,2-dioctylmalonate

To a solution of diethylmalonate (20 g, 0.125 mol) in tetrahydrofuran (500 mL) was added octyl bromide (47 mL, 0.275 mol), followed by sodium hydride (60% in mineral oil, 11 g, 0.275 mol) over 1 h. The reaction mixture was stirred at 25° C. for 3 days. A second portion of sodium hydride (5 g, 0.125 mol) and octyl bromide (15 mL, 0.086) were added and the mixture heated at reflux for 5 h. The reaction was cooled, carefully quenched with water and then diluted with 2M HCl. The reaction mixture was extracted with ethyl acetate, dried over MgSO$_4$ and evaporated. The residue was further purified by flash column chromatography eluting with 1:1 heptane/toluene to toluene to give diethyl 2,2-dioctylmalonate (41.4 g, 86%) as a pale yellow oil. $^1$H-NMR (300 MHz, CDCl$_3$) δ 3.98 (4H, q), 1.70-1.60 (4H, m), 1.15-0.88 (30H, m), 0.69 (6H, t).

Step B—Synthesis of 2-Octyldecanoic acid

To diethyl 2,2-dioctylmalonate (41.4 g, 0.108 mol) was added industrial methylated spirit (50 mL), followed by a solution of KOH (40 g, 0.714 mol) in water (500 mL). The reaction mixture was heated at reflux for 20 h, poured into ice/water and made acidic with 2M HCl. The mixture was then extracted with ethyl acetate and the organic phase dried over MgSO$_4$ before evaporation of the volatiles. The residue was then heated neat at 170° C. until gas evolution had ceased (~5 h) and on cooling 2-octyldecanoic acid (26.4 g, 86%) was obtained as a yellow solid. $^1$H-NMR (300 MHz, CDCl$_3$) δ2.40-2.26 (1H, m), 1.66-1.52 (2H, m), 1.51-1.39 (2H, m), 1.35-1.18 (24H, m), 0.87 (3H, t).

Step C~Synthesis of Chloromethyl 2-octyldecanoate

To a mixture of 2-octyldecanoic acid (12.2 g, 42.9 mmol) and water (90 mL) was added Na$_2$CO$_3$ (17.7 g, 108 mmol), tetrabutylammonium hydrogensulfate (2.8 g, 8.2 mmol), dichloromethane (180 mL) and then chloromethyl chlorosulfate (5.5 mL, 54.3 mmol). The reaction mixture was stirred for 18 h and then diluted with water (300 mL) and dichloromethane (300 mL). The organic phase was separated, dried over MgSO$_4$ and evaporated. The residue was purified on silica eluting with heptane/dichloromethane (8:1) to give chloromethyl 2-octyldecanoate (12.0 g, 84%)

as a colourless oil. $^1$H-NMR (300 MHz, CDCl$_3$) δ 5.72 (2H, s), 2.43-2.33 (1H, m), 1.67-1.52 (2H, m), 1.51-1.40 (2H, m), 1.33-1.18 (24H, m), 0.86 (3H, t).

CIT-3 was synthesized employing chloromethyl 2-octyl-decanoate following general procedure I, steps C and D (above). The final reaction mixture was concentrated and the residue triturated with diethyl ether (×2) and the solvent decanted. The remaining oil was then dissolved in ethyl acetate and washed with water (×2). The organic phase was dried over MgSO$_4$ and concentrated to give CIT-3 (1.30 g, 38%). $^1$H-NMR (300 MHz, CDCl$_3$) δ 7.65-7.59 (2H, m), 7.51-7.44 (3H, m), 7.04 (2H, t), 5.34 (2H, s), 5.20 (2H, dd), 4.07-3.97 (1H, m), 3.91-3.78 (1H, m), 3.25 (6H, s), 2.49-2.42 (1H, m), 2.40-2.27 (2H, m), 1.81-1.71 (2H, s), 1.52-1.48 (2H, m), 1.37-1.13 (24H, m), 0.87 (6H, 2×t).

CIT-4 (Dimethylphenyl Acetate) 3-(5-cyano-1-(4-fluorophenyl)-1,3-dihydroisobenzofuran-1-yl)-N,N-dimethyl-N-(((2-methyl-2-phenylpropanoyl)oxy)methyl)propan-1-aminium iodide

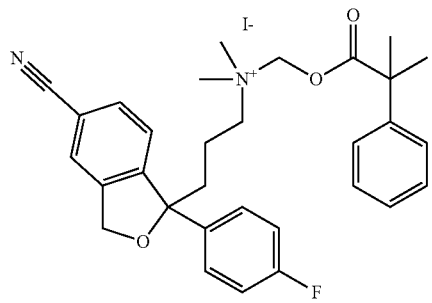 [SMILES: CC(C)(C(=O)OC[N+](C)(C)CCCC1(c2ccc(F)cc2)OCc2cc(C#N)ccc21)c1ccccc1 ; [I-]]

CIT-4 was synthesized employing dimethylphenylacetic acid following general procedure I (above), the final product was triturated with diethyl ether to give CIT-4 (3.8 g, 100%). $^1$H-NMR (300 MHz, CDCl$_3$) δ 7.65-7.55 (2H, m), 7.51 (1H, s), 7.44 (2H, dd), 7.39-7.22 (5H, m), 7.04 (2H, t), 5.32 (2H, s), 5.24 (1H, d), 5.17 (1H, d), 3.70-3.57 (1H, m), 3.46-3.36 (1H, m), 2.91 (6H, s), 2.14 (2H, q), 1.64 (3H, s), 1.60-1.46 (5H, m).

Example 12

Figure 4:
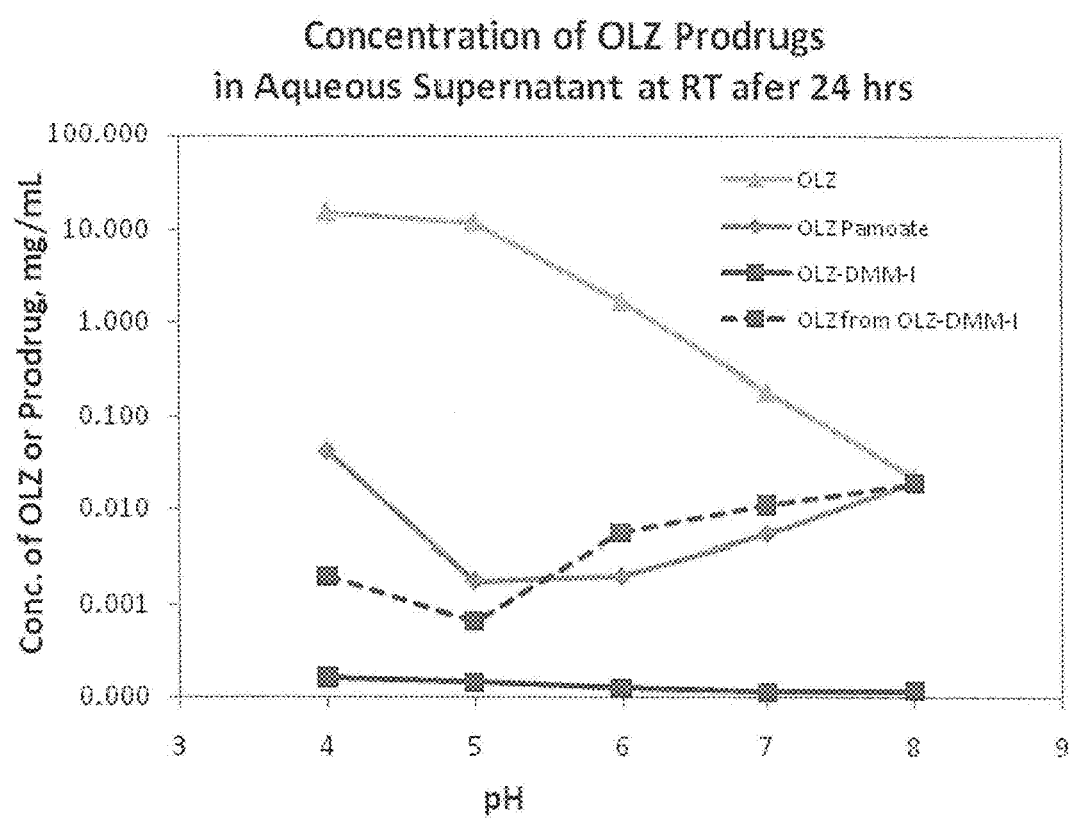
FIG. 4: Solubility of olanzapine base, pamoate salt and prodrug at room temperature as a function of pH.

Solubility of Olanzapine Base, Pamoate Salt and Prodrug at Room Temperature as a Function of pH Equilibrium solubility of olanzapine free base, olanzapine pamoate (the active ingredient in ZYPREXA® REL-PREVV® and ZYPADHERA®) and the iodide salt of dimethylmyristate prodrug (Compound 18; OLZ-DMM-I) was measured in aqueous buffers at room temperature in which the three crystalline materials were suspended and equilibrated to saturation, as evidenced by excess solid in suspension. At pH 4 and 5, 0.1 M citrate buffers were used, while for pH 6, 7 and 8a set of 0.1 M phosphate buffers were used. Each buffer also contained 0.2 M NaCl. No cosolvents or other potentially solubilizing components were included. Buffer preparations were subdivided in order to individually test the solubility of only one material in a given buffer sample. FIG. 4 shows the pH dependence of the solubility of olanzapine base (triangles) illustrating a greater than a 1000-fold variation in solubility (low solubility at pH 9 to high aqueous solubility at pH 4), consistent with the drugs' basic character. The solubility of olanzapine pamoate salt (OLZ Pamoate; diamond symbols) is pH dependent with slightly more than a 10-fold variation of solubility across the pH range studied. Compound 18 of the invention (OLZ DMM-I; square symbols) shows negligible pH dependence of solubility (less than 2-fold) across the pH range of 4-9. The room temperature solubility of the compound is uniformly low in water at between 0.0001 and 0.0002 ug/mL. FIG. 4 also shows the concentration of olanzapine formed by decomposition of Compound 18 as a function of pH(OLZ from DMM-I; square symbols, dashed line).

Example 13

Pharmacokinetic Evaluation of Olanzapine Prodrugs in Rats

Animals: Male Sprague-Dawley rats (Charles River Laboratories, Wilmington, Mass.) were obtained. Approximately 24 rats were used in each study. Rats were approximately 350-375 g at time of arrival. Rats were housed 2 per cage with ad libitum chow and water. Environmental conditions in the housing room: 64-67° F., 30% to 70% relative humidity, and 12:12-h light:dark cycle. All experiments were approved by the institutional animal care and use committee.

Test Compounds: An amount of each test compound was suspended in the vehicle indicated in Table 6 to yield a suspension comprising the equivalent of 3 mg olanzapine in 0.3 mL.

Pharmacokinetics study: Rats were dosed IM by means of a 23 gauge, 1 in. needle with 1 cc syringe. 0.3 mL suspension was withdrawn from the vial containing the test compound. The rat was injected in the muscles of the hind limb after anesthesia with isoflourane. Blood samples were collected via a lateral tail vein after brief anesthesia with Isoflurane. A 27½G needle and 1 cc syringe without an anticoagulant were used for the blood collection. Approximately 250 µL of whole blood was collected at each sampling time point of 6 hours, 24 hours and 2, 5, 7, 9, 12, 14 days after administration. Approximately 450 µL, of whole blood was collected at sampling time points of 21, 28 and 35 days. Once collected, whole blood was immediately transferred to tubes containing K$_2$ EDTA, inverted 10-15 times and immediately placed on ice. The tubes were centrifuged for 2 minutes at >14,000×g (11500 RPM using Eppendorf Centrifuge 5417C, F45-30-11 rotor) at 4-8° C. to separate plasma. Plasma samples were transferred to labeled plain tubes (MICROTAINER®; MFG# BD5962) and stored frozen at <−70° C.

Data Analysis: Drug concentrations in plasma samples were analyzed by liquid chromatography-mass spectroscopy using appropriate parameters for each compound. Half-life, volume of distribution, clearance, maximal concentration, and AUC were calculated by using WinNonlin software, version 5.2 (Pharsight, St. Louis, Mo.).

Results: The results are summarized in Table.

TABLE 7

| Olanzapine Compound # | AUC$_{0-t}$ (ng * day/mL) | T$_{max}$ (day) | T$_{1/2}$ (day) | Vehicle |
|---|---|---|---|---|
| Olanzapine solution control | 193 | 0.03 | 0.15 | 100:1 Captisol:1M HCl |

TABLE 7-continued

| Olanzapine Compound # | AUC$_{0-t}$ (ng * day/mL) | T$_{max}$ (day) | T$_{1/2}$ (day) | Vehicle |
|---|---|---|---|---|
| 13 | 77.3 | 0.3 | 0.9 | 2% CMC in PBS with 0.2% Tween 20. pH 6.6 |
| 10 | 151.0 | 0.3 | 1.6 | 2% CMC in PBS with 0.2% Tween 20. pH 6.7 |
| 18 | 143.0 | 2.0 | 1.3 | 2% CMC in PBS with 0.2% Tween 20. pH 6.8 |
| 2 | 135 | 0.3 | 0.2 | 2% CMC in PBS with 0.2% Tween 20. pH 6.10 |
| 24 | 147.8 | 0.3 | 1.3 | 2% CMC, 0.2% Tween20 PBS buffer at pH 6.73 |
| 11 | 126.0 | 0.3 | 0.6 | 2% CMC, 0.2% Tween20 PBS buffer at pH 6.73 |
| 50 | 99.0 | 2.0 | 1.7 | 2% CMC, 0.2% Tween20 PBS buffer at pH 6.73 |
| 7 | 60.2 | 1.0 | 4.4 | 2% CMC, 0.2% Tween20 PBS buffer at pH 6.73 |
| 20 | 55.0 | 1.0 | 1.6 | 2% CMC, 0.2% Tween20 PBS buffer at pH 6.73 |
| 17 | 37.4 | 0.3 | 0.3 | 2% CMC, 0.2% Tween20 PBS buffer at pH 6.73 |
| 28 | 192.0 | 0.3 | 2.4 | 2% CMC, 0.2% Tween20 PBS buffer at pH 6.73 |
| 36 | 151.0 | 0.04 | 1.9 | 2% CMC, 0.2% Tween20 PBS buffer at pH 6.73 |
| 51 | 66.5 | 0.63 | 2.66 | 2% CMC, 0.2% Tween20 PBS buffer at pH 6.73 |
| 52 | 52.8 | 4.00 | 5.14 | 2% CMC, 0.2% Tween20 PBS buffer at pH 6.73 |
| 22 | 63.1 | 1.83 | 1.11 | 2% CMC, 0.2% Tween20 PBS buffer at pH 6.73 |
| 53 | 127 | 2.00 | NA | 2% CMC, 0.2% Tween20 PBS buffer at pH 6.73 |
| 30 | 7.06 | 0.20 | ND | 2% CMC, 0.2% Tween20 PBS buffer at pH 6.73 |
| 43 | 0.4 | 0.20 | ND | 2% CMC, 0.2% Tween20 PBS buffer at pH 6.8 |
| 49 | 14.2 | 0.25 | ND | 2% CMC, 0.2% Tween20 PBS buffer at pH 6.8 |

The results show that the olanzapine prodrug compounds have a longer T$_{max}$ and/or T$_{1/2}$ than olanzapine. This indicates that these compounds provide delayed release of olanzapine to systemic circulation compared to olanzapine itself.

While this invention has been particularly shown and described with references to preferred embodiments thereof, it will be understood by those skilled in the art that various changes in form and details may be made therein without departing from the scope of the invention encompassed by the appended claims. It should also be understood that the embodiments described herein are not mutually exclusive and that features from the various embodiments may be combined in whole or in part in accordance with the invention.

What is claimed is:

1. A method for sustained delivery of a tertiary amine-containing parent drug to a patient comprising administering a prodrug compound of the parent drug having the formula:

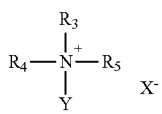

wherein

R$_3$, R$_4$ and R$_5$, together with the nitrogen atom to which they are attached, form a tertiary amine-containing parent drug or a tertiary imine-containing parent drug;

Y is C(R$_7$R$_8$)OC(O)R$_9$, where R$_7$ and R$_8$ are each independently hydrogen or an aliphatic group, and R$_9$ is selected from:
  i) branched, substituted or unsubstituted C$_8$-C$_{24}$ alkyl;
  ii) branched, substituted or unsubstituted C$_8$-C$_{24}$ alkenyl;
  iii) branched, substituted or unsubstituted C$_8$-C$_{24}$ alkynyl;
  iv) substituted or unsubstituted C$_3$-C$_{12}$ cycloalkyl;
  v) substituted or unsubstituted aryl; and
  vi) substituted or unsubstituted heteroaryl; and X$^-$ is a pharmaceutically acceptable anion; and an optional biocompatible delivery system for delivering the prodrug wherein the system is capable of minimizing accelerated hydrolytic cleavage of the prodrug by minimizing exposure of the prodrug to water;

wherein the prodrug compound has lower aqueous solubility at a reference pH as compared to the aqueous solubility of the parent drug at the same reference pH, wherein the reference pH is a pH at which the parent drug is fully protonated and wherein upon administration to the patient, release of the parent drug from the prodrug is sustained release and wherein the parent drug is present in the blood stream of the patient for a period of at least one week.

2. The method of claim 1, wherein R$_7$ and R$_8$ are independently:
  i) hydrogen;
  ii) branched or unbranched, substituted or unsubstituted C$_1$-C$_6$ alkyl;
  iii) branched or unbranched, substituted or unsubstituted C$_2$-C$_6$ alkenyl;
  iv) branched or unbranched, substituted or unsubstituted C$_2$-C$_6$ alkynyl; or
  v) substituted or unsubstituted C$_3$-C$_{12}$ cycloalkyl.

3. The method of claim 1, wherein R$_7$ and R$_8$ are independently:
  i) hydrogen;
  ii) methyl; or
  iii) ethyl.

4. The method of claim 1, wherein R$_9$ is:
  i) C$_8$-C$_{24}$ secondary alkyl group; or
  ii) C$_8$-C$_{24}$ tertiary alkyl group.

5. The method of claim 1, wherein R$_9$ is selected from branched, substituted or unsubstituted C$_9$-C$_{24}$ alkyl.

6. A method for sustained delivery of a tertiary amine-containing parent drug to a patient comprising administering a prodrug compound of the parent drug having the formula:

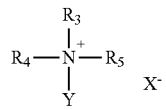

wherein

R$_3$, R$_4$ and R$_5$, together with the nitrogen atom to which they are attached, form a tertiary amine-containing parent drug or a tertiary imine-containing parent drug, Y is C(R$_7$R$_8$)OC(O)R$_9$, where R$_7$ and R$_8$ are each independently hydrogen, methyl or ethyl;

R$_9$ is any aliphatic group that provides a prodrug having lower aqueous solubility at a reference pH as compared to the aqueous solubility of the parent drug, at the same reference pH wherein the reference pH is a pH at which the parent drug is fully protonated;

X⁻ is a pharmaceutically acceptable anion; and
an optional biocompatible delivery system for delivering the prodrug wherein the system is capable of minimizing accelerated hydrolytic cleavage of the prodrug by minimizing exposure of the prodrug to water;
wherein the prodrug compound has lower aqueous solubility at a reference pH as compared to the aqueous solubility of the parent drug at the same reference pH wherein the reference pH is a pH at which the parent drug is fully protonated and wherein upon administration to the patient, release of the parent drug from the prodrug is sustained release and wherein the parent drug is present in the blood stream of the patient for a period of at least one week.

7. A method of reducing a side effect of sedation or coma in a patient as compared to sedation or coma caused by administration of the parent drug of formula IV:

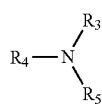

formula IV comprising administering to the patient, a prodrug compound of the parent drug of Formula III:

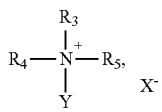

Formula III wherein
$R_3$, $R_4$ and $R_5$, together with the nitrogen atom to which they are attached, form a tertiary amine-containing parent drug or a tertiary imine-containing parent drug;
Y is $C(R_7R_8)OC(O)R_9$, where $R_7$ and $R_8$ are each independently hydrogen or an aliphatic group;
$R_9$ is:
  i) branched, substituted or unsubstituted $C_8$-$C_{24}$ alkyl;
  ii) branched, substituted or unsubstituted $C_8$-$C_{24}$ alkenyl;
  iii) branched, substituted or unsubstituted $C_8$-$C_{24}$ alkynyl; and
  iv) substituted or unsubstituted $C_3$-$C_{12}$ cycloalkyl;
X⁻ is a pharmaceutically acceptable anion; and
an optional biocompatible delivery system for delivering the prodrug wherein the system is capable of minimizing accelerated hydrolytic cleavage of the prodrug by minimizing exposure of the prodrug to water and wherein the prodrug provides pH-independent sustained delivery of the tertiary amine-containing parent drug.

8. A method for sustained delivery of a tertiary amine-containing parent drug to a patient comprising administering a prodrug compound of the parent drug having the formula:

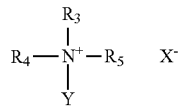

wherein
$R_3$, $R_4$ and $R_5$, together with the nitrogen atom to which they are attached, form a tertiary amine-containing parent drug or a tertiary imine-containing parent drug;
Y is $C(R_7R_8)OC(O)R_9$,
where $R_7$ and $R_8$ are each independently hydrogen or an aliphatic group,
and $R_9$ is selected from:
  i) branched, substituted or unsubstituted $C_7$-$C_{24}$ alkyl;
  ii) branched, substituted or unsubstituted $C_7$-$C_{24}$ alkenyl;
  iii) branched, substituted or unsubstituted $C_7$-$C_{24}$ alkynyl;
  iv) substituted or unsubstituted $C_3$-$C_{12}$ cycloalkyl;
  v) substituted or unsubstituted aryl; and
  vi) substituted or unsubstituted heteroaryl;
X⁻ is a pharmaceutically acceptable anion; wherein the prodrug compound has lower aqueous solubility at a reference pH as compared to the aqueous solubility of the parent drug at the same reference pH, wherein the reference is a at which the parent drug is fully protonated; and
wherein upon administration to the patient, release of the parent drug from the prodrug is sustained release for at least one week and wherein the parent drug is present in the blood stream of the patient for a period of at least one week.

9. The method of claim 8, wherein $R_7$ and $R_8$ are independently:
  i) hydrogen;
  ii) branched or unbranched, substituted or unsubstituted $C_1$-$C_6$ alkyl;
  iii) branched or unbranched, substituted or unsubstituted $C_2$-$C_6$ alkenyl;
  iv) branched or unbranched, substituted or unsubstituted $C_2$-$C_6$ alkynyl; or
  v) substituted or unsubstituted $C_3$-$C_{12}$ cycloalkyl.

10. The method of claim 8, wherein $R_7$ and $R_8$ are independently:
  i) hydrogen;
  ii) methyl; or
  iii) ethyl.

11. The method of claim 8, wherein $R_9$ is:
  i) $C_7$-$C_{24}$ secondary alkyl group; or
  ii) $C_7$-$C_{24}$ tertiary alkyl group.

12. The method of claim 8, wherein $R_7$ and $R_8$ are both hydrogen.

13. The method of claim 12, wherein Y is selected from the group consisting of:

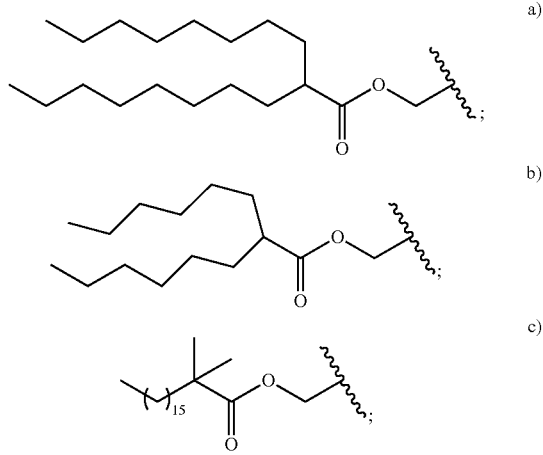

-continued d)

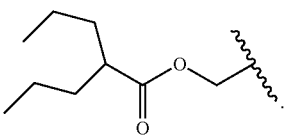

e)

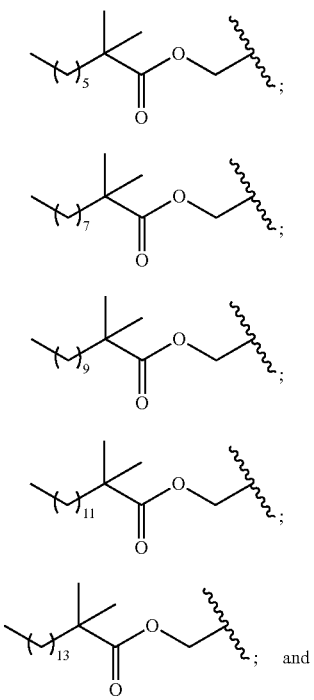

f)

g)

h)

-continued i)

14. The method of claim 8, wherein the administering step is by injection or oral delivery.

15. The method of claim 8, wherein the parent drug is amisulpride, aripiprazole, asenapine, cariprazine, citalopram, dehydroaripiprazole, escitalopram, galantamine, iloperidone, latrepirdine, lurasidone, olanzapine, paliperidone, perospirone, risperidone, or ziprasidone.

16. The method of claim 8, wherein the prodrug has lower aqueous solubility at a reference pH as compared to the aqueous solubility of the parent drug at the same reference pH wherein the reference pH is a pH at which the parent drug is fully protonated.

17. The method of claim 1, wherein the optional biocompatible delivery system is polymeric matrix delivery system.

* * * * *

UNITED STATES PATENT AND TRADEMARK OFFICE
CERTIFICATE OF CORRECTION

PATENT NO. : 9,670,200 B2  Page 1 of 1
APPLICATION NO. : 12/978178
DATED : June 6, 2017
INVENTOR(S) : Almarsson et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 269 days.

Signed and Sealed this
Twenty-fifth Day of September, 2018

Andrei Iancu
*Director of the United States Patent and Trademark Office*